United States Patent
Engelhardt et al.

(10) Patent No.: US 11,529,399 B2
(45) Date of Patent: *Dec. 20, 2022

(54) ANTI-ICOS AGONIST ANTIBODIES AND USES THEREOF

(71) Applicant: BRISTOL-MYERS SQUIBB COMPANY, Princeton, NJ (US)

(72) Inventors: John J. Engelhardt, Fremont, CA (US); Mark J. Selby, San Francisco, CA (US); Alan J. Korman, Piedmont, CA (US); Mary Diane Feingersh, Hayward, CA (US); Brenda L. Stevens, Seattle, WA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 553 days.

This patent is subject to a terminal disclaimer.

(21) Appl. No.: 16/601,231

(22) Filed: Oct. 14, 2019

(65) Prior Publication Data

US 2020/0030425 A1 Jan. 30, 2020

Related U.S. Application Data

(62) Division of application No. 15/946,625, filed on Apr. 5, 2018, now Pat. No. 10,898,556.

(60) Provisional application No. 62/581,412, filed on Nov. 3, 2017, provisional application No. 62/545,732, filed on Aug. 15, 2017, provisional application No. 62/514,151, filed on Jun. 2, 2017, provisional application No. 62/483,158, filed on Apr. 7, 2017.

(51) Int. Cl.
  *C07K 16/28* (2006.01)
  *A61K 39/395* (2006.01)
  *A61K 39/00* (2006.01)
  *A61P 35/00* (2006.01)

(52) U.S. Cl.
  CPC .... *A61K 39/0011* (2013.01); *A61P 35/00* (2013.01); *A61P 35/00* (2018.01); *C07K 16/2818* (2013.01); *C07K 16/2896* (2013.01); *A61K 2039/505* (2013.01); *A61K 2039/507* (2013.01); *C07K 2317/21* (2013.01); *C07K 2317/24* (2013.01); *C07K 2317/33* (2013.01); *C07K 2317/56* (2013.01); *C07K 2317/75* (2013.01); *C07K 2317/92* (2013.01)

(58) Field of Classification Search
  None
  See application file for complete search history.

(56) References Cited

U.S. PATENT DOCUMENTS

| | | |
|---|---|---|
| 7,045,615 B2 | 5/2006 | Tamatani et al. |
| 7,112,655 B1 | 9/2006 | Tamatani et al. |
| 7,259,247 B1 | 8/2007 | Kroczek |
| 7,465,444 B2 | 12/2008 | Watanabe |
| 7,722,872 B2 | 5/2010 | Kroczek |
| 7,998,478 B2 | 8/2011 | Tezuka et al. |
| 8,389,690 B2 | 3/2013 | Tamatani et al. |
| 9,657,106 B2 | 5/2017 | Lazar et al. |
| 9,738,718 B2 | 8/2017 | Liu et al. |
| 9,771,424 B2 | 9/2017 | Liu et al. |
| 10,251,945 B2 | 4/2019 | Engelhardt et al. |
| 10,493,140 B2 | 12/2019 | Engelhardt et al. |
| 10,898,556 B2 | 1/2021 | Engelhardt et al. |
| 11,207,391 B2 * | 12/2021 | Engelhardt ........ A61K 39/0011 |
| 2006/0024298 A1 | 2/2006 | Lazar et al. |
| 2012/0039874 A1 | 2/2012 | Tsuji et al. |
| 2012/0183565 A1 | 7/2012 | Mataraza et al. |
| 2012/0213771 A1 | 8/2012 | Keler et al. |
| 2013/0142783 A1 | 6/2013 | Coyle et al. |
| 2014/0120103 A1 * | 5/2014 | Zhang ..................... A61P 35/02 424/139.1 |

(Continued)

FOREIGN PATENT DOCUMENTS

| | | |
|---|---|---|
| EP | 2482849 A2 | 8/2012 |
| EP | 2679681 B1 | 1/2014 |

(Continued)

OTHER PUBLICATIONS

Zhang, D. et al., "Fc Engineering Approaches to Enhance the Agonism and Effector Functions of an Anti-OX40 Antibody," J Biol Chem., vol. 291(53):27134-27146 (2016).
U.S. Appl. No. 15/946,625, filed Apr. 5, 2018, John J. Engelhardt.
U.S. Appl. No. 16/198,387, filed Nov. 21, 2018, John J. Engelhardt.
U.S. Appl. No. 16/281,447, filed Feb. 21, 2019, John J. Engelhardt.
U.S. Appl. No. 16/351,995, filed Mar. 13, 2019, John J. Engelhardt.
U.S. Appl. No. 15/946,625, Nov. 5, 2018, I. Ouspenski.
U.S. Appl. No. 15/946,625, Jun. 28, 2019, I. Ouspenski.
U.S. Appl. No. 16/198,387, Jan. 2, 2019, I. Ouspenski.

(Continued)

*Primary Examiner* — Ilia I Ouspenski
(74) *Attorney, Agent, or Firm* — Nelson Mullins Riley & Scarborough LLP; Jane E. Remillard, Esq.; Jeanne M. DiGiorgio, Esq.

(57) ABSTRACT

The present invention provides isolated monoclonal antibodies (e.g., humanized and human monoclonal antibodies) that bind to human Inducible T Cell COStimulator (ICOS) and exhibit therapeutically desirable functional properties, e.g., the ability to stimulate human ICOS activity. Nucleic acid molecules encoding the antibodies of the invention, expression vectors, host cells, and methods for expressing the antibodies of the invention are also provided. Immunoconjugates, bispecific molecules, and pharmaceutical compositions comprising the antibodies of the invention are also provided. The antibodies of the invention can be used, for example, as an agonist to stimulate or enhance an immune response in a subject, e.g., antigen-specific T cell responses against a tumor or viral antigen. The antibodies of the invention can also be used in combination with other antibodies (e.g., PD-1, PD-L1, and/or CTLA-4 antibodies) to treat, for example, cancer. Accordingly, the antibodies can be used in therapeutic applications and methods to detect ICOS protein.

32 Claims, 35 Drawing Sheets

Specification includes a Sequence Listing.

(56) References Cited

U.S. PATENT DOCUMENTS

| | | |
|---|---|---|
| 2016/0215059 A1 | 7/2016 | Liu et al. |
| 2016/0304610 A1 | 10/2016 | Sazinsky et al. |
| 2017/0174766 A1 | 6/2017 | Sathish et al. |
| 2017/0233478 A1 | 8/2017 | Faget et al. |
| 2017/0275372 A1 | 9/2017 | Marodon et al. |
| 2018/0030136 A1 | 2/2018 | Liu et al. |
| 2018/0289790 A1 | 10/2018 | Engelhardt et al. |
| 2019/0076515 A1 | 3/2019 | Engelhardt et al. |
| 2019/0175705 A1 | 6/2019 | Engelhardt et al. |
| 2019/0298816 A1 | 10/2019 | Engelhardt et al. |
| 2020/0030425 A1 | 1/2020 | Engelhardt et al. |

FOREIGN PATENT DOCUMENTS

| | | |
|---|---|---|
| EP | 3147297 A1 | 3/2017 |
| JP | 200101108 A | 1/2001 |
| WO | 1998/038216 A1 | 9/1998 |
| WO | 1999/15553 A2 | 4/1999 |
| WO | 0187981 A2 | 11/2001 |
| WO | 2008/137915 A2 | 11/2008 |
| WO | 2011041613 A2 | 4/2011 |
| WO | 2012087928 A2 | 6/2012 |
| WO | 2012131004 A2 | 10/2012 |
| WO | 2014/089113 A1 | 6/2014 |
| WO | 2016120789 A1 | 8/2016 |
| WO | 2016154177 A2 | 9/2016 |
| WO | 2017025871 A1 | 2/2017 |
| WO | 2017/070423 A1 | 4/2017 |
| WO | 2017/220988 A1 | 12/2017 |
| WO | 2018/029474 A2 | 2/2018 |
| WO | 2018/187613 A2 | 10/2018 |

OTHER PUBLICATIONS

U.S. Appl. No. 16/281,447, Jul. 16, 2019, I. Ouspenski.
U.S. Appl. No. 16/281,447, May 14, 2019, I. Ouspenski.
Amatore, F. et al., "Inducible Co-Stimulator (ICOS) as a potential therapeutic target for anti-cancer therapy," Expert Opinion On Therapeutic Targets, vol. 22 (4):343-351 (2018).
Buonfiglio, D. et al., "The T cell activation molecule H4 and the CD28-like molecule ICOS are identical," Eur J Immunol., vol. 30(12): 3463-3467 (2000).
Chu, SY., et al., "Inhibition of B cell receptor-mediated activation of primary human B cells by coengagement of CD19 and FcgammaRIIb with Fc-engineered antibodies.," Mol. Immunol. 45:3926-3933(2008).
Deng Z-B, et al., "An agonist human ICOS monoclonal antibody that induces T cell activation and inhibits proliferation of a myeloma cell line," Hybridoma and Hybridomics, vol. 23(3):176-182 (2004).
Harvey, C. et al., "Efficacy of anti-ICOS agonist monoclonal antibodies in preclinical tumor models provides a rationale for clinical development as cancer immunotherapeutics," J. for ImmunoTherapy of Cancer, vol. 3 (Suppl 2): 09 (2015) 1 page.
International Search Report and Written Opinion, PCT/US2018/026318, dated Oct. 5, 2018, 24 pages.
Invitation to Pay Additional Fees and, Where Applicable Protest Fee, PCT/US2018/026318, dated Jul. 17, 2018, 15 pages.
Invitation to Provide Further Clarification, PCT/US2018/026318, dated Jun. 15, 2018, 5 pages.
Redoglia, V. et al., "Characterization of H4: a mouse T lymphocyte activation molecule functionally associated with the CD3/T cell receptor.," Eur. J. Immunol, vol. 26:2781-2789(1996).
Technical Data Sheet for C398.4A Purified anti-human/mouse/rat CD278 (ICOS) Antibody. Retrieved Jun. 20, 2018. BioLegend. (2 pages).
U.S. Appl. No. 15/946,625, Dec. 2, 2020, I. Ouspenski.
U.S. Appl. No. 15/946,625, Aug. 19, 2020, I. Ouspenski.
U.S. Appl. No. 15/946,625, Feb. 18, 2020, I. Ouspenski.
Gonzales, N. et al: "Minimizing the Immunogenicity of Antibodies for Clinical Application," Tumour Biol., vol. 26 (1):31-43 (2005).
Wu, H., et al.: "Humanization of a Murine Monoclonal Antibody by Simultaneous Optimization of Framework and CDR Residues," J. Mol. Biol., vol. 294:151-162 (1999).

* cited by examiner

MKSGLWYFFLFCLRIKVLTGEINGSANYEMFIFHNGGVQILCKYPDIVQQFKMQLLKGGQ 60
ILCDLTKTKGSGNTVSIKSLKFCHSQLSNNSVSFFLYNLDHSHANYYFCNLSIFDPPPFK 120
VTLTGGYLHIYESQLCCQLKFWLPIGCAAFVVVCILGCILICWLTKKKYSSSVHDPNGEY 180
MFMRAVNTAKKSRLTDVTL (SEQ ID NO:1) 199

FIG.1

ASTKGPSVFP LAPSSKSTSG GTAALGCLVK DYFPEPVTVS WNSGALTSGV HTFPAVLQSS 177

GLYSLSSVVT VPSSSLGTQT YICNVNHKPS NTKVDKRVEP KSCDKTHTCP PCPAPELLGG 237
                                                                                                          D  D

PSVFLFPPKP KDTLMISRTP EVTCVVVDVS HEDPEVKFNW YVDGVEVHNA KTKPREEQYN 297
D                                                                     E D EG

STYRVVSVLT VLHQDWLNGK EYKCKVSNKA LPAPIEKTIS KAKGQPREPQ VYTLPPSREE 357
                                                  F    R

MTKNQVSLTC LVKGFYPSDI AVEWESNGQP ENNYKTTPPV LDSDGSFFLY SKLTVDKSRW 417

QQGNVFSCSV MHEALHNHYT QKSLSLSPG 446

FIG.2

```
                              FR              CDR1          FR2            CDR2
                              * *    *
           VKI 018  DIQMTQSPSSLSASVGDRVTITC  QASQDISNYLN  WYQQKPGKAPKLLIY  DASNLET
         C398.4A VL DIQMTQSPSSLPASLGDRVTINC  QASQDISNYLS  WYQQKPGKAPKLLIY  YTNLLAD
ICOS.33 IgG1f S267E VL DIQMTQSPSSLSASVGDRVTITC  QASQDISNYLS  WYQQKPGKAPKLLIY  YTNLLAE
                                                                                  56

FR3             CDR3         FR4
                              * **     * *    * *                  * *

VKI 018  GVPSRFSGSGSGTDFTFTISSLQPEDIATYYC  QQYDNLP
         C398.4A VL GVPSRFSGSGSGRDYSFTISSLESEDIGSYYC  QQYYNYRT  FGPGTKLEIK
             JK3                                               FT  FGPGTKVDIK
ICOS.33 IgG1f S267E VL GVPSRFSGSGSGTDFTFTISSLQPEDIATYYC  QQYYNYRT  FGPGTKVDIK
                                                                               57

FR1             CDR1         FR2
                              *      *   *                            *

VH3-15  EVQLVESGGGLVKPGGSLRLSCAASGFTFS  NAWMS  WVRQAPGKGLEWVG
         C398.4A VH EVQLVESGGGLVKPAGSLTLSCVASGFTFS  DYFMH  WVRQAPGKGLEWVA
ICOS.33 IgG1f S267E VH EVQLVESGGGLVKPGGSLRLSCAASGFTFS  DYFMH  WVRQAPGKGLEWVG

CDR2                        FR3           94   CDR3
                                          *    ****    * **    *   *

VH3-15  RIKSKTDGGTTDYAAPVKG  RFTISRDDSKNTLYLQMNSLKTEDTAVYYCTT
         C398.4A VH VIDTKSFNYATYYSDLVKG  RFTVSRDDSQGMVYLQMNNLRKEDTATYYCTA  TIAVPYYFDY
ICOS.33 IgG1f S267E VH VIDTKSFNYATYYSDLVKG  RFTISRDDSKNTLYLQMNSLKTEDTAVYYCTA  TIAVPYYFDY
                                FR4
                                *

C398.4A VH      WCQGTMVTVSS
             JH4  YFDY  WGQGTLVTVSS
ICOS.33 IgG1f S267E VH   WGQGTLVTVSS
```

FIG.3

EVQLVESGGGLVKPGGSLRLSCAASGFTFSDYFMHWVRQAPGKGLEWVG
                                  CDR1

VIDTKSFNYATYYSDLVKGRFTISRDDSKNTLYLQMNSLKTEDTAVYYC
      CDR2

TATIAVPYYFDYWGQGTLVTVSS (SEQ ID NO:5)
    CDR3

DIQMTQSPSSLSASVGDRVTITCQASQDISNYLSWYQQKPGKAPKLLIY
                          CDR1

YTNLLAEGVPSRFSGSGSGTDFTFTISSLQPEDIATYYCQQYYNYRTFG
  CDR2                                      CDR3

PGTKVDIK (SEQ ID NO:6)

FIG.4

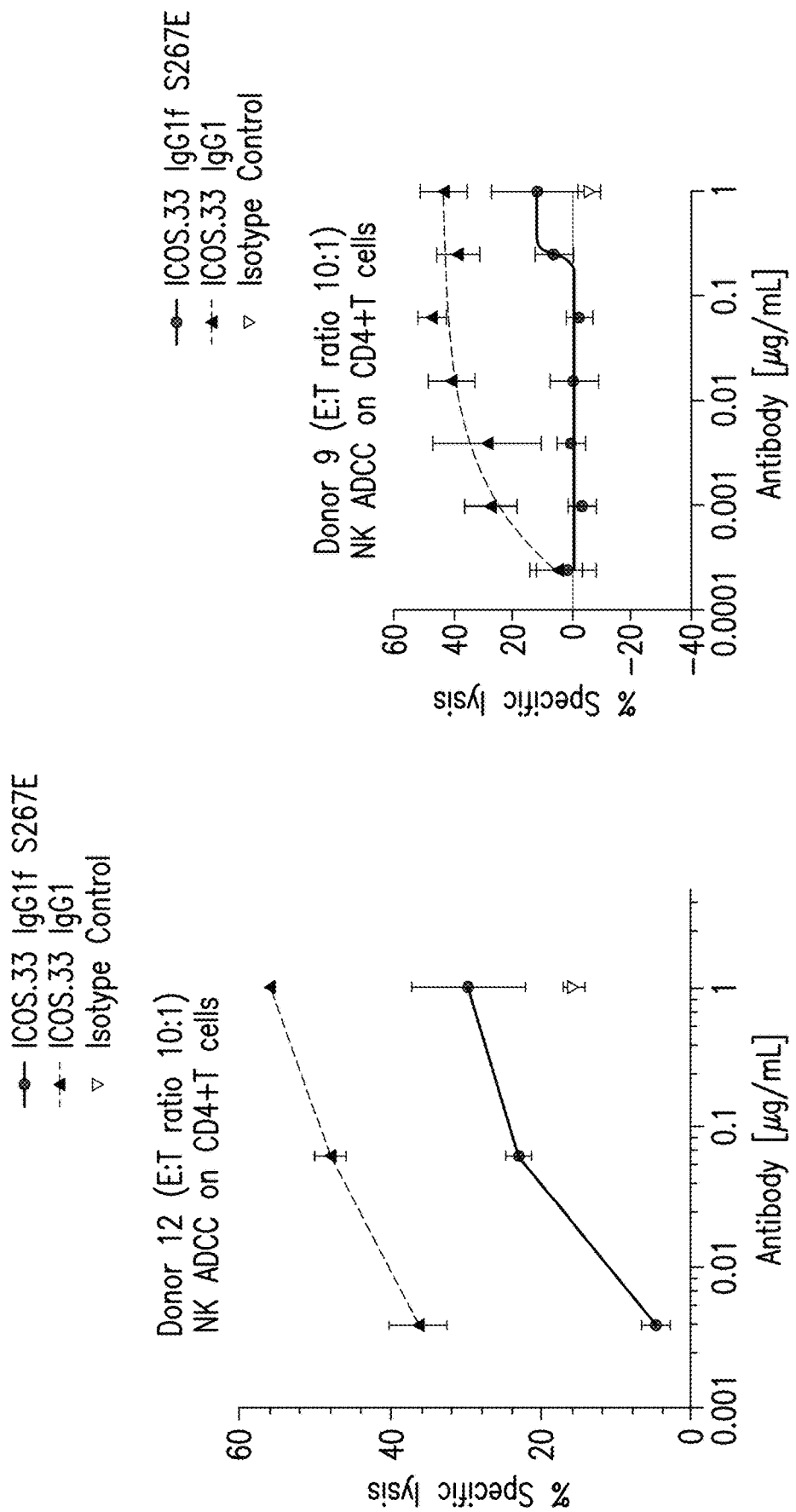

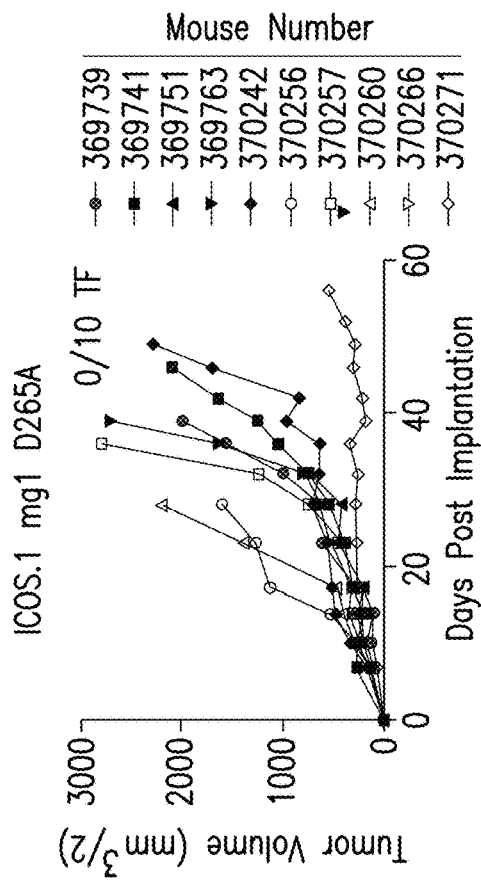
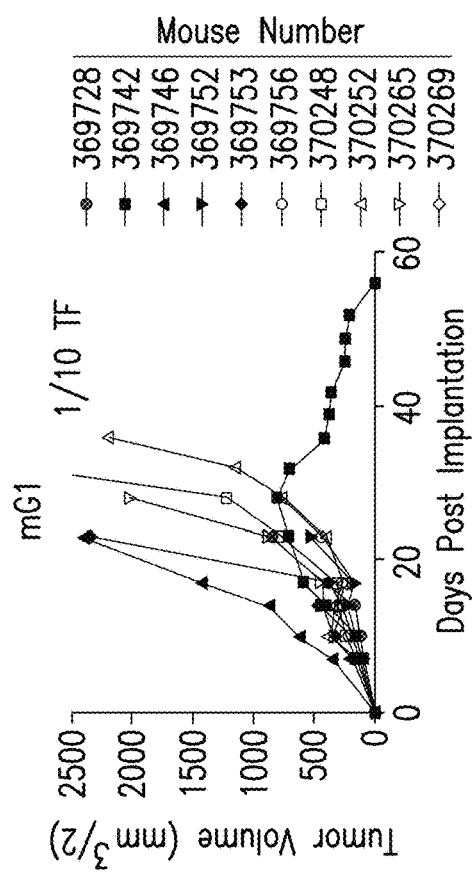
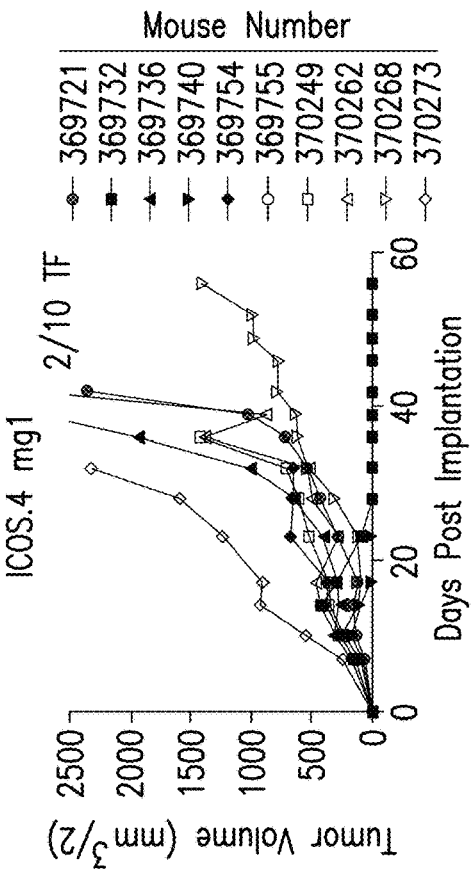
FIG. 12A
FIG. 12B
FIG. 12C

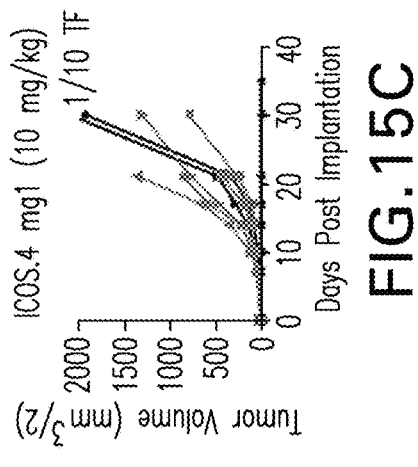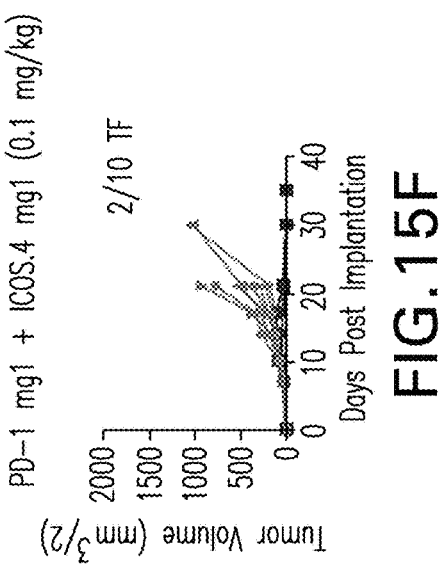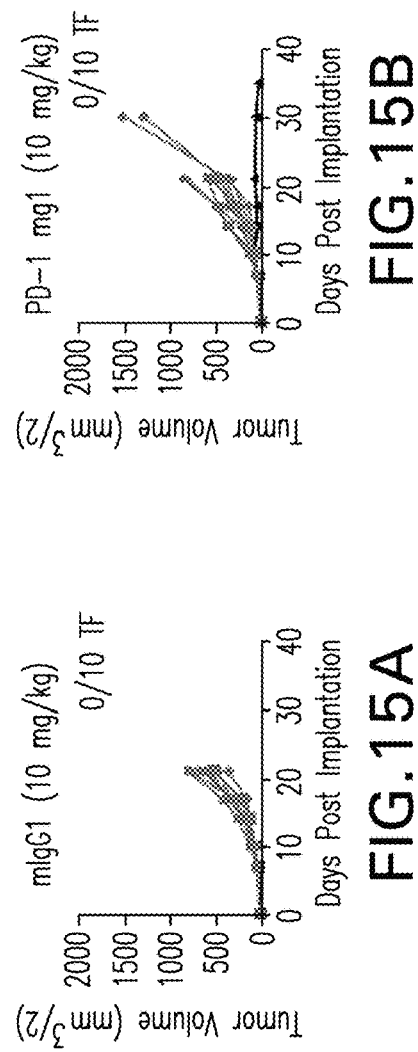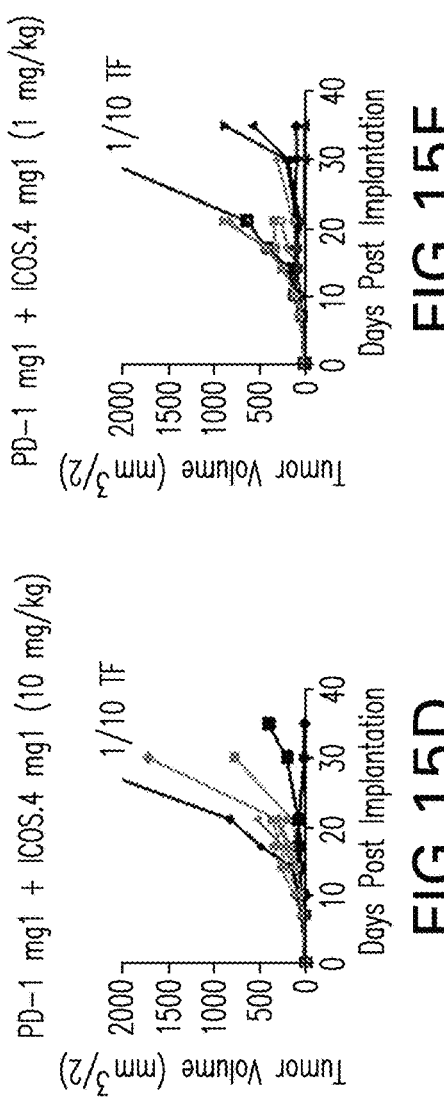

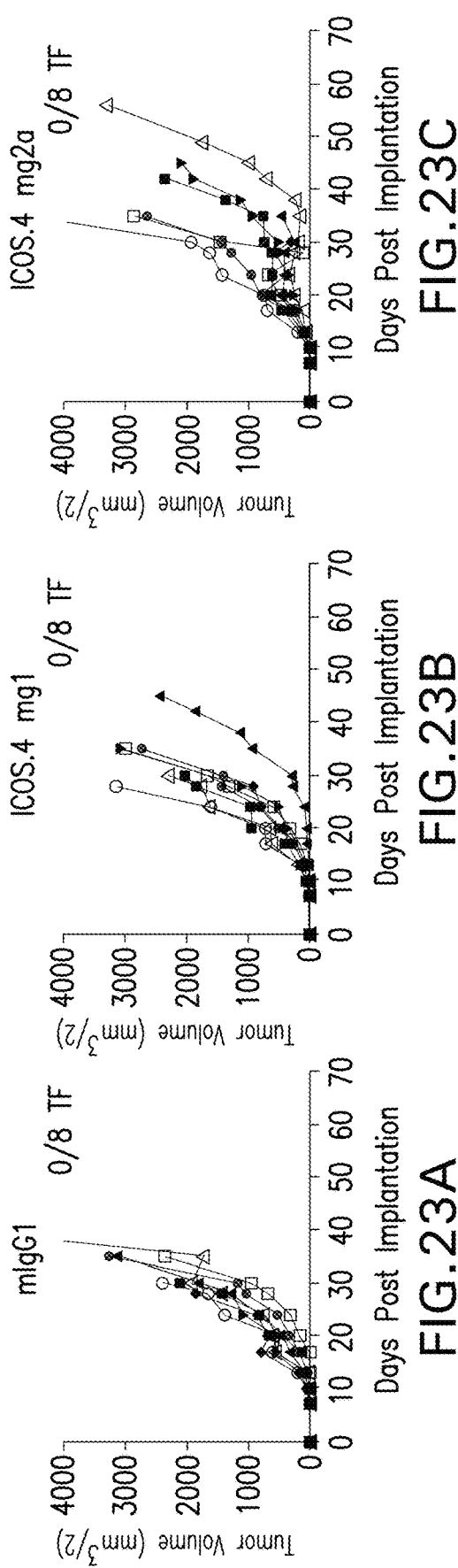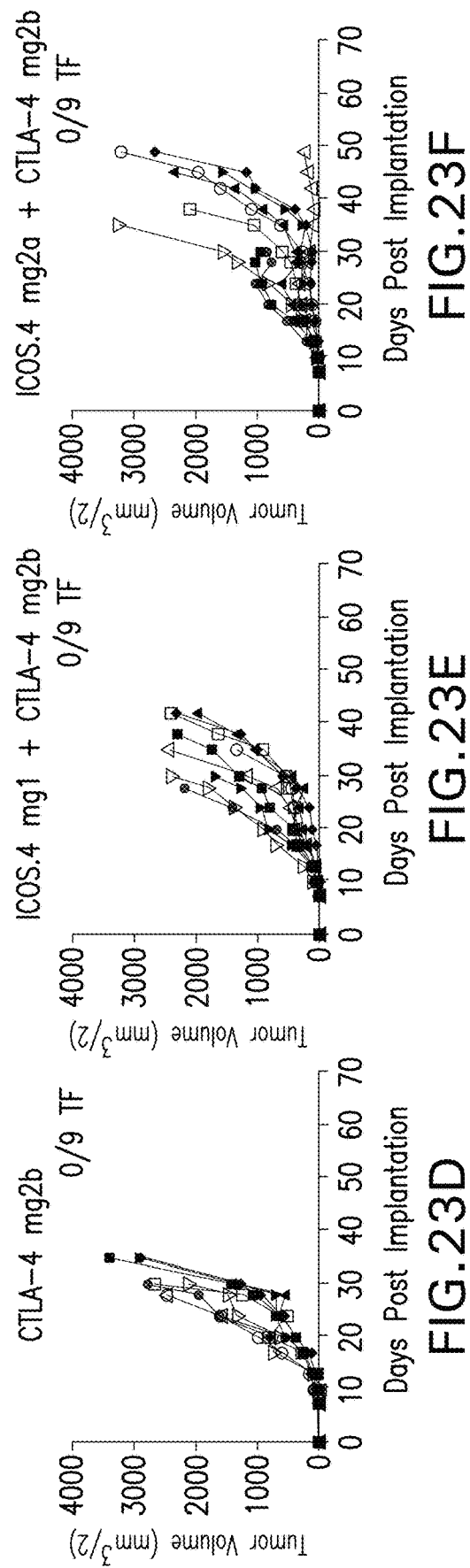

ANTI-ICOS AGONIST ANTIBODIES AND USES THEREOF

RELATED APPLICATIONS

This application is a divisional of U.S. patent application Ser. No. 15/946,625, filed on Apr. 5, 2018, which claims the benefit of priority of U.S. Provisional Application Nos. 62/483,158 (filed on Apr. 7, 2017), 62/514,151 (filed on Jun. 2, 2017), 62/545,732 (filed on Aug. 15, 2017) and 62/581,412 (filed on Nov. 3, 2017). The contents of the aforementioned applications are hereby incorporated by reference in their entireties.

TECHNICAL FIELD

This invention relates to anti-Inducible T Cell COStimulator (ICOS) agonist antibodies and pharmaceutical compositions thereof, and methods for using such antibodies, e.g., for treating cancer by administering the anti-ICOS agonist antibodies and pharmaceutical compositions.

SEQUENCE LISTING

The instant application contains a Sequence Listing which has been filed electronically in ASCII format and is hereby incorporated by reference in its entirety. Said ASCII copy, created on Oct. 14, 2019, is named MXI-556DV4_Sequence_Listing.txt and is 318,969 bytes in size.

BACKGROUND

A need exists to combat the global epidemic of cancer. Cancer is one of the leading causes of disease and the second leading cause of death worldwide. Cancer accounted for 8.8 million deaths in 2015. Globally, nearly one in six deaths is due to cancer. In 2018, there will be an estimated 1,735,350 new cancer cases diagnosed and 609,640 cancer deaths in the United States. In 2012, there were an estimated 3.5 million new cancer cases and 1.9 million cancer deaths in Europe. The World Health Organization estimates in 2018 that the number of new cases of cancer is expected to rise by about 70% over the next two decades.

Traditional cancer treatments include surgery, radiation therapy, and chemotherapy, amongst other therapies. In recent years, immuno-oncology has emerged as a new option to treat cancer. Immuno-oncology is different from traditional cancer treatments, which, for example, has tried to target tumors directly or to disrupt the tumor blood supply. Instead, immuno-oncology is designed to use the patient's own immune response to treat cancer. Understanding how the immune system affects cancer development and how it can be used to treat cancer has been a challenging, complicated problem. For example, patients may not respond to certain immuno-oncology drugs, and some develop resistance mechanisms, such as T cell exhaustion, which is when a T cell, a specific type of white blood cell, no longer functions properly. (Dempke et al., *Eur. J. of Cancer*, 74 55-72 (2017)).

An important role of the immune system is its ability to differentiate between normal cells and "foreign" cells. The immune system can thus attack the foreign cells and leave normal cells alone. To do this, the immune system uses "checkpoints," which are molecules on certain immune cells that need to be activated or inactivated to begin an immune response. Tumor cells can sometimes use these checkpoints to avoid being attacked by the immune system. Some immuno-oncology drugs target these checkpoints by acting as checkpoint inhibitors. Programmed death protein 1 (PD-1) is a checkpoint inhibitor that typically acts as a brake to prevent T cells from attacking other cells in the body. PD-1 does this when it binds to programmed death ligand 1 (PD-L1), a protein on some normal (and cancer) cells. When PD-1 binds to PD-L1, this interaction tells the T cell to not attack other cells. Some cancer cells have large amounts of PD-L1, which helps them evade immune attack. Therapeutic agents such as monoclonal antibodies that target this PD-1/PD-L1 interaction, such as nivolumab (Opdivo®), can block the PD-1/PD-L1 binding to increase the body's immune response against tumor cells.

A need exists for drugs that target different mechanisms of action that work either alone or in combination with checkpoint inhibitors to safely and effectively treat cancer and other diseases or conditions. T cell activation and function are regulated by the innate immune system through costimulatory molecules in the CD28-superfamily (e.g., positive and negative costimulatory molecules that promote or inhibit activation of the T cell receptor signal, respectively). Inducible COStimulator molecule (ICOS), also known as CD278, is an immune checkpoint protein that is a member of this CD28-superfamily. ICOS is a 55-60 kDa type I transmembrane protein that is expressed on T cells after T cell activation and costimulates T-cell activation after binding its ligand, ICOS-L (B7H2). ICOS is expressed by CD4+ cells, CD8+ cells, and regulatory T cells (Treg). ICOS also has been shown to be a key player in the function of follicular helper T cells (Tfhs) and the humoral immune response.

The magnitude and quality of a T cell's immune response depends in part on the complicated balance between co-stimulatory and inhibitory signals to the T cell. To improve patients' response rates after immunotherapy and to overcome drug resistance, a need exists for novel immuno-oncology therapies.

SUMMARY OF THE INVENTION

The present invention provides isolated monoclonal antibodies (e.g., humanized and human monoclonal antibodies) that bind to human ICOS (SEQ ID NO:1), i.e., anti-huICOS antibodies, and exhibit therapeutically desirable functional properties. The antibodies of the invention can be used as an agonist to stimulate or enhance an immune response in a subject, e.g., to stimulate human ICOS activity and/or to provide antigen-specific T cell responses against a tumor or viral antigen. The antibodies of the invention can also be used in combination with other antibodies (e.g., PD-1, PD-L1, and/or CTLA-4 antibodies) to treat various conditions, for example, cancer. Accordingly, the antibodies disclosed herein, either alone or in combination with other agents, can be used to treat various conditions or diseases, including cancer. In other embodiments, the antibodies disclosed herein can be used in methods to detect ICOS protein.

In one aspect, the isolated antibody is a humanized isolated antibody (or antigen binding portion thereof) that binds to human ICOS and blocks the binding and/or the interaction of an ICOS ligand (e.g., human ICOS-L) to human ICOS and (a) induces proliferation and interferon-gamma (IFN-γ) production in CD25– CD4+ T cells with an EC50 of about 0.01 to about 0.16 nM in an in vitro CHO-OKT3-CD32A co-culture assay; and/or (b) induces IFN-γ production in CD25− CD4+ T cells with an EC50 of about 0.002 nM to about 0.4 nM in a staphylococcal enterotoxin B in a CD25− CD4+ T cell and B cell co-culture assay.

In another embodiment, the antibody (or antigen binding portion thereof) exhibits one or more of the following features:

(a) binds to human T cells with an EC50 of about 0.7 nM and cynomolgus T cells with an EC50 of about 0.3 nM;

(b) binds to human activated CD4+ T cells;

(c) does not bind to human CD28 or human CTLA-4;

(d) activates at least one primary T lymphocyte, such as a CD4+ effector T (Teff) cell, a follicular helper T (Tfh) cell, and a regulatory T (Treg) cell;

(e) induces phosphorylation of protein kinase B (pAkt) in an in vitro primary T cell signaling assay with an EC50 of about 30 nM;

(f) induces interleukin-10 (IL-10) production in response to staphylococcal enterotoxin B in a Tfh and naive B cell co-culture assay;

(g) induces a greater proliferation increase of CD3-stimulated Teffs compared to CD45RA+ Tregs and CD45RO+ Tregs in an in vitro assay;

(h) reduces Teff suppression by Tregs;

(i) does not increase cytokine production in a whole blood cell assay at 10 μg/mL;

(j) increases secretion of at least one of IL-10 and IFN-g by Tfh cells in vitro;

(k) stimulates ICOS-mediated signaling;

(l) has increased affinity for CD32B and/or CD32A; and/or (m) has decreased affinity for CD16.

In another embodiment, the isolated antibody is a humanized isolated antibody (or antigen binding portion thereof) that binds to human ICOS and blocks the binding and/or the interaction of an ICOS ligand (e.g., human ICOS-L) to human ICOS and induces proliferation and interferon-gamma (IFN-γ) production in CD25− CD4+ T cells with an EC50 of about 0.083 nM in an in vitro CHO-OKT3-CD32A co-culture assay. In another embodiment, the isolated antibody is a humanized isolated antibody (or antigen binding portion thereof) that binds to human ICOS and blocks the binding and/or the interaction of an ICOS ligand (e.g., human ICOS-L) to human ICOS and induces proliferation and interferon-gamma (IFN-γ) production in CD25− CD4+ T cells with an EC50 of about 0.01 to about 0.1 nM in an in vitro CHO-OKT3-CD32A co-culture assay.

In one aspect, the isolated antibody is a humanized isolated antibody (or antigen binding portion thereof) that binds to human ICOS and blocks the binding and/or the interaction of an ICOS ligand (e.g., human ICOS-L) to human ICOS and induces IFN-γ production in CD25− CD4+ T cells with an EC50 of about 0.2 nM in a staphylococcal enterotoxin B in a CD25− CD4+ T cell and B cell co-culture assay. In another aspect, the isolated antibody is a humanized isolated antibody (or antigen binding portion thereof) that binds to human ICOS and blocks the binding and/or the interaction of an ICOS ligand (e.g., human ICOS-L) to human ICOS and induces IFN-γ production in CD25− CD4+ T cells with an EC50 of about 0.01-0.1 nM in a staphylococcal enterotoxin B in a CD25− CD4+ T cell and B cell co-culture assay.

In another embodiment, the antibody (or antigen binding portion thereof) binds to human, cynomolgus, mouse, and rat ICOS.

In another aspect, the isolated antibody binds to human Inducible COStimulator molecule (ICOS) and comprises:

(a) a heavy chain variable domain comprising CDR1, CDR2, and CDR3 regions comprising the amino acid sequences of SEQ ID NOs: 9, 10 and 11, respectively, and a light chain variable domain comprising CDR1, CDR2, and CDR3 regions comprising the amino acid sequences of SEQ ID NOs: 12, 14 and 15, respectively;

(b) a heavy chain variable domain comprising CDR1, CDR2, and CDR3 regions comprising the amino acid sequences of SEQ ID NOs: 18, 19 and 20, respectively, and a light chain variable domain comprising CDR1, CDR2, and CDR3 regions comprising the amino acid sequences of SEQ ID NOs: 21, 22 and 23, respectively;

(c) a heavy chain variable domain comprising CDR1, CDR2, and CDR3 regions comprising the amino acid sequences of SEQ ID NOs: 26, 27 and 28, respectively, and a light chain variable domain comprising CDR1, CDR2, and CDR3 regions comprising the amino acid sequences of SEQ ID NOs: 29, 30 and 31, respectively;

(d) a heavy chain variable domain comprising CDR1, CDR2, and CDR3 regions comprising the amino acid sequences of SEQ ID NOs: 34, 35 and 36, respectively, and a light chain variable domain comprising CDR1, CDR2, and CDR3 regions comprising the amino acid sequences of SEQ ID NOs: 37, 38 and 39, respectively;

(e) a heavy chain variable domain comprising CDR1, CDR2, and CDR3 regions comprising the amino acid sequences of SEQ ID NOs: 42, 43, and 44, respectively, and a light chain variable domain comprising CDR1, CDR2, and CDR3 regions comprising the amino acid sequences of SEQ ID NOs: 45, 46, and 47, respectively;

(f) a heavy chain variable domain comprising CDR1, CDR2, and CDR3 regions comprising the amino acid sequences of SEQ ID NOs: 42, 43, and 44, respectively, and a light chain variable domain comprising CDR1, CDR2, and CDR3 regions comprising the amino acid sequences of SEQ ID NOs: 49, 50, and 51, respectively; or (g) a heavy chain variable domain comprising CDR1, CDR2, and CDR3 regions comprising the amino acid sequences of SEQ ID NOs: 191, 192, and 193, respectively, and a light chain variable domain comprising CDR1, CDR2, and CDR3 regions comprising the amino acid sequences of SEQ ID NOs: 194, 195, and 196, respectively.

In another aspect, the isolated antibody binds to human Inducible COStimulator molecule (ICOS), and the heavy and light chain variable regions comprise:

(a) the amino acid sequences of SEQ ID NOs: 5 and 6, respectively;

(b) the amino acid sequences of SEQ ID NOs: 16 and 17, respectively;

(c) the amino acid sequences of SEQ ID NOs: 24 and 25, respectively;

(d) the amino acid sequences of SEQ ID NOs: 32 and 33, respectively;

(e) the amino acid sequences of SEQ ID NOs: 40 and 41, respectively;

(f) the amino acid sequences of SEQ ID NOs: 40 and 48, respectively; or (g) the amino acid sequences of SEQ ID NOs: 186 and 189, respectively.

In another aspect, the isolated, full-length, humanized monoclonal antibody that binds to human Inducible COStimulator molecule (ICOS) comprises heavy chains that comprise the amino acid sequence set forth in SEQ ID NO: 7 and light chains that comprise the amino acid sequence set forth in SEQ ID NO: 8.

In one embodiment, the isolated antibody competes for binding to ICOS with or binds to the same epitope as an antibody that blocks the interaction of human ICOS and human ICOS-L. In another embodiment, the isolated antibody specifically binds to one or more residues of SIFDPPPFKVTL (SEQ ID NO: 203) of human ICOS. In another embodiment, the ICOS epitope comprises amino acid residues SIFDPPPFKVTL (SEQ ID NO: 203) of human ICOS.

In one embodiment, the antibodies of the invention are full-length antibodies, for example, of an IgG1, IgG2, IgG2a, or IgG4 isotype. In another embodiment, the antibodies are binding fragments, such as Fab, Fab' or (Fab')2 fragments, or single chain antibodies.

In one aspect, the anti-ICOS antibodies, or antigen binding portions thereof, bind to Fc receptors, such as one or more activating Fc gamma receptors (FcγRs). In certain embodiments, the antibody comprises at least one amino acid substitution in the Fc region compared to human IgG1 sequence (SEQ ID NO: 206), which enhances affinity of the antibody to an FcγR, e.g., FcγRIIb, such as one or more amino acid substitution at a position comprising at least one of 234, 235, 236, 237, 239, 266, 267, 268, 325, 326, 327, 328, and/or 332, according to the EU index, e.g., 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and/or 332E. In other embodiments, the Fc region comprises at least two substitutions of 235Y-267E, 236D-267E, 239D-268D, 239D-267E, 267E-268D, 267E-268E, and/or 267E-328F compared to human IgG1 sequence (SEQ ID NO: 206). In yet another embodiment, the amino acid substitution in the Fc region is S267E compared to human IgG1 sequence as set forth in SEQ ID NO: 206.

In another aspect, the invention provides immunoconjugates comprising an antibody of the invention, or antigen-binding portion thereof, linked to a therapeutic agent, e.g., a cytotoxic agent or a radioactive isotope, as well as a bispecific molecules comprising an antibody, or antigen-binding portion thereof, of the invention, linked to a second functional moiety having a different binding specificity than said antibody, or antigen binding portion thereof.

Compositions (e.g., pharmaceutical compositions) comprising an antibody, or antigen-binding portion thereof, or immunoconjugate or bispecific molecule of the invention and a pharmaceutically acceptable carrier are also provided. In another aspect, the composition further comprises a soluble neutral-active hyaluronidase glycoprotein.

Nucleic acid molecules encoding the antibodies (e.g., cDNA), or antigen-binding portions thereof (e.g., variable regions and/or CDRs), of the invention also are provided, as well as expression vectors comprising such nucleic acids and host cells comprising such expression vectors. Methods for producing anti-ICOS antibodies by expressing the antibody in such host cells and isolating the antibody from the host cell are also provided.

In one aspect, the isolated antibody has reduced antibody-dependent cell-mediated cytotoxicity (ADCC) activity compared to an IgG1 control antibody.

In another aspect, the invention provides methods of stimulating immune responses using anti-ICOS antibodies, or antigen-binding portions thereof, of the invention. In one embodiment, the method includes stimulating an antigen-specific T cell response by contacting T cells with an antibody, or an antigen-binding portion thereof, of the invention, such that an antigen-specific T cell response is stimulated. In another embodiment, interleukin-2 production by the antigen-specific T cell is stimulated. In yet another embodiment, the subject has a tumor(s), and an immune response against the tumor is stimulated. In another embodiment, the subject has a virus, and an immune response against the virus is stimulated.

In yet another aspect, the invention provides a method for inhibiting growth of tumor cells in a subject comprising administering to the subject an antibody, or antigen-binding portion thereof, of the invention, such that growth of the tumor is inhibited in the subject. In another aspect, the invention provides a method for treating viral infection in a subject comprising administering to the subject an antibody, or antigen-binding portion thereof, of the invention such that the viral infection is treated in the subject. Such methods comprise administering an antibody, or an antigen-binding portion thereof, a composition, bispecific, or immunoconjugate of the invention.

In yet another aspect, the invention provides a method for stimulating an immune response in a subject comprising administering to the subject an antibody, or antigen-binding portion thereof, of the invention, e.g., in combination with at least one additional therapeutic agent, such as an anti-PD-1 antibody, an anti-PD-L1 antibody and/or an anti-CTLA-4 antibody, such that an immune response is stimulated in the subject, for example to inhibit tumor growth or to stimulate an anti-viral response. In one embodiment, the additional immunostimulatory antibody is an anti-PD-1 antibody. In another embodiment, the additional immunostimulatory agent is an anti-PD-L1 antibody. In yet another embodiment, the additional immunostimulatory agent is an anti-CTLA-4 antibody. In yet another embodiment, an antibody, or antigen-binding portion thereof, of the invention is administered with a cytokine (e.g., IL-2, modified IL-2, and/or IL-21), or a costimulatory antibody (e.g., an anti-CD137 and/or anti-GITR antibody). In some embodiments, the antibodies are, for example, human, chimeric or humanized antibodies.

In one embodiment, the isolated antibody is administered with one or more additional therapeutic agent(s) to the human subject. In another embodiment, the additional therapeutic agent is a chemotherapeutic agent.

Also provided herein are methods for treating cancer in a subject (e.g., a human patient), comprising administering to the patient an anti-ICOS antibody, or a combination of an anti-ICOS antibody and at least one additional antibody (e.g., an anti-PD-1 antibody, an anti-PD-L1 antibody, and/or an anti-CTLA-4 antibody), wherein the anti-ICOS antibody, or combination of antibodies, are administered according to a particular dosage regimen (i.e., at a particular dose amount and according to a specific dosing schedule). In one aspect, the method comprises at least one administration cycle and, for each of the at least one cycles, at least one dose of the antibody is administered at a dose of about 375 mg. In another aspect, the antibody is administered in an amount or frequency sufficient to achieve and/or maintain a receptor occupancy of less than about 80%. In another embodiment, the method comprises administration at an interval of once a week, once every two weeks, once every three weeks, once every four weeks, once every five weeks, once every six weeks, once every seven weeks, once every eight weeks, once every nine weeks, once every ten weeks, once every eleven weeks, or once every twelve weeks.

The methods disclosed herein include treatment of cancers, such as colorectal cancer (CRC), head and neck squamous cell carcinoma (HNSCC), non-small cell lung cancer (NSCLC), prostate cancer (PRC), urothelial carcinoma (UCC), bladder cancer, breast cancer, uterine/cervical cancer, ovarian cancer, testicular cancer, esophageal cancer, gastrointestinal cancer, pancreatic cancer, colon cancer, kidney cancer, stomach cancer, germ cell cancer, bone cancer, liver cancer, thyroid cancer, skin cancer, neoplasm of the central nervous system, lymphoma, leukemia, myeloma, sarcoma, or virus-related cancer.

In yet another embodiment, the antibodies are formulated for intravenous administration. In another embodiment, the antibodies are formulated for subcutaneous administration. In another embodiment, the antibodies are administered simultaneously (e.g., in a single formulation or concurrently as separate formulations). Alternatively, in another embodiment, the antibodies are administered sequentially (e.g., as separate formulations).

The efficacy of the treatment methods provided herein can be assessed using any suitable means. In some embodiments, the treatment reduces tumor size, reduces the number of metastatic lesions over time, produces a complete response, produces a partial results, and/or results in stable disease.

In another aspect, the invention provides anti-ICOS antibodies, or antigen-binding portions thereof, and compositions of the invention for use in the foregoing methods, or for the manufacture of a medicament for use in the foregoing methods (e.g., for treatment of various conditions).

Also provided are kits that include a pharmaceutical composition containing an anti-ICOS antibody in a therapeutically effective amount adapted for use in the methods described herein. In another embodiment, the kit includes an anti-ICOS antibody and another antibody (e.g., an anti-PD-1 antibody, an anti-PD-L1 antibody, and/or an anti-CTLA-4 antibody) in therapeutically effective amounts adapted for use in the methods described herein. For example, the kit comprises:

(a) a dose of an anti-ICOS antibody;
(b) a dose of an anti-PD-1 antibody, an anti-PD-L1 antibody, and/or an anti-CTLA-4 antibody; and
(c) instructions for using the antibodies in a method of the invention.

In another aspect, an anti-ICOS antibody is provided for administration (or co-administration with another antibody, e.g., an anti-PD-1 antibody, an anti-PD-L1 antibody, and/or an anti-CTLA-4 antibody) according to the methods described herein.

Other features and advantages of the instant disclosure will be apparent from the following detailed description and examples, which should not be construed as limiting. The contents of all references, GenBank entries, patents and published patent applications cited throughout this application are expressly incorporated herein by reference.

BRIEF DESCRIPTION OF THE DRAWINGS

FIG. 1 shows the human ICOS sequence (SEQ ID NO: 1). The results of epitope binding analysis for ICOS.4 using hydrogen/deuterium exchange mass spectrometry (HDX-MS) are shown with the ICOS.4 epitope in bold and underlined.

FIG. 2 shows a portion of the sequence of human IgG1f constant domain (SEQ ID NO: 52, renumbered as residues 118-446) that can be used in the Fc sequence variants disclosed herein. Residues set forth in bold are example residues subject to variation. The altered amino acid is provided in bold below the particular residue. The D270E substitution is underlined. A C-terminal lysine (K) residue has been omitted from the sequence of SEQ ID NO: 52 but, in some embodiments, is present. Likewise, in some embodiments, nucleic acids encoding these embodiments include nucleotides encoding the extra lysine at the 3' end of the nucleic acid.

FIG. 3 shows the sequence alignment of the human heavy and light chain germline sequences used for humanizing the parental hamster antibody (C398.4). VH3-15 was selected for the heavy chain, and VKI O18 was selected for the light chain based on framework sequence homology. Human germline FW4, JK3, was also selected for the light chain based on sequence homology. Human germline FW4, JH4, was selected for the heavy chain based on sequence similarity, and it did not contain residues that could pose a potential liability risk. Asterisks and underlining indicate the amino acid residues that differ between the germline sequences and the parental hamster antibody sequence (C398.4).

FIG. 4 shows the heavy and the light chain variable region sequences of the anti-ICOS antibody ICOS.33 IgG1f S267E. The CDR1, 2, and 3 regions of the heavy and the light chain variable regions are in bold, underlined, and labeled.

FIGS. 9A and 9B are graphs that compare the ability of ICOS.33 IgG1f S267E and ICOS.33 IgG1 to induce ADCC using cells from two different donors (Donors 9 and 12).

FIGS. 12A-E are graphs that show the tumor growth curves by treatment group. Mice were treated with isotype control mG1, ICOS.1 mg1 D265A, ICOS.4 mg1, ICOS.4 hg1, or ICOS.4 mg2a on days 7, 10, and 14 post-Sa1N cell implantation.

FIGS. 15A-J are graphs that show tumor growth curves for individual mice by treatment group: isotype control mIgG1, anti-PD-1 mIgG1 D265A ("PD-1"), and/or anti-ICOS.4 mIgG1 ("ICOS.4 mg1") antibodies.

FIGS. 23A-F are graphs that show the tumor growth curves for individual mice by treatment group: isotype control mIgG1, anti-CTLA-4 mIgG2b ("CTLA-4 mg2b"), anti-ICOS.4 mIgG1 ("ICOS.4 mg1"), and/or anti-ICOS.4 mIgG2a ("ICOS.4 mg2a") antibodies.

DETAILED DESCRIPTION

Figure 5B:
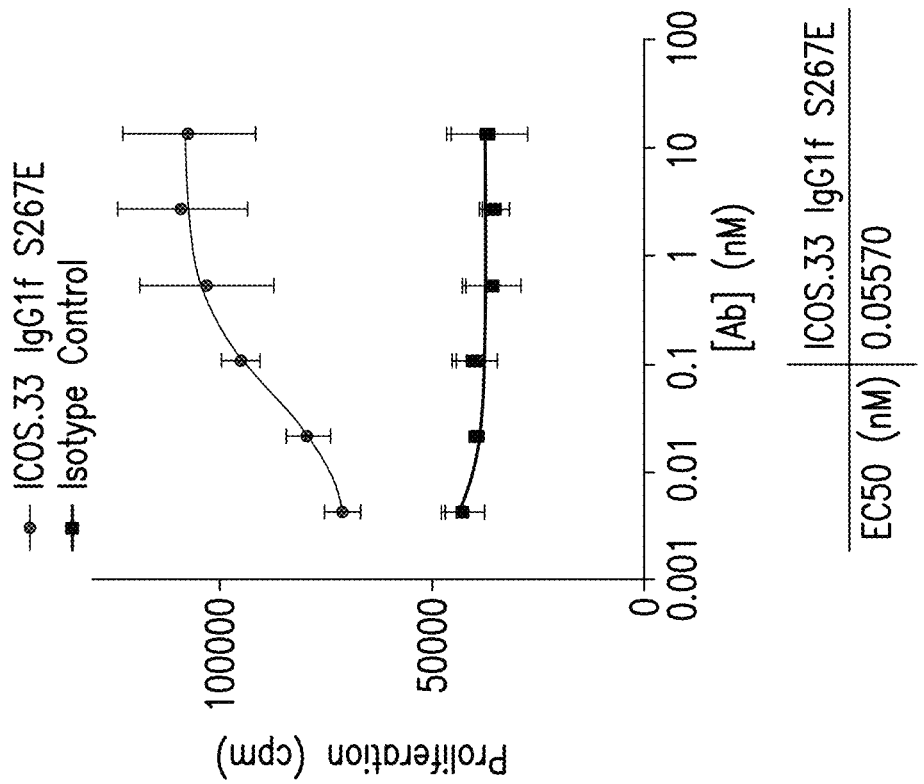
FIGS. 5A and 5B are graphs that show interferon-gamma (IFN-γ) production and cell proliferation induced by ICOS.33 IgG1f S267E in co-cultures of CD25− CD4+ T cells and CHO-OKT3-CD32A cells.

The present invention provides isolated antibodies, such as monoclonal antibodies, e.g., humanized or human monoclonal antibodies, that specifically bind to human ICOS ("huICOS") and have agonist activity to stimulate an immune response. In some embodiments, the antibodies described herein comprise particular structural features such as CDR regions comprising particular amino acid sequences. In other embodiments, the antibodies compete for binding to human ICOS protein with, or bind to the same epitope as, the antibodies of the present invention.

Further provided herein are methods of making such antibodies, immunoconjugates, and bispecific molecules comprising such antibodies or antigen-binding fragments thereof, and pharmaceutical compositions formulated to contain the antibodies or antibody fragments. Also provided herein are methods of using the antibodies, either alone or in combination with other agents, e.g., other immunostimulatory agents (e.g., antibodies), to enhance the immune response to, for example treat cancer and/or infections. Accordingly, the anti-huICOS antibodies described herein may be used to treat a variety of conditions, including, for example, to inhibit tumor growth.

Definitions

In order that the present description may be more readily understood, certain terms are first defined. Additional definitions are set forth throughout the detailed description. The headings provided herein are not limitations of the various aspects of the disclosure, which can be understood by reference to the specification as a whole. Accordingly, the terms defined immediately below are more fully defined by reference to the specification in its entirety.

As used herein, ICOS refers to "inducible T-cell co-stimulator" protein that in humans is encoded by the ICOS gene. ICOS is also known as "inducible co-stimulator," "activation-inducible lymphocyte immunomediatory molecule," AILIM, CVID1, and CD278. Human ICOS is further described at GENE ID NO: 29851 and MIM (Mendelian Inheritance in Man): 604558. The sequence of human ICOS (NP_036224.1), including a 20 amino acid signal sequence, is provided as SEQ ID NO: 1 and shown in FIG. 1.

Below are the amino acid sequences of the two human ICOS isoforms.

```
Isoform 1 (Q9Y6W8)
                                          (SEQ ID NO: 1)
MKSGLWYFFL FCLRIKVLTG EINGSANYEM FIFHNGGVQI

LCKYPDIVQQ FKMQLLKGGQ ILCDLTKTKG SGNTVSIKSL

KFCHSQLSNN SVSFFLYNLD HSHANYYFCN LSIFDPPPFK

VTLTGGYLHI YESQLCCQLK FWLPIGCAAF VVVCILGCIL

ICWLTKKKYS SSVHDPNGEY MFMRAVNTAK KSRLTDVTL

Isoform 2 (Q9Y6W8-2)
                                        (SEQ ID NO: 205)
MKSGLWYFFLFCLRIKVLTGEINGSANYEMFIFHNGGVQILCK

YPDIVQQFKMQLLKGGQILCDLTKTKGSGNTVSIKSLKFCHSQ

LSNNSVSFFLYNLDHSHANYYFCNLSIFDPPPFKVTLTGGYLH

IYESQLCCQLKFWLPIGCAAFVVVCILGCILICWLTKKM
```

The signal sequence of isoforms 1 and 2 correspond to amino acids 1-20 (underlined above). Thus, the mature isoforms 1 and 2 consist of amino acids 21-199 of SEQ ID NO: 1 and amino acids 21-158 of SEQ ID NO: 205.

ICOS interacts with ICOS ligand (ICOS-L), which is also known as ICOSL, ICOS-LG, LICOS, B7H2, B7-H2, B7RP1, B7RP-1, CD275 and GL50. Human ICOS-L is further described at GENE ID NO: 23308 and MIM: 605717. The sequence of human ICOS-L (NP_001269979.1), including 18 amino acid signal sequence, is provided at SEQ ID NO: 2. Thus, the mature form of ICOS-L consists of amino acids 19-302 of SEQ ID NO: 2.

The term "antibody" or "immunoglobulin," which is used interchangeably herein, refers to a protein comprising at least two heavy (H) chains and two light (L) chains interconnected by disulfide bonds. Each heavy chain is comprised of a heavy chain variable region (abbreviated herein as $V_H$) and a heavy chain constant region (abbreviated herein as CH). In certain antibodies, e.g., naturally occurring IgG antibodies, the heavy chain constant region is comprised of a hinge and three domains, CH1, CH2 and CH3. In certain antibodies, e.g., naturally occurring IgG antibodies, each light chain is comprised of a light chain variable region (abbreviated herein as $V_L$) and a light chain constant region. The light chain constant region is comprised of one domain (abbreviated herein as CL). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. A heavy chain may have the C-terminal lysine or not. Unless specified otherwise herein, the amino acids in the variable regions are numbered using the Kabat numbering system and those in the constant regions are numbered using the EU system. An immunoglobulin can be from any of the known isotypes, including IgA, secretory IgA, IgD, IgE, IgG, and IgM. The IgG isotype is divided in subclasses in certain species: IgG1, IgG2, IgG3 and IgG4 in humans, and IgG1, IgG2a, IgG2b and IgG3 in mice. In certain embodiments, the anti-ICOS antibodies described herein are of the IgG1 subtype. Immunoglobulins, e.g., IgG1, exist in several allotypes, which differ from each other in at most a few amino acids. "Antibody" includes, by way of example, both naturally occurring and non-naturally occurring antibodies; monoclonal and polyclonal antibodies; chimeric and humanized antibodies; human and nonhuman antibodies and wholly synthetic antibodies.

As used herein, an "IgG antibody" has the structure of a naturally occurring IgG antibody, i.e., it has the same number of heavy and light chains and disulfide bonds as a naturally occurring IgG antibody of the same subclass. For example, an anti-ICOS IgG1, IgG2, IgG3 or IgG4 antibody consists of two heavy chains (HCs) and two light chains (LCs), wherein the two heavy chains and light chains are linked by the same number and location of disulfide bridges that occur in naturally occurring IgG1, IgG2, IgG3 and IgG4 antibodies, respectively (unless the antibody has been mutated to modify the disulfide bonds).

An "antigen" is a molecule or substance that triggers an immune response and to which an antibody binds. Antibodies typically bind specifically to their cognate antigen with high affinity, reflected by a dissociation constant ($K_D$) of $10^{-7}$ to $10^{-11}$ M or less. Any $K_D$ greater than about $10^{-6}$ M is generally considered to indicate nonspecific binding. As used herein, an antibody that "binds specifically" to an antigen refers to an antibody that binds to the antigen and, in some cases, substantially identical antigens, with high affinity, which means having a $K_D$ of $10^{-7}$ M or less, $10^{-8}$ M or less, $5 \times 10^{-9}$ M or less, or between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, at least 95%, at least 97%, or at least 99% sequence identity to the sequence of the given antigen. By way of example, an antibody that binds specifically to human ICOS, in some embodiments, also cross-reacts with ICOS antigens from certain non-human primate species (e.g., cynomolgus monkey), but does not cross-react with ICOS from other species or with an antigen other than ICOS.

As used herein, the term "antigen-binding portion" or "antigen-binding fragment" of an antibody refers to one or more parts of an antibody that retain the ability to specifically bind to an antigen (e.g., human ICOS). It has been shown that the antigen-binding function of an antibody can be performed by fragments or portions of a full-length antibody. Examples of binding fragments encompassed within the term "antigen-binding portion" or "antigen-binding fragment" of an antibody, e.g., an anti-ICOS antibody described herein, include:

(1) a Fab fragment (fragment from papain cleavage) or a similar monovalent fragment consisting of the $V_L$, $V_H$, LC and CH1 domains;

(2) a F(ab')2 fragment (fragment from pepsin cleavage) or a similar bivalent fragment comprising two Fab fragments linked by a disulfide bridge at the hinge region;

(3) a Fd fragment consisting of the $V_H$ and CH1 domains;

(4) a Fv fragment consisting of the $V_L$ and $V_H$ domains of a single arm of an antibody, (5) a single domain antibody (dAb) fragment (Ward et al., (1989) *Nature* 341:544-46), which consists of a $V_H$ domain;

(6) an isolated complementarity determining region (CDR); and (7) a combination of two or more isolated CDRs, which can optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) *Proc. Natl. Acad. Sci. USA* 85:5879-5883). Such single chain antibodies are also intended to be encompassed within the term "antigen-binding portion" or "antigen-binding fragment" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

The term "acceptor human framework" refers to a framework comprising the amino acid sequence of a light chain variable domain ($V_L$) framework or a heavy chain variable domain ($V_H$) framework derived from a human immunoglobulin framework or a human consensus framework. An acceptor human framework "derived from" a human immunoglobulin framework or a human consensus framework may have the same amino acid sequence as the naturally-occurring human immunoglobulin framework or human consensus framework, or it may have amino acid sequence changes compared to wild-type naturally-occurring human immunoglobulin framework or human consensus framework. In some embodiments, the number of amino acid changes are 10, 9, 8, 7, 6, 5, 4, 3, or 2, or 1. In some embodiments, the $V_L$ acceptor human framework is identical in sequence to the $V_L$ human immunoglobulin framework sequence or human consensus framework sequence.

"Hinge," "hinge domain," or "hinge region," or "antibody hinge region" refers to the domain of a heavy chain constant region that joins the CH1 domain to the CH2 domain and comprises upper, middle, and lower portions. (Roux et al. (1998) *J. Immunol.* 161:4083). Depending on its amino acid sequence, the hinge provides varying levels of flexibility between the antigen binding domain and effector region of an antibody and also provides sites for intermolecular disulfide bonding between the two heavy chain constant regions. As used herein, a hinge starts at E216 and ends at G237 for all IgG isotypes (by EU numbering). Id. The sequences of wildtype IgG1, IgG2, IgG3 and IgG4 hinges are show in Table 1.

the heavy chain constant region that is C-terminal to the CH2 domain in a heavy chain constant domain. As used herein, a CH3 domain starts at G341 and ends at K447.

A "bispecific" or "bifunctional antibody" is an artificial hybrid antibody having two different binding specificities, e.g., two different heavy/light chain pairs, giving rise to two antigen binding sites with specificity for different antigens.

TABLE 1

Hinge Region Sequences

| Ig Type | C-terminal $C_H1$* | Upper Hinge | Middle Hinge | Lower Hinge |
|---|---|---|---|---|
| IgG1 | VDKRV (SEQ ID NO: 66) | EPKSCDKTHT (SEQ ID NO: 67) | CPPCP (SEQ ID NO: 68) | APELLGG (SEQ ID NO: 69) |
| IgG2 | VDKTV (SEQ ID NO: 70) | ERK | CCVECPPCP (SEQ ID NO: 71) | APPVAG (SEQ ID NO: 72) |
| IgG3 (17-15-15-15) | VDKRV (SEQ ID NO: 66) | ELKTPLGDTTHT (SEQ ID NO: 73) | CPRCP (EPKSCDTPPPCPRCP)$_3$ (SEQ ID NO: 74) | APELLGG (SEQ ID NO: 69) |
| IgG3 (17-15-15) | VDKRV (SEQ ID NO: 66) | ELKTPLGDTTHT (SEQ ID NO: 73) | CPRCP (EPKSCDTPPPCPRCP)$_2$ (SEQ ID NO: 75) | APELLGG (SEQ ID NO: 69) |
| IgG3 (17-15) | VDKRV (SEQ ID NO: 66) | ELKTPLGDTTHT (SEQ ID NO: 73) | CPRCP (EPKSCDTPPPCPRCP)$_1$ (SEQ ID NO: 76) | APELLGG (SEQ ID NO: 69) |
| IgG3 (15-15-15) | VDKRV (SEQ ID NO: 66) | EPKS (SEQ ID NO: 77) | CDTPPPCPRCP (EPKSCDTPPPCPRCP)$_2$ (SEQ ID NO: 78) | APELLGG (SEQ ID NO: 69) |
| IgG3 (15) | VDKRV (SEQ ID NO: 66) | EPKS (SEQ ID NO: 77) | CDTPPPCPRCP (SEQ ID NO: 79) | APELLGG (SEQ ID NO: 69) |
| IgG4 | VDKRV (SEQ ID NO: 66) | ESKYGPP (SEQ ID NO: 80) | CPSCP (SEQ ID NO: 81) | APEFLGG (SEQ ID NO: 82) |

*C-terminal amino acid sequences of the CH1 domains.

The term "hinge" includes wild-type hinges (such as those set forth in Table 1), as well as variants thereof (e.g., non-naturally-occurring hinges or modified hinges). For example, the term "IgG2 hinge" includes wildtype IgG2 hinge, as shown in Table 1, and variants having 1 or more mutations (e.g., substitutions, deletions, and/or additions), for example, 1, 2, 3, 4, 5, 1 to 3, 1 to 5, 3 to 5 and/or at most 5, 4, 3, 2, or 1 mutations. Exemplary IgG2 hinge variants include IgG2 hinges in which 1, 2, 3 or all 4 cysteines (C219, C220, C226 and C229) are changed to another amino acid, e.g. serine. In a specific embodiment, the IgG2 hinge region has a C219S substitution. In certain embodiments, the hinge comprises sequences from at least two isotypes. For example, the hinge may comprise the upper, middle, or lower hinge from one isotype, and the remainder of the hinge from one or more other isotypes. For example, the hinge can be an IgG2/IgG1 hinge, and may comprise, e.g., the upper and middle hinges of IgG2 and the lower hinge of IgG1. A hinge may have effector function or be deprived of effector function. For example, the lower hinge of wildtype IgG1 provides effector function. The term "CH1 domain" refers to the heavy chain constant region linking the variable domain to the hinge in a heavy chain constant domain. As used herein, a CH1 domain starts at A118 and ends at V215. The term "CH2 domain" refers to the heavy chain constant region linking the hinge to the CH3 domain in a heavy chain constant domain. As used herein, a CH2 domain starts at P238 and ends at K340. The term "CH3 domain" refers to Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

As used herein, the term "monoclonal antibody" refers to an antibody obtained from a population of substantially homogeneous antibodies, i.e., the individual antibodies in the population are substantially similar and bind the same epitope(s) (e.g., the antibodies display a single binding specificity and affinity), except for possible variants that may arise during production of the monoclonal antibody, such variants generally being present in minor amounts. "Monoclonal" indicates the character of the antibody as having been obtained from a substantially homogenous population of antibodies, and does not require production of the antibody by any particular method. The term "human monoclonal antibody" refers to an antibody from a population of substantially homogeneous antibodies that displays a single binding specificity and that has variable and optional constant regions derived from human germline immunoglobulin sequences. In one embodiment, human monoclonal antibodies are produced by using hybridoma method. Using the hybridoma method, a transgenic non-human animal, e.g., a transgenic mouse, is exposed to an antigen, and a white blood cell known as a B cell produces antibodies that bind to the antigen, which is harvested from the transgenic non-human animal. The isolated B cells are fused with an immortalized cell to produce a hybrid cell line called a hybridoma. In one embodiment, the hybridoma has a genome comprising a human heavy chain transgene and a light chain transgene fused to an immortalized cell.

Antigen binding fragments (including scFvs) of such immunoglobulins are also encompassed by the term "monoclonal antibody" as used herein. Monoclonal antibodies are highly specific, being directed against a single antigenic site. Furthermore, in contrast to conventional (polyclonal) antibody preparations, which typically include different antibodies directed against different epitopes on the antigen, each monoclonal antibody is directed against a single epitope. Monoclonal antibodies can be prepared using any art recognized technique and those described herein such as, for example, a hybridoma method, a transgenic animal, recombinant DNA methods (see, e.g., U.S. Pat. No. 4,816,567), or using phage antibody libraries using the techniques described in, for example, U.S. Pat. No. 7,388,088 and PCT Pub. No. WO 00/31246). Monoclonal antibodies include chimeric antibodies, human antibodies, and humanized antibodies and may occur naturally or be produced recombinantly.

As used herein, the term "recombinant human antibody" includes all human antibodies that are prepared, expressed, created or isolated by recombinant means, such as (1) antibodies isolated from an animal (e.g., a mouse) that is transgenic or transchromosomal for human immunoglobulin genes or a hybridoma prepared therefrom, (2) antibodies isolated from a host cell transformed to express the antibody, e.g., from a transfectoma, (3) antibodies isolated from a recombinant, combinatorial human antibody library, and (4) antibodies prepared, expressed, created, or isolated by any other means that involve splicing of human immunoglobulin gene sequences to other DNA sequences. Such recombinant human antibodies comprise variable and constant regions that use particular human germline immunoglobulin sequences are encoded by the germline genes, but include subsequent rearrangements and mutations that occur, for example, during antibody maturation. As known in the art (see, e.g., Lonberg (2005) *Nature Biotech.* 23(9): 1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase antibody affinity to the foreign antigen. The constant region will change in further response to an antigen (i.e., isotype switch). Thus, the rearranged and somatically mutated nucleic acid molecules that encode the light chain and heavy chain immunoglobulin polypeptides in response to an antigen cannot have sequence identity with the original nucleic acid molecules, but instead will be substantially identical or similar (e.g., have at least 80% identity).

As used herein, a "human antibody" refers to an antibody having variable regions in which both the framework and CDR regions are derived from human germline immunoglobulin sequences. Furthermore, if the antibody contains a constant region, the constant region also is derived from human germline immunoglobulin sequences. The anti-huI-COS antibodies described herein may include amino acid residues not encoded by human germline immunoglobulin sequences (e.g., because of mutations introduced by random or site-specific mutagenesis in vitro or by somatic mutation in vivo). However, the term "human antibody" is not intended to include antibodies in which CDR sequences derived from the germline of another non-human mammalian species, such as a mouse, have been grafted onto human framework sequences. As used herein, the terms "human" and "fully human" antibodies are used interchangeably.

A "humanized" antibody refers to an antibody in which some, most, or all of the amino acids outside the CDR domains of a non-human antibody are replaced with corresponding amino acids derived from human antibodies. In one embodiment of a humanized form of an antibody, some, most, or all of the amino acids outside the CDR domains have been replaced with amino acids from human antibodies, whereas some, most, or all amino acids within one or more CDR regions are unchanged. Small additions, deletions, insertions, substitutions, or modifications of amino acids are permissible as long as they do not prevent the antibody from binding to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody. A "hybrid" antibody refers to an antibody having heavy and light chains of different type, such as a mouse or hamster (parental) heavy chain and a humanized light chain, or vice versa. Chimeric or hybrid antibodies can be constructed, for example by genetic engineering, from immunoglobulin gene segments belonging to different species.

As used herein, "isotype" refers to the antibody class (e.g., IgG (including IgG1, IgG2, IgG3, and IgG4), IgM, IgA (including IgA1 and IgA2), IgD, and IgE antibody) that is encoded by the heavy chain constant region genes of the antibody.

"Allotype" refers to naturally occurring variants within a specific isotype group. (See, e.g., Jefferis et al. (2009) mAbs 1:1).

The terms "an antibody recognizing an antigen" and "an antibody specific for an antigen" are used interchangeably herein with the term "an antibody that binds specifically to an antigen."

As used herein, an "isolated antibody" refers to an antibody that is substantially free of other proteins and cellular materials. As used herein, an "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and down-regulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIb, or equivalently FcγRIIB) receptor. Various exemplary properties of human FcγRs are summarized in Table 2. The majority of innate effector cell types co-express one or more activating FcγR and the inhibitory FcγRIIb, whereas natural killer (NK) cells selectively express one activating Fc receptor (FcγRIII in mice and FcγRIIIA in humans) but not the inhibitory FcγRIIb in mice and humans. Human IgG1 binds to most human Fc receptors and is considered equivalent to murine IgG2a with respect to the types of activating Fc receptors that it binds to.

TABLE 2

Exemplary Properties of Human FcγRs

| Fcγ | Allelic variants | Affinity for human IgG | Isotype preference | Cellular distribution |
|---|---|---|---|---|
| FcγRI | None described | High ($K_D$ = about 10 nM) | IgG1 = 3 > 4 >> 2 | Monocytes, macrophages, activated neutrophils, dendritic cells |
| FcγRIIA | H131 | Low to medium | IgG1 > 3 > 2 > 4 | Neutrophils, monocytes, macrophages, eosinophils, dendritic cells, platelets |
| | R131 | Low | IgG1 > 3 > 4 > 2 | |
| FcγRIIIA | V158 | Medium | IgG1 = 3 >> 4 > 2 | Natural killer (NK) cells, monocytes, macrophages, mast cells, eosinophils, dendritic cells |
| | F158 | Low | IgG1 = 3 >> 4 > 2 | |
| FcγRIIb | I232 | Low | IgG1 = 3 = 4 > 2 | B cells, monocytes, macrophages, dendritic cells, mast cells |
| | T232 | Low | IgG1 = 3 = 4 > 2 | |

As used herein, an "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA, and IgD antibody isotypes, the Fc region comprises CH2 and CH3 constant domains in each of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or an amino acid between these two amino acids) to the carboxy-terminus of the heavy chain, wherein the numbering is according to the EU index as in Kabat. (Kabat et al. (1991) *Sequences of Proteins of Immunological Interest*, National Institutes of Health, Bethesda, Md.). The CH2 domain of a human IgG Fc region extends from about amino acid 231 to about amino acid 340, whereas the CH3 domain is positioned on C-terminal side of a CH2 domain in an Fc region, i.e., it extends from about amino acid 341 to about amino acid 447 of an IgG (including a C-terminal lysine). As used herein, the Fc region may be a native sequence Fc, including any allotypic variant, or a variant Fc (e.g., a non-naturally occurring Fc). Fc region refers to this region in isolation or in the context of an Fc-comprising protein polypeptide such as a "binding protein comprising an Fc region," also referred to as an "Fc fusion protein" (e.g., an antibody or immunoadhesin).

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second (CH2) and third (CH3) constant domains of the antibody's two heavy chains. In IgM and IgE antibody isotypes, the Fc regions comprise three heavy chain constant domains (CH domains 2-4) in each polypeptide chain. For IgG, the Fc region comprises immunoglobulin domains CH2 and CH3 and the hinge between CH1 and CH2 domains. Although the definition of the boundaries of the Fc region of an immunoglobulin heavy chain might vary, as defined herein, the human IgG heavy chain Fc region is defined to stretch from an amino acid residue D221 for IgG1, V222 for IgG2, L221 for IgG3 and P224 for IgG4 to the carboxy-terminus of the heavy chain, wherein the numbering is according to the EU index as in Kabat (Kabat, et al., 1991). The CH2 domain of a human IgG Fc region extends from amino acid 237 to amino acid 340, and the CH3 domain is positioned on C-terminal side of a CH2 domain in an Fc region, i.e., it extends from amino acid 341 to amino acid 447 or 446 (if the C-terminal lysine residue is absent) or 445 (if the C-terminal glycine and lysine residues are absent) of an IgG. As used herein, the Fc region can be a native sequence Fc, including any allotypic variant, or a variant Fc (e.g., a non-naturally occurring Fc). Fc can also refer to this region in isolation or in the context of an Fc-comprising protein polypeptide such as a "binding protein comprising an Fc region," also referred to as an "Fc fusion protein" (e.g., an antibody or immunoadhesin).

A "native sequence Fc region" or "native sequence Fc" has an amino acid sequence that is identical to the amino acid sequence of an Fc region found in nature. Native sequence human Fc regions include a native sequence human IgG1 Fc region (e.g., SEQ ID NO: 206); native sequence human IgG2 Fc region; native sequence human IgG3 Fc region; and native sequence human IgG4 Fc region as well as naturally occurring variants thereof. Native sequence Fc include the various allotypes of Fcs. (See, e.g., Jefferis et al. (2009) *mAbs* 1:1).

The term "epitope" or "antigenic determinant" refers to a site on an antigen (e.g., huICOS) to which an immunoglobulin or antibody specifically binds. Epitopes can be formed both from contiguous amino acids (usually a linear epitope) or noncontiguous amino acids juxtaposed by tertiary folding of the protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14, 15, 16, 17, 18, 19, 20, 21, or 22 amino acids in a unique spatial conformation.

The term "epitope mapping" refers to the process of identifying the molecular determinants on the antigen involved in antibody-antigen recognition. Methods for determining what epitopes are bound by a given antibody are well known in the art and include, for example, immunoblotting and immunoprecipitation assays, wherein overlapping or contiguous peptides from (e.g., from ICOS) are tested for reactivity with a given antibody (e.g., anti-ICOS antibody); x-ray crystallography; antigen mutational analysis, two-dimensional nuclear magnetic resonance; yeast display; and hydrogen/deuterium exchange-mass spectrometry (HDX-MS) (see, e.g., *Epitope Mapping Protocols in Methods in Molecular Biology, Vol. 66*, G. E. Morris, Ed. (1996)).

The term "binds to the same epitope" with reference to two or more antibodies means that the antibodies bind to the same segment of amino acid residues, as determined by a given method. Techniques for determining whether antibodies bind to the "same epitope on ICOS" with the antibodies described herein include, for example, epitope mapping methods, such as x-ray analyses of crystals of antigen: antibody complexes, which provides atomic resolution of the epitope, and HDX-MS. Other methods monitor the binding of the antibody to antigen fragments (e.g. proteolytic fragments) or to mutated variations of the antigen where loss of binding due to a modification of an amino acid residue within the antigen sequence is often considered an indication of an epitope component, such as alanine scanning mutagenesis (Cunningham & Wells (1985) *Science* 244:1081) or yeast display of mutant target sequence variants (see Example 16). In addition, computational combinatorial methods for epitope mapping can also be used. These methods rely on the ability of the antibody of interest to affinity isolate specific short peptides from combinatorial phage display peptide libraries. Antibodies having the same $V_H$ and $V_L$ or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known binding competition experiments, e.g., BIACORE® surface plasmon resonance (SPR) analysis. In certain embodiments, an antibody competes with, and inhibits binding of another antibody to a target by at least 50%, 60%, 70%, 80%, 90% or 100%. The level of inhibition or competition may be different depending on which antibody is the "blocking antibody" (i.e., the antibody that when combined with an antigen blocks another immunologic reaction with the antigen). Competition assays can be conducted as described, for example, in Ed Harlow and David Lane, Cold Spring Harb. Protoc. 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope, or to adjacent epitopes (e.g., as evidenced by steric hindrance). Two antibodies "cross-compete" if antibodies block each other both ways by at least 50%, i.e., regardless of whether one or the other antibody is contacted first with the antigen in the competition experiment.

Competitive binding assays for determining whether two antibodies compete or cross-compete for binding include competition for binding to T cells expressing ICOS, e.g., by flow cytometry. Other methods include: surface plasmon resonance (SPR) (e.g., BIACORE®), solid phase direct or indirect radioimmunoassay (RIA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, Antibodies: A Laboratory Manual, Cold Spring Harbor Press (1988)); solid phase direct label RIA using 1-125 label (see Morel et al., *Mol. Immunol.* 25(1):7 (1988)); solid phase direct biotin-avidin EIA (Cheung et al., *Virology* 176:546 (1990)); and direct labeled RIA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody: (1) binds with an equilibrium dissociation constant ($K_D$) of approximately less than $10^{-7}$M, such as approximately less than $10^{-8}$ M, $10^{-9}$ M or $10^{-10}$ M or even lower when determined by, e.g., SPR technology in a BIACORE® 2000 SPR instrument using the predetermined antigen, e.g., recombinant human ICOS as the analyte and the antibody as the ligand, or Scatchard analysis of binding of the antibody to antigen positive cells, and (2) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human ICOS" refers to an antibody that binds to soluble or cell bound human ICOS with a $K_D$ of $10^{-7}$ M or less, such as approximately less than $10^{-8}$ M, $10^{-9}$M or $10^{-10}$ M or even lower. An antibody that "cross-reacts with cynomolgus ICOS" refers to an antibody that binds to cynomolgus ICOS with a $K_D$ of $10^{-7}$M or less, such as approximately less than $10^{-8}$ M, $10^{-9}$M or $10^{-10}$ M or even lower.

The term "$k_{assoc}$" or "$k_a$", as used herein, refers to the association rate constant of a particular antibody-antigen interaction, whereas the term "$k_{dis}$" or "$k_d$," as used herein, refers to the dissociation rate constant of a particular antibody-antigen interaction. The term "$K_D$", as used herein, refers to the equilibrium dissociation constant, which is obtained from the ratio of $k_d$ to $k_a$ (i.e., $k_d/k_a$) and is expressed as a molar concentration (M). $K_D$ values for antibodies can be determined using methods well established in the art. Available methods for determining the $K_D$ of an antibody is biolayer interferometry (BLI) analysis, such as using a ForteBio Octet RED device, SPR, preferably using a biosensor system such as a BIACORE® SPR system, or flow cytometry and Scatchard analysis.

The term "EC50", in the context of an in vitro or in vivo assay using an antibody or antigen binding fragment thereof, refers to the concentration of an antibody or an antigen-binding fragment thereof that induces a response that is 50% of the maximal response, i.e., halfway between the maximal response and the baseline.

The term "binds to immobilized ICOS" refers to the ability of an antibody described herein to bind to ICOS, for example, expressed on the surface of a cell or attached to a solid support.

The term "cross-reacts," as used herein, refers to the ability of an antibody described herein to bind to ICOS from a different species. For example, an antibody described herein that binds human ICOS may also bind ICOS from another species (e.g., cynomolgus ICOS). As used herein, cross-reactivity may be measured by detecting a specific reactivity with purified antigen in binding assays (e.g., SPR, ELISA) or binding to, or otherwise functionally interacting with, cells physiologically expressing ICOS. Methods for determining cross-reactivity include standard binding assays as described herein, for example, by SPR analysis using a BIACORE® 2000 SPR instrument (Biacore AB, Uppsala, Sweden), or flow cytometric techniques.

"Receptor occupancy" or "occupancy of the receptor," as used herein, refers to the amount of agonistic antibody (e.g., the anti-ICOS antibodies described herein) that is bound to the immunostimulatory receptor (e.g., human ICOS). "% receptor occupancy" or "% occupancy of the receptor" can be calculated using the following formula: ([ΔMFI of Test]/[ΔMFI of Total])×100. ΔMFI (change in mean fluorescence unit) is calculated by subtracting the MFI of background staining with an isotype control antibody from the MFI from the bound agonistic antibody. The total receptor level is determined by adding a saturating amount of agonistic antibody to determine the maximum expression and, therefore, MFI of the particular immunostimulatory receptor. An alternative means to calculate total receptor expression is to use an antibody against the same immunostimulatory receptor that does not compete with the agonistic antibody for which receptor occupancy is being calculated.

As used herein, the term "naturally-occurring" as applied to a substance is a substance that is present in nature that has not been intentionally modified by people. For example, a polypeptide or polynucleotide sequence that is present in an organism (including viruses) that can be isolated from a source in nature and which has not been intentionally modified by people in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or a disulfide bond. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

The term "cDNA" refers to a non-naturally occurring nucleic acid molecule that has been created or derived from mRNA, i.e., the non-coding regions have been removed.

The term "mRNA" or "messenger RNA" is a nucleic acid intermediate that specifies the amino acid sequence of a polypeptide during translation.

As used herein, the term "conservative sequence modifications" refers to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and polymerase chain reaction (PCR)-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine), and aromatic side chains (e.g., tyrosine, phenylalanine, tryptophan, histidine). Thus, one or more amino acid residues within the CDR regions of an antibody of the invention can be replaced with other amino acid residues from the same side chain family and the altered antibody can be tested for retained function (i.e., the functions set forth herein) using the functional assays described herein. In certain embodiments, a predicted nonessential amino acid residue in an anti-ICOS antibody is replaced with another amino acid residue from the same side chain family. Methods of identifying nucleotide and amino acid conservative substitutions that do not eliminate antigen binding are well-known in the art (see, e.g., Brummell et al., *Biochem.* 32: 1180-1187 (1993); Kobayashi et al. *Protein Eng.* 12(10): 879-884 (1999); and Burks et al. *Proc. Natl. Acad. Sci. USA* 94:412-417 (1997)).

For nucleic acids, the term "substantial homology" indicates that two nucleic acids, or designated sequences thereof, when optimally aligned and compared, are identical, with appropriate nucleotide insertions or deletions, in at least about 80% of the nucleotides, at least about 90% to 95%, or at least about 98% to 99.5% of the nucleotides. Alternatively, substantial homology exists when the segments will hybridize under selective hybridization conditions to the complement of the nucleic acid strand.

For polypeptides, the term "substantial homology" indicates that two polypeptides, or designated sequences thereof, when optimally aligned and compared, are identical, with appropriate amino acid insertions or deletions, in at least about 80% of the amino acids, at least about 90% to 95%, or at least about 98% to 99.5% of the amino acids.

The percent identity between two sequences is a function of the number of identical positions shared by the sequences when the sequences are optimally aligned (i.e., % homology=(number of identical positions)/(total number of positions)×100), taking into account the number of gaps and the length of each gap, which need to be introduced for optimal alignment of the two sequences. The comparison of sequences and determination of percent identity between two sequences can be accomplished using a mathematical algorithm, as described below.

The percent identity between two nucleotide sequences can be determined, e.g., using the GAP program in the GCG software package, using a nwsgapdna.cmp matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)), which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm, which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases, for example, to identify related sequences. Such searches can be performed using the NBLAST and)(BLAST programs (version 2.0) of Altschul, et al. (1990) *J Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the) (BLAST program, score=50, wordlength=3 to obtain amino acid sequences homologous to the protein molecules described herein. To obtain gapped alignments for comparison purposes, Gapped BLAST can be used as described in Altschul et al., (1997) *Nucleic Acids Res.* 25(17):3389-3402. When utilizing BLAST and Gapped BLAST programs, the default parameters of the respective programs (e.g.,) (BLAST and NBLAST) can be used. (See, e.g., National Center for Biotechnology Information (NCBI), available at https://www.ncbi.nlm.nih.gov/).

The nucleic acids may be present in whole cells, e.g., a host cell, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. (See, F. Ausubel, et al., ed. Current Protocols in Molecular Biology, Greene Publishing and Wiley Interscience, New York (1987)).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). Expression vectors useful in recombinant DNA techniques include plasmids. As used herein, "plasmid" and "vector" may be used interchangeably, as the plasmid is the most commonly used form of vector. However, also included are other forms of expression vectors, such as viral vectors (e.g., replication defective retroviruses, adenoviruses and adeno-associated viruses), which serve equivalent functions.

The term "host cell" or "recombinant host cell", which are used interchangeably, refers to a cell that comprises a nucleic acid that is not naturally present in the cell, and may be a cell into which a recombinant expression vector has been introduced. It should be understood that such terms refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

An "immune response" is a biological response in an organism against foreign agents, e.g., antigens, that protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the organism's body of invading pathogens, cells or tissues infected with pathogens, cancerous or other abnormal cells, or, in cases of autoimmunity or pathological inflammation, normal cells or tissues, including, for example, human cells or tissues. An immune reaction includes, e.g., activation or inhibition of a T cell, e.g., an effector T cell or a T helper (Th) cell, such as a CD4+ or CD8+ T cell, or the inhibition or depletion of a Treg cell. "Effector T" ("Teff") cells are T cells (e.g., CD4+ and CD8+ T cells) with cytolytic activities. T helper (Th) cells secrete cytokines and activate and direct other immune cells, but does not include regulatory T cells (Treg cells). T regulatory ("Treg") cells are a subpopulation of T cells that modulate the immune system, maintain tolerance to self-antigens, and prevent autoimmune disease. Memory B cells are a B cell sub-type that are formed within germinal centers following primary infection and are important in generating an accelerated and more robust antibody-mediated immune response in the case of re-infection (also known as a secondary immune response). NK cells are a type of cytotoxic lymphocyte critical to the innate immune system. The role NK cells play is analogous to that of cytotoxic T cells in the vertebrate adaptive immune response. NK cells provide rapid responses to viral-infected cells and respond to tumor formation.

As used herein, the term "T cell-mediated response" refers to a response mediated by T cells, e.g., effector T cells (e.g., CD8+ cells) and helper T cells (e.g., CD4+ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated by, for example, CD8+ T cells.

An "immunomodulator" or "immunoregulator" refers to an agent, e.g., a component of a signaling pathway that may be involved in modulating, regulating, or modifying an immune response. "Modulating," "regulating," or "modifying" an immune response refers to any alteration in a cell of the immune system or in the activity of such cell (e.g., an effector T cell, such as a Th1 cell). Such modulation includes stimulation or suppression of the immune system, which may be manifested by an increase or decrease in the number of various cell types, an increase or decrease in the activity of these cells, and/or any other changes that can occur within the immune system. Both inhibitory and stimulatory immunomodulators have been identified, some of which may have enhanced function in a tumor microenvironment. In some embodiments, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with or at risk of contracting or suffering a recurrence of a disease by a method comprising inducing, enhancing, suppressing or otherwise modifying an immune response.

"Immunostimulating therapy" or "immunostimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent, e.g., an anti-ICOS antibody, to a subject, using any of the various methods and delivery systems known to those skilled in the art. "Administering" includes, for example, administration to a human patient by another, such as, for example, one or more healthcare providers, and self-administration by the human patient. Various routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, such as by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, "adjunctive" or "combined" administration (coadministration) includes simultaneous administration of the compounds in the same or different dosage form, or separate administration of the compounds (e.g., sequential administration). Thus, a first antibody, e.g., the anti-ICOS antibody, and a second, third, or more antibodies can be simultaneously administered in a single formulation. Alternatively, the first and second (or more) antibodies can be formulated for separate administration and are administered concurrently or sequentially. "Combination" therapy, as used herein, means administration of two or more therapeutic agents in a coordinated fashion, and includes, but is not limited to, concurrent dosing. Specifically, combination therapy encompasses both co-administration (e.g. administration of a co-formulation or simultaneous administration of separate therapeutic compositions) and serial or sequential administration, provided that administration of one therapeutic agent is conditioned in some way on administration of another therapeutic agent. For example, one therapeutic agent may be administered only after a different therapeutic agent has been administered and allowed to act for a prescribed period of time. (See, e.g., Kohrt et al. (2011) *Blood* 117:2423).

For example, the anti-ICOS antibody can be administered first followed by (e.g., immediately followed by) the administration of a second antibody, or vice versa. In one embodiment, the anti-ICOS antibody is administered prior to administration of the second antibody. In another embodiment, the anti-ICOS antibody is administered, for example, within about 30 minutes of the second antibody. Such concurrent or sequential administration preferably results in both antibodies being simultaneously present in treated patients.

As used herein, the terms "inhibits" or "blocks" are used interchangeably and encompass both partial and complete inhibition/blocking by at least about 50%, 60%, 70%, 80%, 90%, 95%, 99%, or 100%, as determined e.g., by methods described herein.

As used herein, "cancer" refers a broad group of diseases characterized by the uncontrolled growth of abnormal cells in the body. Unregulated cell growth or division may result in the formation of malignant tumors or cells that invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. In contrast, "prophylaxis" or "prevention" refers to administration to a subject who does not have a disease to prevent the disease from occurring. "Treat," "treating," and "treatment" does not encompass prophylaxis or prevention.

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A "prophylactically effective amount" or a "prophylactically effective dosage" of a drug is an amount of the drug that, when administered alone or in combination with another therapeutic agent to a subject at risk of developing a disease or of suffering a recurrence of disease, prevents the development or recurrence of the disease. The ability of a therapeutic agent to promote disease regression or of a prophylactic agent to prevent the development or recurrence of the disease can be evaluated using a variety of methods known to the skilled practitioner, such as in human subjects during clinical trials, in animal model systems predictive of efficacy in humans, or by assaying the activity of the agent in in vitro assays.

The administration of effective amounts of the anti-ICOS antibody alone, or anti-ICOS antibody combined with anti-PD-1 antibody, combined with an anti-PD-L1 antibody, or combined with anti-CTLA-4 antibody, according to any of the methods provided herein, can result in at least one therapeutic effect, including, for example, reduced tumor growth or size, reduced number of metastatic lesions appearing over time, complete remission, partial remission, or stable disease. For example, the methods of treatment produce a comparable clinical benefit rate (CBR=complete remission (CR)+ partial remission (PR)+stable disease (SD) lasting ≥6 months) better than that achieved without administration of the anti-ICOS antibody, or than that achieved with administration of any one of the combined antibodies, e.g., the improvement of clinical benefit rate is about 20% 20%, 30%, 40%, 50%, 60%, 70%, 80% or more.

By way of example, an anti-cancer agent is a drug that slows cancer progression or promotes cancer regression in a subject. In some embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. "Pharmacological effectiveness," "effectiveness," or "efficacy" refers to the ability of the drug to promote cancer regression in the patient. "Physiological safety" refers to an acceptably low level of toxicity or other adverse physiological effects at the cellular, organ and/or organism level (adverse effects) resulting from administration of the drug.

By way of example, for the treatment of tumors, a therapeutically effective amount or dosage of the drug inhibits tumor cell growth by at least about 20%, by at least about 30% by at least about 40%, by at least about 50%, by at least about 60%, by at least above 70%, by at least about 80% relative to untreated subjects, or by at least about 90%. In some embodiments, a therapeutically effective amount or dosage of the drug completely inhibits cell growth or tumor growth, i.e., inhibits cell growth or tumor growth by 100%. The ability of a compound, including an antibody, to inhibit tumor growth can be evaluated using the assays described herein. Alternatively, this property of a composition can be evaluated by examining the ability of the compound to inhibit cell growth; such inhibition can be measured in vitro by assays known to the skilled practitioner. In some embodiments, inhibition of tumor growth may not be immediate after treatment, and may only occur after a period of time or after repeated administration. In other embodiments described herein, tumor regression is observed and continues for at least about 20 days, at least about 30 days, at least about 40 days, at least about 50 days, or at least about 60 days, or longer.

As used herein, the terms "fixed dose", "flat dose" and "flat-fixed dose" are used interchangeably and refer to a dose that is administered to a patient without regard for the weight or body surface area of the patient. The fixed or flat dose is therefore not provided as a mg/kg dose, but rather as an absolute amount of the therapeutic agent.

As used herein, the term "weight based" dose or dosing means that a dose administered to a patient is calculated based on the patient's weight. For example, when a 60 kg patient requires 3 mg/kg of an anti-ICOS antibody, one can calculate and use the appropriate amount of the anti-ICOS antibody (i.e., 180 mg) for administration.

The term "patient" includes human and other mammalian subjects that receive either therapeutic or prophylactic treatment.

The term "subject" includes any human or non-human animal. For example, the methods and compositions herein disclosed can be used to treat a subject having cancer. A non-human animal includes all vertebrates, e.g., mammals and non-mammals, including non-human primates, sheep, dogs, cows, chickens, amphibians, reptiles, etc. In one embodiment, the subject is a human subject.

As used herein, the term "a" or "an" entity refers to one or more of that entity unless otherwise specified; for example, "a nucleotide sequence," is understood to represent one or more nucleotide sequences. As such, the terms "a" or "an", "one or more," and "at least one" can be used interchangeably herein.

As used herein, "and/or" is to be taken as specific disclosure of each of the two specified features or components with or without the other. Thus, the term "and/or" as used in a phrase such as "A and/or B" includes "A and B," "A or B," "A" alone, and "B" alone. Likewise, the term "and/or" as used in a phrase such as "A, B, and/or C" encompasses each of the following: A, B, and C; A, B, or C; A or C; A or B; B or C; A and C; A and B; B and C; A alone; B alone; and C alone.

It is understood that wherever aspects are described herein with the language "comprising," otherwise analogous aspects described in terms of "consisting of" and/or "consisting essentially of" are also provided.

Units, prefixes, and symbols are denoted in their Système International de Unites (SI) accepted form. Numeric ranges are inclusive of the numbers defining the range. Unless otherwise indicated, nucleotide sequences are written left to right in 5' to 3' orientation. Amino acid sequences are written left to right in amino to carboxy orientation.

As used herein, the term "about" means approximately, roughly, around, or in the region of. When the term "about" is used in conjunction with a numerical range, it modifies that range by extending the boundaries above and below the numerical values set forth. In general, the term "about" can modify a numerical value above and below the stated value by a variance of, e.g., 10 percent, up or down (higher or lower).

The headings provided herein are not limitations of the various aspects of the disclosure, and should be read by reference to the specification as a whole. Accordingly, the terms defined immediately below are more fully defined by reference to the specification in its entirety. Various aspects described herein are described in further detail in the following subsections.

I. Anti-ICOS Antibodies

The present invention discloses, in some embodiments, antibodies, such as fully human antibodies, with desirable functions or properties. Described herein are agonistic anti-human ICOS (anti-huICOS) antibodies having desirable properties for use as therapeutic agents in treating diseases such as cancers. These properties include one or more of the ability to bind to human ICOS with high affinity, acceptably low immunogenicity in human subjects, the ability to bind preferentially to FcγRIIb (a specific type of IgG Fc receptor), and the absence of sequence liabilities that reduce the chemical stability of the antibody. The antibodies of the invention are also useful, e.g., for diagnosis of cancer and other disorders associated with ICOS expression and/or activity.

The anti-ICOS antibodies disclosed herein by amino acid sequence bind to specific epitopes on human ICOS, as described in the Examples.

Anti-huICOS Antibodies Having Particular Functional Properties

The antibodies of the invention are characterized by particular functional features or properties. For example, the antibodies specifically bind to human ICOS with high affinity. In some embodiments, the antibodies specifically bind to the site on ICOS to which ICOS-L binds. Binding to human ICOS can be assessed using one or more techniques well established in the art. For example, in some embodiments, the antibody can be tested by a flow cytometry assay in which the antibody is reacted with a cell line that expresses human ICOS, such as CHO cells that have been transfected to express human ICOS on their cell surface. Additionally or alternatively, the binding of the antibody, including the binding kinetics (e.g., $K_D$ value) can be tested in Biacore binding assays. Still other suitable binding assays include ELISA assays using, for example, a recombinant human ICOS protein.

In one embodiment, the antibody, or antigen-binding portion thereof, of the invention binds to an ICOS protein with a $K_D$ of $5 \times 10^{-8}$ M or less, binds to an ICOS protein with a $K_D$ of $2 \times 10^{-8}$ M or less, binds to an ICOS protein with a $K_D$ of $5 \times 10^{-9}$ M or less, binds to an ICOS protein with a $K_D$ of $4 \times 10^{-9}$ M or less, binds to an ICOS protein with a $K_D$ of $3 \times 10^{-9}$ M or less, binds to an ICOS protein with a $K_D$ of $2 \times 10^{-9}$ M or less, binds to an ICOS protein with a $K_D$ of $1 \times 10^{-9}$ M or less, binds to an ICOS protein with a $K_D$ of $5 \times 10^{-10}$ M or less, or binds to an ICOS protein with a $K_D$ of $1 \times 10^{-10}$ M or less.

In another embodiment, the antibody binds one or more residues of SIFDPPPFKVTL (SEQ ID NO: 203) of human ICOS. In another embodiment, the antibody binds to an epitope which comprises amino acid residues SIFDPPPFKVTL (SEQ ID NO: 203) of human ICOS. In another embodiment, the antigen-binding portion of the antibody binds to an epitope which comprises amino acid residues SIFDPPPFKVTL (SEQ ID NO: 203) of human ICOS.

In another embodiment, the antibody binds to human ICOS and stimulates an immune response, e.g., an antigen-specific T cell response. The ability of the antibody to stimulate an immune response can be tested by measuring tumor growth, such as in an in vivo tumor graft model (see, e.g., Examples 6, 7, 8, and 9).

In another embodiment, the antibody, or antigen-binding portion thereof, binds to human ICOS and exhibits at least one of the following properties:
(a) binding to one or more residues within SIFDPPPFKVTL (SEQ ID NO: 203) of human ICOS;
(b) binding to the same epitope on human ICOS as antibody ICOS.33, 17C4, 9D5, 3E8, 1D7, or 2644;
(c) competing for binding to human ICOS with antibody ICOS.33, 17C4, 9D5, 3E8, 1D7, or 2644;
(d) reducing ADCC activity compared to an IgG1 control antibody;
(e) increasing specificity for binding to FcγRIIb receptor;
(f) blocking binding of an ICOS ligand (ICOS-L) to human ICOS;
(g) blocking the interaction of human ICOS and human ICOS-L;
(h) binding to human, cynomolgus, mouse, and rat ICOS;
(i) binding to activated human and cynomolgus T cells;
(j) binds to human T cells with an EC50 of about 0.7 nM and cynomolgus T cells with an EC50 of about 0.3 nM;
(k) no binding to human CD28 or human CTLA-4;
(l) activating at least one primary T lymphocyte, such as a CD4+ Teff cell, a Tfh cell, and a Treg cell;
(m) induces proliferation and interferon-gamma (IFN-γ) production in CD25-CD4+ T cells with an EC50 of about 0.01 to about 0.16 nM in an in vitro CHO-OKT3-CD32A co-culture assay;
(n) inducing protein kinase B (pAkt) in an in vitro primary T cell signaling assay with an EC50 of about 30 nM;
(o) induces IFN-γ production in CD25− CD4+ T cells with an EC50 of about 0.002 to about 0.4 nM in a staphylococcal enterotoxin B in a CD25− CD4+ T cell and B cell co-culture assay.
(p) inducing interleukin 10 (IL-10) production in response to staphylococcal enterotoxin B in a Tfh and naive B cell co-culture assay;
(q) inducing a greater proliferation increase of CD3-stimulated Teffs compared to CD45RA+ Tregs and CD45RO+ Tregs in an in vitro assay;
(r) increasing proliferation in Teffs compared to CD45RA+ Tregs (e.g., wherein the proliferation increase is greater in CD45RA+ Tregs compared to CD45RO+ Tregs);
(s) reducing Teff suppression by Tregs;
(t) wherein about 10 μg/mL of the antibody does not increase cytokine production in a whole blood cell assay;
(u) increasing secretion of at least one of IL-10 and IFN-g by Tfh cells in vitro; and/or
(v) stimulating ICOS-mediated signaling.

In another embodiment, the isolated antibody is a humanized isolated antibody (or antigen binding portion thereof) that binds to human ICOS and blocks the binding and/or the interaction of an ICOS ligand (e.g., human ICOS-L) to human ICOS and induces proliferation and interferon-gamma (IFN-γ) production in CD25− CD4+ T cells with an EC50 of about 0.083 nM in an in vitro CHO-OKT3-CD32A co-culture assay. In another embodiment, the isolated antibody is a humanized isolated antibody (or antigen binding portion thereof) that binds to human ICOS and blocks the binding and/or the interaction of an ICOS ligand (e.g., human ICOS-L) to human ICOS and induces proliferation and interferon-gamma (IFN-γ) production in CD25− CD4+ T cells with an EC50 of about 0.01 to about 0.1 nM in an in vitro CHO-OKT3-CD32A co-culture assay.

In one aspect, the isolated antibody is a humanized isolated antibody (or antigen binding portion thereof) that binds to human ICOS and blocks the binding and/or the interaction of an ICOS ligand (e.g., human ICOS-L) to human ICOS and induces IFN-γ production in CD25− CD4+ T cells with an EC50 of about 0.2 nM in a staphylococcal enterotoxin B in a CD25− CD4+ T cell and B cell co-culture assay. In another aspect, the isolated antibody is a humanized isolated antibody (or antigen binding portion thereof) that binds to human ICOS and blocks the binding and/or the interaction of an ICOS ligand (e.g., human ICOS-L) to human ICOS and induces IFN-γ production in CD25− CD4+ T cells with an EC50 of about 0.01-0.1 nM in a staphylococcal enterotoxin B in a CD25− CD4+ T cell and B cell co-culture assay.

In some embodiments, antibodies of the invention include humanized and fully human monoclonal antibodies. In other embodiments, the antibodies are, for example, chimeric monoclonal antibodies.

Monoclonal Antibodies ICOS.33 IgG1f S267E, 17C4, 9D5, 3E8, 1D7, and 2644

In some embodiments, the antibodies of the invention are the humanized and human monoclonal antibodies ICOS.33 IgG1f S267E, 17C4, 9D5, 3E8, 1D7, and 2644, which are isolated and structurally characterized as described in the following Examples. The $V_H$ amino acid sequences of ICOS.33 IgG1f S267E, 17C4, 9D5, 3E8, 1D7, and 2644 and the $V_L$ amino acid sequences of ICOS.33 IgG1f S267E, 17C4, 9D5, 3E8, 1D7, and 2644 are set forth in Table 35.

Given that each of these antibodies can bind to human ICOS, the $V_H$ and $V_L$ sequences can be "mixed and matched" to create other anti-huICOS binding molecules of the invention. In some embodiments, when $V_H$ and $V_L$ chains are mixed and matched, a $V_H$ sequence from a particular $V_H/V_L$ pairing is replaced with a structurally similar $V_H$ sequence. Likewise, in some embodiments, a $V_L$ sequence from a particular $V_H/V_L$ pairing is replaced with a structurally similar $V_L$ sequence.

Accordingly, in one aspect, this disclosure provides an isolated monoclonal antibody, or antigen binding portion thereof, comprising:

(a) a heavy chain variable region comprising an amino acid sequence set forth in SEQ ID NOs: 5, 16, 24, 32, 40, or 186; and (b) a light chain variable region comprising an amino acid sequence set forth in SEQ ID NOs: 6, 17, 25, 33, 41, 48, or 189;

wherein the antibody specifically binds human ICOS.

In some embodiments, heavy and light chain variable region combinations include:

(a) a heavy chain variable region comprising the amino acid sequence of SEQ ID NO: 5 and a light chain variable region comprising the amino acid sequence of SEQ ID NO: 6;

(b) a heavy chain variable region comprising the amino acid sequence of SEQ ID NO: 16 and a light chain variable region comprising the amino acid sequence of SEQ ID NO: 17;

(c) a heavy chain variable region comprising the amino acid sequence of SEQ ID NO: 24 and a light chain variable region comprising the amino acid sequence of SEQ ID NO: 25;

(d) a heavy chain variable region comprising the amino acid sequence of SEQ ID NO: 32 and a light chain variable region comprising the amino acid sequence of SEQ ID NO: 33;

(e) a heavy chain variable region comprising the amino acid sequence of SEQ ID NO: 40 and a light chain variable region comprising the amino acid sequence of SEQ ID NO: 41;

(f) a heavy chain variable region comprising the amino acid sequence of SEQ ID NO: 40 and a light chain variable region comprising the amino acid sequence of SEQ ID NO: 48; or (g) a heavy chain variable region comprising the amino acid sequence of SEQ ID NO: 186 and a light chain variable region comprising the amino acid sequence of SEQ ID NO: 189.

In another aspect, this disclosure provides antibodies that comprise the heavy chain and light chain CDR1s, CDR2s and CDR3s of ICOS.33 IgG1f S267E, 17C4, 9D5, 3E8, 1D7, and 2644, or combinations thereof. The amino acid sequences of the $V_H$ CDR1s of ICOS.33 IgG1f S267E, 17C4, 9D5, 3E8, 1D7, and 2644 are shown in SEQ ID NOs: 9, 18, 26, 34, 42, and 191, respectively. The amino acid sequences of the $V_H$ CDR2s of ICOS.33 IgG1f S267E, 17C4, 9D5, 3E8, 1D7, and 2644 are shown in SEQ ID NOs: 10, 19, 27, 35, 43, and 192, respectively. The amino acid sequences of the $V_H$ CDR3s of ICOS.33 IgG1f S267E, 17C4, 9D5, 3E8, 1D7, and 2644 are shown in SEQ ID NOs: 11, 20, 28, 36, 44, and 193, respectively. The amino acid sequences of the $V_L$ CDR1s of ICOS.33 IgG1f S267E, 17C4, 9D5, 3E8, 1D7, and 2644 are shown in SEQ ID NOs: 12, 21, 29, 37, 49, and 194, respectively. The amino acid sequences of the $V_L$ CDR2s of ICOS.33 IgG1f S267E, 17C4, 9D5, 3E8, 1D7, and 2644 are shown in SEQ ID NOs: 14, 22, 30, 38, 50, and 195, respectively. The amino acid sequences of the $V_L$ CDR3s of ICOS.33 IgG1f S267E, 17C4, 9D5, 3E8, 1D7, and 2644 are shown in SEQ ID NOs: 15, 23, 31, 39, 51, and 196, respectively. The CDR regions are delineated using the Kabat system (Kabat et al., 1991) Sequences of Proteins of Immunological Interest, Fifth Edition, U.S. Department of Health and Human Services, NIH Publication No. 91-3242).

Given that each of these antibodies can bind to human ICOS and that antigen-binding specificity is provided primarily by the CDR1, CDR2, and CDR3 regions, the $V_H$ CDR1, CDR2, and CDR3 sequences and $V_L$ CDR1, CDR2, and CDR3 sequences can be "mixed and matched" (i.e., CDRs from different antibodies can be mixed and matched, although each antibody must contain a $V_H$ CDR1, CDR2, and CDR3 and a $V_L$ CDR1, CDR2, and CDR3) to create other anti-huICOS binding molecules of the invention. ICOS binding of such "mixed and matched" antibodies can be tested using the binding assays described herein, including in the Examples (e.g., ELISAs, Biacore® analysis). In some embodiments, when $V_H$ CDR sequences are mixed and matched, the CDR1, CDR2 and/or CDR3 sequence from a particular $V_H$ sequence is replaced with a structurally similar CDR sequence(s). Likewise, in some embodiments, when $V_L$ CDR sequences are mixed and matched, the CDR1, CDR2 and/or CDR3 sequence from a particular $V_L$ sequence preferably is replaced with a structurally similar CDR sequence(s). It will be readily apparent to the ordinarily skilled artisan that novel $V_H$ and $V_L$ sequences can be created by substituting one or more $V_H$ and/or $V_L$ CDR region sequences with structurally similar sequences from the CDR sequences disclosed herein for monoclonal antibodies ICOS.33 IgG1f S267E, 17C4, 9D5, 3E8, 1D7, and 2644.

Accordingly, in another aspect, this disclosure provides an isolated monoclonal antibody, or antigen binding portion thereof comprising:

(a) a heavy chain variable region CDR1 comprising an amino acid sequence set forth in SEQ ID NOs: 9, 18, 26, 34, 42, or 191;

(b) a heavy chain variable region CDR2 comprising an amino acid sequence set forth in SEQ ID NOs: 10, 19, 27, 35, 43, or 192;

(c) a heavy chain variable region CDR3 comprising an amino acid sequence offset forth in SEQ ID NOs: 11, 20, 28, 36, 44, or 193;

(d) a light chain variable region CDR1 comprising an amino acid sequence set forth in SEQ ID NOs: 12, 21, 29, 37, 49, or 194;

(e) a light chain variable region CDR2 comprising an amino acid sequence set forth in SEQ ID NOs: 14, 22, 30, 38, 50, or 195; and (f) a light chain variable region CDR3 comprising an amino acid sequence set forth in SEQ ID NOs: 15, 23, 31, 39, 51, or 196;

wherein the antibody specifically binds human ICOS.

In one embodiment, the antibody comprises:

(a) a heavy chain variable region CDR1 comprising SEQ ID NO: 9;

(b) a heavy chain variable region CDR2 comprising SEQ ID NO: 10;

(c) a heavy chain variable region CDR3 comprising SEQ ID NO: 11;

(d) a light chain variable region CDR1 comprising SEQ ID NO: 12;

(e) a light chain variable region CDR2 comprising SEQ ID NO: 14; and (f) a light chain variable region CDR3 comprising SEQ ID NO: 15.

In another embodiment, the antibody comprises:
 (a) a heavy chain variable region CDR1 comprising SEQ ID NO: 18;
 (b) a heavy chain variable region CDR2 comprising SEQ ID NO: 19;
 (c) a heavy chain variable region CDR3 comprising SEQ ID NO: 20;
 (d) a light chain variable region CDR1 comprising SEQ ID NO: 21;
 (e) a light chain variable region CDR2 comprising SEQ ID NO: 22; and
 (f) a light chain variable region CDR3 comprising SEQ ID NO: 23.

In another embodiment, the antibody comprises:
 (a) a heavy chain variable region CDR1 comprising SEQ ID NO: 26;
 (b) a heavy chain variable region CDR2 comprising SEQ ID NO: 27;
 (c) a heavy chain variable region CDR3 comprising SEQ ID NO: 28;
 (d) a light chain variable region CDR1 comprising SEQ ID NO: 29;
 (e) a light chain variable region CDR2 comprising SEQ ID NO: 30; and
 (f) a light chain variable region CDR3 comprising SEQ ID NO: 31.

In another embodiment, the antibody comprises:
 (a) a heavy chain variable region CDR1 comprising SEQ ID NO: 34;
 (b) a heavy chain variable region CDR2 comprising SEQ ID NO: 35;
 (c) a heavy chain variable region CDR3 comprising SEQ ID NO: 36;
 (d) a light chain variable region CDR1 comprising SEQ ID NO: 37;
 (e) a light chain variable region CDR2 comprising SEQ ID NO: 38; and
 (f) a light chain variable region CDR3 comprising SEQ ID NO: 39.

In another embodiment, the antibody comprises:
 (a) a heavy chain variable region CDR1 comprising SEQ ID NO: 42;
 (b) a heavy chain variable region CDR2 comprising SEQ ID NO: 43;
 (c) a heavy chain variable region CDR3 comprising SEQ ID NO: 44;
 (d) a light chain variable region CDR1 comprising SEQ ID NO: 49;
 (e) a light chain variable region CDR2 comprising SEQ ID NO: 50; and
 (f) a light chain variable region CDR3 comprising SEQ ID NO: 51.

In another embodiment, the antibody comprises:
 (a) a heavy chain variable region CDR1 comprising SEQ ID NO: 191;
 (b) a heavy chain variable region CDR2 comprising SEQ ID NO: 192;
 (c) a heavy chain variable region CDR3 comprising SEQ ID NO: 193;
 (d) a light chain variable region CDR1 comprising SEQ ID NO: 194;
 (e) a light chain variable region CDR2 comprising SEQ ID NO: 195; and
 (f) a light chain variable region CDR3 comprising SEQ ID NO: 196.

It is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. (See, e.g., Klimka et al., *British J. of Cancer* 83(2):252-260 (2000). Accordingly, the present disclosure provides monoclonal antibodies comprising one or more heavy and/or light chain CDR3 domains from an antibody derived from a human or non-human animal, wherein the monoclonal antibody is capable of specifically binding to human ICOS. In certain aspects, the present disclosure provides monoclonal antibodies comprising one or more heavy and/or light chain CDR3 domain from a non-human antibody, such as a mouse or rat antibody, wherein the monoclonal antibody is capable of specifically binding to human ICOS. Within some embodiments, such inventive antibodies comprising one or more heavy and/or light chain CDR3 domain from a non-human antibody (a) are capable of competing for binding with; (b) retain the functional characteristics; (c) bind to the same epitope; and/or (d) have a similar binding affinity as the corresponding parental non-human antibody.

In other aspects, the present disclosure provides monoclonal antibodies comprising one or more heavy and/or light chain CDR3 domain from a human antibody, such as, e.g., a human antibody obtained from a non-human animal, wherein the human antibody is capable of specifically binding to human ICOS. In other aspects, the present disclosure provides monoclonal antibodies comprising one or more heavy and/or light chain CDR3 domain from a first human antibody, such as, for example, a human antibody obtained from a non-human animal, wherein the first human antibody is capable of specifically binding to human ICOS, and wherein the CDR3 domain from the first human antibody replaces a CDR3 domain in a human antibody that lacks binding specificity for ICOS to generate a second human antibody that is capable of specifically binding to human ICOS. In some embodiments, such inventive antibodies comprising one or more heavy and/or light chain CDR3 domain from the first human antibody (a) are capable of competing for binding with; (b) retain the functional characteristics; (c) bind to the same epitope; and/or (d) have a similar binding affinity as the corresponding parental non-human antibody.

The present invention also provides anti-huICOS antibodies comprising the novel variable domain sequences disclosed herein and constant domains with modified Fc regions having enhanced affinity for FcγRIIb as compared with their affinity for other Fc receptors. In some embodiments, such agonistic anti-huICOS antibodies with enhanced FcγRIIb-specificity exhibit superior efficacy in treating cancer. In other embodiments, such agonistic anti-huICOS antibodies with enhanced FcγRIIb-specificity exhibit superior efficacy in treating various disorders, e.g., cancer. Without intending to be limited by mechanistic theory, such FcγRIIb-specific agonistic anti-ICOS monoclonal antibodies may exhibit enhanced adjuvant effects by increasing the maturation of dendritic cell, thus, promoting expansion and activation of cytotoxic CD8+ T cells, which leads to enhanced anti-tumor response. Without intending to be limited by theory, FcR-mediated signal enhancement of agonist ICOS antibodies due to increased receptor clustering, or "cross-linking," of the present invention may be a major contributor to therapeutic efficacy. Cross-linking of ICOS agonist antibodies by FcR engagement by the Fc portion of the antibody may increase signal strength and thereby enhance cell activation.

The relative binding affinity of antibodies for activating (A) versus inhibitory (I) Fc receptors can be expressed as the "A/I" ratio, and is typically a function of the structure of the Fc region of an IgG antibody. See WO 2012/087928. Antibodies having enhanced specificity for binding to inhibitory receptor FcγRIIb have lower A/I ratios. In some embodiments, the agonistic anti-huICOS antibodies described herein have A/I ratios of less than 5, 4, 3, 2, 1, 0.5, 0.3, 0.1, 0.05, 0.03 or 0.01.

Examples of human IgG1 constant domains comprising mutations to enhance FcγRIIb specificity are described herein and are also provided in the Sequence Listing. Sequence variants are defined with reference to human IgG1f constant domain sequence provided at SEQ ID NO: 52 and shown in FIG. 2. The nomenclature regarding positions (numbering) of mutations in the Fc region is according to the EU index as in Kabat et al., 1991) *Sequences of Proteins of Immunological Interest*, 5th Ed. Public Health Service, National Institutes of Health, Bethesda, Md.), which facilitates comparison of Fc sequences at equivalent positions in antibodies with differing variable domain lengths. See also Edelman et al. (1969) *Proc. Nat'l Acad. Sci.* (USA) 63:78; WO 2012/130831 (using the same numbering system). Table 3 provides a summary of the Fc sequence variants from which one of skill in the art could readily recognize the corresponding positions in the antibody sequences disclosed herein. SE and SELF variants are described at Chu et al. (2008) *Mol. Immunol.* 45:3926. P238D, V4, V7, V8, V9, V11 and V12 variants are described at Mimoto et al. (2013) *Protein Engineering Design & Selection* 26:589 (e.g. at Table 1 therein).

TABLE 3

Fc Sequence Variants

| Designation | SEQ ID: | Sequence Variants | | | | | |
|---|---|---|---|---|---|---|---|
| IgG1f | 52 | | | | | | |
| SE | 53 | | | S267E | | | |
| SELF | 54 | | | S267E | | L328F | |
| P238D | 55 | | P238D | | | | |
| V4 | 56 | | P238D | | P271G | | |
| V4-D270E | 57 | | P238D | | P271G | | D270E |
| V7 | 58 | E233D | P238D | | P271G | A330R | |
| V8 | 59 | G237D | P238D | H268D | P271G | | |
| V9 | 60 | G237D | P238D | | P271G | A330R | |
| V9-D270E | 61 | G237D | P238D | | P271G | A330R | D270E |
| V11 | 62 | G237D | P238D | H268D | P271G | A330R | |
| V12 | 63 | E233D | G237D | P238D | H268D | P271G | A330R |

Additional Fc sequence variants with enhanced affinity for FcγRIIb are disclosed at Yu et al. (2013) *J. Am. Chem. Soc.* 135:9723 (and WO 2014/184545), including V262E and V264E, e.g. for use in combination with S267E and L328F.

Antibodies with Conservative Modifications

In certain embodiments, an antibody of the invention comprises a heavy chain variable region comprising CDR1, CDR2, and CDR3 sequences and a light chain variable region comprising CDR1, CDR2, and CDR3 sequences, wherein one or more of these CDR sequences comprise specified amino acid sequences based on the antibodies described herein (e.g., ICOS.33 IgG1f S267E, 17C4, 9D5, 3E8, 1D7, and 2644), or conservative modifications thereof, and wherein the antibodies retain the desired functional properties of the anti-huICOS antibodies of the invention. It is understood in the art that certain conservative sequence modifications can be made that do not remove antigen binding. (See, e.g., Brummell et al. (1993) *Biochem* 32:1180-8). Accordingly, this disclosure provides an isolated monoclonal antibody, or antigen binding portion thereof, comprising a heavy chain variable region comprising CDR1, CDR2, and CDR3 sequences and a light chain variable region comprising CDR1, CDR2, and CDR3 sequences, wherein:

(a) the heavy chain variable region comprising a CDR3 sequence comprising an amino acid sequence set forth in SEQ ID NOs: 11, 20, 28, 36, 44, or 193, or conservative modifications thereof;

(b) the light chain variable region comprising a CDR3 sequence comprising an amino acid sequence set forth in SEQ ID NOs: 15, 23, 31, 39, 51, or 196, or conservative modifications thereof; and (c) the antibody, or antigen binding portion thereof, specifically binds human ICOS.

Additionally or alternatively, the antibody can possess one or more of the functional properties described herein, such as high affinity binding to human ICOS, and/or the ability to stimulate antigen-specific T cell responses.

In some embodiments, the heavy chain variable region comprising a CDR2 sequence comprises an amino acid sequence set forth in SEQ ID NOs: 10, 19, 27, 35, 43, or 192, or conservative modifications thereof; and the light chain variable region comprising a CDR2 sequence comprising an amino acid sequence set forth in SEQ ID NOs: 14, 22, 30, 38, 50, or 195, or conservative modifications thereof. In another embodiment, the heavy chain variable region comprises a CDR1 sequence comprising an amino acid sequence set forth in SEQ ID NOs: 9, 18, 26, 34, 42, or 191, or conservative modifications thereof and the light chain variable region comprising a CDR1 sequence comprising an amino acid sequence set forth in SEQ ID NOs: 12, 21, 29, 37, 49, or 194, or conservative modifications thereof.

In various embodiments, the antibody can be, for example, human antibodies, humanized antibodies, or chimeric antibodies.

Antibodies that Bind to the Same Epitope as Anti-huICOS Antibodies

In another embodiment, this disclosure provides antibodies that bind to the same epitope on human ICOS as any of the anti-huICOS monoclonal antibodies of the invention (i.e., antibodies that have the ability to cross-compete for binding to human ICOS with any of the monoclonal antibodies of the invention). In some embodiments, the reference antibody for cross-competition studies are the monoclonal antibodies ICOS.33 IgG1f S267E, 17C4, 9D5, 3E8, 1D7, and 2644.

Such cross-competing antibodies can be identified based on their ability to cross-compete with ICOS.33 IgG1f S267E, 17C4, 9D5, 3E8, 1D7, and/or 2644 in standard human ICOS binding assays. For example, standard ELISA assays can be used in which a recombinant human ICOS protein is immobilized on the plate, one of the antibodies is fluorescently labeled, and the ability of non-labeled antibodies to compete off the binding of the labeled antibody is evaluated. Additionally or alternatively, Biacore analysis can be used to assess the antibodies' ability to cross-compete. The ability of a test antibody to inhibit the binding of, for example, ICOS.33 IgG1f S267E, 17C4, 9D5, 3E8, 1D7, and/or 2644, to human ICOS demonstrates that the test antibody can compete with ICOS.33 IgG1f S267E, 17C4, 9D5, 3E8, 1D7, and/or 2644 for binding to human ICOS and thus binds to the same epitope on human ICOS as ICOS.33 IgG1f S267E, 17C4, 9D5, 3E8, 1D7, and/or 2644. In one embodiment, the antibody that binds to the same epitope on human ICOS as ICOS.33 IgG1f S267E, 17C4, 9D5, 3E8, 1D7, and/or 2644 is a humanized or human monoclonal antibody.

As discussed further in Example 16, the binding of ICOS.33 IgG1f S267E, 3E8, and 9D5 human ICOS has been mapped to residues 112-123 of ICOS (SEQ ID NO: 1), or the amino acid sequence SIFDPPPFKVTL (SEQ ID NO: 203). Accordingly, in one embodiment, the invention provides an anti-huICOS antibody that binds to one or more residues of SIFDPPPFKVTL (SEQ ID NO: 203) of human ICOS, e.g., as determined by HDX-MS. In another embodiment, the anti-huICOS antibody binds to an epitope comprising amino acid residues SIFDPPPFKVTL (SEQ ID NO: 203) of human ICOS.

Such humanized or human monoclonal antibodies can be prepared and isolated as described herein. For example, anti-huICOS antibodies that bind to the same or similar epitopes to the antibodies disclosed herein may be raised using immunization protocols, e.g., those described herein. The resulting antibodies can be screened for high affinity binding to human ICOS. Selected antibodies can then be studied, e.g., in yeast display assay in which sequence variants of huICOS are presented on the surface of yeast cells, or by hydrogen-deuterium exchange experiments, to determine the precise epitope bound by the antibody.

Epitope determinations may be made by any method known in the art. In some embodiments, anti-huICOS antibodies are considered to bind to the same epitope as an anti-huICOS mAb disclosed herein if they make contact with one or more of the same residues within at least one region of huICOS; if they make contacts with a majority of the residues within at least one region of huICOS; if they make contacts with a majority of the residues within each region of huICOS; if they make contact with a majority of contacts along the entire length of huICOS; if they make contacts within all of the same distinct regions of human ICOS; if they make contact with all of the residues at any one region on human ICOS; or if they make contact with all of the same residues at all of the same regions. Epitope "regions" are clusters of residues along, but not necessarily directly adjacent within, the primary sequence.

Techniques for determining antibodies that bind to the "same epitope on huICOS" with the antibodies described herein include x-ray analyses of crystals of antigen:antibody complexes, which provides atomic resolution of the epitope. Other methods monitor the binding of the antibody to antigen fragments or mutated variations of the antigen where loss of binding due to an amino acid modification within the antigen sequence indicates the epitope component. Methods may also rely on the ability of an antibody of interest to affinity isolate specific short peptides (either in native three dimensional form or in denatured form) from combinatorial phage display peptide libraries or from a protease digest of the target protein. The peptides are then regarded as leads for the definition of the epitope corresponding to the antibody used to screen the peptide library. For epitope mapping, computational algorithms have also been developed that have been shown to map conformational discontinuous epitopes.

The epitope or region comprising the epitope can also be identified by screening for binding to a series of overlapping peptides spanning ICOS. Alternatively, the method of Jespers et al. (1994) *Biotechnology* 12:899 may be used to guide the selection of antibodies having the same epitope and therefore similar properties to the anti-ICOS antibodies described herein. Using phage display, first, the heavy chain of the anti-ICOS antibody is paired with a repertoire of (e.g., human) light chains to select an ICOS-binding antibody, and then the new light chain is paired with a repertoire of (e.g., human) heavy chains to select a (e.g., human) ICOS-binding antibody having the same epitope or epitope region as an anti-huICOS antibody described herein. Alternatively, variants of an antibody described herein can be obtained by mutagenesis of cDNA sequences encoding the heavy and light chains of the antibody.

Alanine scanning mutagenesis, as described by Cunningham & Wells (1989) *Science* 244: 1081, or some other form of point mutagenesis of amino acid residues in ICOS (such as the yeast display method provided at Example 16) may also be used to determine the functional epitope for an anti-ICOS antibody.

The epitope or epitope region (an "epitope region" is a region comprising the epitope or overlapping with the epitope) bound by a specific antibody may also be determined by assessing binding of the antibody to peptides comprising ICOS fragments. A series of overlapping peptides encompassing the ICOS sequence (e.g., human ICOS) may be synthesized and screened for binding, e.g. in a direct ELISA, a competitive ELISA (where the peptide is assessed for its ability to prevent binding of an antibody to ICOS bound to a well of a microtiter plate), or on a chip. Such peptide screening methods may not be capable of detecting some discontinuous functional epitopes, i.e., functional epitopes that involve amino acid residues that are not contiguous along the primary sequence of the ICOS polypeptide chain.

An epitope may also be identified by MS-based protein footprinting, such as HDX-MS and Fast Photochemical Oxidation of Proteins (FPOP). HDX-MS may be conducted, e.g., as further described at Wei et al. (2014) *Drug Discovery Today* 19:95, the methods of which are specifically incorporated by reference herein. FPOP may be conducted as described, e.g., in Hambley & Gross (2005) *J. American Soc. Mass Spectrometry* 16:2057, the methods of which are specifically incorporated by reference herein.

The epitope bound by anti-ICOS antibodies may also be determined by structural methods, such as X-ray crystal structure determination (e.g., WO2005/044853), molecular modeling and nuclear magnetic resonance (NMR) spectroscopy, including NMR determination of the H-D exchange rates of labile amide hydrogens in ICOS when free and when bound in a complex with an antibody of interest (Zinn-Justin et al. (1992) *Biochemistry* 31:11335; Zinn-Justin et al. (1993) *Biochemistry* 32:6884).

Unless otherwise indicated, and with reference to the claims, the epitope bound by an antibody is the epitope as determined by HDX-MS methods.

Anti-huICOS Antibodies Derived from Hamster Antibodies

Described herein are examples of chimeric and humanized antibodies that comprise CDRs and/or antibody heavy and/or light chain variable regions that were derived from hamster sequences. Chimeric or humanized antibodies described herein can be prepared based on the sequence of a monoclonal antibody, e.g., mouse or hamster, prepared by various methods known in the art. DNA encoding the heavy and light chain immunoglobulins can be obtained from a hybridoma of interest and engineered to contain human immunoglobulin sequences using standard molecular biology techniques. For example, to create a chimeric antibody, the variable regions of, e.g., a mouse or hamster antibody can be linked to human constant regions using methods known in the art (see e.g., U.S. Pat. No. 4,816,567 to Cabilly et al.). To create a humanized antibody, the CDR regions can be inserted into a human framework using methods known in the art (see e.g., U.S. Pat. No. 5,225,539 to Winter, and U.S. Pat. Nos. 5,530,101; 5,585,089; 5,693,762 and 6,180,370 to Queen et al).

Anti LCOS Antibodies that Bind with High Affinity

In some embodiments, the anti-huICOS antibodies of the present invention bind to huICOS with high affinity, like the anti-huICOS antibodies disclosed herein, making them effective therapeutic agents. In various embodiments, anti-huICOS antibodies of the present invention bind to huICOS with a $K_D$ of less than 10 nM, 5 nM, 2 nM, 1 nM, 300 pM or 100 pM. In other embodiments, the anti-huICOS antibodies of the present invention bind to huICOS with a $K_D$ between 2 nM and 100 pM. Standard assays to evaluate the binding ability of the antibodies toward huICOS include ELISAs, RIAs, Western blots, biolayer interferometry (BLI) and BIACORE® SPR analysis (see Example 10).

Anti LCOS Antibody Sequence Variants

Anti-ICOS antibody sequence variants disclosed herein maintain the desirable functional properties disclosed herein. The CDR regions are delineated using the Kabat system (Kabat, et al., 1991). In some embodiments, the present invention further provides human or humanized anti-huICOS antibodies comprising CDR sequences that are at least 70%, 75%, 80%, 85%, 90%, or 95%, 96%, 97%, 98%, or 99% identical to the CDR sequences of the antibodies disclosed herein. The present invention also provides anti-huICOS antibodies comprising heavy and/or light chain variable domain sequences that are at least 70%, 75%, 80%, 85%, 90%, 95%, 96%, 97%, 98%, or 99% identical to the heavy and/or light chain variable domain sequences of the antibodies disclosed herein, as well as anti-huICOS antibodies comprising full-length heavy and/or light chain sequences that are at least 70%, 75%, 80%, 85%, 90%, 95%, 96%, 97%, 98%, or 99% identical to the heavy and/or light chain sequences of the antibodies disclosed herein.

II. Engineered and Modified Antibodies $V_H$ and $V_L$ Regions

Also provided are engineered and modified antibodies that can be prepared using an antibody having one or more of the $V_H$ and/or $V_L$ sequences disclosed herein as starting material to engineer a modified antibody, which modified antibody may have altered properties from the starting antibody. In some embodiments, an antibody as described herein was engineered by modifying one or more residues within one or both variable regions (i.e., $V_H$ and/or $V_L$), for example, within one or more CDR regions and/or within one or more framework regions. Additionally or alternatively, an antibody as described herein was engineered by modifying residues within the constant region(s), for example, to alter the effector function(s) of the antibody.

In one embodiment, the variable region engineering includes CDR grafting. Such grafting is of particular use in humanizing non-human anti-ICOS antibodies, e.g., anti-huICOS antibodies that compete for binding with the anti-huICOS antibodies disclosed herein and/or bind to the same epitope as the select anti-huICOS antibodies disclosed herein. Antibodies interact with target antigens predominantly through amino acid residues that are located in the heavy and light chain CDRs. The CDRs are hypervariable in sequence and/or form structurally defined loops ("hypervariable loops"). Expression vectors can be constructed such that they include CDR sequences from a specific reference (also called "parental") antibody grafted onto framework sequences from a different antibody (see, e.g., Riechmann, L. et al. (1998) Nature 332:323-327; Jones, P. et al. (1986) Nature 321:522-525; Queen, C. et al. (1989) Proc. Natl. Acad. See. U.S.A. 86:10029-10033; U.S. Pat. No. 5,225,539 to Winter, and U.S. Pat. Nos. 5,530,101; 5,585,089; 5,693, 762 and 6,180,370 to Queen et al.). In some instances, the resulting recombinant antibody has properties that are similar to the parental antibody. The engineered antibody can then be further modified to acquire properties that are distinct from the parental antibody. In other instances, grafting the parental CDR sequences onto a framework abrogates certain characteristics of the parental antibody such that the recombinant antibody no longer has these characteristics. One exemplary characteristic is binding affinity with respect to an antigen. In such instances, it might be advantageous to further modify the engineered antibody to regain the desired characteristics of the parental antibody.

Such framework sequences can be obtained from public DNA databases or published references that include germline antibody gene sequences. For example, germline DNA sequences for human heavy and light chain variable region genes can be found in the "VBase" human germline sequence database, as well as in Kabat, E. A., et al., 1991); Tomlinson, I. M., et al. (1992) "The Repertoire of Human Germline $V_H$ Sequences Reveals about Fifty Groups of $V_H$ Segments with Different Hypervariable Loops" J. Mol. Biol. 227:776-798; and Cox, J. P. L. et al. (1994) "A Directory of Human Germ-line $V_H$ Segments Reveals a Strong Bias in their Usage," Eur. J. Immunol. 24:827-836; the contents of each of which are expressly incorporated herein by reference.

In some embodiments, framework sequences for use in the antibodies described herein are those that are structurally similar to the framework sequences used by antibodies described herein. The $V_H$ CDR1, 2, and 3 sequences and the $V_L$ CDR1, 2, and 3 sequences can be grafted onto framework regions that have the identical sequence as that found in the germline immunoglobulin gene from which the framework sequence derive, or the CDR sequences can be grafted onto framework regions that contain up to 20 amino acid substitutions, including conservative amino acid substitutions, as compared to the germline sequences. For example, it has been found that in certain instances, it is beneficial to mutate residues within the framework regions to maintain or enhance the antigen binding ability of the antibody (see e.g., U.S. Pat. Nos. 5,530,101; 5,585,089; 5,693,762 and 6,180, 370 to Queen et al).

Engineered antibodies described herein include those in which modifications have been made to framework residues within $V_H$ and/or $V_L$, e.g., to improve the properties of the antibody, such as to decrease the immunogenicity of the antibody. For example, one approach is to "back-mutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "back-mutated" to the germline sequence by, for example, site-directed mutagenesis or PCR-mediated mutagenesis. Such "back-mutated" antibodies are also encompassed in this disclosure.

Another type of framework modification involves mutating one or more residues within the framework region, or even within one or more CDR regions, to remove T cell epitopes to thereby reduce the potential immunogenicity of the antibody. This approach is also referred to as "de-immunization" and is described in further detail in U.S. Patent Publication No. 20030153043 by Carr et al.

Another type of variable region modification is to mutate amino acid residues within the CDR regions to improve one or more binding properties (e.g., affinity) of the antibody of interest. Site-directed mutagenesis or PCR-mediated mutagenesis can be performed to introduce the mutation(s) and the effect on antibody binding, or other functional property of interest. Preferably, conservative modifications are introduced. The mutations may be amino acid additions, deletions, or substitutions. In some embodiments, no more than one, two, three, four or five residues within a CDR region are altered.

Methionine residues in CDRs of antibodies can be oxidized, resulting in potential chemical degradation and consequent reduction in antibody potency. Accordingly, also provided herein are anti-ICOS antibodies that have one or more methionine residues in the heavy and/or light chain CDRs replaced with amino acid residues that do not undergo oxidative degradation. Similarly, deamidation sites may be removed from anti-ICOS antibodies, particularly in the CDRs. Also provided herein are antibodies in which potential glycosylation sites within the antigen binding domain were eliminated to prevent glycosylation that may interfere with antigen binding. See, e.g., U.S. Pat. No. 5,714,350.

Antibody Masking

In some embodiments, the antibodies disclosed herein are modified to limit their binding to specific cells and/or tissue. In one embodiment, such antibodies comprise a blocking peptide "mask" that specifically binds to the antigen binding surface of the antibody and interferes with antigen binding. In some embodiments, the mask is linked to each of the binding arms of the antibody by a protease cleavable linker. See, e.g., U.S. Pat. No. 8,518,404 to CytomX. Antibodies with protease cleavable linkers are useful for treatment of cancers in which protease levels are greatly increased in the tumor microenvironment compared with non-tumor tissues. Selective cleavage of the cleavable linker in the tumor microenvironment allows disassociation of the masking/blocking peptide, enabling antigen binding selectively in the tumor, rather than in peripheral tissues in which antigen binding might cause unwanted side effects.

In another embodiment, a bivalent binding compound ("masking ligand") comprising two antigen binding domains is developed that binds to both antigen binding surfaces of the (bivalent) antibody and interferes with antigen binding. In one embodiment, the two binding domain masks are linked to each other (but not the antibody) by a cleavable linker, for example, cleavable by a peptidase. (See, e.g., WO 2010/077643 to Tegopharm Corp). Masking ligands may comprise, or be derived from, the antigen to which the antibody is intended to bind, or may be independently generated (e.g., anti-idiotype binding fragments). Such masking ligands are useful for treatment of cancers in which protease levels are greatly increased in the tumor microenvironment compared with non-tumor tissues. Selective cleavage of the cleavable linker in the tumor microenvironment allows disassociation of the two binding domains from each other, reducing the avidity for the antigen-binding surfaces of the antibody. The resulting dissociation of the masking ligand from the antibody enables antigen binding selectively in the tumor, rather than in peripheral tissues in which antigen binding might cause unwanted side effects.

Fcs and Modified Fc Regions

In one embodiment, the antibodies described herein may comprise Fc regions selected based on the biological activities of the antibody. Salfeld (2007) *Nat. Biotechnol.* 25:1369. Human IgGs, for example, can be classified into four subclasses, IgG1, IgG2, IgG3, and IgG4. Each of these subclasses comprise an Fc region having a unique profile for binding to one or more of Fcγ receptors (activating receptors FcγRI (CD64), FcγRIIA, FcγRIIC (CD32a,c); FcγRIIIA and FcγRIIIB (CD16a,b) and inhibiting receptor FcγRIIB (CD32b), and for the first component of complement (C1q). Human IgG1 and IgG3 bind to all Fcγ receptors; IgG2 binds to FcγRIIA$_{H131}$, and with lower affinity to FcγRIIA$_{R131}$ FcγRIIIA$_{V158}$; IgG4 binds to FcγRI, FcγRIIA, FcγRIIB, FcγRIIC, and FcγRIIIA$_{V158}$; and the inhibitory receptor FcγRIIB has a lower affinity for IgG1, IgG2 and IgG3 than all other Fcγ receptors. (Bruhns et al. (2009) *Blood* 113: 3716). Studies have shown that FcγRI does not bind to IgG2, and FcγRIIIB does not bind to IgG2 or IgG4. Id. In general, with regard to ADCC activity, human IgG1≥IgG3>>IgG4≥IgG2. In some embodiments, an IgG1 constant domain, rather than an IgG2 or IgG4, is chosen, e.g., for use in a therapeutic composition because ADCC is desired. In other embodiments, IgG3 is chosen because activation of FcγRIIIA-expressing NK cells, monocytes or macrophages is desirable. In other embodiments, IgG4 is chosen because the antibody is used to desensitize allergy patients. IgG4 is also selected so that the antibody lacks all effector function.

Anti-huICOS antibody variable regions described herein may be linked (e.g., covalently linked or fused) to an Fc, e.g., an IgG1, IgG2, IgG3 or IgG4 Fc, which may be of any allotype or isoallotype, e.g., for IgG1: G1m, G1m1(a), G1m2(x), G1m3(f), G1m17(z); for IgG2: G2m, G2m23(n); for IgG3: G3m, G3m21(g1), G3m28(g5), G3m11(b0), G3m5(b1), G3m13(b3), G3m14(b4), G3m10(b5), G3m15(s), G3m16(t), G3m6(c3), G3m24(c5), G3m26(u), G3m27(v). (See, e.g., Jefferis et al. (2009) mAbs 1:1). Selection of allotype may be influenced by the potential immunogenicity concerns, e.g. to minimize the formation of anti-drug antibodies.

In some embodiments, anti-ICOS antibodies of the present invention have an Fc region that binds to or has enhanced binding to FcγRIIb, which provides enhanced agonism. See, e.g., WO 2012/087928; Li & Ravetch (2011) *Science* 333: 1030; Wilson et al. (2011) *Cancer Cell* 19:101; White et al. (2011) *J. Immunol.* 187:1754. In some embodiments, variable regions described herein may be linked to Fc variants that enhance affinity for the inhibitory receptor FcγRIIb, e.g., to enhance apoptosis-inducing or adjuvant activity. Li & Ravetch (2012) *Proc. Nat'l Acad. Sci.* (USA) 109:10966; U.S. Pat. App. Pub. 2014/0010812. Such variants provides an antibody with immunomodulatory activities related to FcγRIIb+ cells, including, for example, B cells and monocytes. In one embodiment, the Fc variants provide selectively enhanced affinity to FcγRIIb relative to one or more activating receptors. Such variants may also exhibit enhanced FcR-mediated cross-linking, resulting in enhanced therapeutic efficacy. Modifications for altering binding to FcγRIIb include one or more modifications at, for example, positions 234, 235, 236, 237, 239, 266, 267, 268, 325, 326, 327, 328, or 332, according to the EU index. Exemplary substitutions for enhancing FcγRIIb affinity include but are not limited to 234D, 234E, 234F, 234W, 235D, 235F, 235R, 235Y, 236D, 236N, 237D, 237N, 239D, 239E, 266M, 267D, 267E, 268D, 268E, 327D, 327E, 328F, 328W, 328Y, and 332E. Exemplary substitutions include 235Y, 236D, 239D, 266M, 267E, 268D, 268E, 328F, 328W, and 328Y. Other Fc variants for enhancing binding to FcγRIIb include 235Y-267E, 236D-267E, 239D-268D, 239D-267E, 267E-268D, 267E-268E, and 267E-328F. Specifically, the S267E, G236D, S239D, L328F and I332E variants, including the S267E-L328F double variant, of human IgG1 are of particular value in specifically enhancing affinity for the inhibitory FcγRIIb receptor. Chu et al. (2008) Mol. Immunol. 45:3926; U.S. Pat. App. Pub. 2006/024298; WO 2012/087928. Enhanced specificity for FcγRIIb (as distinguished from FcγRIIa$_{R131}$) may be obtained by adding the P238D substitution and other mutations (Mimoto et al. (2013) Protein. Eng. Des. & Selection 26:589; WO 2012/1152410), as well as V262E and V264E (Yu et al. (2013) J. Am. Chem. Soc. 135:9723, and WO 2014/184545.

Non-IgG2 Heavy Chain Constant Domains with IgG2 Hinge Regions

In some embodiments, anti-ICOS antibodies described herein exhibit increased agonist activity at least in part due to modifications that increased binding to, and/or specificity for, FcγRIIb. An alternative approach is to engineer the Fc region to provide FcγR-independent enhancement of agonism. Examples of antibodies to other targets with modified IgG2 domains providing such enhanced agonism are described at WO 2015/145360 and White et al. (2015) Cancer Cell 27:138, the disclosures of which are hereby incorporated by reference in their entireties. Specifically, disulfide bonds are arranged to "lock" the antibody into a more compact "h2B" conformation, resulting in enhanced agonism. The resulting enhanced agonism is FcγR-independent. (See White et al. (2015) Cancer Cell 27:138). Such FcγR-independent agonism is advantageous in treating some tumors, such as those that have few FcγR-+expressing cells (e.g., few NK cells or macrophages). In one embodiment, anti-ICOS antibodies comprising the CDR or variable domain sequences disclosed herein linked to non-hIgG2 heavy chain constant regions (e.g. IgG1) having hIgG2 hinge regions, or variants thereof, including CH1 domain sequence variants, are provided. In one embodiment, these "IgG2 hinge" antibodies exhibit enhanced agonism compared with antibodies with a fully IgG1 heavy chain constant region, and the enhanced agonism is independent of Fcγ receptor-mediated cross-linking. In some embodiments, these IgG2 hinge anti-ICOS antibodies retain substantially unchanged antigen binding affinity. Also provided herein are methods of enhancing FcγR-independent agonism of non-IgG2 anti-ICOS antibodies comprising replacing the non-IgG2 hinge with an IgG2 hinge. In certain embodiments, a modified heavy chain constant region comprises a hinge of the IgG2 isotype (an "IgG2 hinge") and a CH1, CH2 and CH3 domain, wherein at least one of the CH1, CH2 and CH3 domains is not of the IgG2 isotype. The IgG2 hinge may be a wildtype human IgG2 hinge (e.g., ERKCCVECPPCPAPPVAG, set forth in SEQ ID NO: 96) or a variant thereof that also confers enhanced agonist activity. In certain embodiments, such IgG2 hinge variants have similar rigidity or stiffness as wildtype IgG2 hinge. The rigidity of a hinge can be determined, e.g., by computer modeling, electron microscopy, spectroscopy such as Nuclear Magnetic Resonance (NMR), X-ray crystallography (B-factors), or Sedimentation Velocity Analytical ultracentrifugation to measure or compare the radius of gyration of antibodies comprising the hinge. In some embodiments, human IgG2 hinge variants comprise substitution(s) of one or more of the four cysteine residues (i.e., C219, C220, C226 and C229), for example, with serine. In one embodiment, the IgG2 hinge variant comprises a C219S mutation (e.g., ERKSCVECPPCPAPPVAG, as set forth in SEQ ID NO: 110). Other IgG2 hinge variants comprise C220S, C226S or C229S mutation, any of which may be combined with a C219S mutation.

An IgG2 hinge variant may also comprise non-IgG2 hinge sequence elements (a "chimeric hinge"). In some embodiments, the rigidity of the chimeric hinge is at least similar to that of a wildtype IgG2 hinge. For example, in one embodiment, an IgG2 hinge variant comprises a wildtype IgG1 lower hinge. See Table 2.

Table 4 below provides examples of "IgG2 hinge" human heavy chain constant region sequences differing in the isotypic origins of the CH1, CH2 and CH3 domains. As used herein, "IgG2 hinge antibody" refers not just to antibodies comprising hinge regions derived from IgG2, but also CH1 regions derived from IgG2 CH1. The asterisk (*) in Table 4 indicates that the indicated domain may be of any isotype, or may be completely absent. In certain embodiments, a modified heavy chain constant region comprises a variant CH1 domain, e.g. including A114C and/or T173C mutations. A modified heavy chain constant region may also comprise a variant CH2 domain, e.g. including A330S and/or P331S mutations.

TABLE 4

"IgG2 Hinge" Human Heavy Chain Constant Region Constructs

| CH1 | Hinge | CH2 | CH3 |
| --- | --- | --- | --- |
| * | IgG2 | * | * |
| IgG1 | IgG2 | * | * |
| IgG2 | IgG2 | * | * |
| * | IgG2 | IgG1 | * |
| * | IgG2 | IgG2 | * |
| * | IgG2 | * | IgG1 |
| * | IgG2 | * | IgG2 |
| IgG1 | IgG2 | IgG1 | * |
| IgG1 | IgG2 | IgG2 | * |
| IgG2 | IgG2 | IgG1 | * |
| IgG2 | IgG2 | IgG2 | * |
| IgG1 | IgG2 | * | IgG1 |
| IgG1 | IgG2 | * | IgG2 |
| IgG2 | IgG2 | * | IgG1 |
| IgG2 | IgG2 | * | IgG2 |
| * | IgG2 | IgG1 | IgG1 |
| * | IgG2 | IgG1 | IgG2 |
| * | IgG2 | IgG2 | IgG1 |
| * | IgG2 | IgG2 | IgG2 |
| IgG1 | IgG2 | IgG1 | IgG1 |
| IgG1 | IgG2 | IgG1 | IgG2 |
| IgG1 | IgG2 | IgG2 | IgG1 |
| IgG1 | IgG2 | IgG2 | IgG2 |
| IgG2 | IgG2 | IgG1 | IgG1 |
| IgG2 | IgG2 | IgG1 | IgG2 |

TABLE 4-continued

"IgG2 Hinge" Human Heavy Chain Constant Region Constructs

| CH1 | Hinge | CH2 | CH3 |
|---|---|---|---|
| IgG2 | IgG2 | IgG2 | IgG1 |
| IgG2 | IgG2 | IgG2 | IgG2 |

Examples of antibody constant domains comprising combinations of IgG2 CH1 and hinge sequences with other isotype sequences, and select amino acid substitutions, are provided by Table 5 below.

TABLE 5

Examples of "IgG2 Hinge" Human Heavy Chain Constant Regions

| Construct | SEQ ID NO: | Description |
|---|---|---|
| IgG1f | 104 | wild type IgG1f |
| IgG1.1f | 109 | standard inert IgG1.1f |
| IgG2.3 | 105 | IgG2 A-form (C219S) |
| IgG2.5 | 108 | IgG2 B-form (C131S) |
| IgG2.3G1-KH | 107 | CH1, upper hinge and lower hinge/upper CH2 of IgG2.3, all else IgG1f |
| IgG2.5G1-KH | 116 | CH1, upper hinge and lower hinge/upper CH2 of IgG2.5, all else IgG1f |
| IgG2.3G1-AY | 106 | CH1 and upper hinge of IgG2.3, all else IgG1f |
| IgG2.5G1-AY | 115 | CH1 and upper hinge of IgG2.5, all else IgG1f |
| IgG1-G2.3G1-KH | 119 | CH1 of IgG1, upper hinge and lower hinge/upper CH2 of IgG2.3, all else IgG1f |
| IgG1-G2.3G1-AY | 118 | CH1 of IgG1, upper hinge of IgG2.3, all else IgG1f |
| IgG2.3G1.1f-KH | 110 | CH1, upper hinge and lower hinge/upper CH2 of IgG2.3, all else IgG1.1f |
| IgG2.5G1.1f-KH | 114 | CH1, upper hinge and lower hinge/upper CH2 of IgG2.5, all else IgG1.1f |
| IgG1-deltaTHT | 111 | IgG1 with THT sequence removed from hinge |
| IgG2.3-plusTHT | 112 | IgG2.3 with THT sequence (from IgG1) added into hinge |
| IgG2.5-plusTHT | 117 | IgG2.5 with THT sequence (from IgG1) added into hinge |
| IgG2.3-plusGGG | 113 | IgG2.3 with flexible GGG sequence added into hinge |

Additional specific examples of antibody constant domains comprising combinations of IgG2 CH1 and hinge sequences with other isotype sequences, and select amino acid substitutions, are provided by Table 6 below.

TABLE 6

Additional Examples of "IgG2 Hinge" Human Heavy Chain Constant Regions

| Construct | SEQ ID NO: | Description |
|---|---|---|
| G2-G1-G1-G1 | 120 | CH1 domain of IgG2, with all else IgG1. |
| G2.5-G1-G1-G1 | 121 | Also, Cys > Ser mutant to reduce potential disulfide heterogeneity. |
| G1-G2.3-G2-G2 | 122 | CH1 domain of IgG1 with all else IgG2.3 |
| G1-KRGEGSSNLF | 123 | Swap hinge regions in IgG1 with those of IgG2, either separately or together. |
| G1-KRGEGS | 124 | |
| G1-SNLF | 125 | |
| IgG1-ITNDRTPR | 126 | |
| G1-SNLFPR | 127 | |
| G2-RKEGSGNSFL | 128 | Swap CH1 regions in IgG2 with those of IgG1, either separately or together. |
| G2-RKEGSG | 129 | |
| G2-NSFL | 130 | |
| IgG2-TIDNTRRP | 131 | |
| G2-NSFLRP | 132 | |
| G1-G1-G2-G1-AY | 133 | IgG1 with CH2 domain residues of IgG2 |
| G1-G1-G2-G1-KH | 134 | |
| G2-G2.3-G1-G2-KH | 135 | IgG2 with CH2 domain residues of IgG1 |
| G2.5-G2.3-G1-G2-KH | 136 | |
| G2-G2.3-G1-G2-AY | 137 | |
| G2.5-G2.3-G1-G2-AY | 138 | |
| G1-G2.3-G1-G1-KH | 139 | Swap hinge regions between IgG1 and IgG2. |
| G2-G1-G2-G2-AY | 140 | |
| G2.5-G1-G2-G2-AY | 141 | |
| G1-G2-G1-G1-AY | 142 | |
| G2-G1-G2-G2-KH | 143 | |
| G2.5-G1-G2-G2-KH | 144 | |
| IgG1-deltaHinge | 145 | Hinge truncations |
| IgG2-deltaHinge | 146 | |
| IgG2.5-deltaHinge | 147 | |
| IgG1-deltaG237 | 148 | |
| IgG2-plusG237 | 149 | |
| IgG2.4 | 150 | Other |
| IgG2.3/4 | 151 | |

Anti-ICOS antibodies, including antibodies comprising the CDR and/or variable domain sequences disclosed herein, may incorporate the "IgG2 hinge" constant domain sequences disclosed herein, e.g. to enhance FcγR-independent agonist activity. Examples of such IgG2 hinge constant domains include those disclosed by Table 5 (SEQ ID NOs: 104-108 and 110-119) and Table 6 (SEQ ID NOs: 120-151), and also those disclosed at SEQ ID NOs: 101-108.

Half-Life Extension

In some embodiments, the anti-ICOS antibody is modified to increase its biological half-life, e.g., the antibody's half-life in serum. Various approaches are known in the art. For example, the half-life of an antibody may be extended by increasing the binding affinity of the Fc region for FcRn.

In one embodiment, the antibody is altered within the CH1 or CL region to contain a salvage receptor binding epitope taken from two loops of a CH2 domain of an Fc region of an IgG, as described in U.S. Pat. Nos. 5,869,046 and 6,121,022 by Presta et al. Other exemplary Fc variants that increase binding to FcRn and/or improve pharmacokinetic properties include substitutions at positions 259, 308, and 434, including for example 259I, 308F, 428L, 428M, 434S, 434H, 434F, 434Y, and 434M. Other variants that increase Fc binding to FcRn include: 250E, 250Q, 428L, 428F, 250Q/428L (Hinton et al., 2004, J. Biol. Chem. 279(8): 6213-6216, Hinton et al. 2006 Journal of Immunology 176:346-356), 256A, 272A, 305A, 307A, 311A, 312A, 378Q, 380A, 382A, 434A (Shields et al, *Journal of Biological Chemistry*, 2001, 276(9):6591-6604), 252F, 252Y, 252W, 254T, 256Q, 256E, 256D, 433R, 434F, 434Y, 252Y/254T/256E, 433K/434F/436H (Dall'Acqua et al. *Journal of Immunology*, 2002, 169:5171-5180, Dall'Acqua et al., 2006, Journal of Biological Chemistry 281:23514-23524). See U.S. Pat. No. 8,367,805.

Modification of certain conserved residues in IgG Fc (I253, H310, Q311, H433, N434), such as the N434A variant (Yeung et al. (2009) *J. Immunol.* 182:7663), have been proposed as a way to increase FcRn affinity, thus increasing the half-life of the antibody in circulation. (See, e.g., WO 98/023289). The combination Fc variant comprising M428L and N434S has been shown to increase FcRn binding and increase serum half-life up to five-fold. (Zalevsky et al. (2010) *Nat. Biotechnol.* 28:157). The combination Fc variant comprising T307A, E380A and N434A modifications also extends half-life of IgG1 antibodies. (Petkova et al. (2006) *Int. Immunol.* 18:1759). In addition, combination Fc variants comprising M252Y-M428L, M428L-N434H, M428L-N434F, M428L-N434Y, M428L-N434A, M428L-N434M, and M428L-N434S variants have also been shown to extend half-life. (WO 2009/086320).

Further, a combination Fc variant comprising M252Y, S254T and T256E, increases half-life-nearly four-fold. (Dall'Acqua et al. (2006) *J. Biol. Chem.* 281:23514). A related IgG1 modification providing increased FcRn affinity but reduced pH dependence (M252Y-S254T-T256E-H433K-N434F) has been used to create an IgG1 construct ("MST-HN Abdeg") for use as a competitor to prevent binding of other antibodies to FcRn, resulting in increased clearance of that other antibody, either endogenous IgG (e.g. in an autoimmune setting) or another exogenous (therapeutic) mAb. (Vaccaro et al. (2005) *Nat. Biotechnol.* 23:1283; WO 2006/130834).

Other modifications for increasing FcRn binding are described in Yeung et al. (2010) *J. Immunol.* 182:7663-7671; 6,277,375; 6,821,505; WO 97/34631; WO 2002/060919.

In certain embodiments, hybrid IgG isotypes may be used to increase FcRn binding, and potentially increase half-life. For example, an IgG1/IgG3 hybrid variant may be constructed by substituting IgG1 positions in the CH2 and/or CH3 region with the amino acids from IgG3 at positions where the two isotypes differ. Thus, a hybrid variant IgG antibody may be constructed that comprises one or more substitutions, e.g., 274Q, 276K, 300F, 339T, 356E, 358M, 384S, 392N, 397M, 422I, 435R, and 436F. In other embodiments described herein, an IgG1/IgG2 hybrid variant may be constructed by substituting IgG2 positions in the CH2 and/or CH3 region with amino acids from IgG1 at positions where the two isotypes differ. Thus, a hybrid variant IgG antibody may be constructed that comprises one or more substitutions, e.g., one or more of the following amino acid substitutions: 233E, 234L, 235L, −236G (referring to an insertion of a glycine at position 236), and 327A. See U.S. Pat. No. 8,629,113. A hybrid of IgG1/IgG2/IgG4 sequences has been generated that purportedly increases serum half-life and improves expression. U.S. Pat. No. 7,867,491 (sequence number 18 therein).

The serum half-life of the antibodies described herein can also be increased by pegylation. An antibody can be pegylated, for example, to increase the biological (e.g., serum) half-life of the antibody. To pegylate an antibody, the antibody, or fragment thereof, typically is reacted with a polyethylene glycol (PEG) reagent, such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies described herein. (See, e.g., EP 0154316 by Nishimura et al. and EP 0401384 by Ishikawa et al.

In some instances, it may be desirable to decrease the half-life of an antibody, rather than to increase it. In some embodiments, the antibodies described herein include modifications to decrease their half-life. Modifications such as I253A (Hornick et al. (2000) *J. Nucl. Med.* 41:355) and H435A/R, I253A or H310A (Kim et al. (2000) *Eur. J. Immunol.* 29:2819) in Fc of human IgG1 can decrease FcRn binding, thus decreasing half-life (increasing clearance) for use in situations where rapid clearance is preferred, such as for medical imaging. (See also Kenanova et al. (2005) *Cancer Res.* 65:622). Other means to enhance clearance include formatting the antigen binding domains of the present invention as antibody fragments lacking the ability to bind FcRn, such as Fab fragments. Such modification can, for example, reduce the circulating half-life of an antibody from a couple of weeks to hours. Selective PEGylation of antibody fragments can then be used to increase the half-life of the antibody fragments when desired. (Chapman et al. (1999) *Nat. Biotechnol.* 17:780). Antibody fragments may also be fused to human serum albumin, e.g. in a fusion protein construct, to increase half-life. (Yeh et al. (1992) *Proc. Nat'l Acad. Sci.* 89:1904). Alternatively, a bispecific antibody may be constructed with a first antigen binding domain of the present invention and a second antigen binding domain that binds to human serum albumin (HSA). (See WO 2009/127691 and patent references cited therein). Alternatively, specialized polypeptide sequences can be added to antibody fragments to increase half-life, e.g. "XTEN" polypeptide sequences. (Schellenberger et al. (2009) *Nat. Biotechnol.* 27:1186; Int'l Pat. Appl. Pub. WO 2010/091122).

Additional Fc Variants

In some embodiments, when using an IgG4 constant domain, it can be advantageous to include the substitution S228P, which mimics the hinge sequence in IgG1 and thereby stabilizes IgG4 molecules, e.g. by reducing Fab-arm exchange between the therapeutic antibody and endogenous IgG4 in the patient being treated. (Labrijn et al. (2009) *Nat. Biotechnol.* 27:767; Reddy et al. (2000) *J. Immunol.* 164: 1925).

A potential protease cleavage site in the hinge of IgG1 constructs can be eliminated by D221G and K222S modifications, increasing the stability of the antibody. (WO 2014/043344).

The affinities and binding properties of an Fc variant for its ligands (Fc receptors) may be determined by a variety of in vitro assay methods (e.g., biochemical or immunological based assays) known in the art including but not limited to, equilibrium methods (e.g., enzyme-linked immunosorbent assay (ELISA), or radioimmunoassay (RIA)), or kinetics (e.g., BIACORE® SPR analysis), and other methods such as indirect binding assays, competitive inhibition assays, fluorescence resonance energy transfer (FRET), gel electrophoresis, and chromatography (e.g., gel filtration). These and other methods may use a label on one or more of the components being examined and/or employ various detection methods including but not limited to chromogenic, fluorescent, luminescent, or isotopic labels. A detailed description of binding affinities and kinetics can be found in Paul, W. E., ed., Fundamental Immunology, 4th Ed., Lippincott-Raven, Philadelphia (1999), which focuses on antibody-immunogen interactions.

In still other embodiments, the glycosylation of an antibody is modified to increase or decrease effector function. For example, an aglycoslated antibody can be made that lacks all effector function by mutating the conserved asparagine residue at position 297 (e.g. N297A), thus abolishing complement and FcγRI binding. (Bolt et al. (1993) *Eur. J. Immunol.* 23:403. See also Tao & Morrison (1989) *J. Immunol.* 143:2595 (using N297Q in IgG1 to eliminate glycosylation at position 297)).

Although aglycosylated antibodies generally lack effector function, mutations can be introduced to restore that function. Aglycosylated antibodies, e.g. those resulting from N297A/C/D/or H mutations or produced in systems (e.g. *E. coli*) that do not glycosylate proteins, can be further mutated to restore FcγR binding, e.g. S298G and/or T299A/G/or H (WO 2009/079242), or E382V and M428I (Jung et al. (2010) *Proc. Nat'l Acad. Sci. (USA)* 107:604).

Glycoengineering can also be used to modify the anti-inflammatory properties of an IgG construct by changing the α2,6 sialyl content of the carbohydrate chains attached at Asn297 of the Fc regions, wherein an increased proportion of α2,6 sialylated forms results in enhanced anti-inflammatory effects. (See Nimmerjahn et al. (2008) *Ann. Rev. Immunol.* 26:513). Conversely, reduction in the proportion of antibodies having α2,6 sialylated carbohydrates may be useful in cases where anti-inflammatory properties are not wanted. Methods of modifying α2,6 sialylation content of antibodies, for example, by selective purification of α2,6 sialylated forms or by enzymatic modification, are provided at U.S. Pat. Appl. Pub. No. 2008/0206246. In other embodiments, the amino acid sequence of the Fc region may be modified to mimic the effect of α2,6 sialylation, for example, by inclusion of an F241A modification. (WO 2013/095966).

III. Antibody Physical Properties

In certain embodiments, the antibodies described herein contain one or more glycosylation sites in either the light or heavy chain variable region. Such glycosylation sites may result in increased immunogenicity of the antibody or an altered antibody pharmacokinetics due to altered antigen binding (Marshall et al (1972) *Ann. Rev. Biochem.* 41:673-702; Gala and Morrison (2004) *J. Immunol.* 172:5489-94; Wallick et al (1988) *J. Exp. Med.* 168:1099-109; Spiro (2002) *Glycobiology* 12:43R-56R; Parekh et al (1985) *Nature* 316:452-7; Mimura et al. (2000) *Mol Immunol* 37:697-706). Glycosylation has been known to occur at motifs containing an N—X—S/T sequence. In some embodiments, the anti-huICOS antibody does not contain variable region glycosylation. Such antibodies can be obtained by selecting antibodies that do not contain the glycosylation motif in the variable region or by mutating residues within the glycosylation region.

In certain embodiments, the antibodies described herein do not contain asparagine isomerism sites. The deamidation of asparagine may occur on N-G or D-G sequences and result in the creation of an isoaspartic acid residue that introduces a kink into the polypeptide chain and decreases its stability (known as the isoaspartic acid effect).

In some embodiments, the antibodies described herein have an isoelectric point (pI) in the pH range between 6 and 9.5. In some embodiments, the antibodies described herein have a pI in the pH range of 7-9.5 or 6-8. Antibodies having a pI within a desired pI range can be obtained either by selecting antibodies with a pI in the pH range from a group of candidates or by mutating charged surface residues of a particular antibody.

In some embodiments, the antibodies described herein are selected and/or engineered have a temperature of initial unfolding ($T_{M1}$) greater than 60° C., greater than 65° C., or greater than 70° C. The melting point of an antibody may be measured using differential scanning calorimetry (Chen et al (2003) *Pharm Res* 20:1952-60; Ghirlando et al (1999) *Immunol Lett.* 68:47-52) or circular dichroism (Murray et al. (2002) *J. Chromatogr. Sci.* 40:343-9).

In some embodiments, the antibodies described herein are selected and/or engineered to have advantageous degradation properties, e.g., slow degradation in vitro and/or in vivo. Antibody degradation can be measured using capillary electrophoresis (CE) and MALDI-MS (Alexander A J and Hughes D E (1995) *Anal Chem.* 67:3626-32). In some embodiments, the antibodies described herein are selected and/or engineered to have favorable aggregation properties, e.g., antibodies that show minimal aggregation in vitro and/or in vivo, which may elicit an unwanted immune response and/or altered or unfavorable pharmacokinetic properties. In some embodiments, the antibodies described herein show aggregation of 25% or less, 20% or less, 15% or less, 10% or less, or 5% or less compared to aggregation of the parent antibody. Aggregation can be measured by several techniques, including size-exclusion column (SEC), high performance liquid chromatography (HPLC), and light scattering.

IV. Nucleic Acid Molecules and Recombinant Methods

Another aspect described herein pertains to nucleic acid molecules that encode the anti-huICOS antibodies described herein. The nucleic acids may be present in whole cells e.g., a host cell, in a cell lysate, or in a partially purified or substantially pure form. A nucleic acid is "isolated" or "rendered substantially pure" when purified away from other cellular components or other contaminants, e.g., other cellular nucleic acids (e.g., other chromosomal DNA, e.g., the chromosomal DNA that is linked to the isolated DNA in nature) or proteins, by standard techniques, including alkaline/SDS treatment, CsCl banding, column chromatography, restriction enzymes, agarose gel electrophoresis, and others well known in the art. (See, F. Ausubel, et al., ed. (1987) Current Protocols in Molecular Biology, Greene Publishing and Wiley Interscience, New York). A nucleic acid described herein can be, for example, DNA or RNA and may or may not contain introns. In a certain embodiments, the nucleic acid is a cDNA molecule.

Nucleic acids described herein can be obtained using standard molecular biology techniques. For antibodies expressed by hybridomas (e.g., hybridomas prepared from transgenic mice carrying human immunoglobulin genes as described further below), cDNAs encoding the light and/or heavy chains of the antibody made by the hybridoma can be obtained by standard PCR amplification or cDNA cloning techniques. For antibodies obtained from an immunoglobulin gene library (e.g., using phage display techniques), nucleic acid encoding the antibody can be recovered from the library.

Once DNA fragments encoding $V_H$ and $V_L$ segments are obtained, these DNA fragments can be further manipulated by standard recombinant DNA techniques, for example, to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked," as used in this context, means that the two DNA fragments are joined such that the amino acid sequences encoded by the two DNA fragments remain in-frame.

Isolated DNA encoding the $V_H$ region can be converted to a full-length heavy chain gene by operatively linking the $V_H$-encoding DNA to another DNA molecule encoding heavy chain constant regions (hinge, CH1, CH2 and/or CH3). The sequences of human heavy chain constant region genes are known in the art (see e.g., Kabat, et al., 1991), and DNA fragments encompassing these regions can be obtained by standard PCR amplification. The heavy chain constant region can be an IgG (IgG1, IgG2, IgG3, or IgG4), IgA, IgE, IgM or IgD constant region, for example, an IgG1 region. For a Fab fragment heavy chain gene, the $V_H$-encoding DNA can be operatively linked to another DNA molecule encoding only the heavy chain CH1 constant region.

The isolated DNA encoding the $V_L$ region can be converted to a full-length light chain gene (as well as a Fab light chain gene) by operatively linking the $V_L$-encoding DNA to another DNA molecule encoding the light chain constant region, CL. The sequences of human light chain constant region genes are known in the art (see e.g., Kabat, et al., 1991) Sequences of Proteins of Immunological Interest, Fifth Edition, U.S. Department of Health and Human Services, NIH Publication No. 91-3242), and DNA fragments encompassing these regions can be obtained by standard PCR amplification. The light chain constant region can be a kappa or lambda constant region.

To create a scFv gene, the $V_H$- and $V_L$-encoding DNA fragments are operatively linked to another fragment encoding a flexible linker, e.g., encoding the amino acid sequence $(Gly_4-Ser)_3$, such that the $V_H$ and $V_L$ sequences can be expressed as a contiguous single-chain protein, with the $V_L$ and $V_H$ regions joined by the flexible linker (see e.g., Bird et al. (1988) *Science* 242:423-426; Huston et al. (1988) *Proc. Natl. Acad. Sci. USA* 85:5879-5883; McCafferty et al., (1990) *Nature* 348:552-554).

V. Antibody Generation

Various antibodies of the present invention, e.g. those that bind to the same epitope as selected anti-human ICOS antibodies disclosed herein, can be produced using a variety of known techniques, such as the standard somatic cell hybridization technique described by Kohler and Milstein, *Nature* 256: 495 (1975). Other techniques for producing monoclonal antibodies also can be employed, e.g., viral or oncogenic transformation of B lymphocytes, phage display technique using libraries of human antibody genes.

An exemplary animal system for preparing hybridomas is the murine system. Hybridoma production in the mouse is a well-established procedure. Immunization protocols and techniques for isolation of immunized splenocytes for fusion are known in the art. Fusion partners (e.g., murine myeloma cells) and fusion procedures are also known.

Chimeric or humanized antibodies described herein can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art (see e.g., U.S. Pat. No. 5,225,539 to Winter, and U.S. Pat. Nos. 5,530,101; 5,585,089; 5,693, 762 and 6,180,370 to Queen et al.).

In one embodiment, the antibodies described herein are human monoclonal antibodies. Such human monoclonal antibodies directed against human ICOS can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice."

The HuMAb Mouse® (Medarex, Inc.) contains human immunoglobulin gene miniloci that encode un-rearranged human heavy (μ and γ) and κ light chain immunoglobulin sequences, together with targeted mutations that inactivate the endogenous μ and κ chain loci (see e.g., Lonberg, et al. (1994) *Nature* 368(6474): 856-859). Accordingly, the mice exhibit reduced expression of mouse IgM or κ, and in response to immunization, the introduced human heavy and light chain transgenes undergo class switching and somatic mutation to generate high affinity human IgGκ monoclonal antibodies (Lonberg, N. et al. (1994), supra; reviewed in Lonberg, N. (1994) *Handbook of Experimental Pharmacology* 113:49-101; Lonberg, N. and Huszar, D. (1995) Intern. Rev. Immunol. 13: 65-93, and Harding, F. and Lonberg, N. (1995) *Ann. N.Y. Acad. Sci.* 764:536-546). The preparation and use of HuMab mice, and the genomic modifications carried by such mice, is further described in Taylor, L. et al. (1992) *Nucleic Acids Research* 20:6287-6295; Chen, J. et al. (1993) *International Immunology* 5: 647-656; Tuaillon et al. (1993) *Proc. Natl. Acad. Sci. USA* 90:3720-3724; Choi et al. (1993) *Nature Genetics* 4:117-123; Chen, J. et al. (1993) *EMBO J.* 12: 821-830; Tuaillon et al. (1994) *J. Immunol.* 152:2912-2920; Taylor, L. et al. (1994) *International Immunology* 6: 579-591; and Fishwild, D. et al. (1996) *Nature Biotechnology* 14: 845-851, the contents of all of which are hereby specifically incorporated by reference in their entirety. (See, also, U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay; U.S. Pat. No. 5,545,807 to Surani et al.; PCT Publication Nos. WO 92/03918, WO 93/12227, WO 94/25585, WO 97/13852, WO 98/24884 and WO 99/45962, all to Lonberg and Kay; and PCT Publication No. WO 01/14424 to Korman et al.)

In certain embodiments, antibodies described herein are raised using a mouse that carries human immunoglobulin sequences on transgenes and transchromosomes, such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise anti-huICOS antibodies described herein. For example, an alternative transgenic system referred to as the Xenomouse (Abgenix, Inc.) can be used; such mice are described in, for example, U.S. Pat. Nos. 5,939,598; 6,075,181; 6,114,598; 6, 150,584 and 6,162,963 to Kucherlapati et al.

Moreover, alternative transchromosomic animal systems expressing human immunoglobulin genes are available in the art and can be used to raise anti-ICOS antibodies described herein. For example, mice carrying both a human heavy chain transchromosome and a human light chain transchromosome, referred to as "TC mice" can be used; such mice are described in Tomizuka et al. (2000) Proc. Natl. Acad. Sci. USA 97:722-727. Furthermore, cows carrying human heavy and light chain transchromosomes have been described in the art (Kuroiwa et al. (2002) Nature Biotechnology 20:889-894) and can be used to raise anti-huICOS antibodies described herein.

Additional mouse systems described in the art for raising human antibodies, e.g., human anti-huICOS antibodies, include (i) the VELOCIMMUNE® mouse (Regeneron Pharmaceuticals, Inc.), in which the endogenous mouse heavy and light chain variable regions have been replaced, via homologous recombination, with human heavy and light chain variable regions, operatively linked to the endogenous mouse constant regions, such that chimeric antibodies (human V/mouse C) are raised in the mice, and then subsequently converted to fully human antibodies using standard recombinant DNA techniques; and (ii) the MeMo® mouse (Merus Biopharmaceuticals, Inc.), in which the mouse contains un-rearranged human heavy chain variable regions but a single rearranged human common light chain variable region. Such mice, and use thereof to raise antibodies, are described in, for example, WO 2009/15777, US 2010/0069614, WO 2011/072204, WO 2011/097603, WO 2011/163311, WO 2011/163314, WO 2012/148873, US 2012/0070861 and US 2012/0073004.

Human monoclonal antibodies described herein can also be prepared using phage display methods for screening libraries of human immunoglobulin genes. Such phage display methods for isolating human antibodies are established in the art. (See, e.g., U.S. Pat. Nos. 5,223,409; 5,403,484; and 5,571,698 to Ladner et al.; U.S. Pat. Nos. 5,427,908 and 5,580,717 to Dower et al.; U.S. Pat. Nos. 5,969,108 and 6,172,197 to McCafferty et al.; and U.S. Pat. Nos. 5,885,793; 6,521,404; 6,544,731; 6,555,313; 6,582,915 and 6,593,081 to Griffiths et al.).

Human monoclonal antibodies described herein can also be prepared using mice with severe combined immunodeficiency (SCID) into which human immune cells have been reconstituted such that a human antibody response can be generated upon immunization. Such mice are described in, for example, U.S. Pat. Nos. 5,476,996 and 5,698,767 to Wilson et al.

Immunizations

To generate fully human antibodies to human ICOS, mice or transgenic or transchromosomal mice containing human immunoglobulin genes (e.g., HCo12, HCo7 or KM mice) can be immunized with a purified or enriched preparation of the ICOS antigen and/or cells expressing ICOS, as described for other antigens, for example, by Lonberg et al. (1994) Nature 368(6474): 856-859; Fishwild et al. (1996) Nature Biotechnology 14: 845-851 and WO 98/24884. Alternatively, mice can be immunized with DNA encoding human ICOS. Preferably, the mice will be 6-16 weeks of age upon the first infusion. For example, a purified or enriched preparation (e.g, 5 µg-50 µg) of the recombinant human ICOS antigen can be used to immunize the mice intraperitoneally. If the immunizations using a purified or enriched preparation of the ICOS antigen do not result in antibodies, mice can also be immunized with cells expressing ICOS, e.g., a cell line, to promote immune responses.

The HuMAb transgenic mice can be initially immunized intraperitoneally or subcutaneously (SC) with antigen in Ribi's adjuvant, followed by every other week IP/SC immunizations (up to a total of 10) with antigen in Ribi's adjuvant. The immune response can be monitored over the course of the immunization protocol with plasma samples being obtained by retroorbital bleeds. The plasma can be screened by ELISA and FACS (as described below), and mice with sufficient titers of anti-ICOS human immunoglobulin can be used for fusions. Mice can be boosted intravenously with antigen three days before sacrifice and removal of the spleen and lymph nodes. Two to three fusions for each immunization may be performed. Between 6 and 24 mice can be immunized for each antigen. In some embodiments, HCo7, HCo12, and KM strains are used. In addition, both HCo7 and HCo12 transgene can be bred together into a single mouse having two different human heavy chain transgenes (HCo7/HCo12).

Generation of Hybridomas Producing Monoclonal Antibodies to ICOS

To generate hybridomas producing monoclonal antibodies described herein, splenocytes and/or lymph node cells from immunized mice can be isolated and fused to an appropriate immortalized cell line, such as a mouse myeloma cell line. The resulting hybridomas can be screened for the production of antigen-specific antibodies. For example, single cell suspensions of splenic lymphocytes from immunized mice can be fused to Sp2/0 non-secreting mouse myeloma cells (ATCC, CRL 1581) with 50% PEG. Cells are plated at approximately $2 \times 10^5$ in flat bottom microtiter plate, followed by a two week incubation in selective medium containing 10% fetal Clone Serum, 18% "653" conditioned media, 5% Origen (IGEN), 4 mM L-glutamine, 1 mM sodium pyruvate, 5 mM HEPES, 0.055 mM 2-mercaptoethanol, 50 units/ml penicillin, 50 mg/ml streptomycin, 50 mg/ml gentamycin and 1×HAT (Sigma). After approximately two weeks, cells can be cultured in medium in which the HAT is replaced with HT. Individual wells can then be screened by ELISA for human monoclonal IgM and IgG antibodies. Once extensive hybridoma growth occurs, medium can be observed usually after 10-14 days. The antibody secreting hybridomas can be re-plated, screened again, and, if still positive for human IgG, the monoclonal antibodies can be subcloned at least twice by limiting dilution. The stable subclones can then be cultured in vitro to generate small amounts of antibody in tissue culture medium for characterization.

To purify monoclonal antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

VI. Antibody Manufacture

Generation of Transfectomas Producing Monoclonal Antibodies to ICOS

Antibodies of the present invention, including both specific antibodies for which sequences are provided and other, related anti-ICOS antibodies, can be produced in a host cell transfectoma using, for example, a combination of recombinant DNA techniques and gene transfection methods well known in the art (Morrison, S. (1985) *Science* 229:1202).

For example, to express antibodies, or antibody fragments thereof, DNAs encoding partial or full-length light and heavy chains, can be obtained by standard molecular biology techniques (e.g., PCR amplification or cDNA cloning using a hybridoma that expresses the antibody of interest), and the DNAs can be inserted into expression vectors such that the genes are operatively linked to transcriptional and translational control sequences. In this context, the term "operatively linked" is intended to mean that an antibody gene is ligated into a vector such that transcriptional and translational control sequences within the vector serve their intended function of regulating the transcription and translation of the antibody gene. The expression vector and expression control sequences are chosen to be compatible with the expression host cell used. The antibody light chain gene and the antibody heavy chain gene can be inserted into separate vector or both genes are inserted into the same expression vector. The antibody genes are inserted into the expression vector(s) by standard methods (e.g., ligation of complementary restriction sites on the antibody gene fragment and vector, or blunt end ligation if no restriction sites are present). The light and heavy chain variable regions of the antibodies described herein can be used to create full-length antibody genes of any antibody isotype by inserting them into expression vectors already encoding heavy chain constant and light chain constant regions of the desired isotype such that the $V_H$ segment is operatively linked to the CH segment(s) within the vector and the $V_L$ segment is operatively linked to the CL segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes, recombinant expression vectors may carry regulatory sequences that control the expression of the antibody chain genes in a host cell. The term "regulatory sequence" includes promoters, enhancers, and other expression control elements (e.g., polyadenylation signals) that control the transcription or translation of the antibody chain genes. Such regulatory sequences are described, for example, in Goeddel (Gene Expression Technology. *Methods in Enzymology* 185, Academic Press, San Diego, Calif. (1990)). It will be appreciated by those skilled in the art that the design of the expression vector, including the selection of regulatory sequences, may depend on such factors as the choice of the host cell to be transformed, the level of expression of protein desired, amongst other factors. Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, (e.g., the adenovirus major late promoter (AdMLP), and polyomavirus. Alternatively, nonviral regulatory sequences may be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe, Y. et al. (1988) *Mol. Cell. Biol.* 8:466-472).

In addition to the antibody chain genes and regulatory sequences, recombinant expression vectors may carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216, 4,634,665 and 5,179,017, all by Axel et al.). For example, typically the selectable marker gene confers resistance to drugs, such as G418, hygromycin or methotrexate, on a host cell into which the vector has been introduced. Exemplary selectable marker genes include the dihydrofolate reductase (DHFR) gene (for use in dhfr− host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" encompasses a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies described herein in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody. Prokaryotic expression of antibody genes has been reported to be ineffective for production of high yields of active antibody (Boss, M. A. and Wood, C. R. (1985) *Immunology Today* 6:12-13). Antibodies of the present invention can also be produced in glycol-engineered strains of yeast. (*Pichia pastoris*. Li et al. (2006) *Nat. Biotechnol.* 24:210).

Exemplary mammalian host cells for expressing the recombinant antibodies described herein include Chinese Hamster Ovary (CHO cells) (including dhfr− CHO cells, described in Urlaub and Chasin, (1980) *Proc. Natl. Acad. Sci. USA* 77:4216-4220, used with a dihydrofolate reductase (DHFR) selectable marker, e.g., as described in R. J. Kaufman and P. A. Sharp (1982) *Mol. Biol.* 159:601-621), NSO myeloma cells, COS cells and SP2 cells. In particular, for use with NSO myeloma cells, another exemplary expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The N- and C-termini of antibody polypeptide chains of the present invention may differ from the expected sequence due to commonly observed post-translational modifications.

For example, C-terminal lysine residues are often missing from antibody heavy chains. (Dick et al. (2008) *Biotechnol. Bioeng.* 100:1132). N-terminal glutamine residues, and to a lesser extent glutamate residues, are frequently converted to pyroglutamate residues on both light and heavy chains of therapeutic antibodies. (Dick et al. (2007) *Biotechnol. Bioeng.* 97:544; Liu et al. (2011) *JBC* 28611211; Liu et al. (2011) *J. Biol. Chem.* 286:11211).

Amino acid sequences for various agonist anti-huICOS antibodies of the present invention are provided in the Sequence Listing, which is summarized at Table 35. For the reasons discussed above, the C-terminal lysine is not included in many of sequences in the Sequence Listing for heavy chains or heavy chain constant domains. However, in an alternative embodiment, each heavy chain for the anti-huICOS antibodies of the present invention, and/or genetic construct encoding such antibodies or the heavy or light chains thereof, includes this additional lysine residue at the C-terminus of the heavy chain(s).

VII. Assays

Antibodies described herein can be tested for binding to ICOS by, for example, standard ELISA. For example, microtiter plates are coated with purified ICOS at 1-2 µg/ml in PBS, and then blocked with 5% bovine serum albumin in PBS. Dilutions of antibody (e.g., dilutions of plasma from ICOS-immunized mice) are added to each well and incubated for 1-2 hours at 37° C. The plates are washed with PBS/Tween and then incubated with secondary reagent (e.g., for human antibodies, or antibodies otherwise having a human heavy chain constant region, a goat-anti-human IgG Fc-specific polyclonal reagent) conjugated to horseradish peroxidase (HRP) for 1 hour at 37° C. After washing, the plates are developed with ABTS substrate (Moss Inc, product: ABTS-1000) and analyzed by a spectrophotometer at OD 415-495. Sera from immunized mice are then further screened by flow cytometry for binding to a cell line expressing human ICOS, but not to a control cell line that does not express ICOS. Briefly, the binding of anti-ICOS antibodies is assessed by incubating ICOS expressing CHO cells with the anti-ICOS antibody at 1:20 dilution. The cells are washed and binding is detected with a PE-labeled anti-human IgG Ab. Flow cytometric analyses are performed using a FACScan flow cytometry (Becton Dickinson, San Jose, Calif.). Preferably, mice that develop the highest titers will be used for fusions. Analogous experiments may be performed using anti-mouse detection antibodies if mouse anti-huICOS antibodies are to be detected.

An ELISA, e.g., as described above can be used to screen for antibodies and, thus, hybridomas that produce antibodies that show positive reactivity with the ICOS immunogen. Hybridomas that produce antibodies that bind, preferably with high affinity, to ICOS can then be subcloned and further characterized. One clone from each hybridoma, which retains the reactivity of the parent cells (by ELISA), can then be chosen for making a cell bank, and for antibody purification.

To purify anti-ICOS antibodies, selected hybridomas can be grown in two-liter spinner-flasks for monoclonal antibody purification. Supernatants can be filtered and concentrated before affinity chromatography with protein A-sepharose (Pharmacia, Piscataway, N.J.). Eluted IgG can be checked by gel electrophoresis and high performance liquid chromatography to ensure purity. The buffer solution can be exchanged into PBS, and the concentration can be determined by OD280 using 1.43 extinction coefficient. The monoclonal antibodies can be aliquoted and stored at −80° C.

To determine if the selected anti-ICOS monoclonal antibodies bind to unique epitopes, each antibody can be biotinylated using commercially available reagents (Pierce, Rockford, Ill.). Biotinylated MAb binding can be detected with a streptavidin labeled probe. Competition studies using unlabeled monoclonal antibodies and biotinylated monoclonal antibodies can be performed using ICOS coated-ELISA plates as described above.

To determine the isotype of purified antibodies, isotype ELISAs can be performed using reagents specific for antibodies of a particular isotype. For example, to determine the isotype of a human monoclonal antibody, wells of microtiter plates can be coated with 1 µg/ml of anti-human immunoglobulin overnight at 4° C. After blocking with 1% BSA, the plates are reacted with 1 µg/ml or less of test monoclonal antibodies or purified isotype controls, at ambient temperature for one to two hours. The wells can then be reacted with either human IgG1 or human IgM-specific alkaline phosphatase-conjugated probes. Plates are developed and analyzed as described above.

To test the binding of monoclonal antibodies to live cells expressing ICOS, flow cytometry can be used. Briefly, cell lines expressing membrane-bound ICOS (grown under standard growth conditions) are mixed with various concentrations of monoclonal antibodies in PBS containing 0.1% BSA at 4° C. for one hour. After washing, the cells are reacted with Phycoerythrin (PE)-labeled anti-IgG antibody under the same conditions as the primary antibody staining. The samples can be analyzed by FACScan instrument using light and side scatter properties to gate on single cells and binding of the labeled antibodies is determined. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen.

Anti-huICOS antibodies can be further tested for reactivity with the ICOS antigen by Western blotting. Briefly, cell extracts from cells expressing ICOS can be prepared and subjected to sodium dodecyl sulfate polyacrylamide gel electrophoresis. After electrophoresis, the separated antigens will be transferred to nitrocellulose membranes, blocked with 20% mouse serum, and probed with the monoclonal antibodies to be tested. IgG binding can be detected using anti-IgG alkaline phosphatase and developed with BCIP/NBT substrate tablets (Sigma Chem. Co., St. Louis, Mo.).

Methods for analyzing binding affinity, cross-reactivity, and binding kinetics of various anti-ICOS antibodies include standard assays known in the art, for example, Biolayer Interferometry (BLI) analysis, and BIACORE® SPR analysis using a BIACORE® 2000 SPR instrument (Biacore AB, Uppsala, Sweden).

In one embodiment, an anti-huICOS antibody specifically binds to the extracellular region of human ICOS. In one embodiment, the antibody binds to a particular domain (e.g., a functional domain) within the extracellular domain of ICOS. In one embodiment, the anti-huICOS antibody specifically binds to the extracellular region of human ICOS and the extracellular region of cynomolgus ICOS. In one embodiment, the anti-huICOS antibody binds to human ICOS with high affinity.

VIII. Multispecific Molecules

In certain embodiments, antibodies described herein may be multispecific, e.g., bispecific or trispecific, molecules. Multispecific antigen-binding molecules, such as multispecific antibodies, comprise two or more antigen-binding site, each specific for a different epitope. The different epitope can be part of the same or different antigens. In one embodiment, one antigen-binding site is specific for human ICOS and the other for a different antigen. In one embodiment, an anti-huICOS antibody, or antigen-binding fragments thereof, as described herein is linked to another antigen-binding molecule, e.g., another peptide or protein (e.g., another antibody or antibody fragment, or a ligand for a receptor) having a different binding specificity to generate a bispecific molecule that binds to at least two different binding sites or target molecules. In one embodiment, the antibody described herein is derivatized or linked to more than one other antigen-binding molecule to generate multispecific molecules that bind to more than two different binding sites and/or target molecules. Accordingly, provided herein are bispecific molecules comprising at least one first binding specificity for ICOS and a second binding specificity for a second target epitope. In an embodiment described herein in which the bispecific molecule is multispecific, the molecule can further include a third binding specificity.

In one embodiment, the bispecific molecules described herein comprise as a binding specificity at least one antibody, or an antibody fragment thereof, including, e.g., an Fab, Fab', F(ab')$_2$, Fv, or a single chain Fv. The antibody may also be a light chain or heavy chain dimer, or any minimal fragment thereof such as a Fv or a single chain construct as described in Ladner et al. U.S. Pat. No. 4,946,778, the contents of which is expressly incorporated by reference.

While human monoclonal antibodies are preferred, other antibodies that can be employed in the bispecific molecules described herein are murine, chimeric and humanized monoclonal antibodies.

The bispecific molecules described herein can be prepared by conjugating the constituent binding specificities using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-S-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl) cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. USA* 82:8648). Other methods include those described in Paulus (1985) Behring Ins. Mitt. No. 78, 118-132; Brennan et al. (1985) *Science* 229:81-83), and Glennie et al. (1987) *J. Immunol.* 139: 2367-2375). Preferred conjugating agents are SATA and sulfo-SMCC, both available from Pierce Chemical Co. (Rockford, Ill.).

When the binding specificities are antibodies, they can be conjugated via sulfhydryl bonding of the C-terminus hinge regions of the two heavy chains. In a particularly preferred embodiment, the hinge region is modified to contain an odd number of sulfhydryl residues, preferably one, prior to conjugation.

Alternatively, both binding specificities can be encoded in the same vector and expressed and assembled in the same host cell. This method is particularly useful where the bispecific molecule has a combination of binding specificities such as a (mAb×mAb), (mAb×Fab), (Fab×F(ab')$_2$) or (ligand x Fab) fusion protein. A bispecific molecule described herein can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed using art-recognized methods, such as using ELISA, radioimmunoassay (MA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

IX. Compositions

Further provided are compositions, e.g., a pharmaceutical compositions, containing one or more anti-ICOS antibodies, or antigen-binding fragment(s) thereof, as described herein, formulated together with a pharmaceutically acceptable carrier. Accordingly, the compositions of the present invention include the human or humanized anti-huICOS antibodies (or antigen-binding fragments) thereof having the CDR sequences, the heavy and/or light chain variable region sequences, or the full-length heavy and/or light chain sequences set forth in Table 35. Compositions of the present invention also include anti-huICOS antibodies having sequences which are variants of the sequences set forth in Table 35. For example, such antibodies can comprise sequences that are at least 70%, 75%, 80%, 85%, 90%, or 95%, 96%, 97%, 98%, or 99% identical to the CDR sequences, the heavy and/or light chain variable region sequences, or full-length heavy and/or light chain sequences set forth in Table 35.

Such compositions also may include one or a combination of (e.g., two or more different) antibodies, or immunoconjugates or bispecific molecules described herein. For example, a pharmaceutical composition described herein can comprise a combination of antibodies (or immunoconjugates or bispecific antibodies) that bind to different epitopes on the target antigen or that have complementary activities.

Pharmaceutical compositions described herein also can be administered as combination therapy, i.e., anti-ICOS antibodies combined with other agents. For example, the combination therapy can include an anti-ICOS antibody described herein combined with at least one other anti-cancer and/or T-cell stimulating (e.g., activating) agent. Examples of therapeutic agents that can be used in combination therapy are described in greater detail below in the section on uses of the antibodies described herein.

In some embodiments, pharmaceutical compositions disclosed herein can include other compounds, drugs, and/or agents used for the treatment of cancer. Such compounds, drugs, and/or agents can include, for example, chemotherapy drugs, small molecule drugs or antibodies that stimulate the immune response to a given cancer. In some embodiments, a pharmaceutical composition comprises a first antibody specific for anti-huICOS and a second antibody.

In some embodiments, the first antibody and the second antibody are present in the composition at a fixed dose (i.e., a fixed ratio). In other embodiments, this fixed dose is between at least about 1:200 to at least about 200:1, at least about 1:150 to at least about 150:1, at least about 1:100 to at least about 100:1, at least about 1:75 to at least about 75:1, at least about 1:50 to at least about 50:1, at least about 1:25 to at least about 25:1, at least about 1:10 to at least about 10:1, at least about 1:5 to at least about 5:1, at least about 1:4 to at least about 4:1, at least about 1:3 to at least about 3:1, or at least about 1:2 to at least about 2:1 mg anti-huICOS antibody to mg second antibody. In some embodiments, the fixed dose is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, or about 1:200 anti-huICOS antibody to second antibody. In some embodiments, the fixed dose is at least about 2:1, about 3:1, about 4:1, about 5:1, about 6:1, about 7:1, about 8:1, about 9:1, about 10:1, about 15:1, about 20:1, about 30:1, about 40:1, about 50:1, about 60:1, about 70:1, about 80:1, about 90:1, about 100:1, about 120:1, about 140:1, about 160:1, about 180:1, or about 200:1 mg first antibody to mg second antibody. For example, in one embodiment, the anti-huICOS antibody and the second antibody are administered as described in Example 18.

The additional antibodies include, for example, one or more of an anti-CTLA-4 antibody, an anti-PD-1 antibody, an anti-PD-L1 antibody, an anti-TIGIT antibody, an anti-OX40 (also known as CD134, TNFRSF4, ACT35 and/or TXGP1L) antibody, an anti-LAG-3 antibody, an anti-CD73 antibody, an anti-CD137 antibody, an anti-CD27 antibody, or an anti-CSF-1R antibody.

As used herein, "pharmaceutically acceptable carrier" includes any and all solvents, dispersion media, coatings, antibacterial and antifungal agents, isotonic and absorption delaying agents, and the like that are physiologically compatible. In some embodiments, the carrier is suitable for intravenous, intramuscular, subcutaneous, parenteral, spinal or epidermal administration (e.g., by injection or infusion). In some embodiments, the carrier is suitable for intravenous administration. In other embodiments, the carrier is suitable for subcutaneous administration. In some embodiments, the composition comprising anti-ICOS antibody is delivered subcutaneously using Halozyme's ENHANZE® drug delivery technology, which includes a recombinant human hyaluronidase enzyme (rHuPH20) that temporarily degrades hyaluronan. In some embodiments, the ENHANZE® drug delivery technology allows for subcutaneous administrations of compositions that is more rapid as compared to intravenous administration. In other embodiments, depending on the route of administration, the active compound, i.e., antibody, immunoconjugate, or bispecific molecule, may be coated in a material to protect the compound from the action of acids and other natural conditions that may inactivate the compound.

The pharmaceutical compounds described herein may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) *J. Pharm. Sci.* 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition described herein also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and non-aqueous carriers that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

Pharmaceutically acceptable carriers include sterile aqueous solutions or dispersions and sterile powders for the extemporaneous preparation of sterile injectable solutions or dispersion. Exemplary pharmaceutically acceptable carriers herein further include interstitial drug dispersion agents such as soluble neutral-active hyaluronidase glycoproteins (sHASEGP), for example, human soluble PH-20 hyaluronidase glycoproteins, such as rHuPH20 (HYLENEX™, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

The use of such media and agents for pharmaceutically active substances is known in the art. Except insofar as any conventional media or agent is incompatible with the active compound, use thereof in the pharmaceutical compositions described herein is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, monostearate salts and gelatin.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those described above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient that can be combined with a carrier material to produce a single dosage form will vary depending upon the subject being treated, and the particular mode of administration. The amount of active ingredient that can be combined with a carrier material to produce a single dosage form will generally be that amount of the composition that produces a therapeutic effect. Out of one hundred percent, this amount may range from about 0.01 percent to about ninety-nine percent of active ingredient, e.g., from about 0.1 percent to about 70 percent, e.g., from about 1 percent to about 30 percent of active ingredient in combination with a pharmaceutically acceptable carrier.

In some embodiments, the composition includes an anti-ICOS antibody, such as the ICOS.33 IgG1f S267E antibody, at a concentration of 10 mg/mL. The composition is a sterile, non-pyrogenic, single-use, preservative-free, isotonic aqueous solution for intravenous administration. The composition may be administered undiluted or further diluted with 0.9% sodium chloride injection to the required protein concentrations prior to infusion. In some embodiments, the anti-ICOS antibody includes the following excipients: L-histine, L-histidine hydrochloride monohydrate, sucrose, pentetic acid (also known as diethylenetriaminepentaaceitc acid, polysorbate 80, and water for the injection.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms described herein are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody, the dosage may range from about 0.0001 to 100 mg/kg, and more usually 0.01 to 5 mg/kg, of the host body weight. For example, dosages can be 0.3 mg/kg body weight, 1 mg/kg body weight, 3 mg/kg body weight, 5 mg/kg body weight or 10 mg/kg body weight or within the range of 1-10 mg/kg. Alternatively, administration of the antibody is a flat dose which may range from 2 mg to 800 mg, for example, a dose of 25 mg, 80 mg, 200 mg, or 400 mg. An exemplary treatment regimen entails administration once per week, once every two weeks, once every three weeks, once every four weeks, once a month, once every two months, once every three months, once every four months, once every five months, or once every six months. In some embodiments, the treatment regimen includes an initial dose, and then a maintenance dose of a different dose amount at an intermittent dose interval.

In some embodiments, two or more monoclonal antibodies with different binding specificities are administered simultaneously, in which case the dosage of each antibody administered falls within the ranges indicated. In some embodiments, the therapeutic antibody is administered on multiple occasions. Intervals between single dosages can be, for example, weekly, once every three weeks, once every four weeks, monthly, every three months or yearly. Intervals can also be irregular as indicated by measuring blood levels of antibody to the target antigen in the patient. In some embodiments, dosage is adjusted to achieve a plasma antibody concentration of about 1-1000 µg/ml and in some methods about 25-300 µg/ml.

In some embodiments, the antibody can be administered as a sustained release formulation. Administration via a sustained release formulations might require less frequent administration. Dosage and frequency vary depending on the half-life of the antibody in the patient. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In some embodiments, a relatively high dosage at relatively short intervals is administered for therapeutic treatment. In some embodiments, a relatively high dosage is administered until progression of the disease is reduced or terminated, e.g., until the patient shows partial or complete amelioration of symptoms of disease. In some embodiments, a prophylactic treatment is administered to patient following a therapeutic treatment.

Actual dosage levels of the active ingredients in the pharmaceutical compositions described herein may be varied so as to obtain an amount of the active ingredient that is effective to achieve the desired therapeutic response for a particular patient, composition, and mode of administration, without being toxic to the patient. The selected dosage level will depend upon a variety of pharmacokinetic factors including the activity of the particular compositions described herein employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective dosage" of an anti-ICOS antibody described herein preferably results in a decrease in severity of disease symptoms, an increase in frequency and duration of disease symptom-free periods, or a prevention of impairment or disability due to the disease affliction. In the context of cancer, a therapeutically effective dose preferably prevents further deterioration of physical symptoms associated with cancer. Symptoms of cancer are well-known in the art and include, for example, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like. Therapeutic efficacy may be observable immediately after the first administration of an agonistic anti-huICOS monoclonal antibody of the present invention, or it may only be observed after a period of time and/or a series of doses. Such delayed efficacy my only be observed after several months of treatment, e.g., up to 6, 9 or 12 months.

A therapeutically effective dose may prevent or delay onset of cancer, such as may be desired when early or preliminary signs of the disease are present. Accordingly, any clinical or biochemical assay that monitors any of the foregoing may be used to determine whether a particular treatment is a therapeutically effective dose for treating cancer. One of ordinary skill in the art would be able to determine such amounts based on such factors as the subject's size, the severity of the subject's symptoms, and the particular composition or route of administration selected.

A composition described herein can be administered via one or more routes of administration using one or more of a variety of methods known in the art. As will be appreciated by the skilled artisan, the route and/or mode of administration will vary depending upon the desired results. Exemplary routes of administration for antibodies described herein include intravenous, intramuscular, intradermal, intraperitoneal, subcutaneous, spinal or other parenteral routes of administration, for example by injection or infusion.

Alternatively, an antibody described herein can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

Therapeutic compositions can be administered with medical devices known in the art. For example, in a preferred embodiment, a therapeutic composition described herein can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules for use with anti-huICOS antibodies described herein include: U.S. Pat. No. 4,487,603, which discloses an implantable micro-infusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the anti-huICOS antibodies described herein can be formulated to ensure proper distribution in vivo. For example, the blood-brain barrier (BBB) excludes many highly hydrophilic compounds. To ensure that the therapeutic compounds described herein cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties that are selectively transported into specific cells or organs, thus enhance targeted drug delivery (see, e.g., V. V. Ranade (1989) *J. Clin. Pharmacol.* 29:685). Exemplary targeting moieties include folate or biotin (see, e.g., U.S. Pat. No. 5,416,016 to Low et al.); mannosides (Umezawa et al., (1988) *Biochem. Biophys. Res. Commun.* 153:1038); antibodies (P. G. Bloeman et al. (1995) *FEBS Lett.* 357:140; M. Owais et al. (1995) *Antimicrob. Agents Chemother.* 39:180); surfactant protein A receptor (Briscoe et al. (1995) *Am. J. Physiol.* 1233:134); p 120 (Schreier et al. (1994) *J. Biol. Chem.* 269:9090); see also K. Keinanen; M. L. Laukkanen (1994) *FEBS Lett.* 346:123; J. J. Killion; I. J. Fidler (1994) *Immunomethods* 4:273.

Also within the scope described herein are kits comprising the antibody compositions described herein (e.g., human antibodies, bispecific or multispecific molecules, or immunoconjugates) and instructions for use. The kit can further contain at least one additional reagent, or one or more additional human antibodies described herein. Kits can include a label indicating the intended use of the contents of the kit. The term label includes any writing, or recorded material supplied on or with the kit, or that otherwise accompanies the kit.

X. Methods of Use

The antibodies, antibody compositions and methods described herein have numerous in vitro and in vivo uses involving, for example, enhancement of immune response by stimulating ICOS signaling. In one embodiment, the antibodies described herein are monoclonal human or humanized antibodies. In one embodiment, anti-huICOS antibodies described herein (e.g., ICOS.33 IgG1f S267E, 17C4, 9D5, 3E8, 1D7, and 2644) can be administered to cells in culture, in vitro or ex vivo, or to human subjects to enhance immunity in a variety of diseases. In a particular embodiment, the anti-huICOS antibodies agonistic antibodies, i.e., agonist anti-huICOS antibodies. Provided herein are methods of modifying an immune response in a subject comprising administering to the subject an antibody, or antigen-binding fragment thereof, described herein such that the immune response in the subject is enhanced, stimulated or up-regulated. In one embodiment, administering the anti-huICOS antibody (i.e., the agonist anti-huICOS antibody) according to the methods described herein enhances costimulation of T cell responses. In one embodiment, administering the anti-huICOS antibody according to the methods described herein stimulates, enhances or upregulates antigen-specific T cell responses to a tumor. A tumor may be a solid tumor or a liquid tumor, e.g., a hematological malignancy. In certain embodiments, a tumor is an immunogenic tumor. In certain embodiments, a tumor is non-immunogenic. In certain embodiments, a tumor is PD-L1 positive. In certain embodiments a tumor is PD-L1 negative. A subject may also be a virus-bearing subject and an immune response against the virus is enhanced. In one embodiment, administering the anti-huICOS antibody according to the methods described herein stimulates, enhances or upregulates CD4+ and CD8+ T cell responses. The T cells can be Teff cells, e.g., CD4+ Teff cells, CD8+ Teff cells, T helper ($T_h$) cells and T cytotoxic ($T_c$) cells.

In one embodiment, the methods result in an enhancement of an immune response in a human subject wherein such enhancement has a desirable effect. In one embodiment, the human subject is a human patients having a disorder that can be treated by augmenting an immune response, e.g., the T-cell mediated immune response. In a particular embodiment, the human patient has a cancer. In one embodiment, anti-huICOS antibodies described herein can be administered together with an antigen of interest or the antigen may already be present in the subject to be treated, e.g., a tumor-bearing or virus-bearing subject. When antibodies to ICOS are administered together with another agent, the two can be administered separately or simultaneously.

Further provided are methods for inhibiting growth of a tumor cell in a subject comprising administering to the subject an anti-huICOS antibody described herein such that growth of the tumor cell is inhibited in the subject. Also provided are methods of treating chronic viral infection in a subject comprising administering to the subject an anti-huICOS antibody described herein such that the chronic viral infection is treated in the subject.

In some embodiments, an anti-huICOS agonist antibody is administered to a subject, e.g., a human patient, as an adjunctive therapy, adjuvant therapy, or neo-adjuvant therapy. In some embodiments, treatments of subjects having cancer with an anti-huICOS antibody may lead to a long-term durable response relative to the current standard of care; long term survival of at least 1, 2, 3, 4, 5, 6, 7, 8, 9, 10 or more years, recurrence free survival of at least 1, 2, 3, 4, 5, 6, 7, 8, 9, or 10 or more years. In certain embodiments, treatment of a subject having cancer with an anti-huICOS antibody prevents recurrence of cancer or delays recurrence of cancer by, e.g., 1, 2, 3, 4, 5, 6, 7, 8, 9, or 10 or more years. An anti-ICOS treatment can be used as a first, second, or subsequent line of treatment.

These and other methods described herein are discussed in further detail below.

Cancer

Provided herein are methods for treating a subject having cancer, comprising administering to the subject an anti-huICOS antibody described herein, such that the subject is treated, e.g., such that growth of cancerous tumors is inhibited or reduced and/or that the tumors regress. An anti-huICOS antibody can be used alone to inhibit the growth of cancerous tumors. Alternatively, an anti-huICOS antibody can be used in conjunction with another agent, e.g., other immunogenic agents, standard cancer treatments, or other antibodies, as described below. Combination with an inhibitor of PD-1, such as an anti-PD-1 or an anti-PD-L1 antibody, is also provided. Combination with an inhibitor of CTLA-4, such as an anti-CTLA-4 antibody, is also provided. Combination with an inhibitor of PD-1 and an inhibitor of CTLA-4 is also provided.

In one aspect, provided herein are methods of treating cancer in a subject, comprising administering to the subject a therapeutically effective amount of an anti-huICOS antibody described herein, e.g., a humanized form of a hamster anti-ICOS antibody or antigen-binding fragment thereof. In one embodiment, the anti-huICOS antibody may be a chimeric antibody, a human antibody, or a humanized anti-huICOS antibody, e.g., any of the humanized anti-huICOS antibodies described herein. In one embodiment, the methods of treating a cancer described herein comprise administering a humanized anti-huICOS antibody that contacts human ICOS at one or more amino acid residues of SEQ ID NO: 203 of human ICOS protein. In another embodiment, the method comprises administering ICOS.33 IgG1f 5267E antibody. In another embodiment, the method comprises administering a composition comprising ICOS.33 IgG1f 5267E antibody.

Examples of cancer include, but are not limited to, squamous cell carcinoma, small-cell lung cancer (SCLC), non-small cell lung cancer, squamous non-small cell lung cancer (NSCLC), non NSCLC, glioma, gastrointestinal cancer, renal cancer (e.g. clear cell carcinoma), ovarian cancer, liver cancer, colorectal cancer, endometrial cancer, kidney cancer (e.g., renal cell carcinoma (RCC)), prostate cancer (e.g. hormone refractory prostate adenocarcinoma), thyroid cancer, neuroblastoma, pancreatic cancer, glioblastoma (glioblastoma multiforme), cervical cancer, stomach cancer, bladder cancer, hepatoma, breast cancer, colon carcinoma, and head and neck cancer (or carcinoma), gastric cancer, germ cell tumor, pediatric sarcoma, sinonasal natural killer, melanoma (e.g., metastatic malignant melanoma, such as cutaneous or intraocular malignant melanoma), bone cancer, skin cancer, uterine cancer, cancer of the anal region, testicular cancer, carcinoma of the fallopian tubes, carcinoma of the endometrium, carcinoma of the cervix, carcinoma of the vagina, carcinoma of the vulva, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, cancer of the ureter, carcinoma of the renal pelvis, neoplasm of the central nervous system (CNS), primary CNS lymphoma, tumor angiogenesis, spinal axis tumor, brain cancer including brain stem glioma, pituitary adenoma, Kaposi's sarcoma, epidermoid cancer, squamous cell cancer, T-cell lymphoma, environmentally-induced cancers including those induced by asbestos, virus-related cancers (e.g., human papilloma virus (HPV)-related tumor), and hematologic malignancies derived from either of the two major blood cell lineages, i.e., the myeloid cell line (which produces granulocytes, erythrocytes, thrombocytes, macrophages, and mast cells) or lymphoid cell line (which produces B, T, NK, and plasma cells), such as all types of leukemias, lymphomas, and myelomas, e.g., acute, chronic, lymphocytic and/or myelogenous leukemias, such as acute leukemia (ALL), acute myelogenous leukemia (AML), chronic lymphocytic leukemia (CLL), and chronic myelogenous leukemia (CML), undifferentiated AML (MO), myeloblastic leukemia (M1), myeloblastic leukemia (M2;

with cell maturation), promyelocytic leukemia (M3 or M3 variant [M3V]), myelomonocytic leukemia (M4 or M4 variant with eosinophilia [M4E]), monocytic leukemia (M5), erythroleukemia (M6), megakaryoblastic leukemia (M7), isolated granulocytic sarcoma, and chloroma; lymphomas, such as Hodgkin's lymphoma (HL), non-Hodgkin's lymphoma (NHL), B-cell lymphomas, T-cell lymphomas, lymphoplasmacytoid lymphoma, monocytoid B-cell lymphoma, mucosa-associated lymphoid tissue (MALT) lymphoma, anaplastic (e.g., Ki 1+) large-cell lymphoma, adult T-cell lymphoma/leukemia, mantle cell lymphoma, angio immunoblastic T-cell lymphoma, angiocentric lymphoma, intestinal T-cell lymphoma, primary mediastinal B-cell lymphoma, precursor T-lymphoblastic lymphoma, T-lymphoblastic; and lymphoma/leukemia (T-Lbly/T-ALL), peripheral T-cell lymphoma, lymphoblastic lymphoma, post-transplantation lymphoproliferative disorder, true histiocytic lymphoma, primary central nervous system lymphoma, primary effusion lymphoma, lymphoblastic lymphoma (LBL), hematopoietic tumors of lymphoid lineage, acute lymphoblastic leukemia, diffuse large B-cell lymphoma, Burkitt's lymphoma, follicular lymphoma, diffuse histiocytic lymphoma (DHL), immunoblastic large cell lymphoma, precursor B-lymphoblastic lymphoma, cutaneous T-cell lymphoma (CTLC) (also called mycosis fungoides or Sezary syndrome), and lymphoplasmacytoid lymphoma (LPL) with Waldenstrom's macroglobulinemia; myelomas, such as IgG myeloma, light chain myeloma, nonsecretory myeloma, smoldering myeloma (also called indolent myeloma), solitary plasmocytoma, and multiple myelomas, chronic lymphocytic leukemia (CLL), hairy cell lymphoma; hematopoietic tumors of myeloid lineage, tumors of mesenchymal origin, including fibrosarcoma and rhabdomyoscarcoma; seminoma, teratocarcinoma, tumors of the central and peripheral nervous, including astrocytoma, schwannomas; tumors of mesenchymal origin, including fibrosarcoma, rhabdomyoscaroma, and osteosarcoma; and other tumors, including melanoma, xeroderma pigmentosum, keratoacanthoma, seminoma, thyroid follicular cancer and teratocarcinoma, hematopoietic tumors of lymphoid lineage, for example T-cell and B-cell tumors, including but not limited to T-cell disorders such as T-prolymphocytic leukemia (T-PLL), including of the small cell and cerebriform cell type; large granular lymphocyte leukemia (LGL) preferably of the T-cell type; a/d T-NHL hepatosplenic lymphoma; peripheral/post-thymic T cell lymphoma (pleomorphic and immunoblastic subtypes); angiocentric (nasal) T-cell lymphoma; cancer of the head or neck, renal cancer, rectal cancer, cancer of the thyroid gland; acute myeloid lymphoma, as well as any combinations of said cancers. In one embodiment, the methods described herein may also be used for treatment of metastatic cancers, refractory cancers (e.g., cancers refractory to previous immunotherapy, e.g., with a blocking CTLA-4 and/or PD-1 antibody), and recurrent cancers.

In one embodiment, the anti-huICOS antibody may be administered as a monotherapy. In one embodiment, the anti-huICOS agonist antibody is administered as the only immunostimulating agent. In one embodiment, the anti-human ICOS agonist antibody is administered to a patient with another agent. In one embodiment, an anti-huICOS antibody is administered with an immunogenic agent. In one embodiment, the anti-human ICOS agonist antibody is administered in conjunction with a cancer vaccine. In some embodiments, the cancer vaccine comprises cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). In some embodiments, the cancer vaccine is a peptide cancer vaccine, which in some embodiments is a personalized peptide vaccine. In some embodiments the peptide cancer vaccine is a multivalent long peptide, a multi-peptide, a peptide cocktail, a hybrid peptide, or a peptide-pulsed dendritic cell vaccine (see, e.g., Yamada et al., Cancer Sci, 104:14-21, 2013). In some embodiments, an anti-human ICOS agonist antibody may be administered in conjunction with an adjuvant. Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF. Many experimental strategies for vaccination against tumors have been devised (see Rosenberg, S., 2000, Development of Cancer Vaccines, ASCO Educational Book Spring: 60-62; Logothetis, C., 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita et al. (eds.), 1997, Cancer: Principles and Practice of Oncology, Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination. Dranoff et al. (1993) *Proc. Natl. Acad. Sci. U.S.A.* 90: 3539-43.

Other cancer vaccines can include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen that can be used in conjunction with ICOS inhibition is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot & Srivastava (1995) *Science* 269:1585-1588; Tamura et al. (1997) Science 278: 117-120).

Dendritic cells are potent antigen presenting cells that can be used to prime antigen-specific responses. Dendritic cells can be produced ex vivo and loaded with various protein and peptide antigens as well as tumor cell extracts (Nestle et al. (1998) *Nature Medicine* 4: 328-332). Dendritic cells can also be transduced by genetic means to express these tumor antigens as well. DCs have also been fused directly to tumor cells for the purposes of immunization (Kugler et al. (2000) *Nature Medicine* 6:332-336). As a method of vaccination, Dendritic cell immunization can be effectively combined with ICOS agonism to activate (unleash) more potent anti-tumor responses.

In some embodiments, an anti-human ICOS agonist antibody is administered in conjunction with standard of care, e.g., surgery, radiation, and/or chemotherapy. In some embodiments, an anti-ICOS antibody may be administered in conjunction with a chemotherapeutic agent. In some embodiments, the anti-ICOS antibody is administered in conjunction with one or more of carboplatin, cisplatin, paclitaxel, nab-paclitaxel, gemcitabine or FOLFOX. In some embodiment, an anti-human ICOS agonist antibody may be administered in conjunction with carboplatin or nab-paclitaxel. In some embodiments, an anti-human ICOS agonist antibody may be administered in conjunction with carboplatin and paclitaxel. In some embodiments, an anti-human ICOS agonist antibody may be administered in conjunction with cisplatin and pemetrexed. In some embodiments, an anti-human ICOS agonist antibody may be administered in conjunction with cisplatin and gemcitabine. In some embodiments, an anti-human ICOS agonist antibody may be administered in conjunction with FOLFOX. In some embodiments, an anti-human ICOS agonist antibody may be administered in conjunction with FOLFIRI. In one embodiment, an anti-huICOS antibody is administered in combination with decarbazine for the treatment of melanoma. In some embodiments, cisplatin is intravenously administered as a 100 mg/ml dose once every four weeks. In some embodiments, an anti-human ICOS agonist antibody may be administered in conjunction with doxorubicin (adriamycin), cisplatin bleomycin sulfate, carmustine, chlorambucil, dacarbazine and/or cyclophosphamide hydroxyurea. In some embodiments, adriamycin is intravenously administered as a 60 mg/ml to 75 mg/ml dose once every 21 days. In one embodiment, the anti-huICOS antibody is administered to a human patient that is resistant to treatment with at least one drugs, wherein administration of the anti-huICOS antibody reduces, alleviates, or abrogates resistance to the at least one drug.

The combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent and/or adjuvant. Antibodies of the invention can also be used in combination with radiation therapy.

Another example of such a combination is an anti-huICOS antibody in combination with interleukin-2 (IL-2). In some embodiments, the combination of anti-huICOS antibody and IL-2 is to treat various cancers, including for the treatment of renal cell carcinoma and melanoma. In some embodiments, the anti-huICOS antibodies discussed herein is combined with an IL-2 pathway agonist to treat various cancers. The combination includes various IL-2 pathway agonists, such as those described in WO 2012/065086 (Nektar Therapeutics) and WO 2015/125159 (Nektar Therapeutics), the contents of which are incorporated by reference in their entireties. WO 2006/138572 (Nektar Therapeutics) provides conjugates having a degradable linkage and polymeric reagents useful in preparing such conjugates, as well as methods of making polymeric reagents and conjugates, and is incorporated by reference in its entirety.

In some embodiments, the combination of an anti-huICOS antibody as described herein, such as ICOS.33 IgG1 S267E, and an IL-2 pathway agonist, such as NKTR-214, is administered to patients to treat cancer. As described in more detail below, NKTR-214 is produced by conjugating on average around six FMOC (fluorenylmethyloxycarbonyl chloride)-based polyethylene glycol (PEG) reagents having the following structure (mPEG-C2-fornc-20K—N-Hydroxysuccinimidate Derivative, 20 kDa, ("mPEG2-C2-fmoc-20K-NHS").

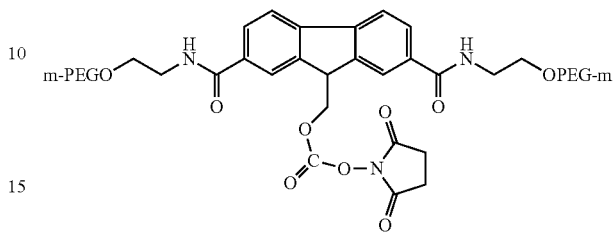

to a protein having the following 132-amino acid sequence:

(SEQ ID NO: 219)
```
PTSSSTKKTQLQLEHLLLDLQMILNGINNYKNPKLTRMLTFKFYMPKKATELKHLQCLEE    60

ELKPLEEVLNLAQSKNFHLRPRDLISNINVIVLELKGSETTFMCEYADETATIVEFLNRW  120

ITFSQSIISTLT                                                  132
```

WO 2012/065086 provides conjugates of an IL-2 moiety and one or more non-peptide, water-soluble polymers, including polytheylene glycol or a derivative thereof. Specifically, Example 2 (paragraphs 202-204) of WO 2012/065086 describes PEGylation of rIL-2 with mPEG2-C2-fmoc-20K-NHS to result in the mPEG2-C2-fmoc-20K-NHS structure set forth above. Example 1 (paragraphs 63-66) WO 2015/125159 describes a scaled-up approach for PEGylating IL-2 with mPEG2-C2-fmoc-20K-NHS that results in RSLAIL-2 (NKTR-214). NKTR-214 is a cytokine that is designed to target CD122, (also known as interleukin-2 receptor beta subunit, IL-2Rβ), a protein found on certain immune cells (e.g., CD8+ T Cells and NK Cells), to expand these cells to promote their anti-tumor effects.

In some embodiments, an anti-huICOS antibody may be administered in combination with an anti-angiogenic agent.

Other combination therapies that may result in synergy with ICOS agonism through cell death are radiation, surgery, and hormone deprivation.

In some embodiments, anti-huICOS antibodies described herein may be administered in conjunction with bispecific antibodies. Bispecific antibodies can be used to target two separate antigens. In one embodiment, anti-huICOS antibodies are used in combination with bispecific antibodies that target Fcα or Fcγ receptor-expressing effectors cells to tumor cells (see, e.g., U.S. Pat. Nos. 5,922,845 and 5,837,243). For example, anti-Fc receptor/anti-tumor antigen (e.g., Her-2/neu) bispecific antibodies have been used to target macrophages to sites of tumor. In one embodiment, the T cell arm of these responses is augmented by agonism of ICOS with an anti-huICOS antibody. Alternatively, antigen may be delivered directly to DCs by the use of bispecific antibodies that bind to tumor antigen and a dendritic cell specific cell surface marker. In some embodiments, anti-huICOS antibodies are used in combination with antibodies that reduce or inactivate the immunosuppressive proteins expressed by a tumor, e.g., anti-TGF-β antibodies, anti-IL-10 antibodies, and anti-Fas ligand antibodies.

Chronic Viral Infections

In another aspect, the invention described herein provides a method of treating an infectious disease in a subject comprising administering to the subject an anti-huICOS antibody, or antigen-binding fragment thereof, such that the subject is treated for the infectious disease.

Similar to its application to tumors as discussed above, antibody-mediated ICOS agonism can be used alone, or as an adjuvant, in combination with vaccines, to enhance the immune response to pathogens, toxins, and self-antigens. Examples of pathogens for which this therapeutic approach can be particularly useful, include pathogens for which there is currently no effective vaccine, or pathogens for which conventional vaccines are less than completely effective. These include, but are not limited to HIV, Hepatitis (A, B, & C), Influenza, Herpes, Giardia, Malaria, Leishmania, *Staphylococcus aureus, Pseudomonas aeruginosa*. ICOS agonism is particularly useful against established infections by agents such as human immunodeficiency virus (HIV) that present altered antigens over the course of the infections. These novel epitopes are recognized as foreign at the time of anti-human ICOS antibody administration, thus provoking a strong T cell response.

Some examples of pathogenic viruses causing infections treatable by methods described herein include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods described herein include chlamydia, rickettsial bacteria, mycobacteria, staphylococci, streptococci, pneumonococci, meningococci and gonococci, klebsiella, proteus, serratia, pseudomonas, legionella, diphtheria, salmonella, bacilli, cholera, tetanus, botulism, anthrax, plague, leptospirosis, and Lyme disease bacteria.

Some examples of pathogenic fungi causing infections treatable by methods described herein include *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods described herein include *Entamoeba histolytica, Balantidium coli, Naegleriafowleri, Acanthamoeba* sp., *Giardia Zambia, Cryptosporidium* sp., *Pneumocystis carinii, Plasmodium vivax, Babesia microti, Trypanosoma brucei, Trypanosoma cruzi, Leishmania donovani, Toxoplasma gondii, Nippostrongylus brasiliensis*.

The methods described herein of administering anti-huICOS antibodies to a subject may be combined with other forms of immunotherapy such as cytokine treatment (e.g., interferons, GM-CSF, G-CSF, IL-2), or bispecific antibody therapy.

Combination Therapies

In one aspect, provided herein are methods of combination therapy, e.g., for the treatment of cancer, in which an anti-huICOS antibody (e.g., an agonist anti-huICOS antibody) is administered in connection with one or more additional agents, e.g., antibodies, that are effective in stimulating immune responses to thereby further enhance, stimulate or upregulate immune responses in a subject. Provided herein are methods for treating or delaying progression of cancer in an individual comprising administering to the individual an anti-huICOS antibody (e.g., ICOS.33 IgG1f S267E, 17C4, 9D5, 3E8, 1D7, and 2644) in conjunction with another anti-cancer agent or cancer therapy. In some embodiments, an anti-huICOS antibody may be administered in conjunction with a chemotherapy or chemotherapeutic agent or with a radiation therapy or radiotherapeutic agent, as described above. In some embodiments, an anti-huICOS antibody may be administered in conjunction. In some embodiments, an anti-huICOS antibody may be administered in conjunction with a targeted therapy or targeted therapeutic agent. In some embodiments, an anti-huICOS antibody may be administered in conjunction with an immunotherapy or immunotherapeutic agent, for example a monoclonal antibody.

In some embodiments, an anti-huICOS antibody described herein can be combined with (i) an agonist of another co-stimulatory receptor and/or (ii) an antagonist of an inhibitory signal on T cells. In some embodiments, a combination therapy comprising an anti-huICOS antibody and the agonist and/or antagonist results in an enhanced antigen-specific T cell response in a subject. In some embodiment, anti-ICOS antibodies described herein may be administered in conjunction with an agent that targets a co-stimulatory and co-inhibitory molecules that is a member of the immunoglobulin super family (IgSF) to increase an immune response. In some embodiment, anti-ICOS antibodies (e.g., ICOS.33 IgG1f S267E, 17C4, 9D5, 3E8, 1D7, and 2644) described herein may be administered in conjunction with an agent that targets a ligand of a co-stimulatory or co-inhibitory molecule. A family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which include CD40, CD40L, OX-40, OX-40L, CD70, CD27L, CD30, CD30L, 4-1BBL, CD137/4-1BB, TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In another aspect, anti-huICOS antibodies can be used in combination with antagonists of cytokines that inhibit T cell activation (e.g., IL-6, IL-10, TGF-ß, VEGF; or other "immunosuppressive cytokines," or cytokines that stimulate T cell activation, for stimulating an immune response, e.g., for treating proliferative diseases, such as cancer.

In one aspect, T cell responses are stimulated by a combination of an anti-huICOS antibody described herein and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, CD40, ICOS-L, OX40, OX40L, GITR, GITRL, CD70, CD27, DR3 and CD28H.

Exemplary agents that modulate one of the above proteins and may be combined with agonist anti-huICOS antibodies, e.g., those described herein, for treating cancer, include: YERVOY®/ipilimumab or tremelimumab (to CTLA-4), galiximab (to B7.1), BMS-936558 (to PD-1), pidilizumab/ CT-011 (to PD-1), KEYTRUDA®/pembrolizumab/MK-3475 (to PD-1), AMP224 (to B7-DC/PD-L2), BMS-936559 (to B7-H1), MPDL3280A (to B7-H1), CP-870893 or dacetuzumab/SGN-40 (CD40—Kirkwood et al. (2012) *CA Cancer J. Clin.* 62:309; Vanderheide & Glennie (2013) *Clin. Cancer Res.* 19:1035), AMG557 (to B7H2), MGA271 (to B7H3—WO 11/109400), IMP321 (to LAG-3), urelumab/ BMS-663513 and PF-05082566 (to CD137/4-1BB), varlilumab/CDX-1127 (to CD27), MEDI-6383 and MEDI-6469 (to OX40), RG-7888 (to OX40L—WO 06/029879), Atacicept (to TACT), muromonab-CD3 (to CD3), ipilumumab (to CTLA-4). Accordingly, in one embodiment an anti-huICOS antibody (such as ICOS.33 IgG1f S267E) is combined with an anti-PD-1 antibody (such as nivolumab) and/or an anti-CTLA-4 antibody (such as ipilimumab).

Other molecules that can be combined with agonist anti-huICOS antibodies for the treatment of cancer include antagonists of inhibitory receptors on NK cells or agonists of activating receptors on NK cells. For example, agonist anti-huICOS antibodies can be combined with antagonists of KIR (e.g., lirilumab).

Yet other agents for combination therapies include agents that inhibit or deplete macrophages or monocytes, including but not limited to CSF-1R antagonists such as CSF-1R antagonist antibodies including RG7155 (WO 11/70024, WO 11/107553, WO 11/131407, WO 13/87699, WO 13/119716, WO 13/132044) or FPA-008 (WO 11/140249; WO 13/169264; WO 14/036357).

In some embodiments, agonist anti-huICOS antibodies described herein are used together with one or more of agonistic agents that ligate positive co-stimulatory receptors, blocking agents that attenuate signaling through inhibitory receptors, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

Provided herein are methods for stimulating an immune response in a subject comprising administering to the subject a ICOS agonist, e.g., an antibody, and one or more additional immunostimulatory antibodies, such as a PD-1 antagonist, e.g., antagonist antibody, a PD-L1 antagonist, e.g., antagonist antibody, a CTLA-4 antagonist, e.g., antagonist antibody and/or a LAG3 antagonist, e.g., an antagonist antibody, such that an immune response is stimulated in the subject, for example to inhibit tumor growth or to stimulate an anti-viral response. In one embodiment, the subject is administered an agonist anti-huICOS antibody and an antagonist anti-PD-1 antibody. In one embodiment, the subject is administered an agonist anti-huICOS antibody and an antagonist anti-PD-L1 antibody. In one embodiment, the subject is administered an agonist anti-huICOS antibody and an antagonist anti-CTLA-4 antibody. In one embodiment, the at least one additional immunostimulatory antibody (e.g., an antagonist anti-PD-1, an antagonist anti-PD-L1, an antagonist anti-CTLA-4 and/or an antagonist anti-LAG3 antibody) is a human antibody. Alternatively, the at least one additional immunostimulatory antibody can be, for example, a chimeric or humanized antibody (e.g., prepared from a mouse or hamster anti-PD-1, anti-PD-L1, anti-CTLA-4 and/ or anti-LAG3 antibody).

Provided herein are methods for treating a hyperproliferative disease (e.g., cancer), comprising administering an agonist anti-huICOS antibody and an antagonist PD-1 antibody to a subject. In some embodiments the cancer is non-small cell lung cancer (NSCLC) or colorectal cancer (CRC). In some embodiments the cancer is characterized by tumors with (i) elevated expression of CD32A/CD32B (FcγRIIa/Fcγ), and/or (ii-a) elevated expression of ICOS or (ii-b) reduced expression of ICOS-L, for example as detected by flow cytometry or immunohistochemistry (IHC). Tumor types with moderate to high ICOS RNA expression include head and neck, lung, cervical, kidney, pancreatic, breast and colorectal cancers, suggesting that these cancers might also exhibit elevated ICOS protein expression. In certain embodiments, the agonist is administered at a subtherapeutic dose, the anti-PD-1 antibody is administered at a subtherapeutic dose, or both are administered at a subtherapeutic dose. Also provided herein are methods for altering an adverse event associated with treatment of a hyperproliferative disease with an immunostimulatory agent. In one embodiment, the method comprises administering an agonist anti-huICOS antibody and a subtherapeutic dose of anti-PD-1 antibody to a subject. In some embodiments, the subject is a human. In some embodiments, the anti-PD-1 antibody is a human monoclonal antibody and the agonist anti-huICOS antibody is a humanized monoclonal antibody, such as an antibody comprising the CDRs or variable regions of the antibodies disclosed herein.

Anti-PD-1 antibodies that are known in the art can be used in the presently described methods. Various human monoclonal antibodies that bind specifically to PD-1 with high affinity have been disclosed in U.S. Pat. No. 8,008,449. Anti-PD-1 human antibodies disclosed in U.S. Pat. No. 8,008,449 have been demonstrated to exhibit one or more of the following characteristics: (a) bind to human PD-1 with a $K_D$ of $1 \times 10^{-7}$ M or less, as determined by surface plasmon resonance using a Biacore biosensor system; (b) do not substantially bind to human CD28, CTLA-4 or ICOS; (c) increase T-cell proliferation in a Mixed Lymphocyte Reaction (MLR) assay; (d) increase interferon-γ production in an MLR assay; (e) increase IL-2 secretion in an MLR assay; (f) bind to human PD-1 and cynomolgus monkey PD-1; (g) inhibit the binding of PD-L1 and/or PD-L2 to PD-1; (h) stimulate antigen-specific memory responses; (i) stimulate antibody responses; and (j) inhibit tumor cell growth in vivo. Anti-PD-1 antibodies usable in the present invention include monoclonal antibodies that bind specifically to human PD-1 and exhibit at least one, in some embodiments, at least five, of the preceding characteristics.

Other anti-PD-1 monoclonal antibodies have been described in, for example, U.S. Pat. Nos. 6,808,710, 7,488, 802, 8,168,757 and 8,354,509, US Publication No. 2016/ 0272708, and PCT Publication Nos. WO 2012/145493, WO 2008/156712, WO 2015/112900, WO 2012/145493, WO 2015/112800, WO 2014/206107, WO 2015/35606, WO 2015/085847, WO 2014/179664, WO 2017/020291, WO 2017/020858, WO 2016/197367, WO 2017/024515, WO 2017/025051, WO 2017/123557, WO 2016/106159, WO 2014/194302, WO 2017/040790, WO 2017/133540, WO 2017/132827, WO 2017/024465, WO 2017/025016, WO 2017/106061, WO 2017/19846, WO 2017/024465, WO 2017/025016, WO 2017/132825, and WO 2017/133540 each of which is incorporated by reference in its entirety.

In some embodiments, the anti-PD-1 antibody is nivolumab (also known as OPDIVO®, 5C4, BMS-936558, MDX-1106, and ONO-4538), pembrolizumab (Merck; also known as KEYTRUDA®, lambrolizumab, and MK-3475; see WO2008/156712), PDR001 (Novartis; see WO 2015/112900), MEDI-0680 (AstraZeneca; also known as AMP-514; see WO 2012/145493), cemiplimab (Regeneron; also known as REGN-2810; see WO 2015/112800), JS001 (TAIZHOU JUNSHI PHARMA; see Si-Yang Liu et al., *J. Hematol. Oncol.* 10:136 (2017)), BGB-A317 (Beigene; see WO 2015/35606 and US 2015/0079109), INCSHR1210 (Jiangsu Hengrui Medicine; also known as SHR-1210; see WO 2015/085847; Si-Yang Liu et al., J. Hematol. Oncol. 10:136 (2017)), TSR-042 (Tesaro Biopharmaceutical; also known as ANB011; see WO2014/179664), GLS-010 (Wuxi/Harbin Gloria Pharmaceuticals; also known as WBP3055; see Si-Yang Liu et al., *J. Hematol. Oncol.* 10:136 (2017)), AM-0001 (Armo), STI-1110 (Sorrento Therapeutics; see WO 2014/194302), AGEN2034 (Agenus; see WO 2017/040790), MGA012 (Macrogenics, see WO 2017/19846), or IBI308 (Innovent; see WO 2017/024465, WO 2017/025016, WO 2017/132825, and WO 2017/133540).

In one embodiment, the anti-PD-1 antibody is nivolumab. Nivolumab is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions (U.S. Pat. No. 8,008,449; Wang et al., 2014 *Cancer Immunol Res.* 2(9):846-56).

In another embodiment, the anti-PD-1 antibody is pembrolizumab. Pembrolizumab is a humanized monoclonal IgG4 (S228P) antibody directed against human cell surface receptor PD-1 (programmed death-1 or programmed cell death-1). Pembrolizumab is described, for example, in U.S. Pat. Nos. 8,354,509 and 8,900,587.

Anti-PD-1 antibodies usable in the disclosed methods also include isolated antibodies that bind specifically to human PD-1 and cross-compete for binding to human PD-1 with any anti-PD-1 antibody disclosed herein, e.g., nivolumab (see, e.g., U.S. Pat. Nos. 8,008,449 and 8,779,105; WO 2013/173223). In some embodiments, the anti-PD-1 antibody binds the same epitope as any of the anti-PD-1 antibodies described herein, e.g., nivolumab. The ability of antibodies to cross-compete for binding to an antigen indicates that these monoclonal antibodies bind to the same epitope region of the antigen and sterically hinder the binding of other cross-competing antibodies to that particular epitope region. These cross-competing antibodies are expected to have functional properties very similar those of the reference antibody, e.g., nivolumab, by virtue of their binding to the same epitope region of PD-1. Cross-competing antibodies can be readily identified based on their ability to cross-compete with nivolumab in standard PD-1 binding assays such as Biacore analysis, ELISA assays or flow cytometry (see, e.g., WO 2013/173223).

In certain embodiments, the antibodies that cross-compete for binding to human PD-1 with, or bind to the same epitope region of human PD-1 antibody, nivolumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-1 antibodies usable in the methods of the disclosed invention also include antigen-binding portions of the above antibodies. It has been amply demonstrated that the antigen-binding function of an antibody can be performed by fragments of a full-length antibody.

Anti-PD-1 antibodies suitable for use in the disclosed methods or compositions are antibodies that bind to PD-1 with high specificity and affinity, block the binding of PD-L1 and or PD-L2, and inhibit the immunosuppressive effect of the PD-1 signaling pathway. In any of the compositions or methods disclosed herein, an anti-PD-1 "antibody" includes an antigen-binding portion or fragment that binds to the PD-1 receptor and exhibits the functional properties similar to those of whole antibodies in inhibiting ligand binding and up-regulating the immune system. In certain embodiments, the anti-PD-1 antibody or antigen-binding portion thereof cross-competes with nivolumab for binding to human PD-1.

Provided herein are methods for treating a hyperproliferative disease (e.g., cancer), comprising administering an agonist anti-huICOS antibody and an antagonist PD-L1 antibody to a subject. In certain embodiments, the agonist anti-huICOS antibody is administered at a subtherapeutic dose, the anti-PD-L1 antibody is administered at a subtherapeutic dose, or both are administered at a subtherapeutic dose. Provided herein are methods for altering an adverse event associated with treatment of a hyperproliferative disease with an immunostimulatory agent, comprising administering an agonist anti-huICOS antibody and a subtherapeutic dose of anti-PD-L1 antibody to a subject. In certain embodiments, the subject is human. In certain embodiments, the anti-PD-L1 antibody is a human sequence monoclonal antibody and the agonist anti-huICOS antibody is a humanized monoclonal antibody, such as an antibody comprising the CDRs or variable regions of the antibodies disclosed herein.

Anti-PD-L1 antibodies that are known in the art can be used in the methods of the present disclosure. Examples of anti-PD-L1 antibodies useful in the methods of the present disclosure include the antibodies disclosed in U.S. Pat. No. 9,580,507. Anti-PD-L1 human monoclonal antibodies disclosed in U.S. Pat. No. 9,580,507 have been demonstrated to exhibit one or more of the following characteristics: (a) bind to human PD-L1 with a $K_D$ of 1×10-7 M or less, as determined by SPR using a Biacore biosensor system; (b) increase T-cell proliferation in a Mixed Lymphocyte Reaction (MLR) assay; (c) increase interferon-γ production in an MLR assay; (d) increase IL-2 secretion in an MLR assay; (e) stimulate antibody responses; and (f) reverse the effect of T regulatory cells on T cell effector cells and/or dendritic cells. Anti-PD-L1 antibodies usable in the present invention include monoclonal antibodies that bind specifically to human PD-L1 and exhibit at least one, in some embodiments, at least five, of the preceding characteristics.

In certain embodiments, the anti-PD-L1 antibody is BMS-936559 (also known as 12A4, MDX-1105; see, e.g., U.S. Pat. No. 7,943,743 and WO 2013/173223), atezolizumab (Roche; also known as TECENTRIQ®; MPDL3280A, RG7446; see U.S. Pat. No. 8,217,149; see, also, Herbst et al. (2013) J Clin Oncol 31(suppl):3000), durvalumab (AstraZeneca; also known as IMFINZI™, MEDI-4736; see WO 2011/066389), avelumab (Pfizer; also known as BAVEN-CIO®, MSB-0010718C; see WO 2013/079174), STI-1014 (Sorrento; see WO2013/181634), CX-072 (Cytomx; see WO2016/149201), KN035 (3D Med/Alphamab; see Zhang et al., Cell Discov. 7:3 (March 2017), LY3300054 (Eli Lilly Co.; see, e.g., WO 2017/034916), or CK-301 (Checkpoint Therapeutics; see Gorelik et al., AACR:Abstract 4606 (April 2016)).

In certain embodiments, the PD-L1 antibody is atezolizumab (TECENTRIQ®)). Atezolizumab is a fully humanized IgG1 monoclonal anti-PD-L1 antibody.

In certain embodiments, the PD-L1 antibody is durvalumab (IMFINZI™). Durvalumab is a human IgG1 kappa monoclonal anti-PD-L1 antibody.

In certain embodiments, the PD-L1 antibody is avelumab (BAVENCIO®). Avelumab is a human IgG1 lambda monoclonal anti-PD-L1 antibody.

In other embodiments, the anti-PD-L1 monoclonal antibody is 28-8, 28-1, 28-12, 29-8, 5H1, or any combination thereof.

Anti-PD-L1 antibodies usable in the disclosed methods also include isolated antibodies that bind specifically to human PD-L1 and cross-compete for binding to human PD-L1 with any anti-PD-L1 antibody disclosed herein, e.g., atezolizumab, durvalumab, and/or avelumab. In some embodiments, the anti-PD-L1 antibody binds the same epitope as any of the anti-PD-L1 antibodies described herein, e.g., atezolizumab, durvalumab, and/or avelumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., atezolizumab and/or avelumab, by virtue of their binding to the same epitope region of PD-L1. Cross-competing antibodies can be readily identified based on their ability to cross-compete with atezolizumab and/or avelumab in standard PD-L1 binding assays such as Biacore analysis, ELISA assays or flow cytometry (see, e.g., WO 2013/173223).

In certain embodiments, the antibodies that cross-compete for binding to human PD-L1 with, or bind to the same epitope region of human PD-L1 antibody as, atezolizumab, durvalumab, and/or avelumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-PD-L1 antibodies usable in the methods of the disclosed invention also include antigen-binding portions of the above antibodies. It has been amply demonstrated that the antigen-binding function of an antibody can be performed by fragments of a full-length antibody.

Anti-PD-L1 antibodies suitable for use in the disclosed methods or compositions are antibodies that bind to PD-L1 with high specificity and affinity, block the binding of PD-1, and inhibit the immunosuppressive effect of the PD-1 signaling pathway. In any of the compositions or methods disclosed herein, an anti-PD-L1 "antibody" includes an antigen-binding portion or fragment that binds to PD-L1 and exhibits the functional properties similar to those of whole antibodies in inhibiting receptor binding and up-regulating the immune system. In certain embodiments, the anti-PD-L1 antibody or antigen-binding portion thereof cross-competes with atezolizumab, durvalumab, and/or avelumab for binding to human PD-L1.

In one embodiment, the agonist anti-huICOS antibody of the present invention is combined with an antagonist of PD-1/PD-L1 signaling, such as a PD-1 antagonist (e.g., nivolumab, also known as MDX1106, as described in WO 06/121168) or a PD-L1 antagonist, in combination with a third immunotherapeutic agent (e.g., an anti-ICOS antibody, such as ICOS.33 IgG1f S267E, combined with nivolumab and ipilimumab). In one embodiment the third immunotherapeutic agent is a CTLA-4 antagonist antibody. In certain embodiments, the anti-CTLA-4 antibody is YERVOY® (ipilimumab or antibody 10D1, described in PCT Publication WO 01/14424) or tremelimumab (formerly ticilimumab, CP-675,206). In one embodiment the third immunotherapeutic agent is a GITR antagonist or an OX-40 antagonist, such as the anti-GITR or anti-OX40 antibodies disclosed herein. In one embodiment, the third immunotherapeutic agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683). In one embodiment, the third immunotherapeutic agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

Provided herein are methods for treating a hyperproliferative disease (e.g., cancer), comprising administering an agonist anti-huICOS antibody described herein and a CTLA-4 antagonist antibody to a subject. In certain embodiments, the agonist anti-huICOS antibody is administered at a subtherapeutic dose, the anti-CTLA-4 antibody is administered at a subtherapeutic dose, or both are administered at a subtherapeutic dose. Provided herein are methods for altering an adverse event associated with treatment of a hyperproliferative disease with an immunostimulatory agent, comprising administering an agonist anti-huICOS antibody and a subtherapeutic dose of anti-CTLA-4 antibody to a subject. In certain embodiments, the subject is human.

Anti-CTLA-4 antibodies that are known in the art can be used in the methods of the present disclosure. Anti-CTLA-4 antibodies of the instant invention bind to human CTLA-4 so as to disrupt the interaction of CTLA-4 with a human B7 receptor. Because the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

Human monoclonal antibodies that bind specifically to CTLA-4 with high affinity have been disclosed in U.S. Pat. No. 6,984,720. Other anti-CTLA-4 monoclonal antibodies have been described in, for example, U.S. Pat. Nos. 5,977,318, 6,051,227, 6,682,736, and 7,034,121 and International Publication Nos. WO 2012/122444, WO 2007/113648, WO 2016/196237, and WO 2000/037504, each of which is incorporated by reference herein in its entirety. The anti-CTLA-4 human monoclonal antibodies disclosed in U.S. Pat. No. 6,984,720 have been demonstrated to exhibit one or more of the following characteristics: (a) binds specifically to human CTLA-4 with a binding affinity reflected by an equilibrium association constant ($K_a$) of at least about $10^7$ $M^{-1}$, or about $10^9$ $M^{-1}$, or about $10^{10}$ $M^{-1}$ to $10^{11}$ $M^{-1}$ or higher, as determined by Biacore analysis; (b) a kinetic association constant ($k_a$) of at least about $10^3$, about $10^4$, or about $10^5$ $m^{-1}s^{-1}$; (c) a kinetic disassociation constant ($k_d$) of at least about $10^3$, about $10^4$, or about $10^5$ $m^{-1}s^{-1}$; and (d) inhibits the binding of CTLA-4 to B7-1 (CD80) and B7-2 (CD86). Anti-CTLA-4 antibodies useful for the present invention include monoclonal antibodies that bind specifically to human CTLA-4 and exhibit at least one, at least two, or at least three of the preceding characteristics.

In certain embodiments, the CTLA-4 antibody is ipilimumab (also known as YERVOY®, MDX-010, 10D1; see U.S. Pat. No. 6,984,720), MK-1308 (Merck), AGEN-1884 (Agenus Inc.; see WO 2016/196237), or tremelimumab (AstraZeneca; also known as ticilimumab, CP-675,206; see WO 2000/037504 and Ribas, *Update Cancer Ther.* 2(3): 133-39 (2007)). In particular embodiments, the anti-CTLA-4 antibody is ipilimumab.

In particular embodiments, the CTLA-4 antibody is ipilimumab for use in the methods disclosed herein. Ipilimumab is a fully human, IgG1 monoclonal antibody that blocks the binding of CTLA-4 to its B7 ligands, thereby stimulating T cell activation and improving overall survival (OS) in patients with advanced melanoma.

In particular embodiments, the CTLA-4 antibody is tremelimumab.

In particular embodiments, the CTLA-4 antibody is MK-1308.

In particular embodiments, the CTLA-4 antibody is AGEN-1884.

Anti-CTLA-4 antibodies usable in the disclosed methods also include isolated antibodies that bind specifically to human CTLA-4 and cross-compete for binding to human CTLA-4 with any anti-CTLA-4 antibody disclosed herein, e.g., ipilimumab and/or tremelimumab. In some embodiments, the anti-CTLA-4 antibody binds the same epitope as any of the anti-CTLA-4 antibodies described herein, e.g., ipilimumab and/or tremelimumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of the reference antibody, e.g., ipilimumab and/or tremelimumab, by virtue of their binding to the same epitope region of CTLA-4. Cross-competing antibodies can be readily identified based on their ability to cross-compete with ipilimumab and/or tremelimumab in standard CTLA-4 binding assays such as Biacore analysis, ELISA assays or flow cytometry (see, e.g., WO 2013/173223).

In certain embodiments, the antibodies that cross-compete for binding to human CTLA-4 with, or bind to the same epitope region of human CTLA-4 antibody as, ipilimumab and/or tremelimumab, are monoclonal antibodies. For administration to human subjects, these cross-competing antibodies are chimeric antibodies, engineered antibodies, or humanized or human antibodies. Such chimeric, engineered, humanized or human monoclonal antibodies can be prepared and isolated by methods well known in the art.

Anti-CTLA-4 antibodies usable in the methods of the disclosed invention also include antigen-binding portions of the above antibodies. It has been amply demonstrated that the antigen-binding function of an antibody can be performed by fragments of a full-length antibody.

Anti-CTLA-4 antibodies suitable for use in the disclosed methods or compositions are antibodies that bind to CTLA-4 with high specificity and affinity, block the activity of CTLA-4, and disrupt the interaction of CTLA-4 with a human B7 receptor. In any of the compositions or methods disclosed herein, an anti-CTLA-4 "antibody" includes an antigen-binding portion or fragment that binds to CTLA-4 and exhibits the functional properties similar to those of whole antibodies in inhibiting the interaction of CTLA-4 with a human B7 receptor and up-regulating the immune system. In certain embodiments, the anti-CTLA-4 antibody or antigen-binding portion thereof cross-competes with ipilimumab and/or tremelimumab for binding to human CTLA-4.

In one embodiment, the agonist anti-huICOS antibody of the present invention is combined with an anti-CTLA-4 antibody, in combination with a third immunotherapeutic agent. In one embodiment the third immunotherapeutic agent is a GITR antagonist or an OX-40 antagonist, such as the anti-GITR or anti-OX40 antibodies disclosed herein. In one embodiment, the third immunotherapeutic agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683). In one embodiment, the third immunotherapeutic agent is an IDO antagonist. Suitable IDO antagonists include, for example, INCB-024360 (WO2006/122150, WO07/75598, WO08/36653, WO08/36642), indoximod, or NLG-919 (WO09/73620, WO09/1156652, WO11/56652, WO12/142237).

Provided herein are methods for treating a hyperproliferative disease (e.g., cancer), comprising administering an agonist anti-huICOS antibody and an anti-LAG-3 antibody to a subject. In further embodiments, the agonist anti-huICOS antibody is administered at a subtherapeutic dose, the anti-LAG-3 antibody is administered at a subtherapeutic dose, or both are administered at a subtherapeutic dose. Provided herein are methods for altering an adverse event associated with treatment of a hyperproliferative disease with an immunostimulatory agent, comprising administering an agonist anti-huICOS antibody and a subtherapeutic dose of anti-LAG-3 antibody to a subject. In certain embodiments, the subject is human. In certain embodiments, the anti-LAG-3 antibody is a human sequence monoclonal antibody and the agonist anti-huICOS antibody is a humanized monoclonal antibody, such as an antibody comprising the CDRs or variable regions of the antibodies disclosed herein. Examples of anti-LAG3 antibodies include antibodies comprising the CDRs or variable regions of antibodies 25F7, 26H10, 25E3, 8B7, 11F2 or 17E5, which are described in U.S. Patent Publication No. US2011/0150892 and WO2014/008218. In one embodiment, an anti-LAG-3 antibody is BMS-986016. Other anti-LAG-3 antibodies that can be used include IMP731 described in US 2011/007023 or IMP-321. Anti-LAG-3 antibodies that compete with and/or bind to the same epitope as that of any of these antibodies may also be used in combination treatments.

In certain embodiments, the anti-LAG-3 antibody binds to human LAG-3 with a $K_D$ of $5 \times 10^{-8}$ M or less, binds to human LAG-3 with a $K_D$ of $1 \times 10^{-8}$ M or less, binds to human LAG-3 with a $K_D$ of $5 \times 10^{-9}$ M or less, or binds to human LAG-3 with a $K_D$ of between $1 \times 10^{-8}$ M and $1 \times 10^{-10}$ M or less.

Administration of agonist anti-huICOS antibodies described herein and antagonists, e.g., antagonist antibodies, to one or more second target antigens such as LAG-3 and/or CTLA-4 and/or PD-1 and/or PD-L1 can enhance the immune response to cancerous cells in the patient. Cancers whose growth may be inhibited using the antibodies of the instant disclosure include cancers typically responsive to immunotherapy. Examples of cancers for treatment with the combination therapy described herein include, but are not limited to, the described above in the discussion of monotherapy with agonist anti-huICOS antibodies.

In certain embodiments, the combination of therapeutic antibodies discussed herein can be administered concurrently as a single composition in a pharmaceutically acceptable carrier, or concurrently as separate compositions with each antibody in a pharmaceutically acceptable carrier. In another embodiment, the combination of therapeutic antibodies can be administered sequentially. For example, an anti-CTLA-4 antibody and an agonist anti-huICOS antibody can be administered sequentially, such as anti-CTLA-4 antibody being administered first and agonist anti-huICOS antibody second, or agonist anti-huICOS antibody being administered first and anti-CTLA-4 antibody second. Additionally or alternatively, an anti-PD-1 antibody and an agonist anti-huICOS antibody can be administered sequentially, such as anti-PD-1 antibody being administered first and agonist anti-huICOS antibody second, or agonist anti-huICOS antibody being administered first and anti-PD-1 antibody second. Additionally or alternatively, an anti-PD-L1 antibody and an agonist anti-huICOS antibody can be administered sequentially, such as anti-PD-L1 antibody being administered first and agonist anti-huICOS antibody second, or agonist anti-huICOS antibody being administered first and anti-PD-L1 antibody second. Additionally or alternatively, an anti-LAG-3 antibody and an agonist anti-huICOS antibody can be administered sequentially, such as anti-LAG-3 antibody being administered first and agonist anti-huICOS antibody second, or agonist anti-huICOS antibody being administered first and anti-LAG-3 antibody second.

Furthermore, if more than one dose of the combination therapy is administered sequentially, the order of the sequential administration can be reversed or kept in the same order at each time point of administration, sequential administrations can be combined with concurrent administrations, or any combination thereof. For example, the first administration of a combination anti-CTLA-4 antibody and agonist anti-huICOS antibody can be concurrent, the second administration can be sequential with anti-CTLA-4 antibody first and agonist anti-huICOS antibody second, and the third administration can be sequential with agonist anti-huICOS antibody first and anti-CTLA-4 antibody second, etc. Additionally or alternatively, the first administration of a combination anti-PD-1 antibody and agonist anti-huICOS antibody can be concurrent, the second administration can be sequential with anti-PD-1 antibody first and agonist anti-huICOS antibody second, and the third administration can be sequential with agonist anti-huICOS antibody first and anti-PD-1 antibody second, etc. Additionally or alternatively, the first administration of a combination anti-PD-L1 antibody and agonist anti-huICOS antibody can be concurrent, the second administration can be sequential with anti-PD-L1 antibody first and agonist anti-huICOS antibody second, and the third administration can be sequential with agonist anti-huICOS antibody first and anti-PD-L1 antibody second, etc. Additionally or alternatively, the first administration of a combination anti-LAG-3 antibody and agonist anti-huICOS antibody can be concurrent, the second administration can be sequential with anti-LAG-3 antibody first and agonist anti-huICOS antibody second, and the third administration can be sequential with agonist anti-huICOS antibody first and anti-LAG-3 antibody second, etc. Another representative dosing scheme can involve a first administration that is sequential with agonist anti-huICOS first and anti-CTLA-4 antibody (and/or anti-PD-1 antibody and/or anti-PD-L1 antibody and/or anti-LAG-3 antibody) second, and subsequent administrations may be concurrent.

In one embodiment, an agonist anti-huICOS antibody, as sole immunotherapeutic agent, or the combination of an agonist anti-huICOS antibody and one or more additional immunotherapeutic antibodies (e.g., anti-CTLA-4 and/or anti-PD-1 and/or anti-PD-L1 and/or anti-LAG-3 antibody) may be further combined with an immunogenic agent, such as cancerous cells, purified tumor antigens (including recombinant proteins, peptides, and carbohydrate molecules), cells, and cells transfected with genes encoding immune stimulating cytokines (He et al. (2004) *J. Immunol.* 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF (discussed further below). An ICOS agonist and one or more additional antibodies (e.g., CTLA-4 and/or PD-1 and/or PD-L1 and/or LAG-3 blockade) can also be further combined with standard cancer treatments. For example, an ICOS agonist and one or more additional antibodies (e.g., CTLA-4 and/or PD-1 and/or PD-L1 and/or LAG-3 blockade) may be combined with chemotherapeutic regimes. In one embodiment, an anti-huICOS agonist antibody is administered to a patient with an anti-CTLA-4 antibody and/or anti-PD-1 antibody and/or anti-PD-L1 antibody and/or anti-LAG-3 antibody in combination with decarbazine for the treatment of melanoma. In one embodiment, an anti-huICOS agonist antibody is administered to a patient with an anti-CTLA-4 antibody and/or anti-PD-1 antibody and/or anti-PD-L1 antibody and/or anti-LAG-3 antibody in combination with interleukin-2 (IL-2) for the treatment of cancer, including melanoma. Without wishing to be bound to theory, combined use of ICOS agonism and CTLA-4 and/or PD-1 and/or PD-L1 and/or LAG-3 antagonism with chemotherapy may function synergistically as the cytotoxic action of most chemotherapeutic compounds may result in increased levels of tumor antigen in the antigen presentation pathway. Other combination therapies that may result in synergy with a combined ICOS agonism with or without and CTLA-4 and/or PD-1 and/or PD-L1 and/or LAG-3 antagonism through cytotoxicity include radiation, surgery, or hormone deprivation. In another embodiment, angiogenesis inhibitors may be combined with an anti-huICOS antibody and CTLA-4 and/or PD-1 and/or PD-L1 and/or LAG-3 antagonism.

In one embodiment, an anti-huICOS antibody as sole immunotherapeutic agent, or a combination of an anti-huICOS antibody and CTLA-4 and/or PD-1 and/or PD-L1 and/or LAG-3 blocking antibodies can also be used in combination with bispecific antibodies that target Fcα or Fcγ receptor-expressing effector cells to tumor cells. See, e.g., U.S. Pat. Nos. 5,922,845 and 5,837,243. Bispecific antibodies can be used to target two separate antigens. The T cell arm of these responses would be augmented by the use of a combined ICOS agonism and CTLA-4 and/or PD-1 and/or PD-L1 and/or LAG-3 blockade.

In one embodiment an anti-ICOS antibody as sole immunotherapeutic agent or a combination of an anti-ICOS antibody and additional immunostimulating agent, e.g., anti-CTLA-4 antibody and/or anti-PD-1 antibody and/or anti-PD-L1 antibody and/or anti-LAG-3 antibody, can be used in conjunction with an anti-neoplastic agent, such as RIT-UXAN® (rituximab), HERCEPTIN® (trastuzumab), BEXXAR® (tositumomab), ZEVALIN® (ibritumomab), CAMPATH® (alemtuzumab), LYIVIPHOCIDE® (epr-tuzumab), AVASTIN® (bevacizumab), and TARCEVA® (erlotinib). By way of example and not wishing to be bound by theory, treatment with an anti-cancer antibody or an anti-cancer antibody conjugated to a toxin can lead to cancer cell death (e.g., tumor cells) which may potentiate an immune response mediated by the immunostimulating agent, e.g., anti-ICOS antibody, anti-TIGIT antibody, anti-CTLA-4 antibody, anti-PD-1 antibody, anti-PD-L1 antibody or anti-LAG-3 antibody. In one embodiment, a treatment of a hyperproliferative disease (e.g., a cancer tumor) can include an anti-cancer agent, e.g., antibody, in combination with an agonist anti-huICOS antibody and optionally an additional immunostimulating agent, e.g., anti-CTLA-4 antibody and/or anti-PD-1 antibody and/or anti-PD-L1 antibody and/or anti-LAG-3 antibody, concurrently or sequentially or any combination thereof, which can potentiate an anti-tumor immune responses by the host.

Provided herein are methods for reducing, ameliorating or abrogating an adverse event associated with treatment of a hyperproliferative disease (e.g., cancer) with an immunostimulatory agent, comprising administering an agonist anti-huICOS antibody with or without an anti-CTLA-4 and/or anti-PD-1 and/or anti-PD-L1 and/or anti-LAG-3 antibody, to a subject. In one embodiment, the method reduces the incidence of immunostimulatory therapeutic antibody-induced colitis or diarrhea by administering a non-absorbable steroid to the patient. As used herein, a "non-absorbable steroid" is a glucocorticoid that exhibits extensive first pass metabolism such that, following metabolism in the liver, the bioavailability of the steroid is low, i.e., less than about 20%. In one embodiment described herein, the non-absorbable steroid is budesonide. Budesonide is a locally-acting glucocorticosteroid, which is extensively metabolized, primarily by the liver, following oral administration. ENTOCORT EC® (Astra-Zeneca) is a pH- and time-dependent oral formulation of budesonide developed to optimize drug delivery to the ileum and throughout the colon. ENTOCORT EC® is approved in the U.S. for the treatment of mild to moderate Crohn's disease involving the ileum and/or ascending colon. The usual oral dosage of ENTOCORT EC® for the treatment of Crohn's disease is 6 to 9 mg/day. ENTOCORT EC® is released in the intestines before being absorbed and retained in the gut mucosa. Once it passes through the gut mucosa target tissue, ENTOCORT EC® is extensively metabolized by the cytochrome P450 system in the liver to metabolites with negligible glucocorticoid activity. Therefore, the bioavailability is low (about 10%). The low bioavailability of budesonide results in an improved therapeutic ratio compared to other glucocorticoids with less extensive first-pass metabolism. Budesonide results in fewer adverse effects, including less hypothalamic-pituitary suppression, than systemically-acting corticosteroids. However, chronic administration of ENTOCORT EC® can result in systemic glucocorticoid effects such as hypercorticism and adrenal suppression. See PDR 58$^{th}$ ed. 2004; 608-610.

In one embodiment, an anti-ICOS antibody with or without CTLA-4 and/or PD-1 and/or PD-L1 and/or LAG-3 antagonist (i.e., immunostimulatory therapeutic antibodies against ICOS and optionally anti-CTLA-4 and/or anti-PD-1 and/or anti-PD-L1 and/or anti-LAG-3 antibodies) in conjunction with a non-absorbable steroid can be further combined with a salicylate. Salicylates include 5-ASA agents such as, for example: sulfasalazine (AZULFIDINE®, Pharmacia & UpJohn); olsalazine (DIPENTUM®, Pharmacia & UpJohn); balsalazide (COLAZAL®, Salix Pharmaceuticals, Inc.); and mesalamine (ASACOL Procter & Gamble Pharmaceuticals; PENTASA®, Shire US; CANASA®, Axcan Scandipharm, Inc.; ROWASA®, Solvay).

In accordance with the methods described herein, a salicylate administered in combination with an anti-huICOS antibody with or without anti-CTLA-4 and/or anti-PD-1 and/or anti-PD-L1 and/or anti-LAG-3 antibodies and a non-absorbable steroid may include any overlapping or sequential administration of the salicylate and the non-absorbable steroid for the purpose of decreasing the incidence of colitis induced by the immunostimulatory antibodies. Thus, for example, methods for reducing the incidence of colitis induced by the immunostimulatory antibodies described herein encompass administering a salicylate and a non-absorbable steroid concurrently or sequentially (e.g., a salicylate is administered 6 hours after a non-absorbable steroid), or any combination thereof. Further, a salicylate and a non-absorbable steroid can be administered by the same route (e.g., both are administered orally) or by different routes (e.g., a salicylate is administered orally and a non-absorbable steroid is administered rectally), which may differ from the route(s) used to administer the anti-huICOS and anti-CTLA-4 and/or anti-PD-1 and/or anti-PD-L1 and/or anti-LAG-3 antibodies.

The agonist anti-huICOS antibodies and combination antibody therapies described herein may also be used in conjunction with other well-known therapies that are selected for their particular usefulness against the indication being treated (e.g., cancer). Combinations of the agonist anti-huICOS antibodies described herein may be used sequentially with known pharmaceutically acceptable agent(s).

In one embodiment, the agonist anti-huICOS antibodies and combination antibody therapies described herein can be used in combination (e.g., simultaneously or separately) with an additional treatment, such as irradiation, chemotherapy (e.g., using camptothecin (CPT-11), 5-fluorouracil (5-FU), cisplatin, doxorubicin, irinotecan, paclitaxel, gemcitabine, cisplatin, paclitaxel, carboplatin-paclitaxel (Taxol), doxorubicin, 5-fu, or camptothecin+apo21/TRAIL (a 6× combo)), one or more proteasome inhibitors (e.g., bortezomib or MG132), one or more Bcl-2 inhibitors (e.g., BH3I-2' (bcl-xl inhibitor), indoleamine dioxygenase-1 (IDO1) inhibitor (e.g., INCB24360), AT-101 (R-(−)-gossypol derivative), ABT-263 (small molecule), GX-15-070 (obatoclax), or MCL-1 (myeloid leukemia cell differentiation protein-1) antagonists), iAP (inhibitor of apoptosis protein) antagonists (e.g., smac7, smac4, small molecule smac mimetic, synthetic smac peptides (see Fulda et al., *Nat Med* 2002; 8:808-15), ISIS23722 (LY2181308), or AEG-35156 (GEM-640)), HDAC (histone deacetylase) inhibitors, anti-CD20 antibodies (e.g., rituximab), angiogenesis inhibitors (e.g., bevacizumab), anti-angiogenic agents targeting VEGF and VEGFR (e.g., AVASTIN®), synthetic triterpenoids (see Hyer et al., *Cancer Research* 2005; 65:4799-808), c-FLIP (cellular FLICE-inhibitory protein) modulators (e.g., natural and synthetic ligands of PPARγ (peroxisome proliferator-activated receptor γ), 5809354 or 5569100), kinase inhibitors (e.g., Sorafenib), trastuzumab, cetuximab, Temsirolimus, mTOR inhibitors such as rapamycin and temsirolimus, Bortezomib, JAK2 inhibitors, HSP90 inhibitors, PI3K-AKT inhibitors, Lenalildomide, GSKβ inhibitors, IAP inhibitors and/or genotoxic drugs.

The agonist anti-huICOS antibodies and combination antibody therapies described herein can further be used in combination with one or more anti-proliferative cytotoxic agents. Classes of compounds that may be used as anti-proliferative cytotoxic agents include, but are not limited to, the following:

Alkylating agents (including, without limitation, nitrogen mustards, ethylenimine derivatives, alkyl sulfonates, nitrosoureas and triazenes): Uracil mustard, Chlormethine, Cyclophosphamide (CYTOXAN™) fosfamide, Melphalan, Chlorambucil, Pipobroman, Triethylenemelamine, Triethylenethiophoshoramine, Busulfan, Carmustine, Lomustine, Streptozocin, Dacarbazine, and Temozolomide.

Antimetabolites (including, without limitation, folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Suitable anti-proliferative agents for combining with agonist anti-huICOS antibodies, without limitation, taxanes, paclitaxel (paclitaxel is commercially available as TAXOL™), docetaxel, discodermolide (DDM), dictyostatin (DCT), Peloruside A, epothilones, epothilone A, epothilone B, epothilone C, epothilone D, epothilone E, epothilone F, furanoepothilone D, desoxyepothilone B1, [17]-dehydrodesoxyepothilone B, [18]dehydrodesoxyepothilones B, C12,13-cyclopropyl-epothilone A, C6-C8 bridged epothilone A, trans-9,10-dehydroepothilone D, cis-9,10-dehydroepothilone D, 16-desmethylepothilone B, epothilone B10, discodermolide, patupilone (EPO-906), KOS-862, KOS-1584, ZK-EPO, ABJ-789, XAA296A (Discodermolide), TZT-1027 (soblidotin), ILX-651 (tasidotin hydrochloride), Halichondrin B, Eribulin mesylate (E-7389), Hemiasterlin (HTI-286), E-7974, Cyrptohycins, LY-355703, Maytansinoid immunoconjugates (DM-1), MKC-1, ABT-751, T1-38067, T-900607, SB-715992 (ispinesib), SB-743921, MK-0731, STA-5312, eleutherobin, 17beta-acetoxy-2-ethoxy-6-oxo-B-homo-estra-1,3,5(10)-trien-3-ol, cyclostreptin, isolaulimalide, laulimalide, 4-epi-7-dehydroxy-14,16-didemethyl-(+)-discodermolides, and cryptothilone 1, in addition to other microtubuline stabilizing agents known in the art.

In some embodiments it may be desirable to render aberrantly proliferative cells quiescent in conjunction with or prior to treatment with agonist anti-huICOS antibodies described herein, e.g., by administering to the patient hormones and steroids (including synthetic analogs), such as 17a-Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, ZOLADEX™. When employing the methods or compositions described herein, other agents used in the modulation of tumor growth or metastasis in a clinical setting, such as antimimetics, can also be administered as desired.

Methods for the safe and effective administration of chemotherapeutic agents are known to those skilled in the art. In addition, their administration is described in the standard literature. For example, the administration of many of the chemotherapeutic agents is described in the Physicians' Desk Reference (PDR), e.g., 1996 edition (Medical Economics Company, Montvale, N.J. 07645-1742, USA); the disclosure of which is incorporated herein by reference thereto.

The chemotherapeutic agent(s) and/or radiation therapy can be administered according to therapeutic protocols known in the art. It will be apparent to those skilled in the art that the administration of the chemotherapeutic agent(s) and/or radiation therapy can be varied depending on the disease being treated and the known effects of the chemotherapeutic agent(s) and/or radiation therapy on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the disease to the administered therapeutic agents.

Outcomes

Tumor response is determined, for example, by modified Response Evaluation Criteria in Solid Tumors (RECIST) established by the NCI.

With respect to target lesions, responses to therapy may include:

| | |
|---|---|
| Complete Response (CR) (RECIST V1.1) | Disappearance of all target lesions. Any pathological lymph nodes (whether target or non-target) must have reduction in short axis to <10 mm. |
| Partial Response (PR) (RECIST V1.1) | At least a 30% decrease in the sum of the diameters of target lesions, taking as reference the baseline sum diameters. |
| Progressive Disease (PD) (RECIST V1.1) | At least a 20% increase in the sum of the diameters of target lesions, taking as reference the smallest sum on study (this includes the baseline sum if that is the smallest on study). In addition to the relative increase of 20%, the sum must also demonstrate an absolute increase of at least 5 mm. (Note: the appearance of one or more new lesions is also considered progression). |
| Stable Disease (SD) (RECIST V1.1) | Neither sufficient shrinkage to qualify for PR nor sufficient increase to qualify for PD, taking as reference the smallest sum diameters while on study. |
| Immune-related Complete Response (irCR) (irRECIST) | Disappearance of all target lesions. Any pathological lymph nodes (whether target or non-target) must have reduction in short axis to <10 mm. |
| Immune-related Partial Response (irPR) (irRECIST) | At least a 30% decrease in the sum of diameters of target lesions and all new measurable lesions (ie Percentage Change in Tumor Burden), taking as reference the baseline sum diameters. Note: the appearance of new measurable lesions is factored into the overall Tumor Burden, but does not automatically qualify as progressive disease until the sum of the diameters increases by ≥20% when compared to nadir. |
| Immune-related Progressive Disease (irPD) (irRECIST) | At least a 20% increase in Tumor Burden (ie the sum of diameters of target lesions, and any new measurable lesions) taking as reference the smallest sum on study (this includes the baseline sum if that is the smallest on study). In addition to the relative increase of 20%, the sum must also demonstrate an absolute increase of at least 5 mm. Tumor assessments using immune-related criteria for progressive disease incorporates the contribution of new measurable lesions. Each net percentage change in tumor burden per assessment accounts for the size and growth kinetics of both old and new lesions as they appear. |
| Immune-related Stable Disease (irSD) (irRECIST) | Neither sufficient shrinkage to qualify for irPR nor sufficient increase to qualify for irPD, taking as reference the smallest sum diameters while on study. |

With respect to non-target lesions, responses to therapy may include:

| | |
|---|---|
| Complete Response (CR) (RECIST V1.1) | Disappearance of all non-target lesions. All lymph nodes must be non-pathological in size (<10 mm short axis). |
| Non-CR/Non-PD (RECIST V1.1) | Persistence of one or more non-target lesion(s). |
| Progressive Disease (PD) (RECIST V1.1) | Unequivocal progression of existing non-target lesions. The appearance of one or more new lesions is also considered progression. |

| | |
|---|---|
| Immune-related Complete Response (irCR) (irRECIST) | Disappearance of all non-target lesions. All lymph nodes must be non-pathological in size (<10 mm short axis). |
| Immune-related Progressive Disease (irPD) (irRECIST) | Increases in number or size of non-target lesion(s) does not constitute progressive disease unless/until Tumor Burden increases by 20% (ie the sum of the diameters at nadir of target lesions and any new measurable lesions increases by the required amount). Non-target lesions are not considered in the definition of Stable Disease and Partial Response. |

Patients treated according to the methods disclosed herein preferably experience improvement in at least one sign of cancer. In one embodiment, improvement is measured by a reduction in the quantity and/or size of measurable tumor lesions. In another embodiment, lesions can be measured on chest x-rays or CT or MRI films. In another embodiment, cytology or histology can be used to evaluate responsiveness to a therapy.

In one embodiment, the patient treated exhibits a complete response (CR), a partial response (PR), stable disease (SD), immune-related complete disease (irCR), immune-related partial response (irPR), or immune-related stable disease (irSD). In another embodiment, the patient treated experiences tumor shrinkage and/or decrease in growth rate, i.e., suppression of tumor growth. In another embodiment, unwanted cell proliferation is reduced or inhibited. In yet another embodiment, one or more of the following can occur: the number of cancer cells can be reduced; tumor size can be reduced; cancer cell infiltration into peripheral organs can be inhibited, retarded, slowed, or stopped; tumor metastasis can be slowed or inhibited; tumor growth can be inhibited; recurrence of tumor can be prevented or delayed; one or more of the symptoms associated with cancer can be relieved to some extent.

In other embodiments, administration of effective amounts of the anti-ICOS antibody (or combinations of anti-ICOS antibody and at least one additional antibody, e.g., an anti-PD-1 antibody or anti-CTLA-4 antibody) according to any of the methods provided herein produces a reduction in size of a tumor, reduction in number of metastatic lesions appearing over time, complete remission, partial remission, or stable disease. In still other embodiments, the methods of treatment produce a comparable clinical benefit rate (CBR=CR+PR+SD≥6 months) better than that achieved by an anti-ICOS antibody alone (or any one of the combined antibodies alone). In other embodiments, the improvement of clinical benefit rate is about 20% 20%, 30%, 40%, 50%, 60%, 70%, 80% or more compared to the anti-ICOS antibody alone (or any one of the combined antibodies alone).

Vaccine Adjuvants

Anti-huICOS antibodies described herein can be used to enhance antigen-specific immune responses by co-administration of an anti-huICOS antibody with an antigen of interest, e.g., a vaccine. Accordingly, provided herein are methods of enhancing an immune response to an antigen in a subject, comprising administering to the subject: (i) the antigen; and (ii) an anti-huICOS antibody, or antigen-binding fragment thereof, such that an immune response to the antigen in the subject is enhanced. The antigen can be, for example, a tumor antigen, a viral antigen, a bacterial antigen or an antigen from a pathogen. Non-limiting examples of such antigens include those discussed in the sections above, such as the tumor antigens (or tumor vaccines) discussed above, or antigens from the viruses, bacteria or other pathogens described above.

Detection and Diagnostics

In another aspect, provided herein are methods for detecting the presence of human ICOS antigen in a sample, or measuring the amount of human ICOS antigen, comprising contacting the sample, and a control sample, with an anti-ICOS antibody, e.g., a monoclonal anti-human ICOS antibody, or an antigen binding fragment thereof, that specifically binds to human ICOS, under conditions that allow for formation of a complex between the antibody or fragment thereof and human ICOS. The formation of a complex is then detected, wherein a difference complex formation between the sample compared to the control sample is indicative the presence of human ICOS antigen in the sample. Moreover, the anti-ICOS antibodies described herein can be used to purify human ICOS via immunoaffinity purification.

The present disclosure is further illustrated by the following examples, which should not be construed as limiting. The contents of all figures and all references, Genbank sequences, patents and published patent applications cited throughout this application are expressly incorporated herein by reference.

EXAMPLES

The following are non-limiting examples of antibodies, compositions and methods of the invention. It is understood that various other embodiments may be practiced consistent with the general description provided herein.

Example 1

Generation of Fully Human Anti-huICOS Antibodies

Fully human anti-huICOS monoclonal antibodies, and fully human antibodies that bind to the same epitope and/or cross-block the binding of the fully human anti-ICOS antibodies are disclosed herein. Such antibodies may be generated using transgenic mice that express human antibody genes, as described in the following example.

A. Hybridoma Technology Using HuMab Mouse® and/or a Kunming (KM) Mouse®

Anti LCOS Antibodies were Generated

Human anti-ICOS monoclonal antibodies were generated by immunizing the HC2/KCo7 strain of HuMAb® transgenic mice (HuMAb® is a trademark of Medarex, Inc., Princeton, N.J.) and KM mice (the KM Mouse® strain contains the SC20 transchromosome as described in WO 02/43478) with 1) a soluble human ICOS antigen and 2) a Hek293T cell line that was transfected with human ICOS gene that expresses human ICOS, a Chinese Hamster Ovary (CHO) cell line that expresses ICOS, and a 300-19 cell line that expresses ICOS. HC2/KCo7 HuMAb mice and KM mice were generated as described in U.S. Pat. Nos. 5,770, 429 and 5,545,806, the entire disclosures of which are hereby incorporated by reference.

Antigen and Immunization

The antigens were a soluble fusion protein comprising an ICOS extracellular domain fused with an antibody Fc domain (recombinant human ICOS-mouse Fc chimeric protein), Hek293T cells, CHO cells, or 300-19 cells that was transfected for surface expression of human ICOS. The antigens were mixed with RIM monophosphoryl lipid A (MPL) plus TDM adjuvant system (Sigma) for the immunizations. The mice described above that were immunized with the soluble ICOS protein in 15-25 µg soluble recombinant ICOS antigen in PBS or 1×10⁷ CHO cells, Hek293T cells, or 300-19 cells transfected for surface expression of human ICOS in PBS were mixed 1:1 with the adjuvant. Mice were injected with 200 µl of the prepared antigens into the peritoneal cavity or subcutaneous or foot pad every two to fourteen days. Mice were injected with 100-200 µl of recombinant moue IL21 following the ICOS antigen immunizations. Mice that developed anti-ICOS titers were given an intravenous injection and/or foot pad injection of 10-20 µg soluble recombinant ICOS antigen or 5×10⁶ CHO cells, or 300-19 cells transfected for surface expression of human ICOS or plus intraperitoneal injection of 15 µg recombinant mouse IL21 protein in 100 µl of PBS three to two days prior to fusion. Mouse lymph nodes and or spleens were harvested, and the isolated lymph node cells and/or splenocytes were used for hybridoma preparation.

Selection of HuMab Mouse® or KM Mouse® that Produced Anti-ICOS Antibodies

To select a HuMab Mouse® or KM Mouse® that produced ICOS-binding antibodies, sera from immunized mice was tested by enzyme-linked immunosorbent assay (ELISA). Briefly, microtiter plates were coated with purified recombinant human ICOS-mouse Fc at 1-2 µg/ml in PBS; 50 µl/wells were incubated 4° C. overnight, then blocked with 200 µl/well of 5% chicken serum in PBS/Tween (0.05%). Dilutions of plasma from ICOS-immunized mice were added to each well and incubated for one hour at ambient temperature. The plates were washed with PBS/Tween and then incubated with a goat-anti-human IgG Fc polyclonal antibody conjugated with horseradish peroxidase (HRP) for one hour at room temperature. After washing, the plates were developed with ABTS substrate (Moss Inc., product: ABTS-1000) and analyzed by spectrophotometer at 415-495 Optical Density (OD). Sera from immunized mice were then further screened by flow cytometry for binding to a cell line that expressed human ICOS, but not to a control cell line that did not express ICOS. Briefly, the binding of anti-ICOS antibodies was assessed by incubating ICOS-expressing CHO cells or 300-19 cells with the anti-ICOS antibody at 1:20 dilution. The cells were washed and binding was detected with a phycoerythrin (PE)-labeled anti-human IgG antibody. Flow cytometric analyses were performed using a FACScan™ flow cytometer (Becton Dickinson, San Jose, Calif.). Mice that developed the highest titers of anti-ICOS antibodies were used for fusions. Fusions were performed as described below. Hybridoma supernatants were tested for anti-ICOS activity by ELISA and fluorescence-activated cell cytometry (FACS).

Hybridoma Preparation

The mouse splenocytes and/or lymphocytes isolated from a HuMab Mouse® and/or a KM Mouse® were fused with a mouse myeloma cell line using electric field-based electrofusion using a Cyto Pulse large chamber cell fusion electroporator (Cyto Pulse Sciences, Inc., Glen Burnie, Md.). Briefly, single cell suspensions of splenic lymphocytes from immunized mice were fused to equal number of Sp2/0 non-secreting mouse myeloma cells (ATCC, CRL 1581 cell lines). Cells were plated at approximately 2×10⁴/well in flat bottom microtiter plates, followed by about two weeks incubation in selective medium containing 10% fetal bovine serum, 10% P388D1 (ATCC, CRL TIB-63) conditioned medium, 3-5% Origen (IGEN) in DMEM (Mediatech, CRL 10013, with high glucose, L-glutamine and sodium pyruvate) plus 5 mM HEPES, 0.055 mM 2-mercaptoethanol, 50 mg/ml gentamycin and 1× hypoxanthine-aminopterin-thymidine (HAT) medium (Sigma, CRL P-7185). After one to two weeks, cells were cultured in medium in which the HAT was replaced with hypoxanthine and thymidine (HT) medium. Approximately 10-14 days after cell plating, supernatants from individual wells were screened first for whether they contained human gamma and kappa antibodies. The supernatants that were scored positive for human gamma and kappa antibodies were then subsequently screened by ELISA and FACS for human anti-ICOS monoclonal IgG antibodies. The antibody-secreting hybridomas were transferred to 24-well plates, screened again and, if still positive for human anti-ICOS monoclonal antibodies, were subcloned at least twice by limiting dilution. The stable subclones were then cultured in vitro to generate small amounts of antibody in tissue culture medium for further characterization. The human monoclonal antibodies produced were then purified by protein A column chromatography. Isolated antibodies of particular interest were designated as 17C4, 9D5, 3E8, 1D7-a, and 1D7-b, as described in Table 7 below.

TABLE 7

Isolated Antibodies

| Antibody Name | Heavy Chain CDR 1, 2, and 3 SEQ ID NOs | Light Chain CDR 1, 2, and 3 SEQ ID NOs | Heavy Chain Variable Domain SEQ ID NO | Light Chain Variable Domain SEQ ID NO |
|---|---|---|---|---|
| 17C4 | 18, 19, and 20 | 21, 22, and 23 | 16 | 17 |
| 9D5 | 26, 27, and 28 | 29, 30, and 31 | 24 | 25 |
| 3E8 | 34, 35, and 36 | 37, 38, and 39 | 32 | 33 |
| 1D7-a | 42, 43, and 44 | 45, 46, and 47 | 40 | 41 |
| 1D7-b | 42, 43, and 44 | 49, 50, and 51 | 40 | 48 |

B. PROfusion® mRNA Display System

KM mice #333819 and #333821 were immunized with CHO cells overexpressing human ICOS, and the spleen and lymph nodes were subsequently harvested. Total RNA was extracted from the spleen and lymph node cells and was reverse transcribed using primers specific to antibody constant regions. The antibody cDNA was used to generate a single-chain variable fragment (scFv) library that was expressed in mRNA display, where each scFv protein was fused to its encoding mRNA via a puromycin linkage. The library was selected against 10 nM recombinant human ICOS-Fc, and any bound molecules were recovered using capture with Protein G magnetic beads and amplified by polymerase chain reaction (PCR) to proceed into the next round. A total of six rounds were completed, after which a significant ICOS binding signal was observed by quantitative PCR (qPCR). The final population was sequenced and unique variable regions were cloned into IgG expression vectors. IgG proteins were expressed using transient transfection of Hek293T cells to generate material for binding and functional assays. Antibody IgG-2644, as described in Table 8 below, was selected.

TABLE 8

| | | | | | |
|---|---|---|---|---|---|
| Antibody Name | Heavy Chain CDR 1, 2, and 3 SEQ ID NOs | Light Chain CDR 1, 2, and 3 SEQ ID NOs | Heavy Chain Variable Domain SEQ ID NO | Light Chain Variable Domain SEQ ID NO | Heavy Chain Domain SEQ ID NO | Light Chain Domain SEQ ID NO |
| 2644 | 191, 192, and 193 | 194, 195, and 196 | 186 | 189 | 185 | 188 |

Antibody IgG-2644

Example 2

Generation of Humanized Anti-ICOS Antibodies

Sequence Determination of Hamster ICOS Antibody C398.4A

A hamster anti-rat ICOS monoclonal antibody, C398.4A (anti-H4/ICOS) Monoclonal Antibody, referred to herein as "parental hamster antibody" or antibody "C398.4A," was obtained from BioLegend®. The C398.4A antibody was sequenced using mass spectrometry. Specifically, C398.4A was denatured in 5.3 M guanidine HCl, reduced with dithiolthreitol (40 mM), and alkylated with iodoacetamide (80 mM). After desalting with a 6 kDa MW cutoff Zeba desalting column, the antibody was enzymatically digested with trypsin, chymotrypsin, pepsin, Lys-C, AspN, or GluC and analyzed by mass spectrometry. Peptide mapping and MS/MS was used to identify the resulting peptides and to confirm the amino acid sequence. The intact heavy and light chain masses were generated by cleaving the glycan off with PNGaseF, reducing the antibody with dithiolthreitol, and alkylating with iodoacetic acid. The resulting antibody chains were analyzed by LC-MS.

The resulting peptide fragmentation data was aligned to a custom protein database consisting of three light chain and heavy chain antibody sequences for *Cricetulus migratorius* present in GenBank along with antibody sequences determined in-house through RNA sequencing of monoclonal antibodies derived from Armenian hamsters. A database search identified the GenBank sequence gene locus CMU17870 (Accession U17870) as similar to the C398.4A light chain. Amino acid substitutions in CDR3 and the framework region were observed in the C398.4A sequence when compared to the CMU17870 light chain sequence. The database search identified the GenBank sequence gene locus CMU17166 (Accession U17166) as similar to the C398.4A heavy chain variable region. The J-region matched an internally identified hamster sequence HA-VH-7. The constant region of the heavy chain matched the same isotype as the antibody HL4E10 (Accession HM369133). The D-region was determined to be novel and was identified by de novo sequencing of the peptide fragmentation data. Amino acid substitutions in CDR1, CDR2, CDR3, and the variable framework region were observed when compared to the CMU17166 and HA-V$_H$-7 heavy chain sequences.

Generation and Evaluation of Chimeric Antibody ICOS. 4 Based on Antibody C398.4A The C398.4A antibody protein sequence was back-translated into cDNA sequence. The isoleucine/leucine (I/L) residue at position 96 in the D region (CDRH3) was expressed with either isoleucine or leucine at this position. The variable regions were cloned into expression vectors containing a signal sequence and human IgG1f constant regions, and transfected into CHO-S cells for the expression of chimeric human antibody, ICOS.4. The chimeric antibody were purified using 2 L supernatant each using 250 mL Protein A column on the AKTA Avant and were screened for activity in the CHO-OKT3-CD32a/CD25-CD4+ T cell assay. The CHO-OKT3-CD32a/CD25-CD4+ T cell assay was a co-culture of irradiated (growth arrested) CHO cells transfected with a low level of single-chain-CD3 (clone OKT3) and a higher level of CD32A (to cross-link antibody) with CD25-depleted-CD4+ T cells at a CHO:T cell ratio of 1:4. The CHO cell line was grown in shaker flasks and irradiated on the day of assay set-up. The T cells were selected from a fresh buffy coat (Stanford Blood Bank) using the RosetteSep® CD4+ T cell isolation kit (Catalog 15062) followed by depletion of CD25+ cells using the Miltenyi® CD25-microbeads (Catalog 130-092-983), following kit instructions for depletion on the AutoMACS®.

ICOS antibody or isotype control were titrated from 5 pg/mL by 5-fold serial dilutions, with each condition set up in triplicate. The cultures were set up in flat-bottom TC-treated Costar® 96-well plates with $5\times10^4$ T cells and $1.25\times10^4$ CHO cells in 200 µL complete medium (RPMI-1640 (Corning®, Catalog 10-040-CM)+10% fetal bovine serum (FBS) (Gibco®, Catalog 25140)+1x Pen Strep (Corning Catalog 30-002-CL)+10 mM HEPES (Corning Catalog 25-000-CL)+1 mM sodium pyruvate (Corning Catalog 25-000Cl)+1xMEM (Corning Catalog 25030-CL) per well and incubated for three days at 37° C. and 5% $CO_2$.

Culture supernatants (50 µL/well) were harvested at Day 3 for analysis of interferon-gamma concentrations using homogeneous time resolved fluorescence (HTRF) assay (Cisbio®), reading out using the Rubystar® microplate reader, and calculating the concentrations from a standard curve using Softmax Pro® software. ICOS.4 antibody was tested in a functional T cell assay using CHO-OKT3-CD32 and CD4+CD25-T cells with the antibody titrated to compare the relative levels of dose-dependent co-stimulation, as measured by interferon-gamma secretion. ICOS.4 exhibited an EC50 value of 0.018 µg/mL.

Isotype Selection

Isotype selection for immuno-oncology therapeutic antibodies and, specifically, for agonist targets, is influenced by two different considerations downstream of binding to FcRs. As detailed by Ravetch and colleagues (Li and Ravetch, Science 2011; 333:1030-4; Otten et al., J Immunol. 2008; 181:6829-36), binding of antibodies to activating receptors can lead to antibody-dependent cell-mediated cytotoxicity (ADCC) or antibody-dependent cellular phagocytosis (ADCP) of cells expressing the target. On the other hand, binding of antibodies preferentially to the inhibitory FcR can mediate multivalent crosslinking of the receptor and agonist signaling. Because ICOS can be highly expressed on CD8+ and CD4+ Teffs in the tumor microenvironment, use of an isotype that can mediate ADCC or ADCP was considered a less attractive option. In vitro ADCC activity of anti-ICOS antibodies also suggested that the anti-ICOS antibodies were highly competent at mediating ADCC and supported the idea that ADCC-inducing isotypes should be avoided. Antibodies that increase the affinity of human IgG1 for CD32B were instead considered as alternative isotypes. The isotypes considered were the IgG1 S267E mutation, SELF mutations, and V12 mutations of the human IgG1, as shown in Table 3 above. These mutations all increase affinity for CD32B and to varying degrees CD32A, while decreasing the affinity for CD16 (as shown in Table 9). This decrease was predicted to lower ADCC activity, as this is the FcR likely mediating depletion of T cells in the tumor.

TABLE 9

Comparison of Binding Properties of Wild Type and S267E Variant of Human IgG1 (μM Kd)

| Protein | IgG1f | IgG1f-S267E |
|---|---|---|
| CD16-V | 97 | 950 |
| CD16-F | 200 | >5000 |
| CD32A-H131 | 530 | 650 |
| CD32A-R131 | 960 | 31 |
| CD32B | 3400 | 87 |
| CD64 | 0.2 | 0.2 |
| C1q | + | ++ |

In vitro activity in the SEB assay using CD4+ T cells and B cells showed superior activity of the IgG1f S267E antibody compared to the human IgG1 and other isotypes, as described above. Based on the data from these functional experiments, IgG1f S267E was chosen as the lead antibody. One complication in the choice of IgG1f S267E was that this isotype binds to complement C1q with higher affinity than the human IgG1, which posed a possible increased risk of complement dependent cytolysis (CDC). Surprisingly, IgG1f S267E did not have higher CDC activity compared to human IgG1 in in vitro testing. Therefore, the S267E mutation did not result in an increased risk of CDC.

Humanization of Antibody ICOS.4

Antibody ICOS.4 was humanized by grafting hamster CDRs onto human germline genes (FIG. 3), VH3-15 was selected for the heavy chain and VKI 018 was selected for the light chain based on framework sequence homology. Human germline FW4, JK3, was also selected for the light chain based on sequence homology. Human germline FW4, JH4, was selected for the heavy chain based on sequence similarity, and it did not contain residues that could pose a potential liability risk. A panel of 26 antibodies was evaluated in the CHO-OKT3-CD32A/CD4+CD25-T cell assay, with an antibody range starting at 0.2 μg/mL and titrated by four-fold dilutions, to identify humanized sequences that retain binding similar to the parental hamster antibody (C398.4A, i.e., the parental hamster antibody having heavy and light chain region sequences set forth in SEQ ID NOs: 3 and 4, respectively).

One amino acid residue substitution was identified (T94A) to restore binding of the humanized CDR grafted antibody, and it is located at the junction of FR3 and CDRH3. In addition, three chimeric antibodies with liability mutations at the D56, G57 sequence were also evaluated to see if the potential isomerization site in the VL could be removed without affecting activity. The residue substitution D56E was selected to eliminate the potential isomerization site (D56, G57) in the light chain and incorporated into the humanized sequence. The humanized antibodies were screened with the IgG1f isotype, however, ICOS.33 IgG1f S267E was re-expressed using the IgG1f S267E isotype. A description of the antibodies generated is provided in Table 10 below.

TABLE 10

Summary of Antibodies Generated

| | Antibody Name | Description |
|---|---|---|
| 1 | C398.4A | Parental hamster antibody |
| 2 | ICOS.1 mG1 | Mouse IgG1 anti-mouse ICOS antibody derived from rat 17G9 (does not bind to human ICOS) |
| 3 | ICOS.4 | Chimeric antibody with variable regions of C398.4A made as four different variants (listed below) |
| 4a | ICOS.4 mG1 | Mouse IgG1 variant of ICOS.4 |
| 4b | ICOS.4 mIgG2a | Mouse IgG2a variant of ICOS.4 |
| 4c | ICOS.4 hg1 | Human IgG1 variant of ICOS.4 |
| 4d | ICOS.4 hg1 SE | Human IgG1 variant of ICOS.4 with S267E mutation |
| 5 | ICOS.33 | Humanized (IgG1 isotype) ICOS.4 with parental CDRs grafted onto human framework and T94A and D56E mutations |
| 6 | ICOS.33 IgG1f S267E | ICOS.33 with S267E substitution |
| 7 | ICOS.34 G1f | Humanized (IgG1 isotype) ICOS.4 with parental CDRs grafted onto human framework (also referred to as "C398.4A-03") |
| 8 | ICOS.35 G1f | ICOS.34 plus T94A mutation |

A set of four humanized antibodies based on C398.4A were tested in the CHO-OKT3-CD32a/CD4+CD25− T cell functional assay, comparing to the original hamster chimeric antibody, as described below in Example 3. ICOS.33 IgG1f S267E was selected for further characterization and development. The heavy and light chain variable region sequences for ICOS.33 IgG1f S267E are shown in SEQ ID NOs: 5 and 6, respectively, and in FIG. 4.

Example 3

Antibody Selection

CHO-scFv-CD3-CD32A/CD25-CD4+ T Cell Assay

Initial functional assay screening was performed using CHO cells expressing single-chain variable fragment (scFv) anti-CD3 (OKT3) and human CD32A to stimulate primary human T cells. This assay was a co-culture of irradiated (growth arrested) CHO cells transfected with a low level of single-chain variable fragment-CD3 (clone OKT3) and a higher level of CD32A (to cross-link antibody) with CD25-depleted-CD4+ T cells at a CHO:T cell ratio of 1:4. The CHO cell line was grown in shaker flasks and irradiated on the day of assay set-up. The T cells were selected from fresh buffy coats (Stanford Blood Bank) using the RosetteSep CD4+ T cell isolation kit. CD25+ cells were depleted using Miltenyi CD25-microbeads, following kit instructions for depletion on the AutoMACS.

ICOS antibody or isotype control (i.e., antibody of the same isotype as the ICOS antibody, but that does not bind any naturally-occurring human protein, e.g., antibodies against keyhole limpet hemocyanin (KLH), diphtheria toxin, amongst others) was titrated from 2 µg/mL by five-fold serial dilutions, with each condition set up in triplicate using T cells from two donors. The cultures were set up in flat-bottom TC-treated 96-well plates (Costar) with $5 \times 10^4$ T cells and $1.25 \times 10^4$ CHO cells in 200 µL complete medium per well and incubated for three days at 37° C. and 5% $CO_2$.

Culture supernatants (50 µL/well) were harvested on Day 3 for analysis of interferon-gamma (IFN-γ) concentrations using the homogeneous time resolved fluorescence (HTRF) assay (Cisbio). Concentrations were determined using the Rubystar microplate reader and calculated from a standard curve using Softmax Pro software. The plates were then pulsed with 0.5 µCi tritiated thymidine per well for eight hours and frozen. The cells were harvested onto filter plates (Perkin Elmer) for analysis of tritiated thymidine incorporation to assess proliferation.

Figure 5A:
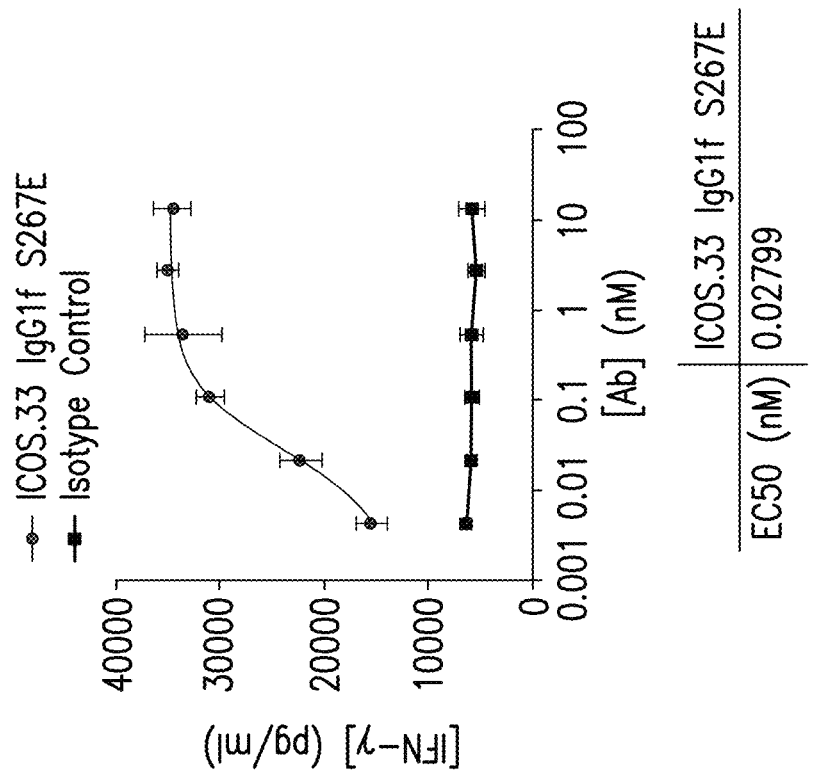

The FcR CD32A permitted crosslinking of antibodies regardless of antibody Fc subtype. This crosslinking allowed for the costimulation of T cells through ICOS agonism, resulting in enhanced proliferation and cytokine release in comparison to isotype control-treated cells. This activity was seen on CD8+, CD4+, and CD25− CD4+ T cells. Because of superior signal-to-noise in the depleted CD25− CD4+ T cell assay, these cells were used for screening hybridomas. The best performing antibodies were selected for sub-cloning, purification, and further characterization. The parental hamster monoclonal antibody was included in the analysis of the panel of antibodies. As described above, activity in the CHO-CD3-CD32 assay was used to select a lead panel of antibodies, which were re-expressed as human IgG1 antibodies or other modified versions of human IgG1. ICOS.33 IgG1f S267E exhibited dose-dependent induction of IFN-γ secretion and proliferation in the CHO-scFv-CD3-CD32A/CD25-CD4+ T cell assay, as shown in FIG. 5. The mean EC50 of this effect was 0.083 nM (±0.067, n=6) for proliferation and 0.083 nM (±0.074, n=6) for IFN-γ induction. Proliferation induction ranged from 2- to 5-fold at the three highest concentrations tested in a total of 6 donors, while IFN-γ induction ranged from 2-fold to 9-fold in the same experiments compared to control. Previous experiments using CHO-scFv-CD3 (no CD32A) confirmed that cross-linking is required for agonistic activity of all ICOS antibodies tested.

CD25-CD4+ T Cell and B Cell-SEB Assay

Further characterization of anti-ICOS antibodies functional activity was performed using Staphylococcal Enterotoxin B (SEB) as a T cell receptor (TCR) stimulus and addition of anti-ICOS antibodies to test for co-stimulation. When human peripheral blood cells (PBMC) were used in the assay, anti-ICOS antibodies showed no functional activity. However, when CD4+ T cells (either CD25-depleted or total CD4+ T cells) were used along with purified B cells, anti-ICOS antibodies showed enhanced interferon gamma (IFN-γ) secretion compared to control antibodies.

This assay involved a co-culture of autologous CD25-CD4+ T cells and B cells. SEB was added to a final fixed concentration of 85 ng/mL to provide submaximal stimulation, and ICOS antibody was titrated to show a dose-dependent costimulation effect. The purpose of this assay was to measure the ability of ICOS antibodies to enhance activation of T cells in the context of a primary activating signal (SEB+B cells) as evidenced by levels of IFN-γ induction. It is beneficial to induce higher levels of IFN-γ because it is a measure of T cell activation that reflects the potency of the different antibodies exhibiting agonism of the ICOS receptor, and IFN-γ is a known mediator of anti-tumor immunity.

T cells were isolated by positive selection from two fresh buffy coats followed by detachment of beads to generate untouched CD4+ T cells (Invitrogen). CD25+ cells were then depleted from the CD4+ T cells using CD25-microbeads (Miltenyi), following kit instructions for depletion using the AutoMACS. The negative fractions from the CD4 isolations were then used to isolate the autologous B cells using Miltenyi CD20 beads, following kit instructions for positive selection using the AutoMACS.

The T cells were plated in 96-well flat-bottom TC-treated culture plates at $5 \times 10^4$ cells/well with autologous B cells at 3 to $5 \times 10^4$ cells/well (depending on yield from each donor) with SEB included for a final concentration of 85 ng/mL. ICOS antibody or isotype control was titrated from 5 µg/mL by 5-fold serial dilutions for a total of seven points, each tested in triplicate. The assay was set up in complete medium with 200 µL/well final volume. The plates were incubated for 3 days at 37° C. and 5% $CO_2$.

Culture supernatants (50 µL/well) were harvested on Day 3 for analysis of IFN-γ concentrations using the HTRF assay (Cisbio). Concentrations were determined using the Rubystar microplate reader and calculated from a standard curve using Softmax Pro software.

Figure 6:
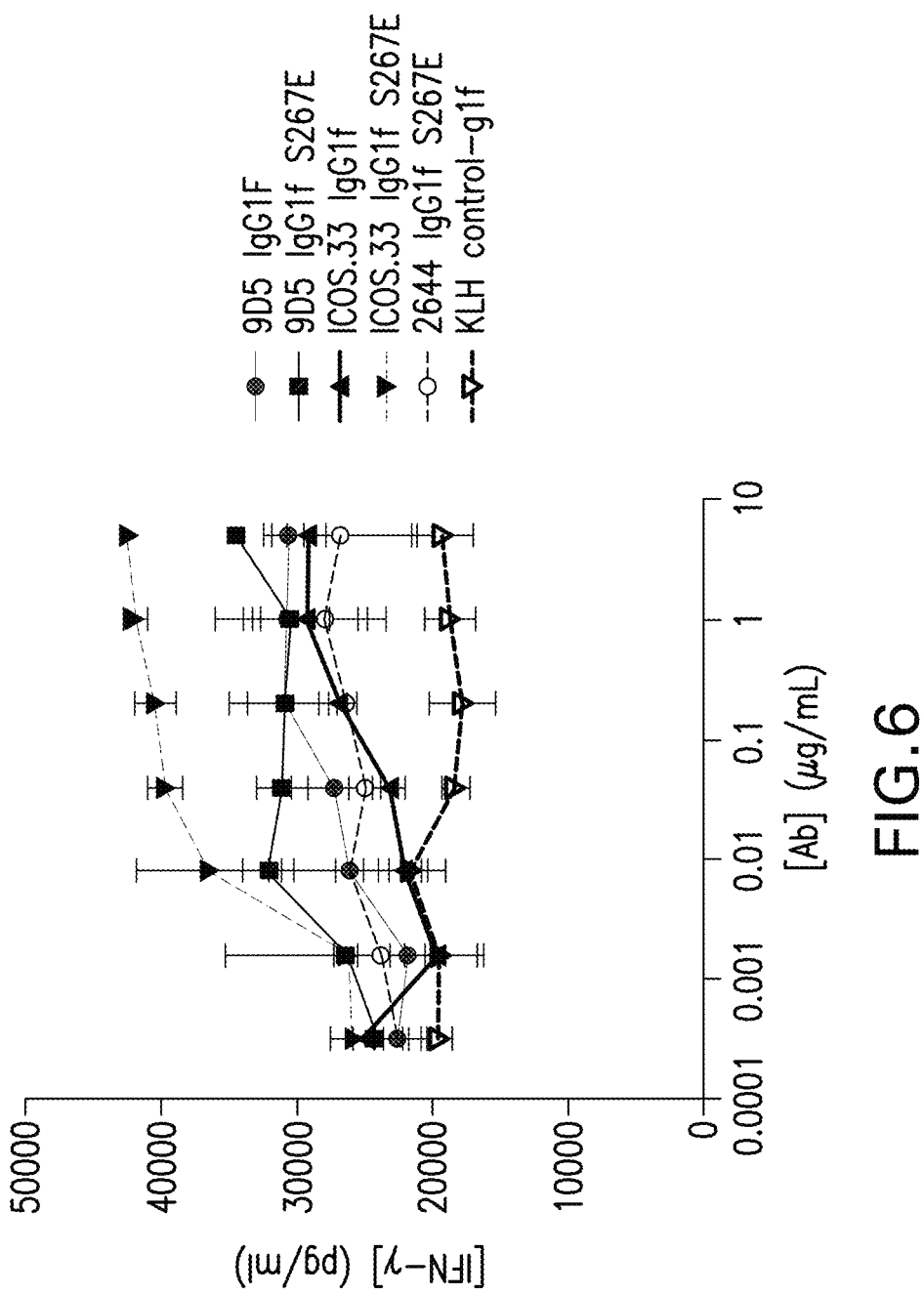
FIG. 6 is a graph that illustrates IFN-γ induction by anti-ICOS antibodies in a CD25-CD4+ T cell and B cell SEB co-culture assay.

SEB co-culture experiments compared IFN-γ production for anti-ICOS antibodies ICOS.33 IgG1f, ICOS.33 IgG1f S267E, 9D5 IgG1f, 9D5 IgG1f S267E, 2644 IgG1f S267E, and control antibody KLH control Ig1f (FIG. 6). The humanized lead antibody ICOS.33 with the S267E mutation (ICOS.33 IgG if S267E, as depicted in the full downward triangle in FIG. 6) induced higher levels of IFN-γ than the same antibody with wild type Fc (ICOS.33 IgG1f). The other comparator antibodies tested, that is, 95D IgG1f, 9D5 IgG1f S267E, and 2644 IgG1, also exhibited lower activity than ICOS.33 IgG1f S267E. The KLH control Ig1f did not exhibit any activity. ICOS.33 IgG1f S267E antibody increased IFN-γ production up to 2.3-fold compared to the control antibody in a dose-dependent manner in CD25-CD4+ T and B cell co-cultures stimulated by a suboptimal dose of SEB. A total of 20 donors were tested using this assay, all showing the greatest agonist activity by ICOS.33 IgG1f S267E, with an EC50 of 0.020 nM (±0.018).

Figure 7A:
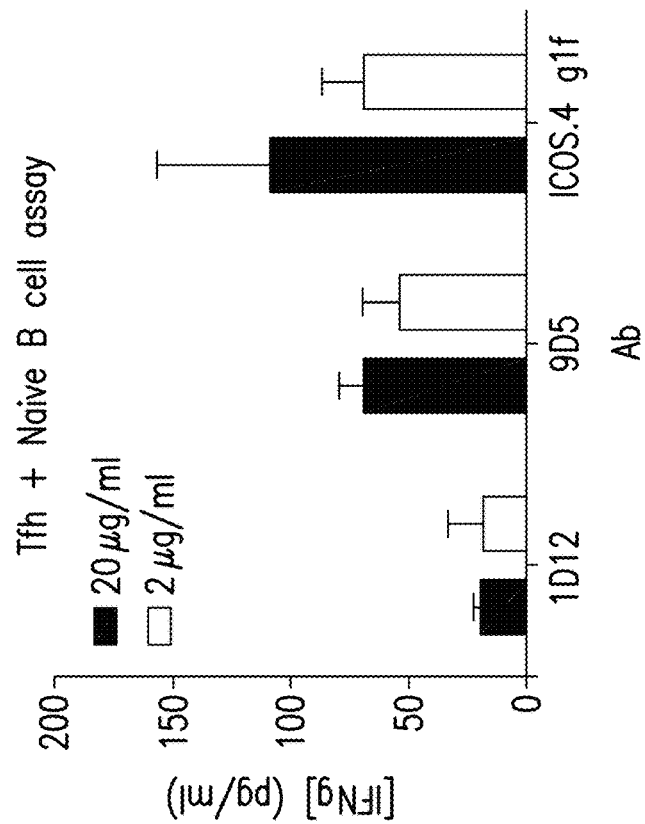
FIGS. 7A and 7B are a graphs that show IL-10 and IFN-γ induction in an SEB stimulated Tfh and naive B cell co-culture assay. Average: 4.4-fold induction.
Figure 7B:
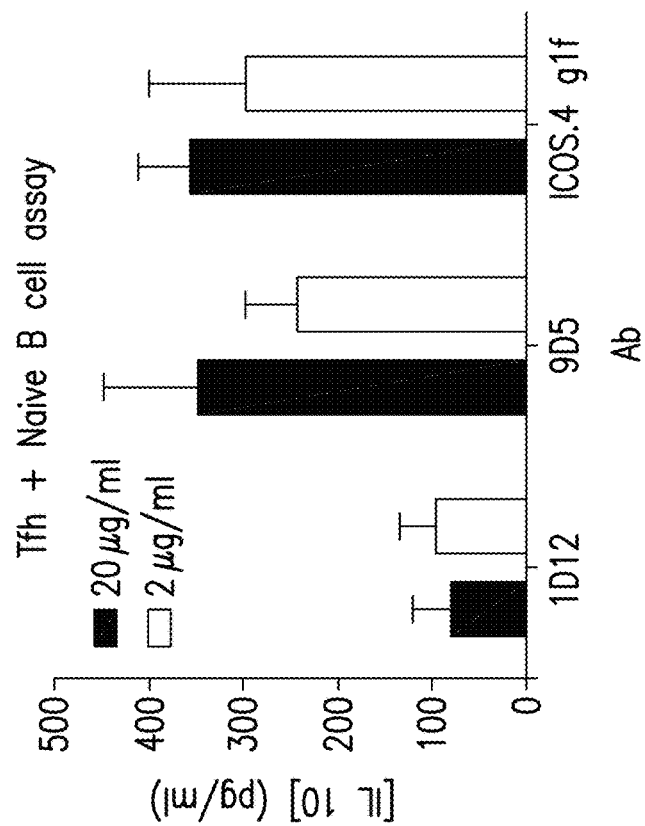

The activity of ICOS antibodies on T follicular helper cells (Tfhs) was tested in this manner. Compared to control antibody 1D12, enhanced secretion of IL-10 was observed after adding the anti-ICOS antibodies 9D5 and ICOS.4. Tfh cells were sorted from PBMCs after enrichment by CD4 selection (Invitrogen kit) by staining the CD4 enriched cells for CD4, CD14, CXCR5, CD45RA and CD123 and sorting for Tfh cells (CD4+CXCR5+CD45RA-CD123-CD14-) using the Aria II FACS. Naive B cells were isolated from the CD4-negative fraction using the Miltenyi kit. The Tfh and naive B cells were co-cultured in 96-well flat-bottom TC plates with 5e4 cells/well of each and stimulated with SEB for 2 days when IL-10 and IFNγ were measured by ELISA (BD) and shown to be enhanced by ICOS antibodies. This enhanced cytokine secretion did not require an exogenous crosslinker and could be enhanced by including the S267E mutation to the human IgG1 (FIGS. 7A and 7B).

ICOS.33 IgG1f S267E was selected for further development because of its ability to stimulate IFN-γ production in the CHO FcR assay and induce cell proliferation (FIG. 5), as well as its higher functional activity in the SEB assay compared to the other anti-ICOS antibodies tested (FIG. 6).

Example 4

Reversal of Regulatory T Cell Suppression by ICOS.33 IgG1f S267E

The objective of this study was to determine the effect of ICOS.33 IgG1f S267E on effector T cell (Teff) proliferation and Treg-mediated suppression.

U-bottom plates were coated for three hours at 37° C. with anti-CD3 (3 μg/mL) in combination with either ICOS.33 IgG1f S267E (10 μg/mL) or anti-KLH, an isotype control that does not bind ICOS protein (10 μg/mL) in PBS. CD4+ T cells were isolated from whole fresh buffy coats using RosetteSep CD4+ T enrichment cocktail in conjunction with Ficoll-Paque separation, following the RosetteSep manufacturer's instructions. Enriched CD4+ T cells were stained with fluorophore-conjugated monoclonal antibodies directed against CD4, CD25, CD127, CD45RA, and CD45RO in FACS sort buffer. CD4+ T cells were then sorted into Teff (CD4+CD25loCD127hi), RA+ Treg (CD4+CD25hiCD127lo/CD45RA+/CD45RO−) and RO+ Treg (CD4+CD25hiCD127lo/CD45RA−/CD45RO+) cell populations using a FACSAria II cell sorter. Sorted Tregs were labeled with CellTrace™Violet (CTV) proliferation dye according to manufacturer's instructions at a concentration of 5 μM. Sorted Teffs were labeled with CellTrace CFSE™ proliferation dye (CFSE) according to manufacturer's instructions, except that it was used at a higher dilution of 1.25 μM to reduce cytotoxic effects observed in previous experiments.

Fifty-thousand sorted and CFSE-labeled Teffs in 100 μL of complete medium were added to each well of the 96-well plate coated with anti-CD3 and ICOS.33 IgG1f S267E or isotype control. These were prepared with or without anti-CD28 added at 2 μg/mL (for a final concentration of 1 μg/mL). Titrating numbers of sorted and CTV-labeled Tregs in 100 μL of complete medium were then added to each well beginning with $5 \times 10^4$ Tregs (1:1 Treg to Teff) and decreasing 2-fold in subsequent wells (1:2, 1:4, etc).

The cultures were incubated for six days at 37° C. when the cells were stained with the fixable viability dye Ghost Red-780 to exclude dead cells. Flow cytometry data were collected using a BD FACSCanto II flow cytometer. Percent Teff proliferation was determined using FACSDiva flow cytometry analysis software. The percent proliferation of Teffs was determined by gating on Teffs that had diluted their CellTrace CFSE proliferation dye following at least one round of division.

Figure 8B:
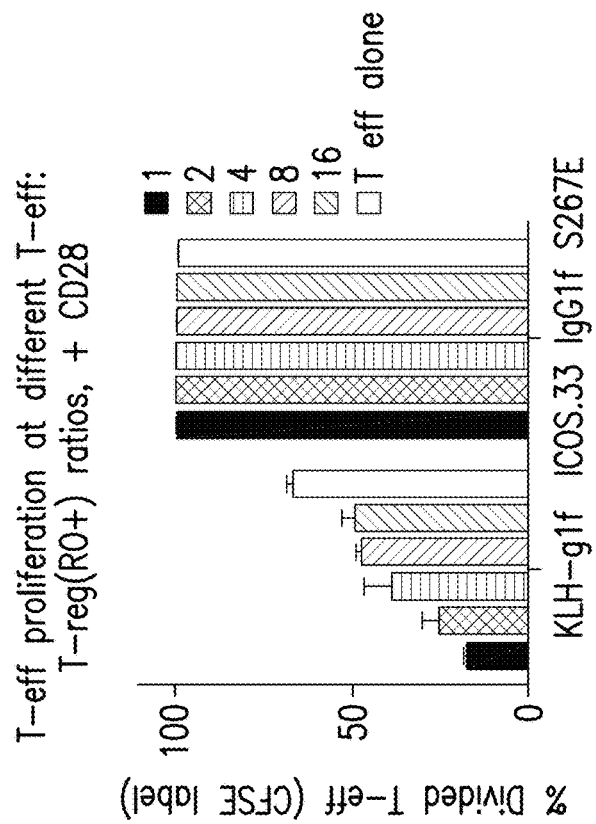
FIGS. 8A and 8B are graphs that show the elimination of Teff suppression by Tregs with anti-ICOS antibody costimulation.
Figure 8A:
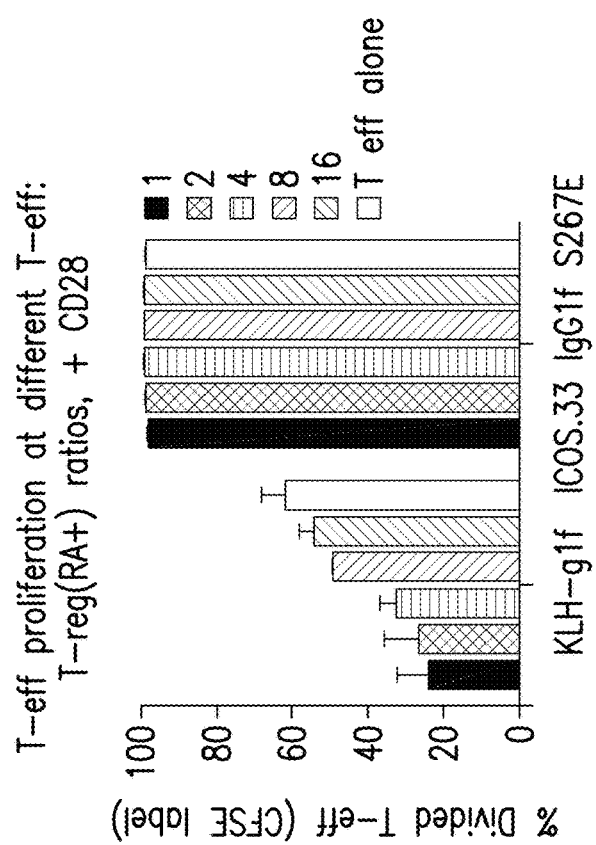

This Example showed that ICOS.33 IgG1f S267E both reversed Treg-mediated suppression and enhanced Teff proliferation, as shown in FIGS. 8A and 8B. The values shown in the legend in FIGS. 8A and 8B are the Teff:Teg ratios. Hence, a value of 1 means a ratio of 1 Teff to 1 Treg, a value of 2 means 2 Teff to 1 Treg, and so on, essentially titrating down the Tregs. At the 1:1 ratio, ICOS.33 IgG1f S267E showed an approximately 4-fold increase of proliferation and apparent reversal of RA+ Treg-mediated suppression. A 7-fold increase in proliferation and apparent reversal of RO+ Treg mediated suppression, as measured by the difference in percent of dividing Teff between isotype control and ICOS antibody, was also observed. As the Tregs were titrated out, there was a proportional decrease of apparent suppression and in the absence of Treg there was approximately a 1.5-fold increase in the percent of divided Teff relative to the isotype control. The effect in the presence of Treg could be a result of decreasing Teff susceptibility to Treg suppression or a decreasing suppressive capacity of Tregs. It is beneficial that ICOS.33 IgG1f S267E reversed Treg-mediated suppression and enhanced Teff proliferation, as this showed that ICOS.33 IgG1f S267E stimulated the immune response.

Example 5

In Vitro Fc Effector Function of ICOS.33 IgG1f S267E

The objective of this study was to assess the antibody-dependent cellular cytotoxicity (ADCC) and complement C1q factor binding activities of ICOS.33 IgG1f S267E.

Target Cell Labeling with Calcein AM

CD4+ T cells from Donor 2 (Stanford Blood ID WO70516511239) were isolated, activated and labeled with Calcein AM. Briefly, peripheral blood mononuclear cells (PBMC) were purified from heparinized buffy coat by density gradient centrifugation and washed with phosphatebuffered saline (PBS) supplemented with 2% FBS (HyClone). CD4+ T cells were isolated by negative selection using a magnetic bead-based separation kit (StemCell Technologies) and automated RoboSep cell separator (StemCell Technologies). From the CD4+ T cell isolation, CD25+ Tregs were depleted using a magnetic bead-based separation kit (Miltenyi Biotec). Purified CD4+ T cells were re-suspended at $2.5 \times 10^6$ cells/mL in R10 media and activated with the T Cell Activation/Expansion kit (Miltenyi Biotec) at one bead per two cells for three days at 37° C. On day 3, cells were counted, pelleted, and re-suspended at $1 \times 10^6$ cells/mL in PBS in a 15 mL conical tube. Calcein AM reagent was prepared by adding 20 μL of ultrapure DMSO to the reagent tube containing 50 μg of lyophilized reagent. A volume of 2 μL of reconstituted Calcein AM was added to the suspended cells for every 1 mL of volume. The cells were vortexed and placed in a 37° C. incubator for 30 minutes. After the incubation period, the labeled target cells were washed three times with ADCC assay media, and their concentration was adjusted to $10^5$ cells/mL in assay media.

Antibody-Dependent Cellular Cytotoxicity (ADCC) Assay with Activated CD4+ T Cells as Targets Primary human NK effector cells were purified from fresh PBMC from two different donors (BDC Donors 9 and 12) and stimulated with IL-2. Briefly, PBMC were purified from heparinized whole blood samples by density gradient centrifugation and washed with PBS supplemented with 2% FBS (HyClone). NK cells were isolated from PBMC by negative selection using a magnetic bead-based separation kit (Miltenyi Biotech) and autoMACs Separator (Miltenyi Biotech). Purified NK cells were re-suspended at $1 \times 10^6$ cells/mL in MyeloCult media supplemented with 500 IU/mL IL-2 and incubated overnight at 37° C.

The following day, activated NK effector cells were washed twice in assay media and their concentration was adjusted to 4.33-5×10⁵ cells/mL in assay media. Labeled target cells (50 µL/well) were added to a U-bottom 96-well plate containing 50 µL/well of test or control antibody. Activated NK effector cells were then added (100 µL/well) to result in a final effector cell-to-target cell ratio (E:T) of 10:1 and a final antibody concentration ranging from 0.0002 µg/mL to 1 µg/mL. The plate was then placed in a humidified 37° C. incubator for two hours. Supernatant (50 µL/well) was transferred into an optical 96-well black plate, and fluorescence intensity was read on an EnVision plate reader set to 485 excitation and 535 emission filters.

Target cells incubated with effector cells in the absence of antibody provided the control for background of antibody-independent lysis (spontaneous lysis), while target cells lysed with 20 µL or 100 µL/well Delfia Lysis buffer represented maximal release in the assay.

The percentage of antibody-dependent cell lysis was calculated based on mean fluorescence intensity (MFI) with the following formula:

$$\left(\frac{test\ MFI - mean\ background}{mean\ maximum - mean\ background}\right) \times 100$$

Percentage of target cell lysis was plotted for each antibody using Prism v5.01 software from GraphPad Inc.

Results

Primary NK ADCC with Activated CD4+ T Cells as Targets

Anti-ICOS antibody ICOS.33 IgG1f S267E was tested for its ability to induce ADCC of ICOS-expressing CD4+ T cells as targets and compared ADCC induced by ICOS.33 IgG1. Two experiments were run with target cells and NK cell donor pairs. In each case, ICOS.33 IgG1f S267E with the modified IgG1 isotype induced less ADCC of activated CD4+ T cells than ICOS.33 IgG1. Data from these experiments are summarized in Table 11 and FIGS. 9A and 9B.

TABLE 11

Comparison of ADCC Mediated by Anti-ICOS IgG1 and Modified IgG1 Isotypes

| CD4+ Target Cell Donar | Effector Cell Donar | Antibody | Concentration (µg/mL) | Percent Target Cell Lysis | | |
|---|---|---|---|---|---|---|
| | | | | Well 1 | Well 2 | Well 3 |
| 2 | 12 | ICOS.33 IgG1fS267E | 1.0000 | 31 | 16 | 42 |
| | | | 0.0625 | 20 | 23 | 26 |
| | | | 0.0039 | 6 | 1 | 7 |
| | | ICOS.33 IgG1 | 1.0000 | 57 | 56 | 55 |
| | | | 0.0625 | 52 | 47 | 45 |
| | | | 0.0039 | 42 | 38 | 29 |
| | | Isotype Control | 1.0000 | 16 | 13 | 18 |
| 2 | 9 | ICOS.33 IgG1fS267E | 1.0000 | 41 | −11 | 16 |
| | | | 0.2500 | 8 | 22 | 1 |
| | | | 0.0625 | 1 | 10 | −5 |
| | | | 0.0156 | 21 | −3 | −4 |
| | | | 0.0039 | 17 | −1 | 1 |
| | | | 0.0010 | 7 | 9 | −6 |
| | | | 0.0002 | 8 | 20 | −10 |
| | | ICOS.33 IgG1 | 1.0000 | 36 | 43 | 62 |
| | | | 0.2500 | 48 | 29 | 51 |
| | | | 0.0625 | 61 | 47 | 51 |
| | | | 0.0156 | 59 | 34 | 45 |
| | | | 0.0039 | 41 | −3 | 59 |
| | | | 0.0010 | 46 | 20 | 27 |
| | | | 0.0002 | 25 | −6 | 9 |
| | | Isotype Control | 1.0000 | −3 | 2 | −8 |

C1q Binding Assay

The binding of ICOS.33 IgG1f S267E to human C1q was investigated by ELISA. All antibodies were coated on a high-binding immunoassay plate at 10 µg/mL in PBS at 50 per well. A nonspecific binding control with wells coated with PBS only was included. The plate was incubated overnight at 4° C. The next day, the plate and all reagents were equilibrated to room temperature; all subsequent steps were performed at ambient room temperature. Unoccupied protein binding sites were blocked with SmartBlock® at 200 per well for 30 minutes. The plate was washed 3 times with washing solution (PBS+0.05% Tween-20) at 200 µL/well. Graded doses of human C1q (48.00 to 0.76 µM) in ELISA assay buffer were added at 50 µL/well. The plate was incubated for two hours and washed three times with washing solution. Binding of human C1q to the immobilized antibodies was detected by a biotinylated mouse anti-C1q mAb diluted 1:1000 in ELISA assay buffer and incubated for one hour. After the plate was washed three times, streptavidin-poly-HRP, diluted 1:5000 in conjugate buffer, was added at 50 µL/well and incubated for 30 minutes. A final washing step was completed, and the plate was developed with TMB substrate at 50 µL/well for 5 minutes. The optical density was read at 650 nm on the SpectraMax 340PC384 Microplate Reader (Molecular Device). The data was graphed using Prism, Version 5.01.

Results

ICOS. 33 IgG1f S267E Binds C1q Component of Human Complement

Figure 10:
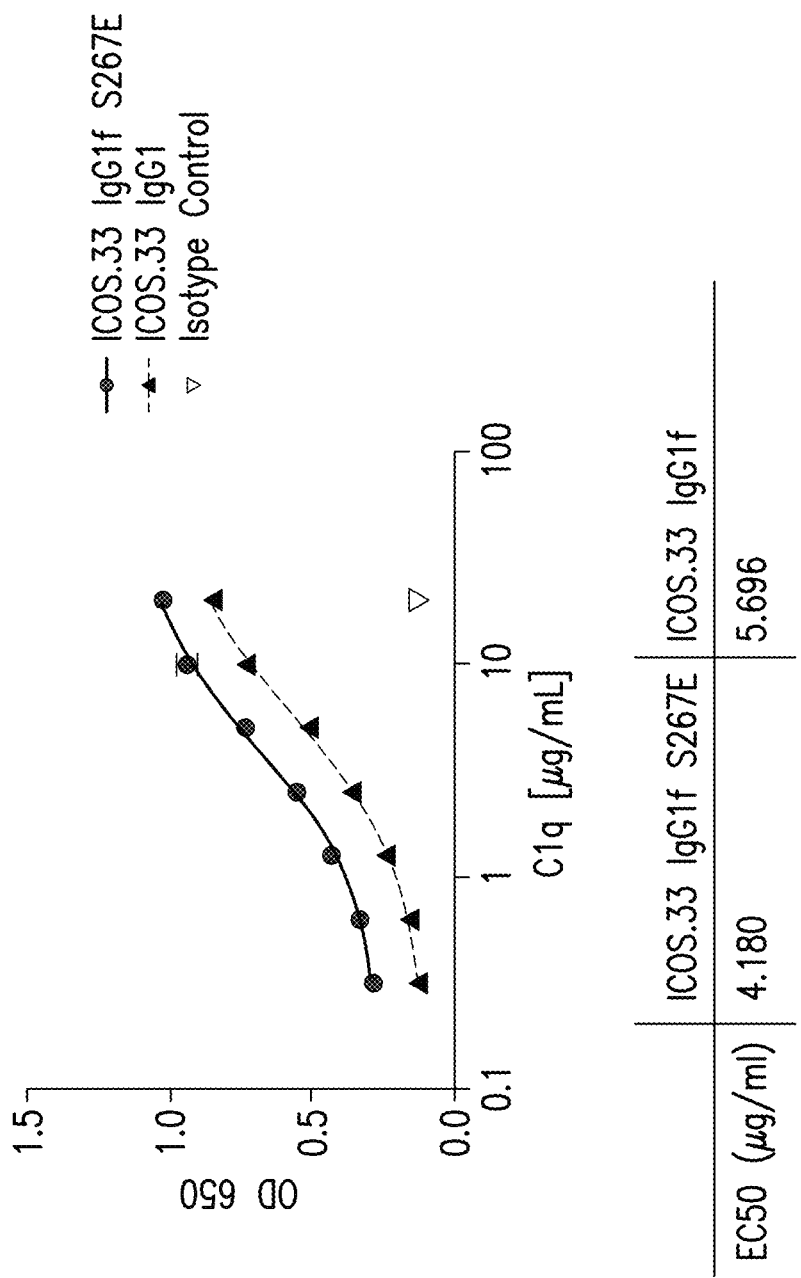
FIG. 10 is a graph of results from an ELISA assay comparing the ability of ICOS.33 IgG1f S267E and ICOS.33 IgG1 to bind C1q component of human complement.

Anti-ICOS antibody ICOS.33 IgG1f S267E was tested for its ability to bind C1q component of human complement compared to ICOS.33 IgG1 in an ELISA assay. ICOS.33 IgG1f S267E was found to bind human C1q with higher affinity than ICOS.33 IgG1. Data are summarized in FIG. 10 and Table 12.

TABLE 12

ICOS.33 IgG1f S267E Binds Human C1q

| C1q (μg/mL) | ICOS.33 IgG1 | | | ICOS.33 IgG1f S267E | | | Background |
|---|---|---|---|---|---|---|---|
| | | | | OD 650 nm | | | |
| 20.000 | 0.8363 | 0.8463 | 0.8704 | 0.9977 | 1.0367 | 1.0318 | 0.1168 |
| 10.000 | 0.7742 | 0.1753 | 0.7053 | 0.9207 | 1.0096 | 0.8919 | n/a |
| 5.000 | 0.5254 | 0.4921 | 0.5139 | 0.7107 | 0.7528 | 0.7405 | n/a |
| 2.500 | 0.3531 | 0.3600 | 0.3591 | 0.5393 | 0.5667 | 0.5590 | n/a |
| 1.250 | 0.2561 | 0.2298 | 0.2309 | 0.4255 | 0.4460 | 0.4259 | n/a |
| 0.625 | 0.1724 | 0.1616 | 0.1630 | 0.3306 | 0.3415 | 0.3302 | n/a |
| 0.313 | 0.1249 | 0.1260 | 0.1230 | 0.2843 | 0.2784 | 0.2815 | n/a |

Conclusion

ICOS.33 IgG1f S267E with a modified IgG1 induced less ADCC-mediated killing of ICOS-expressing CD4+ T cells, yet bound with higher affinity to human C1q than an anti-ICOS antibody with wildtype IgG1.

Example 6

In Vivo Anti-Tumor Activity

Antitumor Activity of Anti-Mouse ICOS as Monotherapy or Combined with Other Agents Variations in the isotype of antibodies that are specific for T cell surface receptors (both co-stimulatory and co-inhibitory) can alter antitumor activity. Mouse Fc isotype variants of both 17G9 and ICOS.4 were generated and expressed as mouse IgG2a isotypes. Both showed superior antitumor activity compared to mouse IgG1 variants, as described below. Although not bound by any theory, this was likely due to depletion of T regulatory cells (Tregs) at the tumor site as well as to effector T cell (Teff) expansion from antibody-mediated agonism of ICOS. Mouse studies with the 17G9 Ab also exhibited downregulation of ICOS receptor on T cell populations both in the spleen and tumor. ICOS expression was observed to be lower in mice treated with Ab isotypes that engage FcR (mIgG1 and mIgG2a), while receptor levels were unchanged in the mice treated with a non-FcγR binding Ab (mIgG1 D265A, also referred to as "ICOS.1 D265A"). The dependence on FcγR interaction suggested that crosslinking is required for this downregulation. Importantly, antitumor activity was demonstrated even though receptor was downregulated.

Mouse IgG1 variants of both 17G9 (ICOS.1) and of the parental hamster antibody (ICOS.4), were both expected to have agonist activity due to the ability to bind to FcRII (inhibitory receptor). As summarized in Table 13, both mouse IgG1 variants demonstrated antitumor activity at a detectable but lower level relative to the IgG2a isotype, and a smaller reduction in tumor Tregs. In contrast, an anti-ICOS antibody that does not bind FcRs (17G9-IgG1-D265A) showed no antitumor activity. Although a depleting isotype such as the mouse IgG2a showed higher antitumor activity than the agonistic mIgG1, the high expression of ICOS on Teffs makes this mechanism of action less favorable when considered in conjunction with another treatment, such as an anti-CTLA-4 antibody treatment, which is expected to deplete Tregs more selectively. Consistent with the in vitro findings of better agonist activity in isotypes with the S267E mutation, these isotypes also showed slightly higher or equivalent antitumor activity than the human IgG1 in human FcR transgenic mice.

TABLE 13

Summary of Efficacy Studies Using Anti-Mouse ICOS as Monotherapy or Combined with Other Agents

| Tumor | mAbs | Antitumor Activity |
|---|---|---|
| Colon CT26 | Anti-ICOS parental-mIgG2a or mIgG1 (ICOS.4) Anti-PD-1 4H2-mIgG1-D265A Anti-CTLA-4 9D9-mIgG2b | Monotherapy with anti-ICOS IgG2a 69% TGI, 1/10 TF and with ICOS IgG1 15% TGI, 0/10 TF Monotherapy 5% TGI, 0/10 TF Combined with anti-ICOS IgG1 83% TGI, 3/10 TF Monotherapy 15% TGI, 0/9 TF Combined with anti-ICOS IgG1 48% TGI, 0/9 TF |
| Colon MC38 | Anti-ICOS parental-mIgG2a or mIgG1 or anti-ICOS 17G9 rat IgG2b Anti-PD-1 4H2 mIgG1-D265A | Monotherapy with ICOS rat IgG2b 25% TGI 0/9 TF and with anti-ICOS IgG1 6% TGI, 0/10 TF Monotherapy 73% TGI, 1/9 TF Combined with anti-ICOS rat IgG2b 92% TGI, 5/9 TF |
| Thymoma EG7 | Anti-ICOS parental-mIgG2a or mIgG1 | Monotherapy with ICOS IgG2a 69% TGI, 2/8 TF and with anti-ICOS IgG1 11% TGI, 1/8 TF |
| Sarcoma 1956 | Anti-ICOS parental-mIgG2a or mIgG1 | Monotherapy with anti-ICOS IgG2a 94% TGI, 0/8 TF and with anti-ICOS IgG1 50% TGI, 2/10 TF |
| Fibrosarcoma SA1N | Anti-ICOS parental-mIgG2a or mIgG1 | Monotherapy with anti-ICOS IgG2a 84% TGI, 6/10 TF and with anti-ICOS IgG1 55% TGI, 5/10 TF |

Antitumor Activity of ICOS IgG1 Fc Variants

To determine if human IgG1 S267E behaves similar to mouse IgG1 antibodies, but with more potency with respect to FcR binding to CD32, and agonistic receptor engagement, additional tumor model experiments were performed. Specifically, to evaluate anti-human ICOS isotype variants in human Fc receptor (FcR)-transgenic mice, the following antibodies were constructed:

(a) Anti-ICOS hIgG1—Monoclonal antibody to mouse ICOS, chimeric hamster/mouse anti-mouse ICOS, isotype IgG1 (ICOS.4 hg1);

(b) Anti-ICOS hIgG1 SE—monoclonal antibody to mouse ICOS, chimeric hamster/mouse anti-mouse ICOS, isotype IgG1 SE (ICOS.4 hg1 SE), which has a mutation that allows it to bind to CD32R and CD32B better than the unmodified version; and (c) IgG1 Isotype Control—a fully human IgG1 isotype control (DT-1D12 hg1).

Figure 11A:
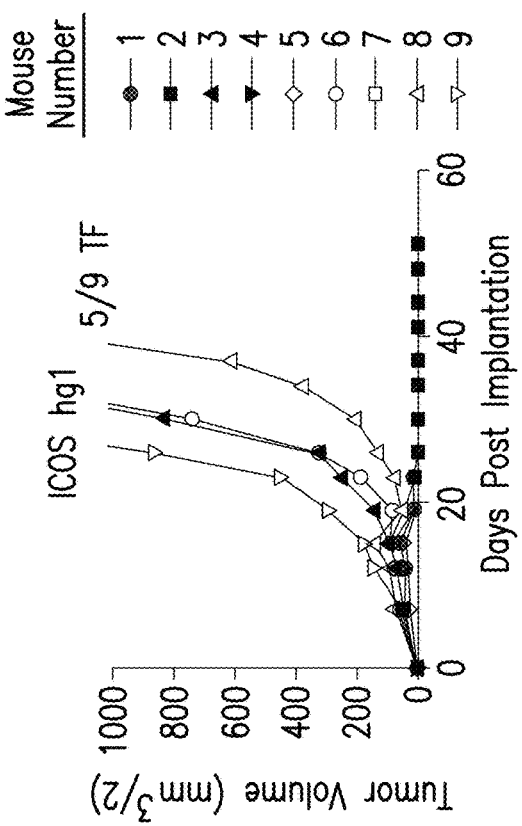
FIGS. 11A-C are graphs that show the anti-tumor activity of ICOS Fc variants, ICOS IgG1 SE ("ICOS hg1 SE") and ICOS IgG1 ("ICOS hg1") antibodies, and an IgG1 isotype control antibody ("hIgG1") in an MC38 tumor model.
Figure 11B:
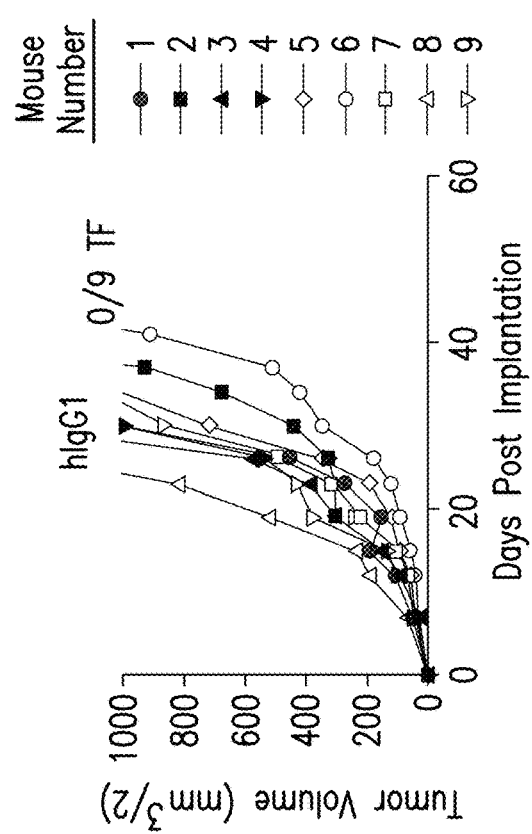
Figure 11C:
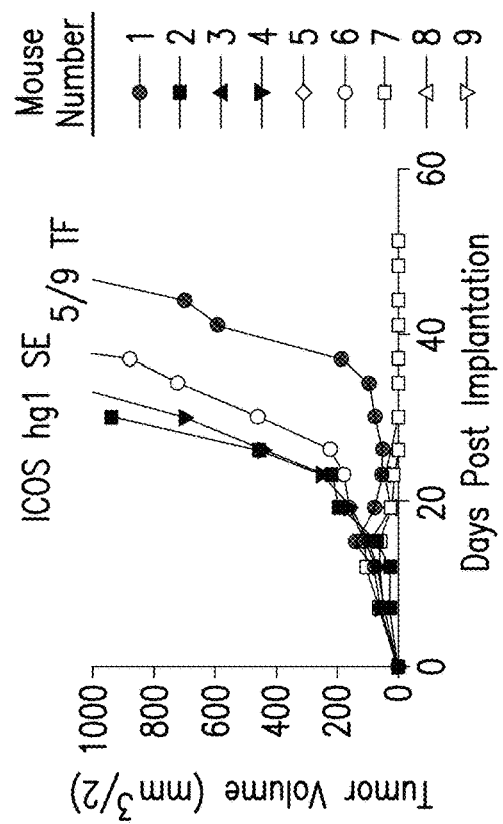
Figure 12E:
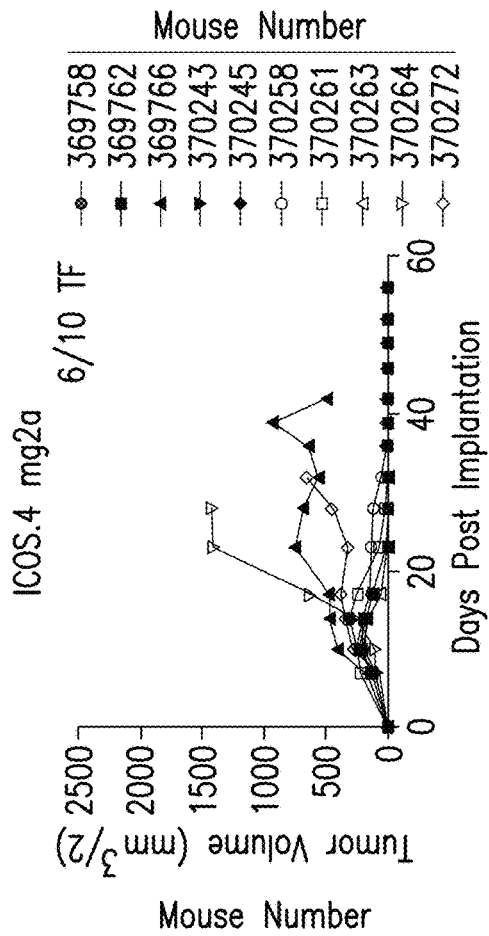
Figure 12D:
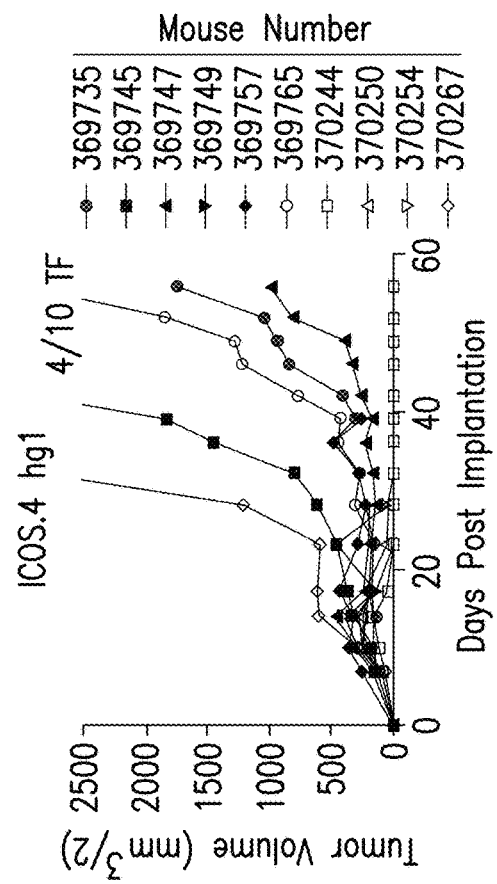

MC38 murine colon carcinoma cells were implanted subcutaneously in the right flanks of mice. Mice were divided into three treatment groups and dosed with 60 μg of (1) anti-ICOS IgG1 or (2) anti-ICOS IgG1 SE, or (3) IgG1 isotype control antibody (i.e., antibody of the same isotype as the ICOS antibody, but that does not bind any naturally-occurring murine protein, e.g., antibodies against KLH, diphtheria toxin, amongst others) on Days 7, 10, and 14 post implantation. Body weight and tumor size were measured twice weekly through study termination on Day 52. If tumors were ≥2000 mm$^3$ or appeared ulcerated, the animal was euthanized. Enhancement of antitumor activity was observed with anti-ICOS IgG1 SE mAb treatment at 60 μg per mouse; mean tumor growth inhibition (TGI) was 76% compared with 63% for anti-ICOS IgG1 without the SE modification, as shown in Table 14 and FIGS. 11A-C. No significant changes in body weight were associated with the treatments nor were any overt signs of clinical toxicity observed.

Results

In the human FcR-transgenic mice model, administration of ICOS IgG1 SE and ICOS IgG1 mAbs resulted in 76% and 63% mean tumor growth inhibition (TGI), respectively (as shown in Table 14). Five complete regressions were observed in each group at the dose level (60 μg/mouse) tested (Tables 14 and FIGS. 11A-C). No physical signs of toxicity or body weight loss were observed.

TABLE 14

Antitumor Activity of ICOS IgG1 Fc Variants

| Treatment (μg/mouse) | Mean % TGI on Day 30 | Complete Regressions[a] |
|---|---|---|
| IgG1 Isotype Control, 60 μg | N/A | 0/9 |
| Anti-ICOS.4 hg1[b], 60 μg | 63 | 5/9 |
| Anti-ICOS.4 hg1[c] SE, 60 μg | 76 | 5/9 |

[a]Complete regression = mouse with tumors <20 mm$^3$ for at least 3 measurements on last day of study.
[b]ICOS.4 with human IgG1
[c]ICOS.4 with human IgG1 and S267E mutation Conclusions In a Ravetch syngeneic tumor model study (summarized in Table 15), both anti-ICOS monotherapies promoted modest antitumor activity, with anti-ICOS IgG1 SE demonstrating slightly greater efficacy at Day 30 (76% vs. 63% mean TGI) (Table 14). No significant changes in body weight were associated with the treatments nor were any overt signs of clinical toxicity observed. Overall, anti-ICOS monotherapies promoted antitumor activity, with anti-ICOS IgG1 SE demonstrating slightly greater efficacy at Day 30 (76% vs. 63% mean TGI). Both treatments resulted in five mice rejecting their tumor. No significant changes in body weight were associated with the treatments nor were any overt signs of clinical toxicity observed.

TABLE 15

In vivo Pharmacology Studies

| Type of Study/ Species/Strain | Schedule/Route/Duration of Study/Vehicle/ Formulation | Range of Doses (μg/mouse) | Animals per group (M/F) |
|---|---|---|---|
| Antitumor activity MC38 tumor model/human FcγR transgenic C57/B6 mice | Antibodies administered IP on post-implantation Days 7, 10, and 14 Human IgG1 isotype control Anti-ICOS.4 hg1 Anti-ICOS.4 hg1 SE | 60 μg/mouse | 9 per group; mixed gender cohorts |

Example 7

Sa1N Tumor Model

The Sa1N fibrosarcoma mouse model was used to evaluate antitumor activity of chimeric anti-ICOS monoclonal antibodies. The ICOS.4 mIgG1 is a good surrogate for ICOS.33 IgG1 s S267E because this ICOS.4 variant preferentially binds to the mouse inhibitory Fc receptor. Because the tumor model is performed in a mouse expressing mouse Fc receptor, this makes the ICOS.4 variant a good surrogate for the human antibody. The ICOS.4 mIgG2a variant is a good surrogate for the ICOS.33 IgG1 antibody because this ICOS.4 variant is more similar to human IgG1, as it binds to the mouse activating Fc receptors. Furthermore, these variants were particularly relevant as surrogates, as no modifications were required in their variable regions, which already cross-reacted with both mouse and human ICOS protein. In contrast, anti-ICOS.1 murine IgG1 (mIgG1) D265A does not bind FcRs. An IgG1 antibody that does not bind to ICOS protein was used as an isotype control.

To evaluate antitumor activity in the Sa1N fibrosarcoma model after treatment with chimeric anti-ICOS surrogate monoclonal antibodies, Sa1N cells were implanted subcutaneously in the right flanks of mice. Mice were dosed with mAb in five treatment groups on Days 7, 10, and 14 post implantation:

(1) chimeric anti-ICOS.1 murine IgG1 (mIgG1) D265A,
(2) anti-ICOS.4 mIgG1
(3) anti-ICOS.4 hIgG1,
(4) anti-ICOS.4 mIgG2a, or
(5) IgG1 isotype control,
each at 10 mg/kg.

On Day 15, tumor and spleen were harvested from four mice per group for immuno-monitoring analysis. In the remaining mice, body weight and tumor size were measured twice weekly through study termination on Day 56. If tumors were ≥2000 mm$^3$ or appeared ulcerated, animals were euthanized.

On Day 23 post implantation, the last day when the median tumor growth inhibition (TGI) could be calculated based on 60% of treatment group animals remaining alive, the treatment efficacy of the anti-ICOS isotypes on Sa1N tumors was evident when compared with isotype control treatment. Median TGI values were 21% (ICOS.1 mIgG1 D265A), 55% (ICOS.4 mIgG1), 69% (ICOS.4 hIgG1), and 84% (ICOS.4 mIgG2a). No toxicity was apparent in any treatment group as demonstrated by mean and median body weight losses remaining below 20%.

Immuno-monitoring data indicated varying levels of intratumoral Treg depletion in all anti-ICOS isotypes. In addition, elevated levels of intratumoral CD8+ T cells were observed in all anti-mICOS.4 treatments.

Tumor responses were in part correlated with Treg reduction at Day 15, which agrees with the relative binding of these mAbs to Fc receptors. These data suggested that an anti-ICOS mAb that reduced Tregs would be more potent than one that does not.

Antitumor Treatment

On Day 7 post implantation (2 Feb. 2015), 70 mice were randomized to five groups of 14 mice according to tumor volume (L×W×H/2). Average tumor volumes were approximately 134 mm³ for each group. On Days 7, 10, and 14, isotype control or the designated mAb was administered. Mice were dosed intraperitoneally (IP).

Immuno Monitoring of T Cell Populations

To further study antitumor activity at the cellular level, immuno-monitoring was performed to look at subsets of immune cells in tumor sites and to determine whether a link exists between antibody treatment and changes in lymphoid cell populations. On Day 15, four mice from each treatment group were harvested by the animal facility operator for tumors and spleens. The tissues were first processed on a gentleMACS Octo Dissociator™ (Miltenyi, San Diego, Calif.) and then stained for different T cell markers. Samples were analyzed by flow cytometry on the Fortessa cytometer (BD Biosciences, San Jose, Calif.).

Post-Treatment Monitoring

The mice's tumors and body weights were measured twice weekly through study termination. Tumors were measured in three dimensions with an electronic digital caliper, and data was electronically recorded using StudyDirector software from Studylog Systems (South San Francisco, Calif.). Mice were checked daily for postural, grooming, and respiratory changes, as well as lethargy. Mice were euthanized when the tumors reached the 2000 mm³ endpoint or appeared ulcerated.

Results

Tumor Response

The last day all mice in the study were alive was Day 14 post implantation, the last day of IP dosing. As a result, mean tumor growth inhibition (TGI) could not be calculated. On Day 23 post implantation, the last day when median TGI could be calculated, the treatment efficacy of the anti-ICOS isotypes on Sa1N tumors was evident when compared with isotype control treatment. Median TGI values were 21% (ICOS.1 mIgG1 D265A), 55% (ICOS.4 mIgG1), 69% (ICOS.4 hIgG1), and 84% (ICOS.4 mIgG2a).

Figure 13B:
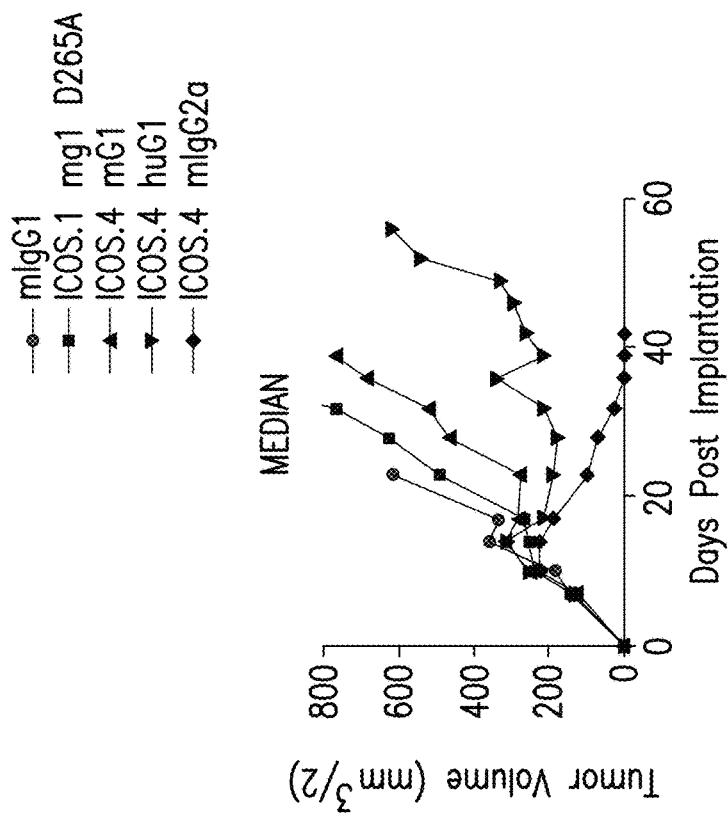
FIGS. 13A and 13B are graphs that illustrate mean and median tumor growth curves by treatment group. Mice were treated with isotype control mG1, ICOS.1 mg1 D265A, ICOS.4 mg1, ICOS.4 hg1, or ICOS.4 mg2a on days 7, 10, and 14 post-Sa1N cell implantation.
Figure 13A:
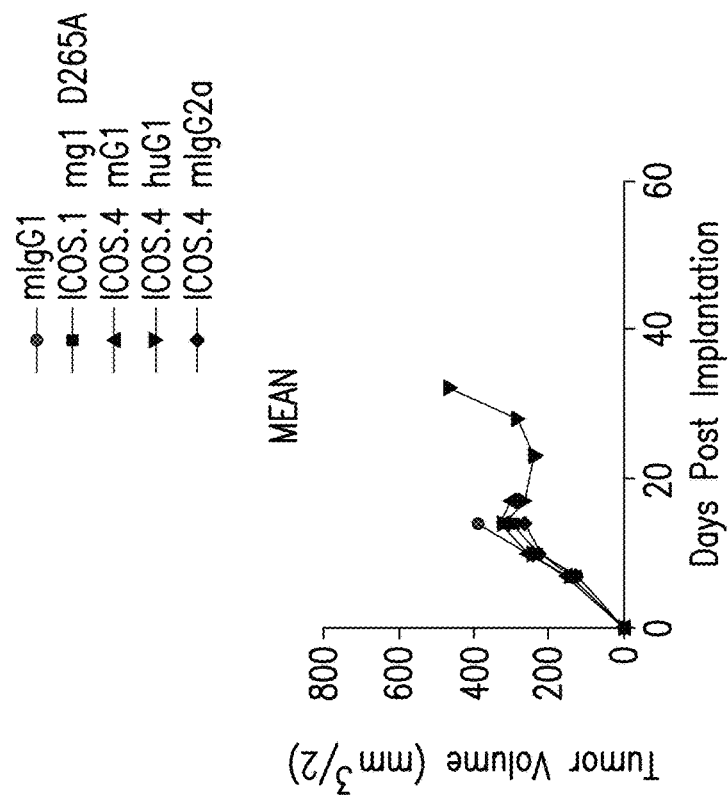
Figure 14A:
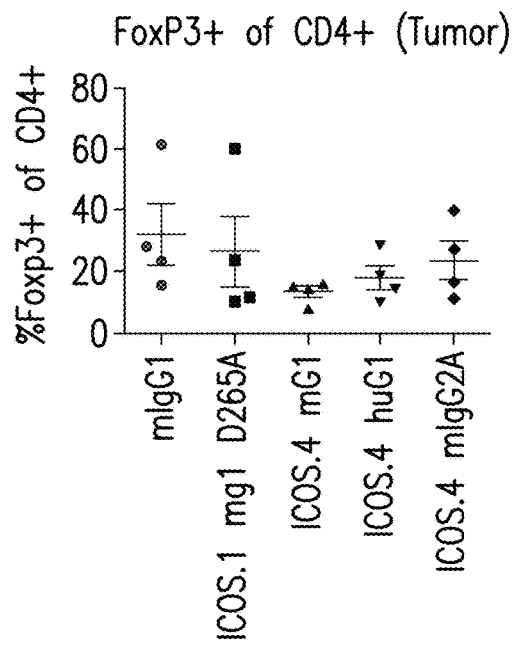
FIGS. 14A-D are graphs that show the percentage of Foxp3+ Treg cells, CD4+ Teff cells, and CD8+ T cells in tumors at Day 15. Mice were treated with isotype control mG1, ICOS.1 mg1 D265A, ICOS.4 mg1, ICOS.4 hg1, or ICOS.4 mg2a on days 7, 10, and 14 post-Sa1N cell implantation.
Figure 14B:
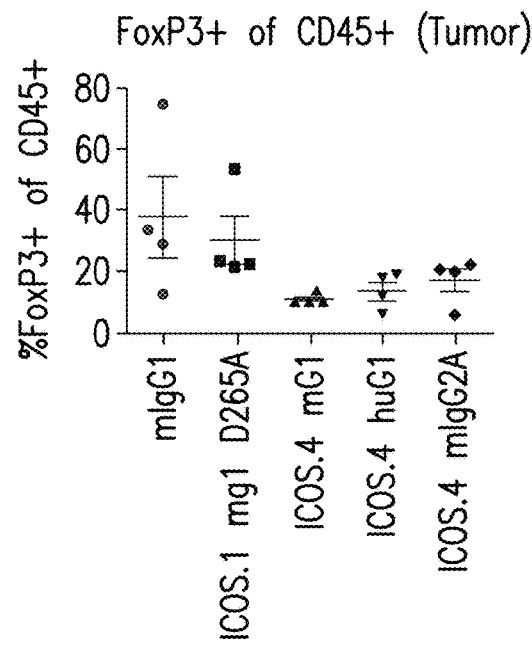
Figure 14C:
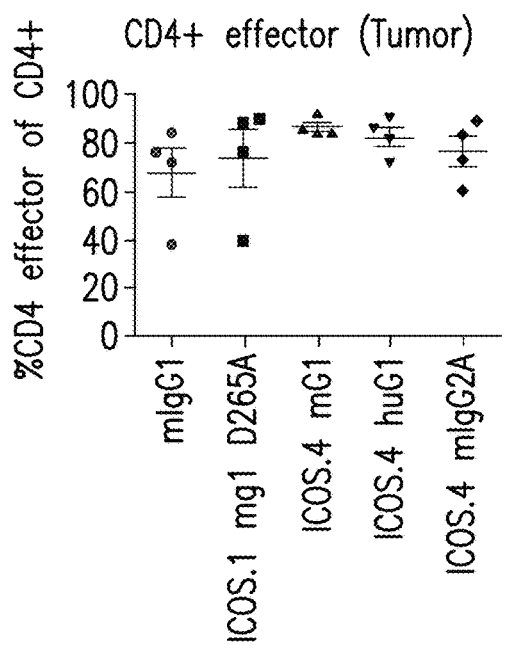
Figure 14D:
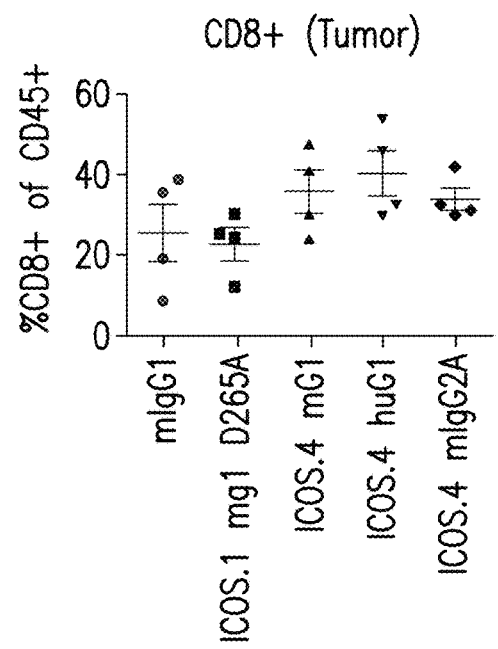
Figure 15G:
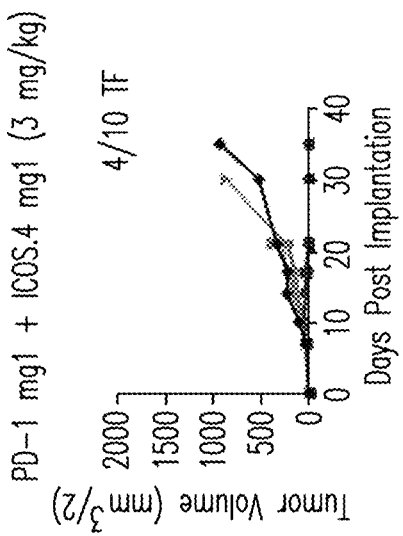
Figure 15H:
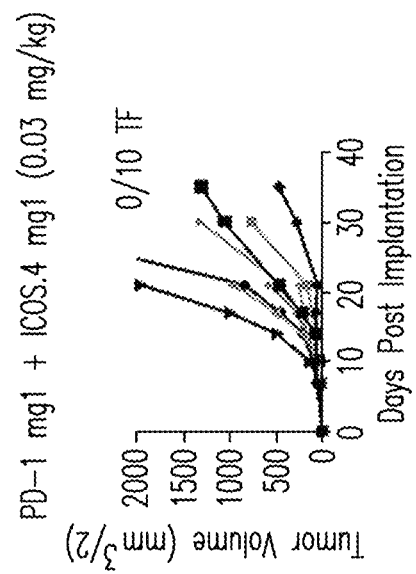
Figure 15I:
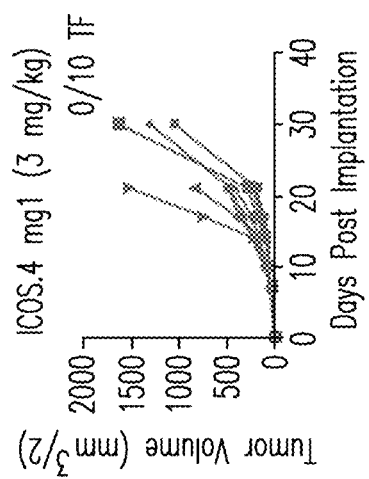
Figure 15J:
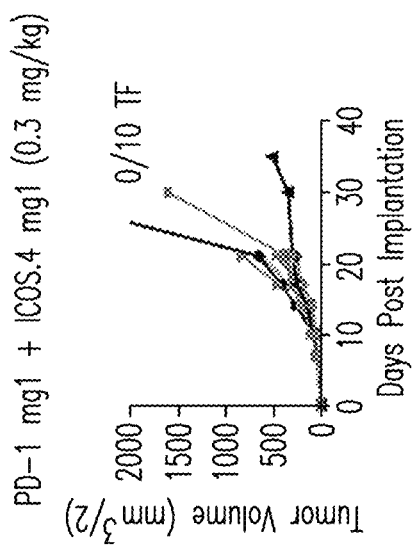

Tumor growth curves by treatment group are shown in FIGS. 12A-E. TGI is summarized by treatment group in Table 16. Mean and median tumor growth curves by treatment group are presented in FIGS. 13A and 13B.

The efficacy differences among the anti-ICOS isotypes demonstrated a hierarchy of mIgG2a>hIgG1>mIgG1>mIgG1 D265A. The inert mIgG1 D265A variant, which cannot bind FcR, exhibited some antitumor activity with 21% median TGI on Day 23. The unmodified mIgG1 isotype, which can engage the inhibitory Fc receptor, FcγRIIB, may potentiate agonism and in this study showed 55% median TGI on Day 23. Consistent with their higher TGI values, the mIgG2a and hIgG1 isotypes can bind murine activating receptors and mediate ADCC or antibody-dependent cellular phagocytosis (ADCP) of Tregs expressing ICOS. In addition, reduced levels of intratumoral Tregs have been associated with increased tumor regression in mouse tumor models. No toxicity was apparent in any treatment group, as the mean and median body weight changes were below 20%.

Changes in T Cell Populations

Treg depletion was observed at Day 15 in groups treated with mIgG2a and hIgG1 variants of the anti-ICOS.4 mAb since the percentages of Foxp3+ cells were significantly lower in these groups than in the isotype control group, as shown in FIGS. 14A-D. The same trend was also observed in the group treated with non-depleting anti-ICOS antibody (mIgG1). In addition, increased CD4+ effector T cells (Teffs) were evident in all of the treatment groups with the following ranking: mIgG1>hIgG1>mIgG2a. This observation suggested that some CD4+ Teffs, which are likely to be ICOS+, may have been depleted by the mIgG2a isotype, which has the highest depleting potential. Elevated levels of intratumoral CD8+ T cells were also observed in all anti-mICOS.4 treatments.

Conclusion

As summarized in Table 17, in a staged Sa1N syngeneic tumor model, chimeric anti-ICOS isotypes promoted varying levels of antitumor activity, ranging from 21% to 84% median TGI at Day 23. The antitumor potencies of isotype variants in this study ranked as follows: mIgG2a>hIgG1>mIgG1>mIgG1 D265A. Tumor responses were in part correlated with Treg depletion at Day 15, which agrees with the relative binding of these mAbs to Fc receptors.

Results from this study showed that choice of isotype is an important determinant of anti-ICOS antibody treatment. The anti-ICOS mIgG2a isotype, which binds activating Fcγ receptors equivalently to the human IgG1 isotype, was able to deplete intratumoral Tregs and showed the greatest efficacy in inhibiting tumor growth. Chimeric anti-ICOS isotype variants promoted varying levels of antitumor activity. Tumor responses were in part correlated with Treg depletion at Day 15, in agreement with the relative binding of these mAbs to Fc receptors. Results suggested mg2a promoted the best antitumor activity.

TABLE 16

Tumor Growth by Treatment Group

| | Day 14 | | Day 23 | |
|---|---|---|---|---|
| Treatment Group | Mean Tumor Volume (mm³) | TGI (%) | Median Tumor Volume (mm³) | TGI (%) |
| Isotype Control mIgG1, 10 mg/kg | 387 | N/A | 621 | N/A |
| Anti ICOS.1 mIgG1 D265A, 10 mg/kg | 295 | 24 | 493 | 21 |
| Anti ICOS.4 mIgG1, 10 mg/kg | 326 | 16 | 282 | 55 |
| Anti ICOS.4 hIgG1, 10 mg/kg | 322 | 17 | 190 | 69 |
| Anti ICOS.4 mIgG2a, 10 mg/kg | 264 | 32 | 101 | 84 |

TABLE 17

In vivo Pharmacology Studies

| Type of Study/ Species/Strain | Schedule/Route/ Duration of Study/ Vehicle/ Formulation | Range of Doses (μg/mouse) | Animals per group (M/F) |
|---|---|---|---|
| Antitumor activity of anti-ICOS isotype variants in the Sa1N tumor model with immunomonitoring | Antibodies administered IP on post-implantation Days 7, 10, and 14; Mouse IgG1 isotype control, Anti-ICOS.1 mIgG1 D265A, Anti-ICOS.4 mIgG1, | 10 mg/kg | 14 per group; F |

TABLE 17-continued

In vivo Pharmacology Studies

| Type of Study/<br>Species/Strain | Schedule/Route/<br>Duration of Study/<br>Vehicle/<br>Formulation | Range of<br>Doses<br>(μg/mouse) | Animals<br>per group<br>(M/F) |
|---|---|---|---|
| of immune<br>cell subsets/<br>A/J mice | Anti-ICOS.4 hIgG1,<br>Anti-ICOS.4 mIgG2a | | |

Example 8

Combination of Anti-ICOS Antibodies with an Anti-PD-1 Antibody

Study 1

To evaluate antitumor activity in the CT26 colorectal carcinoma model after treatment with an anti-ICOS surrogate monoclonal antibody, ICOS.4 (mouse IgG1 variant of the parental hamster antibody), at varying doses and/or anti-PD-1 mAb, CT26 cells were implanted subcutaneously in the right flanks of mice. When tumors reached 31 mm$^3$, mice were randomized into nine treatment groups of 10 to 14 mice each. Each mouse was dosed on post-implantation Days 7, 10, and 14 with mAb or an isotype control (i.e., an antibody of the same isotype, but that does not bind any naturally-occurring mouse protein, e.g., antibodies against KLH, diphtheria toxin, amongst others).

Mice were weighed and tumors were measured twice weekly through study termination at Day 35. If tumors were ≥2000 mm$^3$ or appeared ulcerated, animals were euthanized. On Day 15 after implantation, four mice in four treatment groups were sacrificed for spleen and tumor harvest. Tissues were processed into single cell suspensions, and cells were stained using flow cytometry antibodies to analyze T cell populations.

On Day 21 post implantation, the last day when the mean tumor growth inhibition (TGI) relative to the isotype control antibody could be calculated, TGI values for anti-ICOS monotherapy were 37% and 33% at 3 mg/kg and 10 mg/kg, respectively; TGI value for anti-PD-1 monotherapy was 22%. When anti-ICOS at 10 mg/kg, 3 mg/kg, or 1 mg/kg was combined with anti-PD-1 mAb, median TGI values >54% were observed. When anti-ICOS at 0.3, 0.1, or 0.03 mg/kg was combined with anti-PD-1 mAb, median TGI values <40 but >20% were observed. No toxicity was apparent in any treatment group.

Antibody Treatment

On Day 7 post-CT26 cell implantation, 120 mice were randomized to 10 groups of 10 to 14 mice each according to tumor volume. Groups had an average tumor volume of approximately 31 mm$^3$. Mice were dosed with the antibodies on Days 7, 10, and 14.

Post-Treatment Monitoring

Mice were checked daily for postural, grooming, and respiratory changes, as well as lethargy. Animals were weighed at least twice weekly and were euthanized if weight loss was ≥20%. The flanks of each animal were checked for the presence and size of tumors at least twice weekly until death, euthanasia, or end of the study period. Tumors were measured in three dimensions (length [L], width [W], and height [H]) with electronic digital calipers and recorded. Tumor volumes were calculated using the equation: Volume=(L×W×H×0.5). Response to treatment was measured as a function of tumor growth inhibition (TGI) and was calculated as: (reference mm$^3$−test article mm$^3$)/reference mm$^3$×100. When the tumor reached a volume greater than approximately 2000 mm$^3$ or appeared ulcerated, the animal was euthanized.

Immunomonitoring of T Cell Populations

To investigate the effect of ICOS antibody on T cell populations, tissues were harvested from four mice each in four treatment groups on Day 15 post-implantation. Spleens and tumors were homogenized on a gentleMACS Octo Dissociator™ (Miltenyi, San Diego, Calif.). Single-cell suspensions were stained for T cell markers using fluorochrome-conjugated antibodies. Antibody fluorescence was detected by flow cytometry on a Fortessa cytometer (BD Biosciences, San Jose, Calif.), and the results were analyzed using FlowJo software (FlowJo, LLC, Ashland, Oreg.).

Statistical Analysis

Figure 16B:
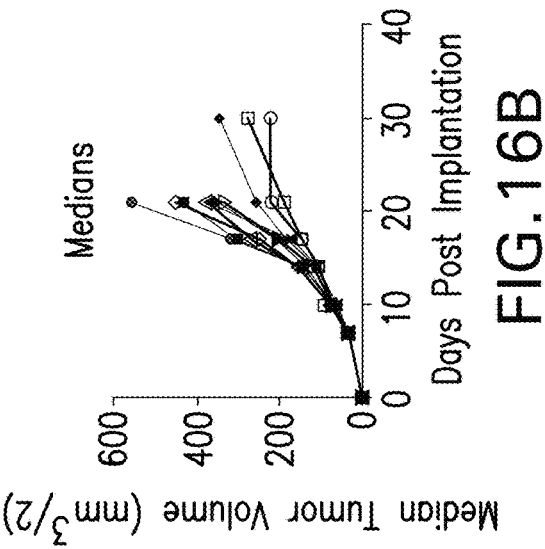
FIGS. 16A and 16B are graphs that show the mean and median tumor growth curves by treatment group: isotype control mIgG1, anti-PD-1 mg1, and/or anti-ICOS.4 mIgG1 ("ICOS.4 mg1") antibodies.
Figure 16A:
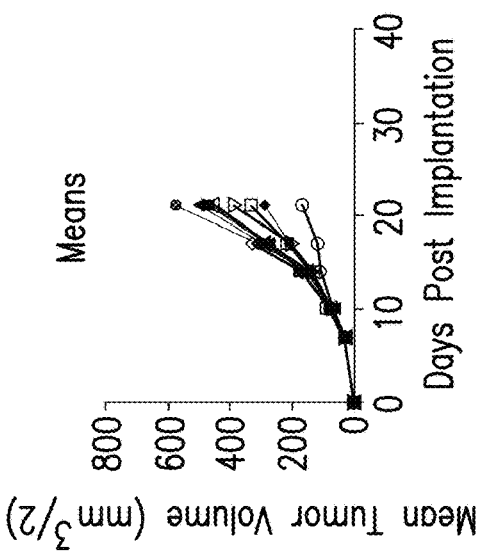

The mean, standard deviation (SD), and median values of tumor sizes and the mean body weight values were calculated. The mean value was calculated while 100% of study animals remained alive; and the median value was calculated while at least 60% of study animals remained alive. One-way analysis of variance (ANOVA) was used to determine whether means between treatment groups were statistically significantly different; p values 0.05 were considered significantly different. GraphPad Prism® Version 5.01 software (GraphPad Software, La Jolla, Calif.) was used to plot data and determine statistical differences between groups. Tumor growth curves for individual mice by treatment group can be seen in FIGS. 15A-J. Mean and median tumor growth curves by treatment group are presented in FIGS. 16A and 16B.

Results

Tumor Growth Inhibition

On Day 21 post tumor implantation, the last day when the median TGI could be calculated, mice treated with anti-ICOS.4 mIgG1 as monotherapy at 10 mg/kg showed 33% median TGI relative to control mIgG1 antibody-treated mice. Mice treated with anti-ICOS.4 mIgG1 monotherapy at 3 mg/kg showed 37% TGI and single-agent anti-PD-1 4H2 mAb showed 22% TGI. At the end of the study period (Day 35), proportions of tumor-free mice were 0/10 in the control antibody group, 0/10 in the anti-PD-1 group, 1/10 in the anti-ICOS.4 mIgG1 group at 10 mg/kg, and 0/10 in the anti-ICOS.4 mIgG1 group at 3 mg/kg. The combination of anti-mouse PD-1 with anti-ICOS.4 mIgG1 at various doses (10, 3, or 1 mg/kg) showed antitumor activity superior to that of either monotherapy (TGI values 54%, 60%, and 66%, respectively). The numbers of tumor-free mice at the end of study were the same in these groups (1/10 tumor-free mice) with the exception of the 3 mg/kg dose which had 4/10 tumor-free mice. In addition, median TGI was also calculated over the 21 days using the relative difference in the area under the effect curve between control and treatment groups (Table 18).

TABLE 18

Tumor Growth Inhibition by Treatment Group (Relative to Isotype Control)

| | | Day 21 | |
|---|---|---|---|
| Treatment Group | Day 35<br>Tumor<br>Free<br>Mice | Median<br>Tumor<br>Volume<br>(mm$^3$) | Median<br>TGI$^a$ | Median<br>TGI<br>(over 21<br>days)$^b$ |
| 10 mg/kg mIgG1 control mAb | 0/10 | 558 | — | — |
| 10 mg/kg anti-PD-1 4H2 mAb | 0/10 | 433 | 22% | 11% |

TABLE 18-continued

Tumor Growth Inhibition by Treatment Group
(Relative to Isotype Control)

| Treatment Group | Day 35 Tumor Free Mice | Median Tumor Volume (mm³) | Day 21 Median TGI[a] | Median TGI (over 21 days)[b] |
|---|---|---|---|---|
| 10 mg/kg anti-ICOS.4 mIgG1 mAb | 0/10 | 376 | 33% | 42% |
| 3 mg/kg anti-ICOS.4 mIgG1 mAb | 0/10 | 349 | 37% | 29% |
| 10 mg/kg anti-ICOS.4 mIgG1 mAb + 10 mg/kg anti-PD-1 4H2 mAb | 1/10 | 256 | 54% | 42% |
| 3 mg/kg anti-ICOS.4 mIgG1 mAb + 10 mg/kg anti-PD-1 4H2 mAb | 4/10 | 222 | 60% | 44% |
| 1 mg/kg anti-ICOS.4 mIgG1 mAb + 10 mg/kg anti-PD-1 4H2 mAb | 1/10 | 190 | 66% | 48% |
| 0.3 mg/kg anti-ICOS.4 mIgG1 mAb + 10 mg/kg anti-PD-1 4H2 mAb | 0/10 | 377 | 32% | 14% |
| 0.1 mg/kg anti-ICOS.4 mIgG1 mAb + 10 mg/kg anti-PD-1 4H2 mAb | 2/10 | 333 | 40% | 28% |
| 0.03 mg/kg anti-ICOS.4 mIgG1 mAb + 10 mg/kg anti-PD-1 4H2 mAb | 0/10 | 452 | 19% | 21% |

Figure 17B:
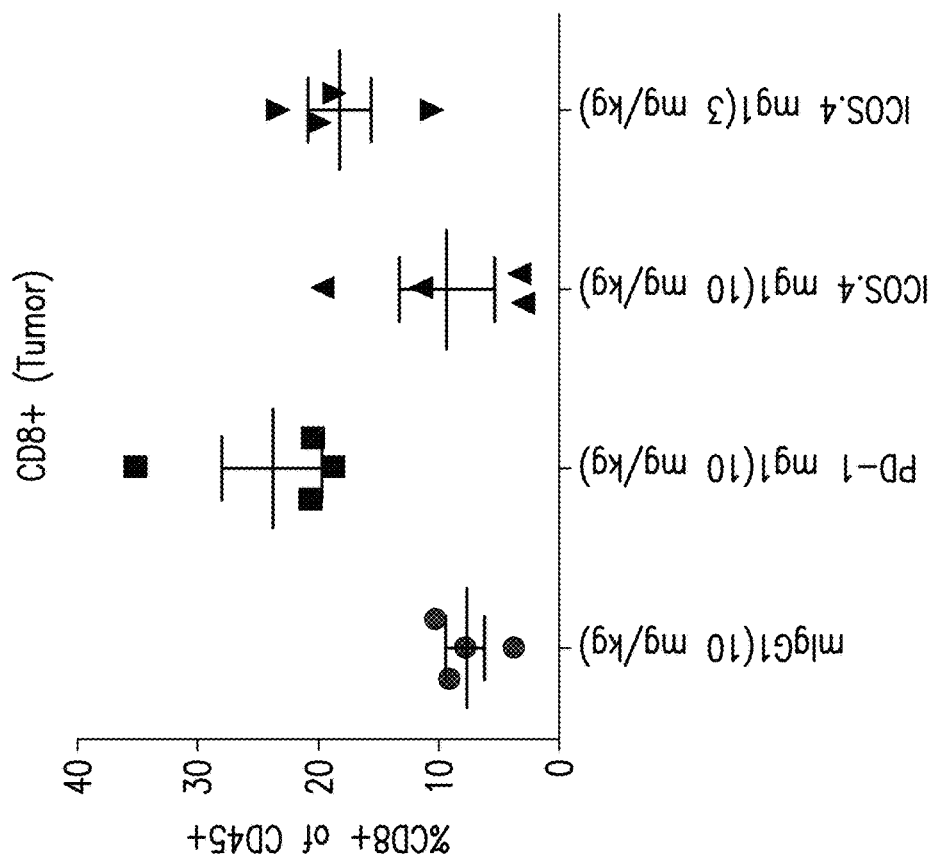
FIGS. 17A-D are graphs that show the mean (SEM) percentages of Foxp3+, CD8+, Ki-67, and Granzyme B in tumors. Mice were treated with isotype control mIgG1, anti-PD-1 mg1, and/or anti-ICOS.4 mIgG1 ("ICOS.4 mg1") antibodies.
Figure 17A:
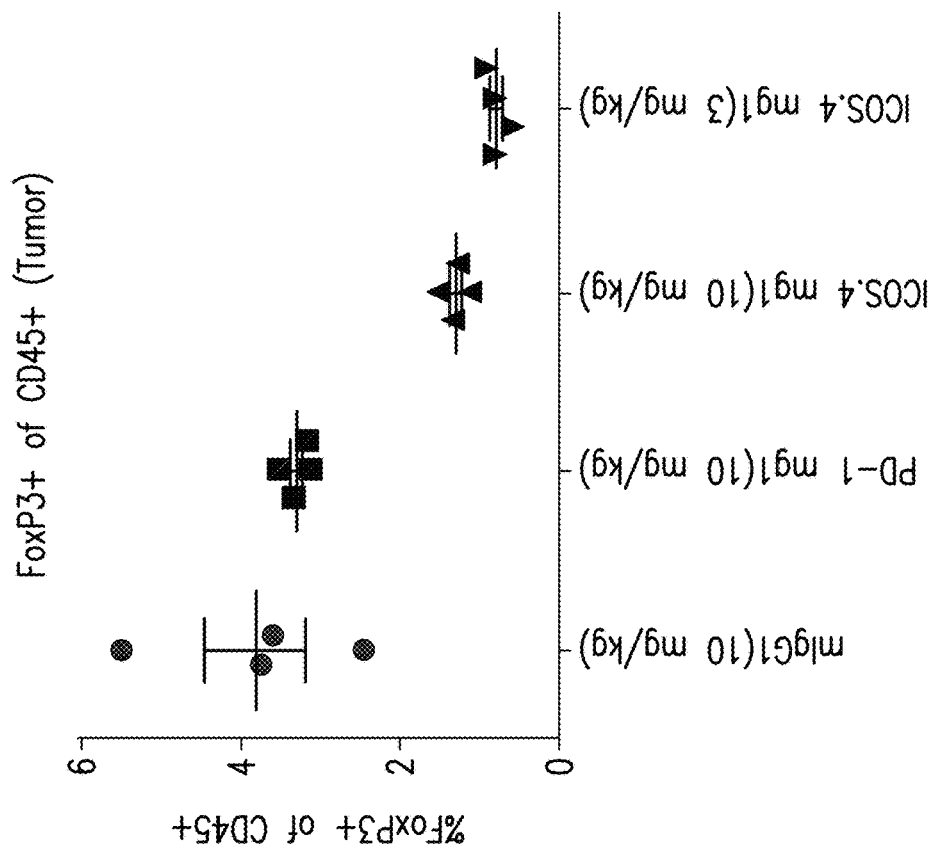

[a]% Median TGI was calculated on Day 21
[b]% Median TGI (over 21 days) was calculated using the relative difference in the area under the effect curve between control and treatment group over 21 days Immunomonitoring Analysis Immunomonitoring was performed at Day 15 post-implantation in certain treatment groups (FIGS. 17A-D). A depletion of Foxp3+ Tregs on tumor-infiltrating lymphocytes (TILs) was observed in the single-agent anti-ICOS.4 mIgG1 treated groups (10 mg/kg and 3 mg/kg) (FIG. 17A). The mice treated with anti-PD-1 mIgG1 did not show a reduction in TIL Tregs. The groups treated with anti-PD1 mIgG1 or anti-ICOS.4 at 3 mg/kg also showed an increase in the CD8+ T cell subset in TILs (FIG. 17B). At 10 mg/kg, the single-agent anti-ICOS.4 treatment seemed to have the similar levels of this subset compared with the control group.

Figure 17D:
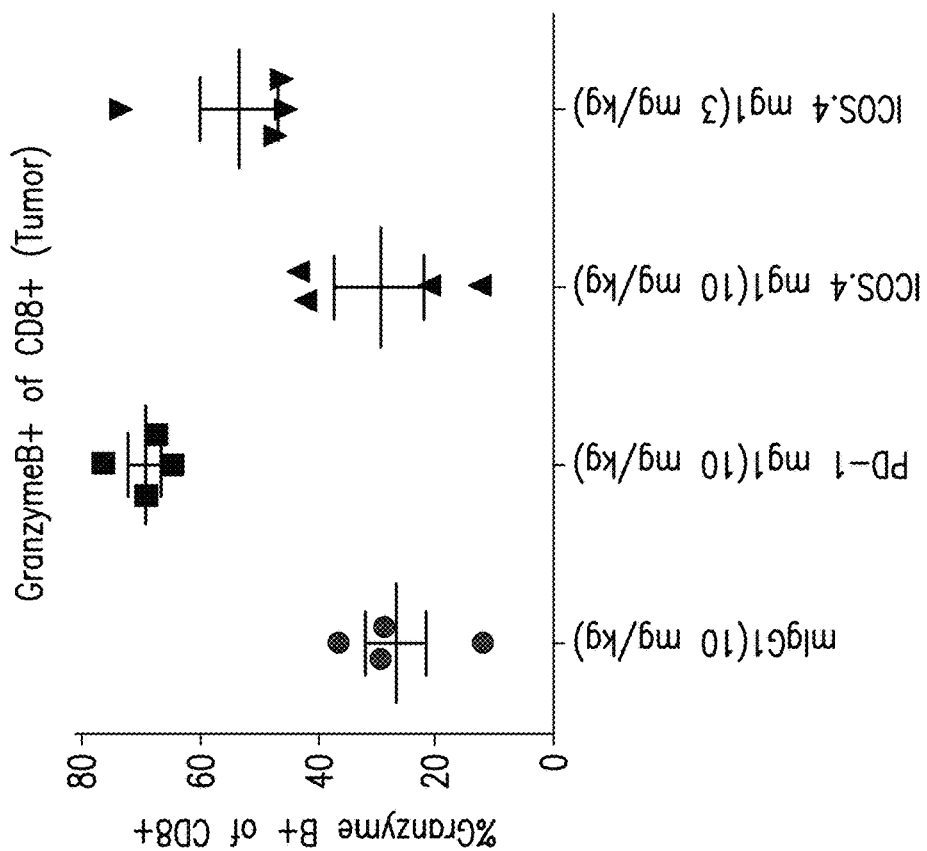
Figure 17C:
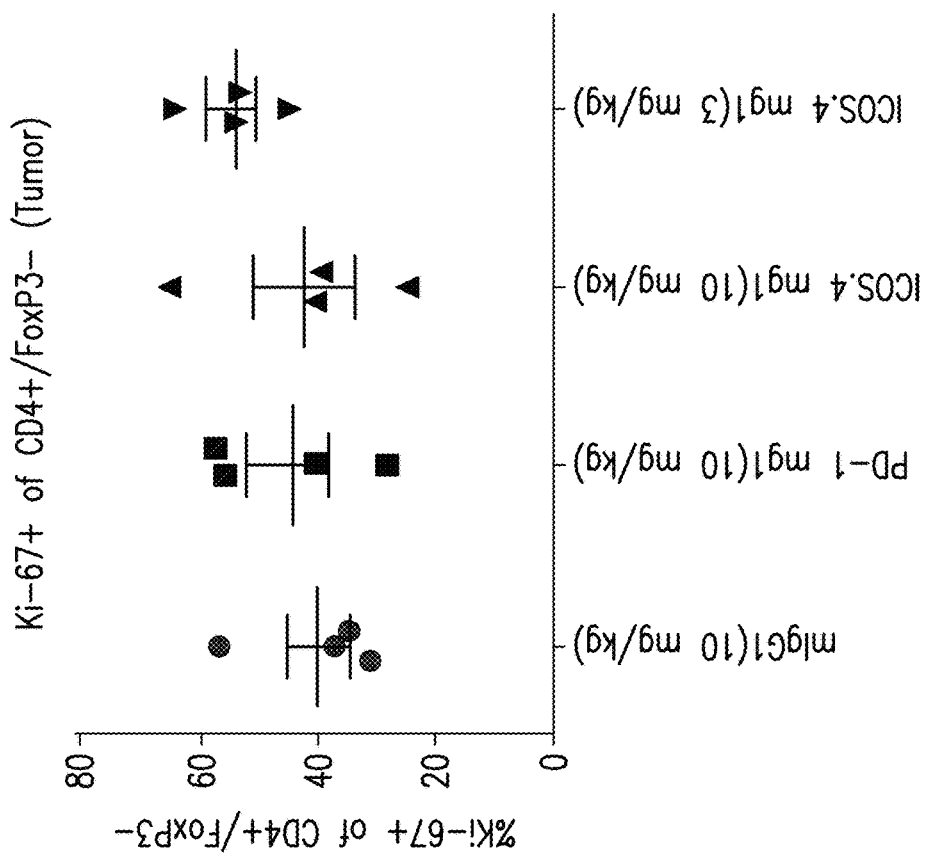
Figure 18A:
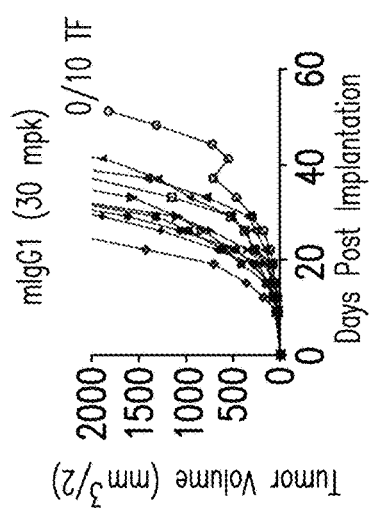
FIGS. 18A-I are graphs that show the tumor growth curves for individual mice by treatment group: isotype control mIgG1, anti-PD-1 mIgG1 D265A ("PD-1"), and/or anti-ICOS.4 mIgG1 ("ICOS") antibodies.
Figure 18B:
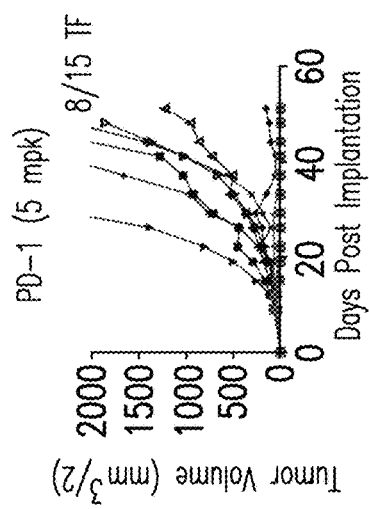
Figure 18C:
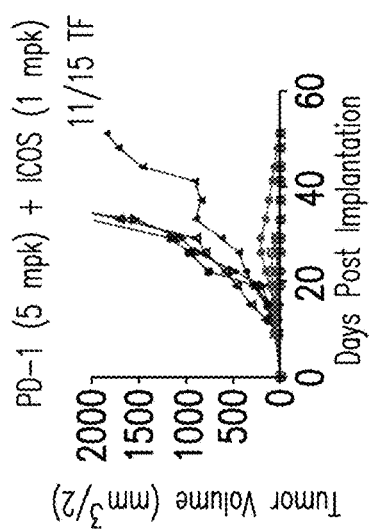
Figure 18D:
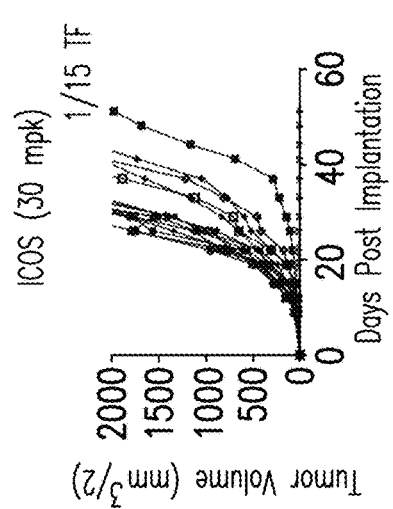
Figure 18E:
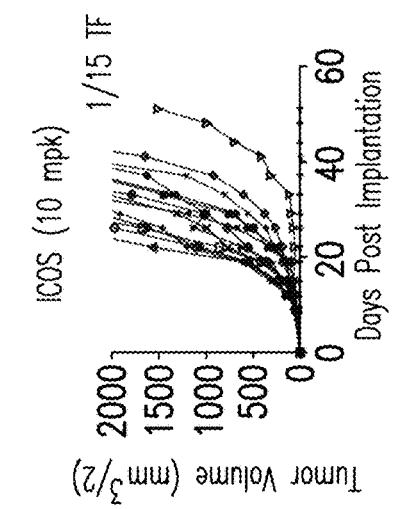
Figure 18F:
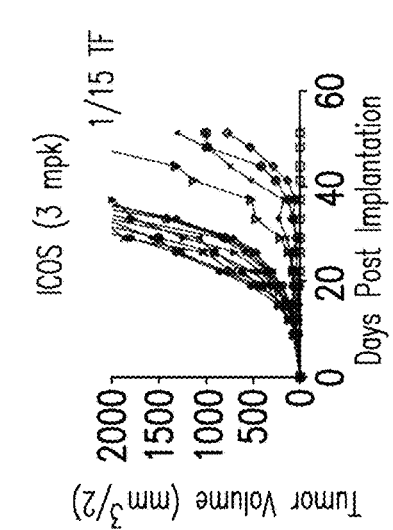
Figure 18I:
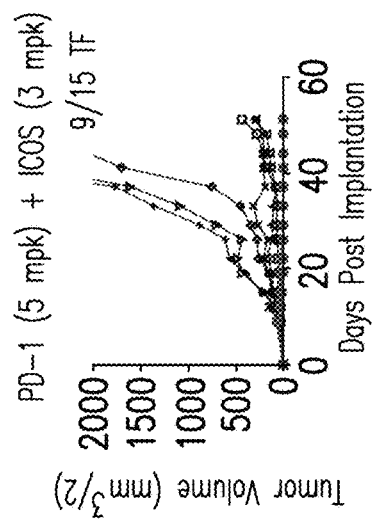
Figure 18H:
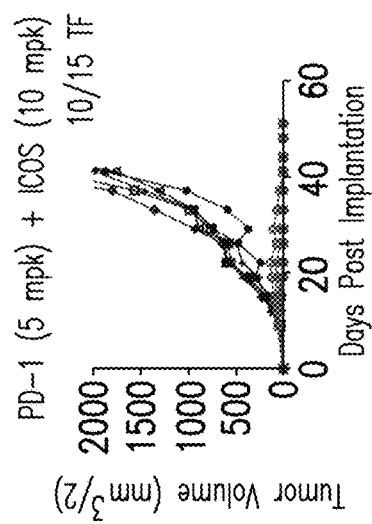
Figure 18G:
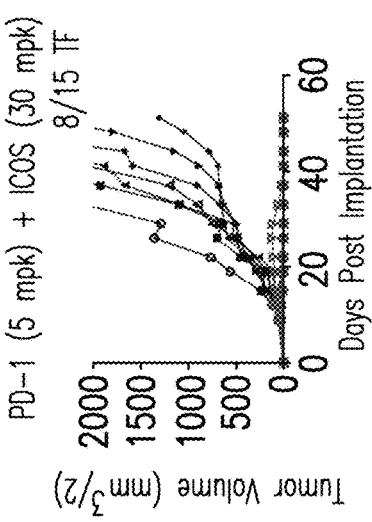

Levels of Ki-67, a marker for cell proliferation, were increased in the CD4+ effector T cell subset after single-agent treatment with anti-ICOS.4 mIgG1 at 3 mg/kg (FIG. 17C). The percent of cells positive for granzyme B, a marker for cytolytic activity on CD8+ T cells, was also found to be higher in groups treated with either anti-ICOS mIgG1 at 3 mg/kg or with anti-PD-1 alone (FIG. 17D).

Conclusion

In a staged CT26 syngeneic tumor model, anti-ICOS.4 mIgG1 as a monotherapy demonstrated more potent TGI when anti-ICOS.4 mIgG1 was dosed at 3 mg/kg (37% TGI on Day 21, 0/10 tumor-free mice) vs. 10 mg/kg (33% TGI on Day 21, 0/10 tumor-free mice). Immunomonitoring data showed a higher percentage of CD8+ T cells, higher Ki-67 levels in CD4+ effectors, and higher granzyme B levels in CD8+ T cells in the anti-ICOS mIgG1 3 mg/kg treatment group than in the 10 mg/kg treatment group. These data suggest that for anti-ICOS monotherapy, a 3 mg/kg dose has more antitumor activity than a 10 mg/kg dose.

The combination treatment of anti-ICOS.4 mIgG1 mAb at 10 mg/kg, 3 mg/kg, and 1 mg/kg, with anti-PD-1 mIgG1 resulted in median TGI values >54%, with 1/10 mice tumor free for these treatment groups, except anti-ICOS.4 at 3 mg/kg, which had 4/10 mice tumor free. These results suggest comparable levels of antitumor activity of the anti-ICOS mIgG1 in combination with anti-PD-1 mIgG1 treatments at the three highest doses.

Study 2

This study was designed to evaluate antitumor activity in the CT26 colorectal carcinoma model after treatment with an anti-ICOS surrogate monoclonal antibody, ICOS.4 (mouse IgG1 variant of the parental hamster antibody) at varying doses and/or anti-PD-1 mAb. CT26 cells were implanted subcutaneously in the right flanks of mice. When tumors reached 45 mm³, mice were randomized into nine treatment groups of 15 to 20 mice each. Each mouse was dosed on post-implantation Days 9, 12, and 15 with mAb or irrelevant isotype control. Mice were weighed and tumors were measured twice weekly through study termination at Day 51. If tumors were >2000 mm³ or appeared ulcerated, animals were euthanized. Whole blood samples were taken from mice at various time points (Day 9, Day 15, and Day 16 post-tumor implantation) for analysis. On Day 16 after tumor implantation, five mice in eight treatment groups were sacrificed for spleen and tumor harvest. Tissues were processed into single cell suspensions, and cells were stained using flow cytometry antibodies to analyze T cell populations.

On Day 29 post-tumor implantation, the last day when the mean tumor growth inhibition (TGI) relative to the isotype control antibody could be calculated, TGI values for anti-ICOS monotherapy were 5% at 30 mg/kg and 33% at 3 mg/kg; anti-PD-1 monotherapy showed a TGI value of 74%. When anti-ICOS at 30 mg/kg, 10 mg/kg, 3 mg/kg, or 1 mg/kg was combined with anti-PD-1 mAb, mean TGI values >74% were observed. No toxicity was apparent in any treatment group.

Antibody Treatment

On Day 9 post-tumor implantation, 200 mice were randomized to nine groups of 15 to 20 mice each according to tumor volume. Groups had an average tumor volume of approximately 45 mm³. Mice were dosed with the antibodies on Days 9, 12, and 15.

Post-Treatment Monitoring

Animals were checked daily for postural, grooming, and respiratory changes, as well as lethargy. Animals were weighed at least twice weekly and were euthanized if weight loss was ≥20%. The flanks of each animal were checked for the presence and size of tumors at least twice weekly until death, euthanasia, or end of the study period. Tumors were measured in three dimensions (length [L], width [W], and height [H]) with electronic digital calipers and recorded. Tumor volumes were calculated using the equation: Volume=(L×W×H×0.5). Response to treatment was measured as a function of tumor growth inhibition (TGI) and was calculated as: (reference mm³−test article mm³)/reference mm³×100. When the tumor reached a volume greater than approximately 2000 mm³ or appeared ulcerated, the animal was euthanized.

Immunomonitoring of T Cell Populations

Various methods were used to investigate the effect of ICOS antibody on T and B cell populations. Whole blood samples were taken from mice at various time points (Day 9, Day 15, and Day 16) and then processed for analysis. Additionally, tissues were harvested from five mice each in eight treatment groups on Day 16 post-implantation. Spleens and tumors were homogenized on a gentleMACS Octo Dissociator™ (Miltenyi, San Diego, Calif.). Single-cell suspensions were stained for T cell markers using the fluorochrome-conjugated antibodies. Antibody fluorescence was detected by flow cytometry on a Fortessa cytometer (BD Biosciences, San Jose, Calif.), and the results were analyzed using FlowJo software (FlowJo, LLC, Ashland, Oreg.).

Statistical Analysis

Figure 19A:
FIGS. 19A and 19B are graphs that show the mean and median tumor growth curves by treatment group: isotype control mIgG1, anti-PD-1 mIgG1 D265A ("PD-1"), and/or anti-ICOS.4 mIgG1 ("ICOS") antibodies.
Figure 19B:
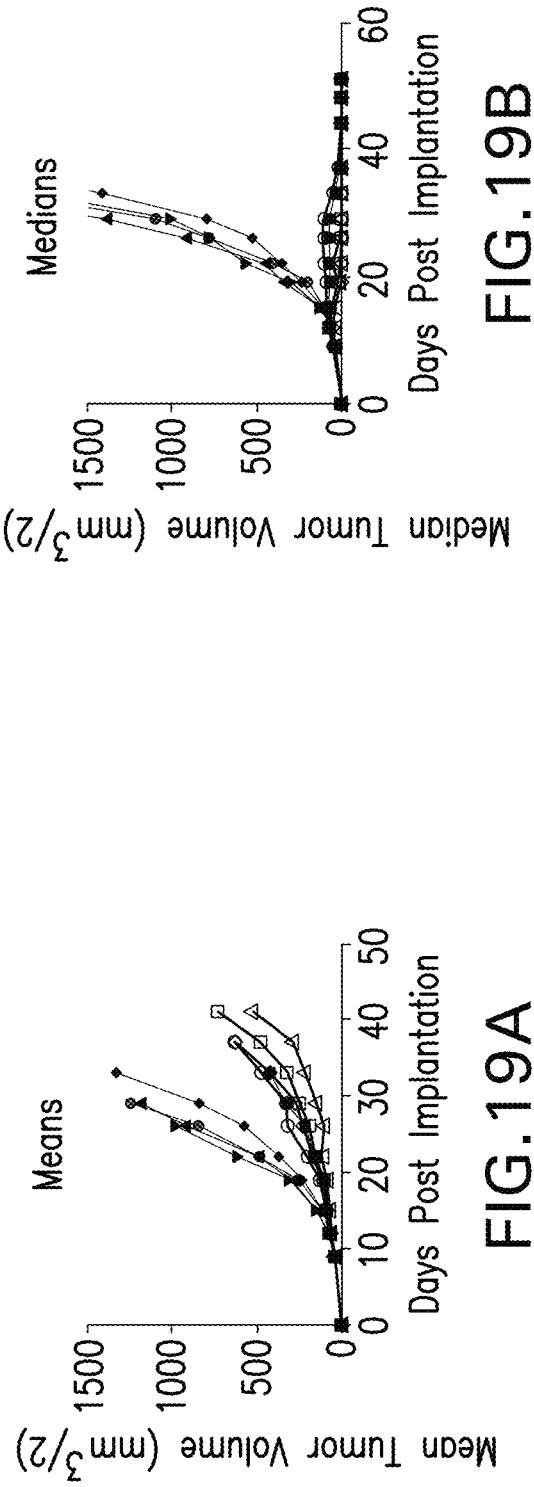

The mean, standard deviation (SD), and median values of tumor sizes and the mean body weight values were calculated. The mean value was calculated while 100% of study animals remained alive; the median value was calculated while at least 60% of study animals remained alive. One-way analysis of variance (ANOVA) was used to determine whether means between treatment groups were statistically significantly different; p values 0.05 were considered significantly different. GraphPad Prism® Version 7.02 software (GraphPad Software, La Jolla, Calif.) was used to plot data and determine statistical differences between groups. Tumor growth curves for individual mice by treatment group can be seen in FIGS. 18A-I. Mean and median tumor growth curves by treatment group are presented in FIGS. 19A and 19B.

Results

Tumor Growth Inhibition

At Day 29 post-tumor implantation, the last day the mean TGI could be calculated, the treatment efficacy of the anti-ICOS mAb therapies on CT26 tumors was observed as both monotherapy and in combination with anti-PD-1 mAb (Table 19). Mice treated with anti-ICOS.4 mIgG1 monotherapy at 3 mg/kg showed 33% TGI and single-agent anti-PD-1 4H2 mAb showed 74% TGI. At the end of the study period (Day 51), the number of tumor-free mice were 0/10 in the control antibody group, 8/15 in the anti-PD-1 group, and 1/15 across all anti-ICOS.4 mIgG1 doses (30 mg/kg, 10 mg/kg, or 3 mg/kg). The combination of anti-PD-1 with anti-ICOS.4 mIgG1 at various doses (30 mg/kg, 10 mg/kg, 3 mg/kg, and 1 mg/kg) showed antitumor activity superior or equal to that of the monotherapy (TGI values 74%, 80%, 87%, and 78% respectively). The number of tumor-free mice at the end of study ranged from 8-11/15 across the four combination groups.

TABLE 19

Tumor Growth Inhibition by Treatment Group (Relative to Isotype Control)

| Treatment Group | Day 29 | |
|---|---|---|
| | Mean Tumor Volume (mm³) | Mean % TGI |
| 30 mg/kg mIgG1 control mAb | 1248 | N/A |
| 5 mg/kg anti-PD-1 4H2 mAb | 327 | 74% |
| 30 mg/kg anti-ICOS.4 mIgG1 mAb | 1182 | 5% |
| 10 mg/kg anti-ICOS.4 mIgG1 mAb | N/A | N/A |
| 3 mg/kg anti-ICOS.4 mIgG1 mAb | 838 | 33% |
| 30 mg/kg anti-ICOS.4 mIgG1 mAb + 5 mg/kg anti-PD-1 4H2 mAb | 328 | 74% |
| 10 mg/kg anti-ICOS.4 mIgG1 mAb + 5 mg/kg anti-PD-1 4H2 mAb | 252 | 80% |
| 3 mg/kg anti-ICOS.4 mIgG1 mAb + 5 mg/kg anti-PD-1 4H2 mAb | 158 | 87% |
| 1 mg/kg anti-ICOS.4 mIgG1 mAb + 5 mg/kg anti-PD-1 4H2 mAb | 271 | 78% |

Immunomonitoring Analysis

Figure 20B:
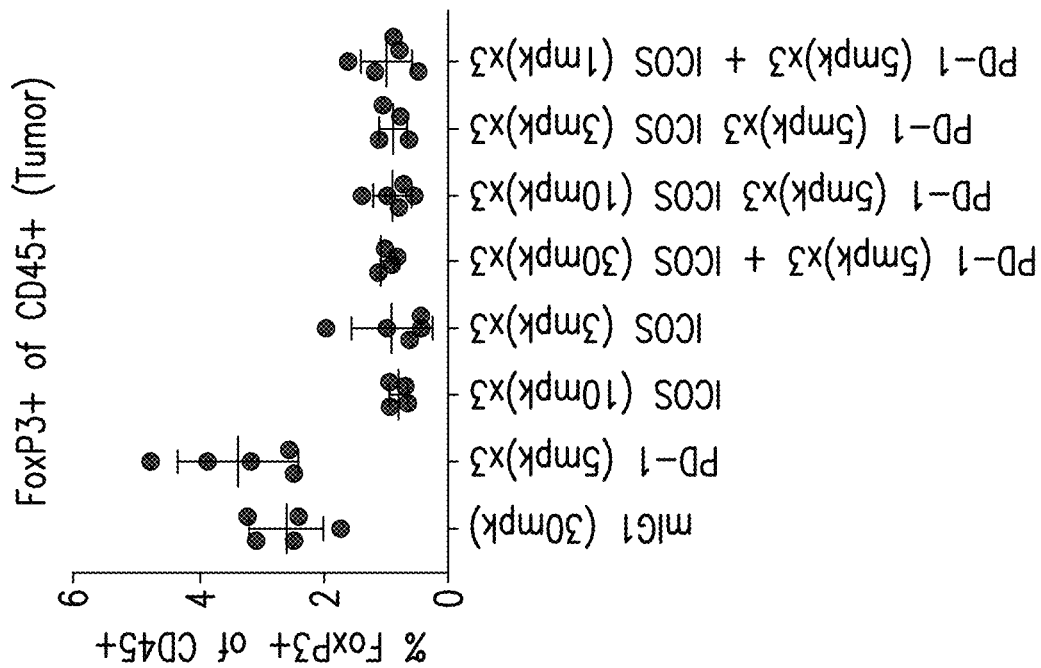
FIGS. 20A-D are graphs that show the percentage of Foxp3+ Treg cells, CD4+ Teff cells, and CD8+ T cells in tumors. Mice were treated with isotype control mIgG1, anti-PD-1 mIgG1 D265A ("PD-1"), and/or anti-ICOS.4 mIgG1 ("ICOS") antibodies.
Figure 20A:
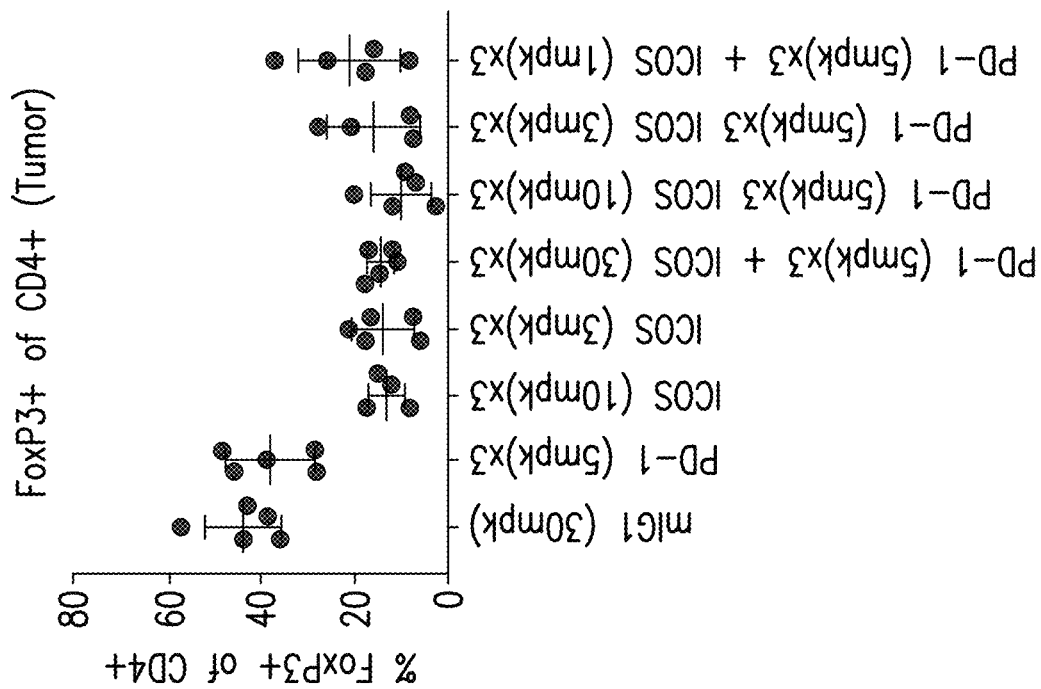
Figure 20D:
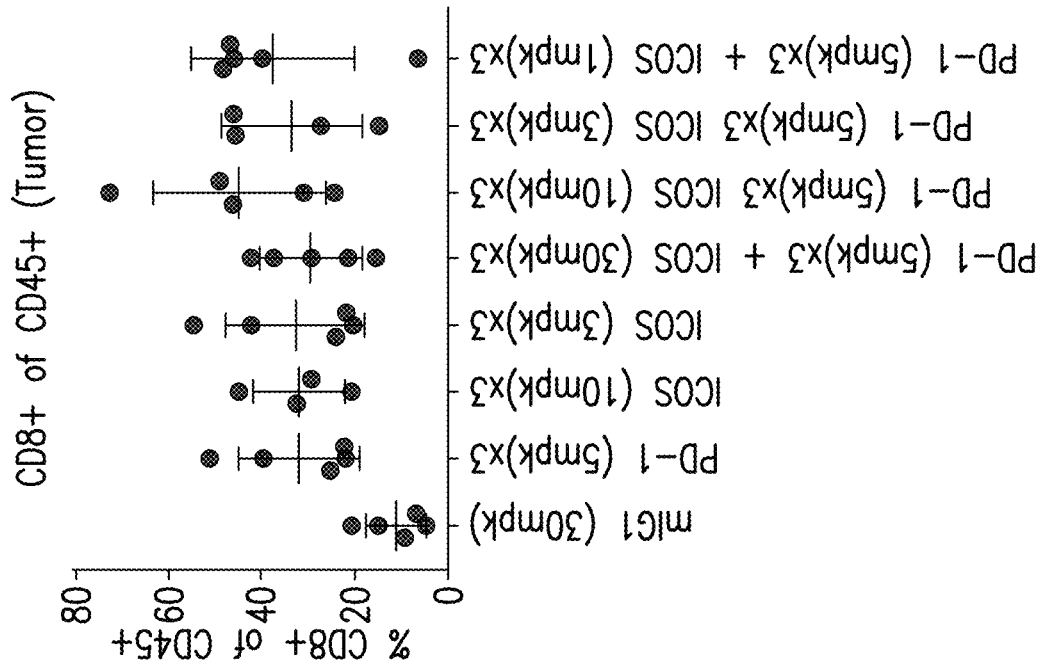
Figure 20C:
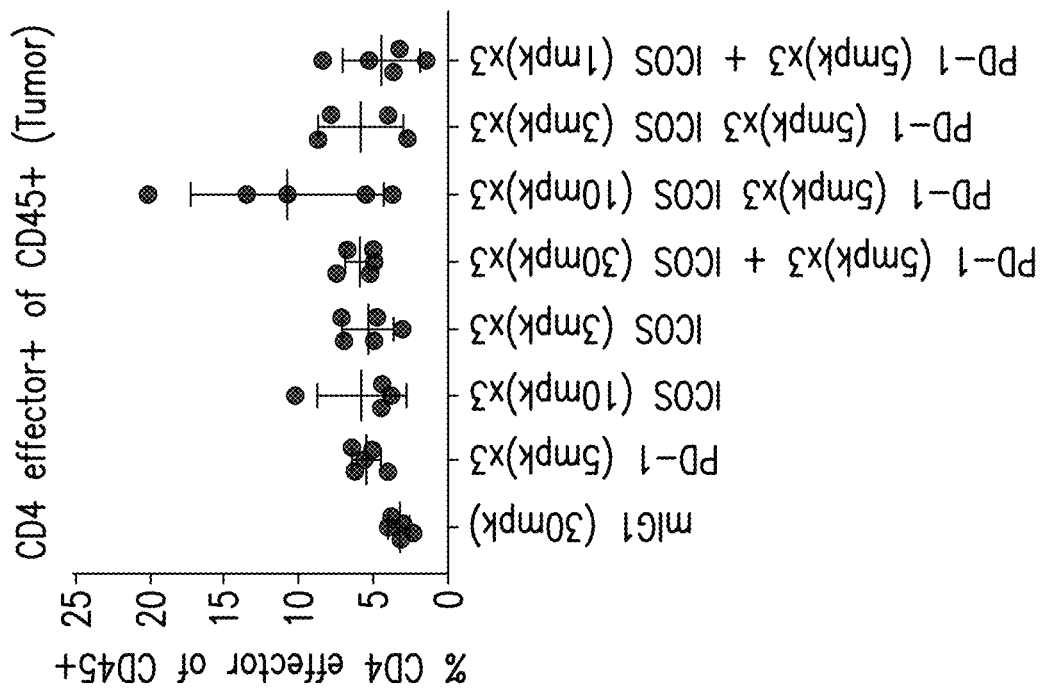

Immunomonitoring was performed at various time points post-implantation in certain treatment groups (FIGS. 20A-D). On Day 16 post-tumor implantation, a depletion of FoxP3+ Tregs on tumor-infiltrating lymphocytes (TILs) was observed in all groups treated with anti-ICOS.4 mIgG1 mAb (FIGS. 20A and 20B). The CT26 tumor-bearing mice treated with anti-PD-1 mIgG1 alone did not show a reduction in TIL Tregs. Although more variable, CD8+ T cells increased on TILs in all treatment groups versus control (FIG. 20D).

Figure 21B:
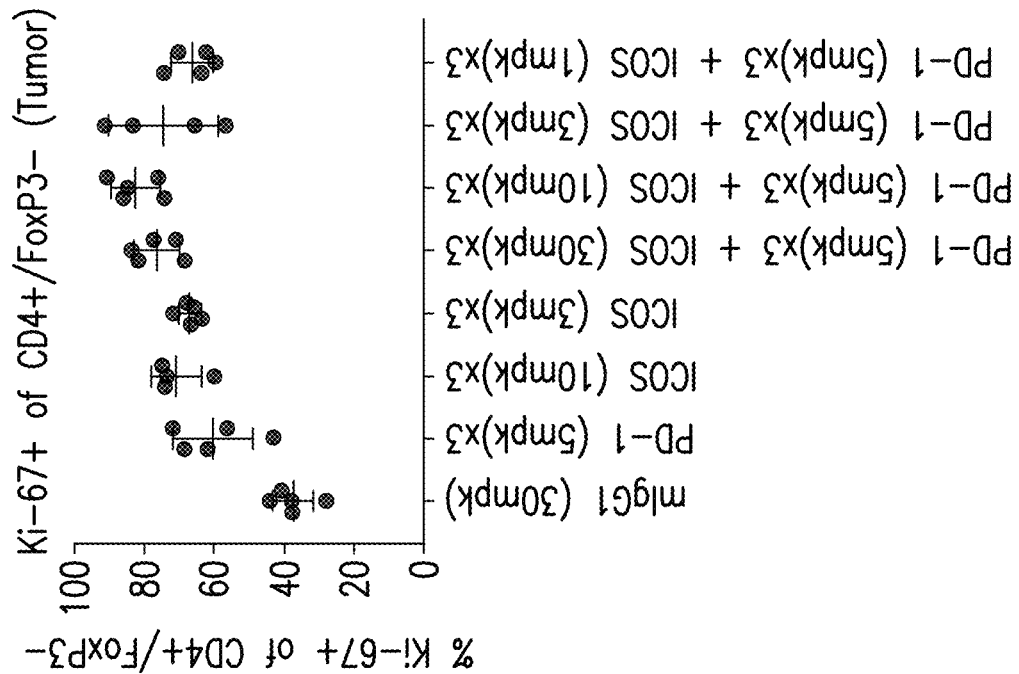
FIGS. 21A-C are graphs that show the mean percentages of Ki-67 in tumors. Mice were treated with isotype control mIgG1, anti-PD-1 mIgG1 D265A ("PD-1"), and/or anti-ICOS.4 mIgG1 ("ICOS") antibodies.
Figure 21A:
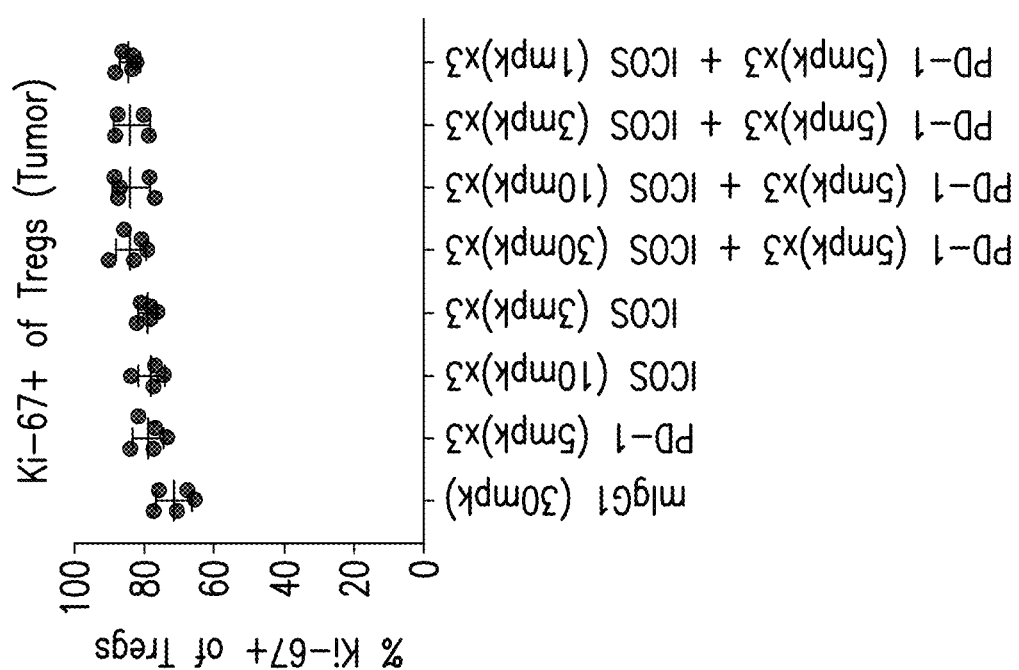
Figure 21C:
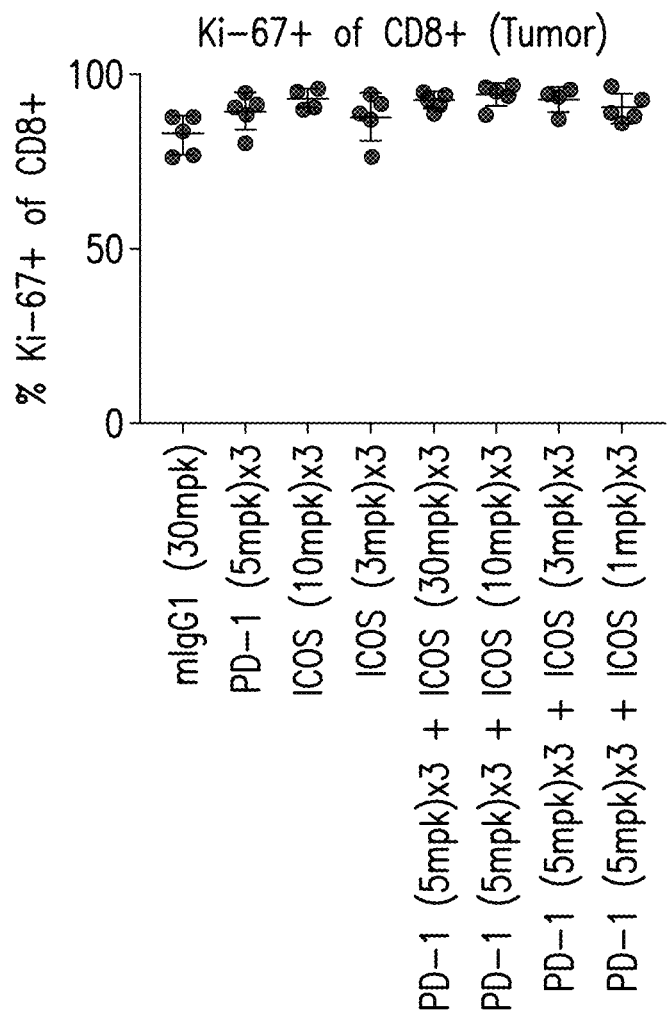
Figure 22B:
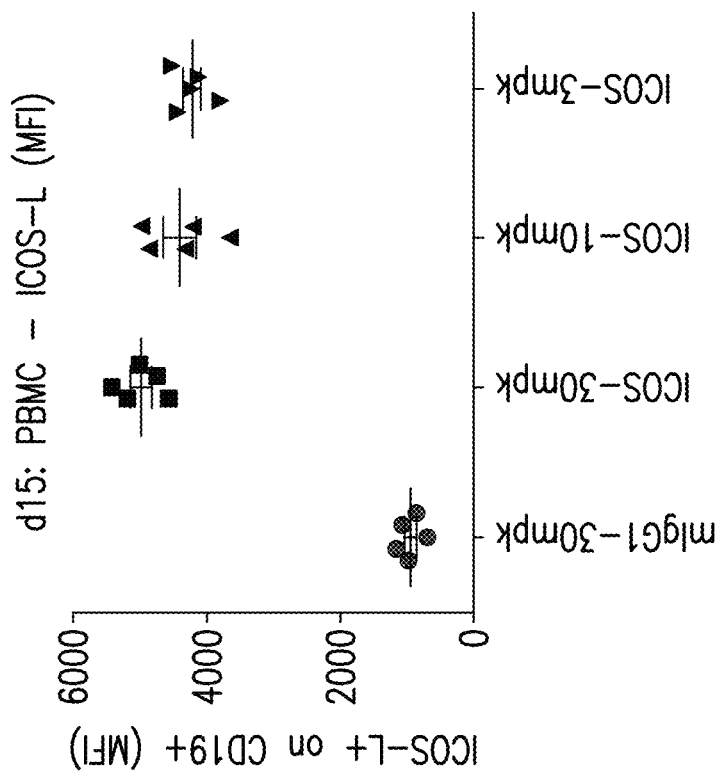
FIGS. 22A-D are graphs that show the expression of ICOS-L on B cells in spleen and PBMC. Mice were treated with isotype control mIgG1, anti-PD-1 mIgG1 D265A ("PD-1"), and/or anti-ICOS.4 mIgG1 ("ICOS") antibodies.
Figure 22A:
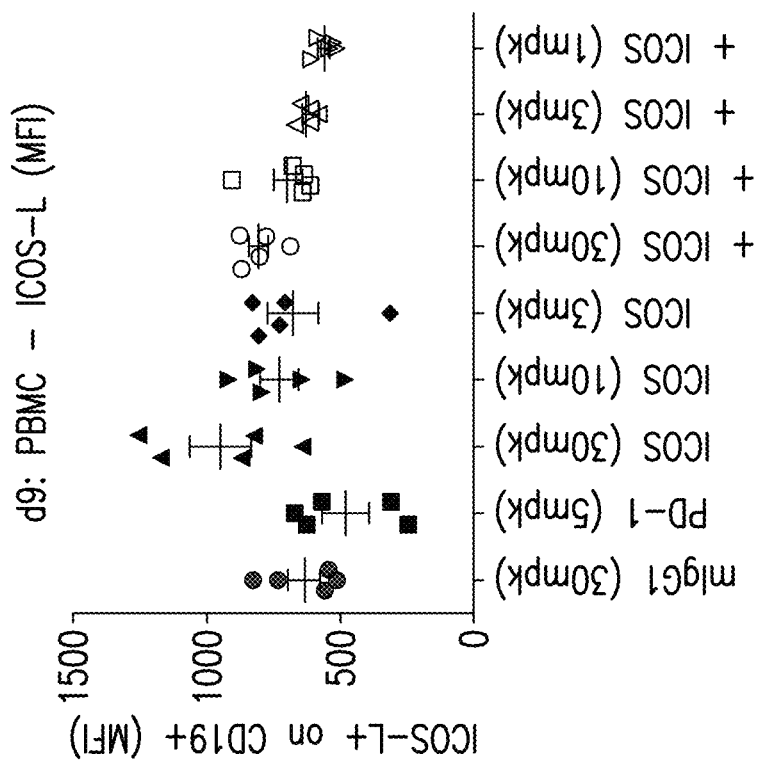
Figure 22D:
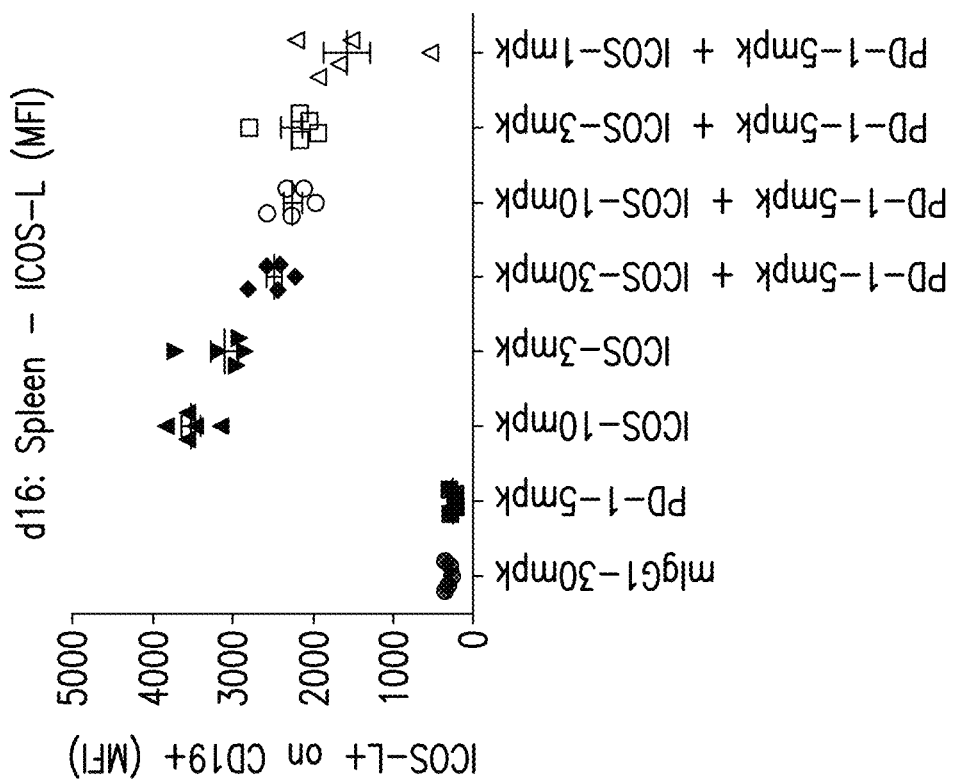
Figure 22C:
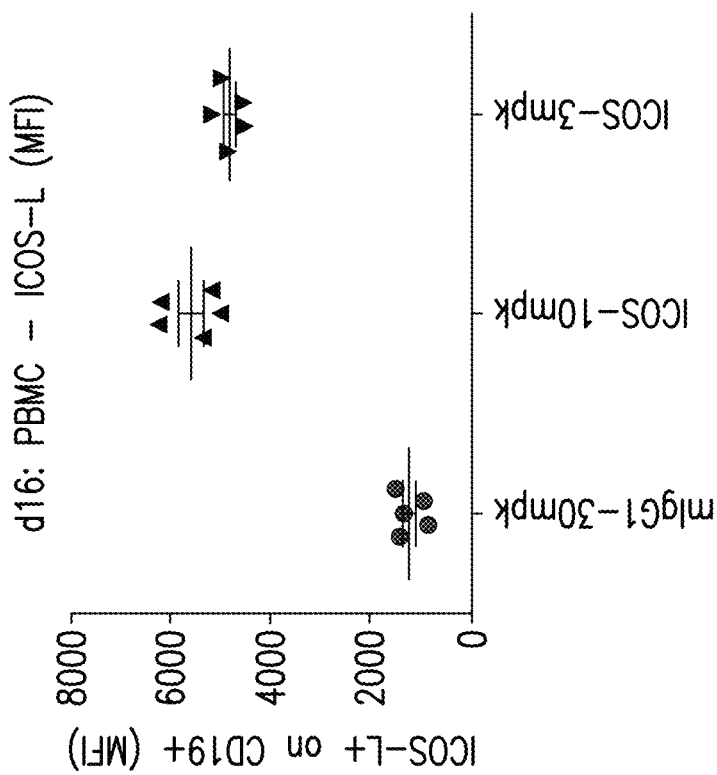

Levels of Ki-67 protein, a marker for cell proliferation, increased in the CD4+ effector T cell subset after single-agent treatment with either anti-PD-1 (moderate increase) or anti-ICOS.4 mIgG1 (high increase) (FIGS. 21A-C). Further increase in Ki-67 levels were observed in the anti-PD-1 and anti-ICOS.4 mIgG1 combination treatment groups.

ICOS-L, the ligand for ICOS, showed higher mean fluorescence intensity (MFI) levels on B cells after treatment with anti-ICOS.4 antibodies. MFI levels of ICOS-L were also elevated in whole blood taken at Day 9, Day 15, and Day 16 post-tumor implantation, and in spleen on Day 16 post-tumor implantation. A trend seems to emerge where the highest dose of anti-ICOS.4 mIgG1 has the highest MFI for ICOS-L (FIGS. 22A-D).

Looking at ICOS levels, loss of receptor expression on CD4+ T cells was observed after antibody treatment. This was most apparent in the tumor TILS (Table 20). Higher doses of anti-ICOS.4 mIgG1 correlated with lower levels of ICOS. Dosing of antibodies (Isotype Control at 30 mg/kg and Anti-PD-1 mIgG1 D265A at 5 mg/kg; Anti-ICOS.4 mIgG1 mAb at 1 mg/kg, 3 mg/kg, 10 mg/kg, and 30 mg/kg dose levels) was by intraperitoneal injection on days 9, 12, and 15 post-CT26 cell implantation. Whole blood was collected at various timepoints (day 9, day 15 and day 16 post implantation), and tumor was harvested on day 16 post implantation from five mice in certain treatment groups. Immuno-monitoring analysis via flow cytometry was performed on processed samples.

TABLE 20

Expression of ICOS on CD4+ T Cells

| Tissue analyzed | Day post-implantation | mIgG1 (30 mpk) [% ICOS] | ICOS.4 mIgG1 [% ICOS] | | |
|---|---|---|---|---|---|
| | | | 30 mpk | 10 mpk | 3 mpk |
| PBMC | 9 | 100% | 67% | 75% | 86% |
| PBMC | 15 | 100% | 65% | 50% | 65% |
| PBMC | 16 | 100% | — | 43% | 50% |
| Tumor | 16 | 100% | — | 18% | 15% |

Conclusions

As summarized in Table 21, in a staged CT26 syngeneic tumor model, treatment with anti-ICOS.4 mIgG1 mAb showed antitumor activity both as a single agent or when combined with anti-PD-1 mAb. As a monotherapy, similar levels of anti-tumor activity were observed when anti-ICOS.4 mIgG1 was dosed at 30 mg/kg, 10 mg/kg, or 3 mg/kg, although the 3 mg/kg dose had the highest mean TGI (33%) on Day 29. Immunomonitoring data showed an increased depletion of FoxP3+ Tregs (tumor), higher percentage of CD8+ T cells (tumor), higher Ki-67 protein levels in CD4+ effectors (tumor), higher ICOS-L levels in B cells (whole blood and spleen), and loss of ICOS expression in CD4+ T cells (whole blood and spleen) with across all doses of groups treated with anti-ICOS.4 mIgG1. These data showed that anti-ICOS monotherapy has good efficacy in this tumor model.

Anti-PD-1 mIgG1 treatment had very strong activity in this experiment. The combination treatment of anti-ICOS.4 mIgG1 mAb at 30 mg/kg, 10 mg/kg, 3 mg/kg, and 1 mg/kg, with anti-PD-1 mIgG1 resulted in mean TGI values ≥74%, with 8-11/15 mice tumor free for these treatment groups. These results showed comparable levels of antitumor activity of the anti-ICOS mIgG1 in combination with anti-PD-1 mIgG1 treatments across all doses. Improved antitumor efficacy in the CT26 model was observed when combining anti-ICOS and anti-PD-1 mAb. Tumor growth inhibition was ≥74% for each of the four doses (1 mg/kg, 3 mg/kg, 10 mg/kg, 30 mg/kg) anti-ICOS treatment groups in combination with anti-PD-1, with at least 8/15 mice tumor free in each of these groups. Tumor growth inhibition of anti-ICOS mAb as a single agent was 33% with 1/15 mice tumor free when dosed at 3 mg/kg. Immunomonitoring also showed lower FoxP3+ Tregs, higher percentages of CD8+ T cells, higher Ki-67 levels in CD4+ effectors, higher ICOS-L levels in B cells, and lower ICOS receptor expression levels in the anti-ICOS monotherapy.

TABLE 21

In vivo Nonclinical Pharmacology Studies

| Type of Study/ Species/Strain | Schedule/Route/ Duration of Study/ Vehicle/ Formulation | Range of Doses (µg/mouse) | Animals per group (M/F) |
|---|---|---|---|
| Antitumor activity of anti-ICOS mAb in combination with anti-PD-1 mAb in the CT26 tumor model with immunomonitoring of immune cell subsets/ Balb/c mice | Antibodies administered IP on post-implantation Days 9, 12, and 15; Mouse IgG1 isotype control, Anti-ICOS.4 mIgG1, Anti-PD-1 clone 4H2 mIgG1 | 1-30 mg/kg | 15-20 per group; F |

Example 9

Antitumor Activity of Anti-ICOS Antibody in Combination with Anti-CTLA-4 in a CT26 Tumor Model Summary To evaluate antitumor activity in the CT26 colorectal carcinoma model after treatment with an anti-ICOS surrogate monoclonal antibody of varying Fcs, ICOS.4 (mouse IgG1 or IgG2 variant of the parental hamster antibody), and/or anti-CTLA-4 mAb, CT26 cells were implanted subcutaneously in the right flanks of mice. When tumors reached 96 mm³, mice were randomized into six treatment groups of 10 to 15 mice each. Each mouse was dosed on post-implantation Days 13, 16, and 20 with mAb or isotype control (i.e., antibody of the same isotype, but that does not bind any naturally-occurring mouse protein, e.g., antibodies against KLH, diphtheria toxin, amongst others). Mice were weighed and tumors were measured twice weekly through study termination at Day 66. If tumors were ≥2000 mm³ or appeared ulcerated, animals were euthanized.

On Day 30 post implantation, the last day when the median tumor growth inhibition (TGI) relative to the isotype control antibody could be calculated, TGI values for anti-ICOS monotherapy were 15% and 69% with mIgG1 and mIgG2a variants (e.g., chimeric mouse antibody with $V_H/V_L$ sequences SEQ ID NOs: 3 and 4+IgG1 or IgG2), respectively; anti-CTLA-4 monotherapy showed a TGI value of −7%. When anti-ICOS mAbs were combined with anti-CTLA-4 mAb, mean TGI values of 40% (mIgG1) and 79% (mIgG2a) were observed. No toxicity was apparent in any treatment group.

Experimental Procedures
Test Antibodies and Controls
The following antibodies were constructed:
(a) Anti-Mouse ICOS Mouse IgG1 Antibody—Anti-ICOS.4 mAb, isotype mouse IgG1, was expressed from Chinese hamster ovary (CHO) cell lines;
(b) Anti-Mouse ICOS Mouse IgG2a Antibody—Anti-ICOS.4 mAb, isotype mouse IgG2a, was expressed from CHO cell lines;
(c) Anti-Mouse CTLA-4 9D9 Mouse IgG2b Antibody—Monoclonal antibody to mouse CTLA-4 clone 9D9, isotype mouse IgG2b, was expressed from a transfected CHO cell line and formulated in PBS; and
(d) Mouse IgG1 Isotype Control—A fully murine IgG1 antibody, non-binding to ICOS; prepared at 10 mg/kg in PBS.

Preparation of Tumor Cells
CT26 murine colon carcinoma cells were purchased from American Type Culture Collection (ATCC, Catalog CRL-2638) and maintained in vitro in sterile culture of Dulbecco's modified eagle medium (DMEM)+10% heat-inactivated fetal bovine serum (FBS), for less than 10 passages. Cells were confirmed to be virus-free via mouse antibody production testing.

Tumor Implantation
CT26 cells were cultured in RPMI-1640 medium (HyClone/GE Healthcare, Logan Utah, Catalog 10-040-CM, Lot 16915003) supplemented with 10% fetal bovine serum (FBS) (Gibco, Life Technologies, Catalog 26140-079, Lot 1704315). Cells were split 1:10 every three to four days. The right flank of each mouse was subcutaneously implanted with 1×10⁶ CT26 cells in 0.2 mL PBS using a 1-cm syringe and a 26-gauge half-inch needle.

Antibody Treatment
On Day 13 post-CT26 cell implantation, 120 mice were randomized to six groups of 10 to 15 mice each according to tumor volume. Groups had an average tumor volume of approximately 96 mm³. Mice were dosed with the antibodies on Days 13, 16, and 20.

Post-Treatment Monitoring
Animals were checked daily for postural, grooming, and respiratory changes, as well as lethargy. Animals were weighed at least twice weekly and were euthanized if weight loss was greater than or equal to 20%. The flanks of each animal were checked for the presence and size of tumors at least twice weekly until death, euthanasia, or end of the study period. Tumors were measured in three dimensions (length [L], width [W], and height [H]) with electronic digital calipers and recorded. Tumor volumes were calculated using the equation: Volume=(L×W×H×0.5). Response to treatment was measured as a function of tumor growth inhibition (TGI) and was calculated as: (reference mm³ −test article mm³)/reference mm³×100. When the tumor reached a volume greater than approximately 2000 mm³ or appeared ulcerated, the animal was euthanized.

Results
As shown in Table 22, at Day 30 post-tumor implantation, the last day the median TGI could be calculated, the treatment efficacy of the anti-ICOS mAb therapies on CT26 tumors was observed as both monotherapy and in combination with anti-CTLA-4 mAb. Mice treated with anti-ICOS.4 variants as monotherapy showed 15% median TGI (mIgG1) and 69% TGI (mIgG2a). The combination of anti-CTLA-4 mAb (−7% TGI), resulted in higher median TGIs as the anti-ICOS.4 mIgG1 variant had 40% TGI, and the anti-ICOS.4 mg2a variant had 79% TGI. At the end of the study period (Day 66), the number of tumor-free mice was 0 for all groups. Tumor growth curves for individual mice by treatment group are shown in FIGS. 23A-F. Dosing of antibodies (isotype control at 20 mg/kg; anti-CTLA-4 mIgG2b, anti-ICOS.4 mIgG1, and anti-ICOS.4 mIgG2a at 10 mg/kg) was by intraperitoneal injection on days 13, 16, and 20 post-CT26 cell implantation.

Figure 24A:
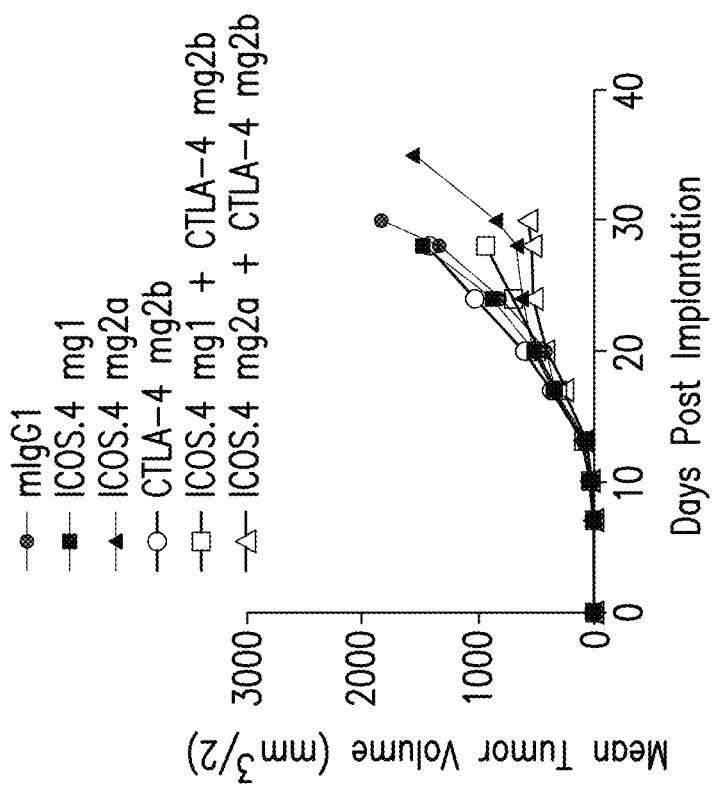
FIGS. 24A and 24B are graphs that show the mean and median tumor growth curves by treatment group: isotype control mIgG1, anti-CTLA-4 mIgG2b ("CTLA-4 mg2b"), anti-ICOS.4 mIgG1 ("ICOS.4 mg1"), and/or anti-ICOS.4 mIgG2a ("ICOS.4 mg2a") antibodies.
Figure 24B:
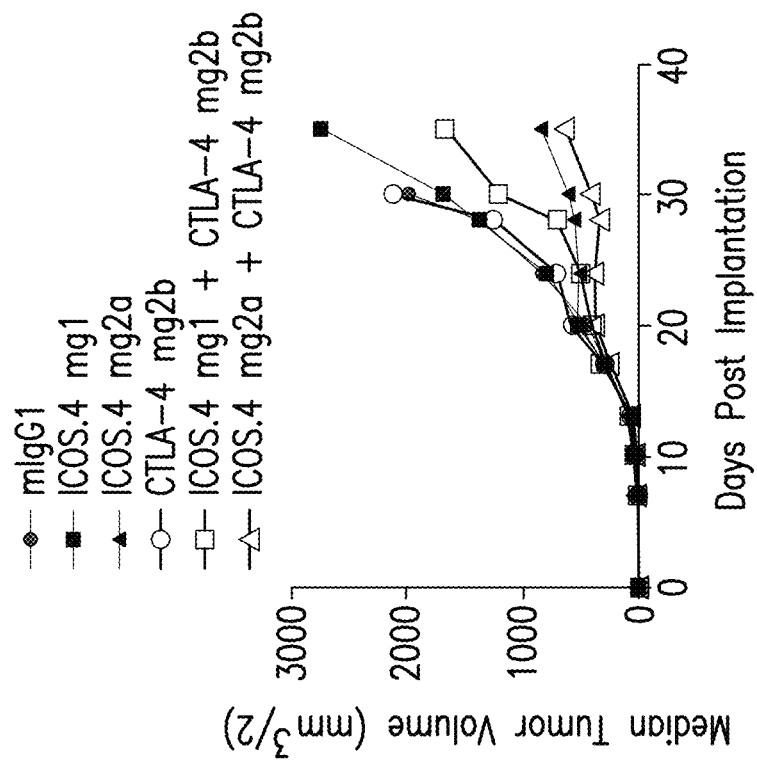

Mean and median tumor growth curves by treatment group are presented in FIGS. 24A and 24B. No toxicity was apparent in any treatment group, as the mean and median body weight changes were below 20%.

TABLE 22

Tumor Growth Inhibition by Treatment Group

|  | Day 30 | |
| --- | --- | --- |
| Treatment Group | Median Tumor Volume (mm$^3$) | Median % TGI |
| mIgG1 isotype control, 20 mg/kg | 1981 | N/A |
| Anti-ICOS.4 mIgG1, 10 mg/kg | 1686 | 15% |
| Anti-ICOS.4 mIgG2a, 10 mg/kg | 614 | 69% |
| Anti-CTLA-4 9D9 mIgG2b, 10 mg/kg | 2114 | −7% |
| Anti-ICOS.4 mIgG1, 10 mg/kg + Anti-CTLA-4 9D9 mIgG2b, 10 mg/kg | 1195 | 40% |
| Anti-ICOS.4 mIgG2a, 10 mg/kg + Anti-CTLA-4 9D9 mIgG2b, 10 mg/kg | 410 | 79% |

Conclusions

As summarized in Table 23, in a staged CT26 syngeneic tumor model, both anti-ICOS Fc variant monotherapies (i.e., ICOS.4 mouse IgG1 or IgG2 variant of the parental hamster antibody) promoted modest antitumor activity, with anti-ICOS.4 mIgG2a demonstrating greater efficacy than anti-ICOS.4 mIgG1 at Day 30 (69% versus 15% median TGI). The combination of the anti-ICOS.4 treatments with anti-CTLA-4 mAb increased efficacy with the median TGIs increasing to 79% (mIgG2a) and 40% (mIgG1). No significant changes in body weight were associated with the treatments nor were any overt signs of clinical toxicity observed. Anti-ICOS monotherapies promoted antitumor activity, with anti-ICOS.4 mIgG2a demonstrating greater antitumor efficacy at Day 30 (69% versus 15% median TGI). Antitumor efficacy increased when combined with anti-CTLA-4 mAb treatment, with anti-ICOS.4 mIgG2a combination group at 79% TGI and anti-ICOS.4 mIgG1 at 40% TGI.

TABLE 23

In vivo Pharmacology Studies

| Type of Study/ Species/Strain | Schedule/Route/ Duration of Study/ Vehicle/ Formulation | Range of Doses (µg/mouse) | Animals per group (M/F) |
| --- | --- | --- | --- |
| Antitumor activity of anti-ICOS mAb in combination with anti-CTLA-4 mAb in the CT26 tumor model/ Balb/c mice | Antibodies administered IP on post-implantation Days 13, 16, and 20; 66 days; Mouse IgG1 isotype control, Anti-ICOS.4 mIgG1, Anti-ICOS.4 mIgG2a, Anti-CTLA-4 9D9 mIgG2b, in PBS | 10-20 mg/kg | 10-15 per group; F (female) |

Example 10

Affinity, Binding, Biophysical Properties, Forced Stability, and Immunogenicity Characterization of Binding Properties Human CD4+ T cells, cynomolgus PBMC and mouse and rat splenocytes were activated by incubation with plate-bound species-specific anti-CD3 (coated in a 6-well plate with 2 mL/well of a 4 µg/mL solution in PBS for 3 hours at 37° C. and washed twice with 1 mL medium), +1 µg/mL soluble species-specific anti-CD28 in fresh medium with 1-2×10$^6$ cells/mL for 3-4 days. It should be noted that the cynomolgus PBMC and mouse and rat splenocytes become primarily T cells after three to four days of CD3/CD28 activation. The cells were harvested, counted, spun down and re-suspended in staining buffer+100 µg/mL mouse IgG to block for 15 minutes at room temperature. ICOS.33 IgG1f S267E was titrated from 2 µg/mL by 4-fold serial dilutions down to 0.002 µg/mL in staining buffer and incubated with the activated human, cynomolgus monkey, rat or mouse cells for 30 minutes at 4-8° C. in a U-bottom plate. The cells were then washed twice in 150-200 µL of staining wash buffer and re-suspended in 50 µL of APC-Goat Anti-Human IgG (Fc gamma) diluted 1:200 in staining buffer, gently vortexed, and incubated 30 minutes at 4-8° C. in the dark. The cells were then washed once in 200 µL staining wash buffer, re-suspended in same and analyzed on the FACS Canto flow cytometer.

Figure 25A:
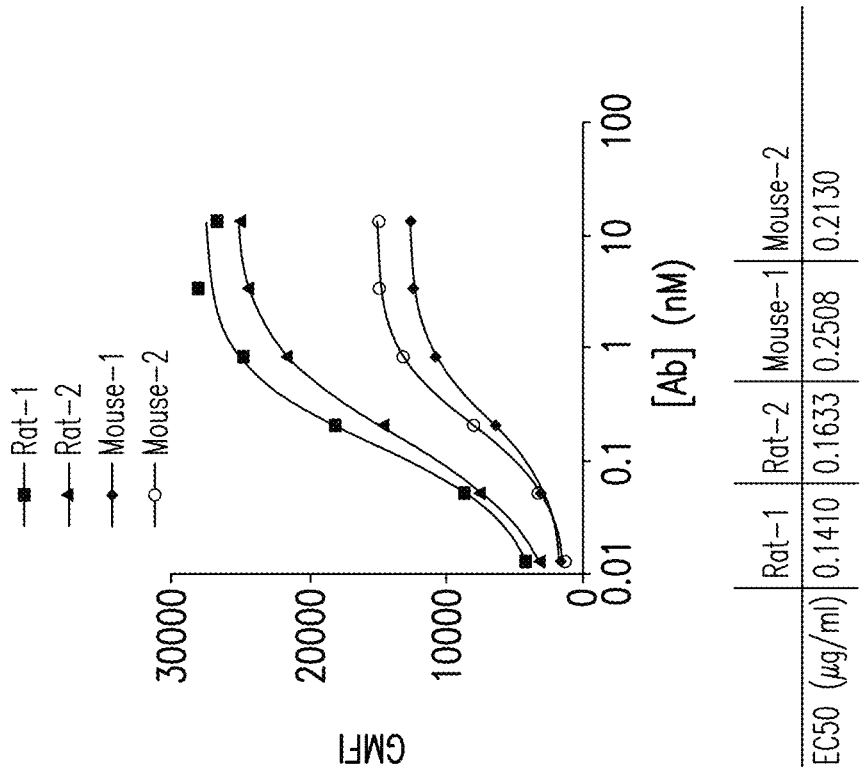
FIGS. 25A and 25B are graphs that show ICOS.33 IgG1f S267E binding to human, cynomolgus monkey, rat and mouse T cells, as measured using FACS.
Figure 25B:
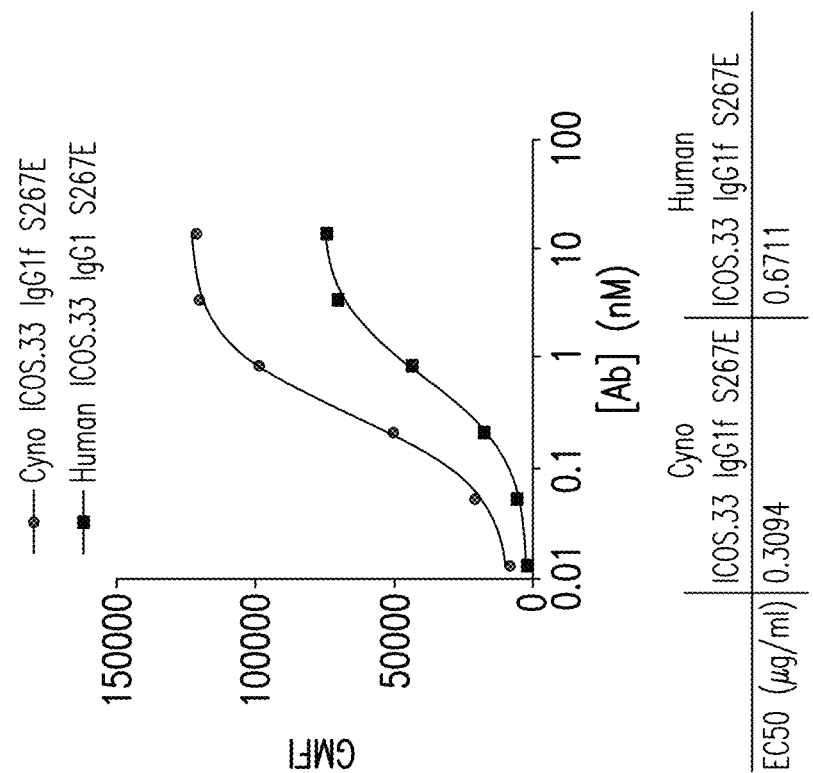

As illustrated in FIGS. 25A and 25B, ICOS.33 IgG1f S267E exhibits strong binding to human, cynomolgus monkey, rat and mouse T cells with EC50 values that are not significantly different among the three species.

Figures 26A, 26B:
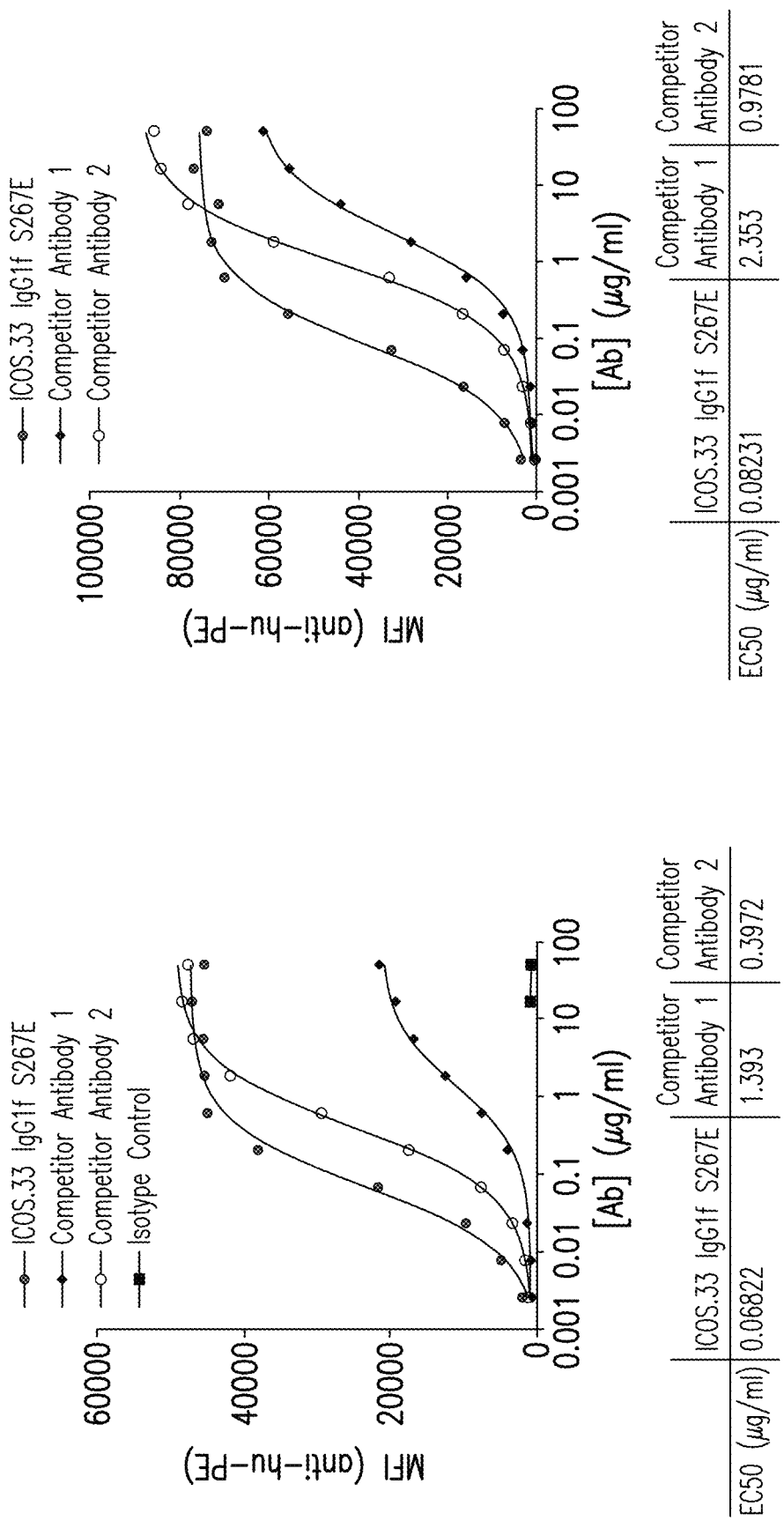
FIGS. 26A and 26B are graphs that show that the ICOS.33 IgG1f antibody has greater binding avidity to CD4+ T cells as calculated by EC50 values compared to two competitor anti-ICOS antibodies.

In addition, the binding avidity of ICOS.33 IgG1f S257E was compared to two different anti-ICOS competitor antibodies. Briefly, the antibodies were incubated with activated CD4+ T cells on ice for thirty minutes. The cells were then washed, and the bound antibodies were detected with an anti-human-IgG-PE secondary reagent. The signal was measured by flow cytometry, and the mean fluorescence intensity was calculated. As shown in FIGS. 26A-B, ICOS.33 IgG1f S267E showed greater binding avidity to activated CD4+ T cells as calculated by EC50 compared to the two competitor antibodies. As discussed herein, the term "EC50", in the context of an in vitro assay using an antibody or antigen binding fragment thereof, refers to the concentration of an antibody or an antigen-binding fragment thereof that induces a response that is 50% of the maximal response, i.e., halfway between the maximal response and the baseline. In FIG. 26A, the EC50 of ICOS.33 IgG1f S267E was about 0.07 µg/mL, whereas the EC50 of competitor antibody 1 was about 1.4 µg/mL, and the EC50 of competitor antibody 2 was about 0.4 µg/mL. In other words, the EC50 of ICOS.33 IgG1f S267E was about 20-fold less than the EC50 of competitor antibody 1, and about 6-fold less than the EC50 for competitor antibody 2. In FIG. 26B, the EC50 of ICOS.33 IgG1f S267E was about 0.08 µg/mL, whereas the EC50 of competitor antibody 1 was about 2.4 µg/mL, and the EC50 of competitor antibody 2 was about 1.0 µg/mL. In other words, the EC50 of ICOS.33 IgG1f S267E was about 30-fold less than the EC50 of competitor antibody 1, and about 12-fold less than the EC50 for competitor antibody 2.

Affinity Studies

Since monomeric human ICOS was not available, experiments to determine the true affinity of ICOS.33 IgG1f S267E were done using ICOS.33 IgG1f S267E Fab fragment (Lot PC-1804-04) and human ICOS Fc (R&D Systems, 169-CS-050) antigen with Biacore™ T200 equipment. The binding experiments were done at 37° C. to obtain (or model) the affinity of the antibody to the antigen under in vivo conditions. A CM4 chip was covalently coated with anti-hFc capture reagent from Biacore. The surface was blocked with ethylenediamine. Next, human ICOS with an Fc tag was captured on the CM4 chip and the Fab fragment of ICOS.33 IgG1f S267E was flowed on it at 0.91, 2.7, 25, 74, 667, and 2000 nM concentrations.

The association rate constant (kon) and disassociation rate constant (koff) were plotted by time and response units (RU) using BIAevaluation software, Version 3.2. The data were fit to a 1:1 Langmuir model. The ratio of koff/kon was represented by the dissociation constant ($K_D$) of the antibody-antigen complex. The Biacore chip was regenerated with 50 mM sodium hydroxide solution at a flow rate of 100 µL/min. The affinity of the antibody for the human ICOS antigen as measured by Fab fragment of ICOS.33 IgG1f S267E was 52 nM to 65 nM.

Biophysical Analysis

The identity of ICOS.33 IgG1f S267E was confirmed by liquid chromatography/mass spectrometry (LC-MS). For heavy and light chain mass measurements, the sample was deglycosylated, reduced, and alkylated per the standard test method and analyzed using a Waters LCT Premier ESI-TOF instrument. The mass of ICOS.33 IgG1f S267E light and heavy chains were equivalent to their predicted mass assignments of 23,795 Da and 50,161 Da, respectively, based on amino acid sequence derived from DNA sequence.

The identity of the antibody was determined by Edman sequence analysis. N-terminal amino acid sequencing of antibody heavy and light chains was performed with an ABI Procise Automated Protein Sequence Analyzer. The observed N-terminal amino acid sequences of ICOS.33 IgG1f S267E matched the predicted amino acid sequences for the light and heavy chains.

Using the Agilent 2100 BioAnalyzer system, it was determined that ICOS.33 IgG1f S267E migrated at approximately 160 kDa under non-reducing (NR) conditions. Under reducing conditions (R), the heavy chain migrated at about 60 kDa and the light chain migrated at about 25 kDa.

The purity of ICOS.33 IgG1f S267E was determined by capillary electrophoresis-sodium dodecyl sulfate (CE-SDS). Samples were analyzed with a Beckman Coulter Proteome Lab PA 800 plus under non-reducing and reducing conditions. ICOS.33 IgG1f S267E comprised 93.45% intact IgG by CE-SDS under non-reducing conditions. The antibody fragments detected were as follows: a light chain (1.85%), a heavy-light chain (0.45%), two heavy chains (0.88%) and two heavy and one light chain (3.37%). The purity of ICOS.33 IgG1f S267E was 96.51% (62.22% heavy chain+ 34.29% light chain) by CE-SDS under reducing conditions.

ICOS.33 IgG1f S267E was characterized by hydrophobic interaction chromatography (HIC) to determine the level of product heterogeneity. ICOS.33 IgG1f S267E showed low heterogeneity with 98.1% main peak, 0.4% peak in front of the main peak, and 1.5% tailing shoulder, indicating low chemical or conformational heterogeneity.

Capillary isoelectric focusing (cIEF) was utilized to characterize ICOS.33 IgG1f S267E for charge isoforms. The sample was analyzed using an iCE Analyzer Model iCE3. ICOS.33 IgG1f S267E displayed an isoelectric point (pI) range of 7.30 to 7.72 with a major peak at 7.72 (45.19%). Other peaks observed were at 7.30 (7.51%), 7.40 (16.21%) and 7.56 (31.10%). The observed pI range was within the normal range expected for IgG1 antibody samples.

Size-exclusion chromatography (SEC; gel filtration) coupled with multi-angle light scattering (MALS) was performed to determine the monomer content and MW distribution of the major impurities of ICOS.33 IgG1f S267E. It was found that ICOS.33 IgG1f S267E comprised more than 99.8% monomer. The MW assignment by MALS indicated that the monomeric component had a MW of 144,300 Da. A very small amount of aggregate had an apparent MW of 626,800 Da.

Peptide fingerprinting and sequencing was performed by analyzing digested peptides by LC-MS on a Waters Acquity UPLC with an Acquity UPLC BEH C18 1.7 µm (2.1×150 mm; Waters Corporation) coupled to an LTQ-Orbitrap XL mass spectrometer. The heavy and light chain sequence identification was 100% using the MS/MS data from various digests including trypsin, chymotrypsin, and pepsin. Peptide sequencing confirmed that the allotype was human IgG1 and matched the expected amino acid sequence as predicted by the DNA sequence. A single N-glycosylation site was confirmed to be N297 on the heavy chain. The disulfide bonds were found to be as expected for a human IgG1 monoclonal antibody. The S267E mutation made to enhance the CD32b receptor binding was also identified in the sequence.

The oligosaccharide profile of N-linked sugars present on ICOS.33 IgG1f S267E was determined by capillary laser-induced fluorescence (cLIF) using a Beckman MDQ instrument. N-linked glycans present on ICOS.33 IgG1f S267E comprised a mixture of asialo-biantennary sugars without fucose that varied with respect to the level of galactose incorporation. The major glycan structures were G0F (30.64%) and G1F (43.65%), and to a lesser degree, G2F (19.07%).

A VP-capillary differential scanning calorimeter was used to determine thermal stability and reversibility of the antibody. Data were analyzed using the Origin 7 software program. Thermal stability was within acceptable range for a typical human monoclonal antibody. In thermal scanning experiments, many antibodies show three resolvable melting temperatures; the first one is due to the unfolding of CH2 domain, the second is due to the unfolding of the Fab domain, and the third is due to the unfolding of CH3 domain. ICOS.33 IgG1f S267E displayed a thermogram with these three unfolding temperatures: 65.2° C. (Tm1), 83.2° C. (Tm2), 86.3° C. (Tm3). Thermal reversibility is a marker for the ability of a protein to refold back to its native conformation after a perturbation, in this case heat. Thermal reversibility experiments at 83.2° C. (the second melting temperature) showed 55.2% reversibility, which suggests that the antibody has robust refolding properties.

The stability of ICOS.33 IgG1f S267E is summarized in Table 24.

TABLE 24

Stability of ICOS.33 IgG1f S267E

| Property | Method | Results |
| --- | --- | --- |
| Freeze/Thaw (1 h at −80° C., 1 h at RT × 6) | UV, SEC | No F/T stability risk revealed |
| Solubility/ Concentration Profile | UV, SEC | At least 50 mg/ml in buffer (20 mM histidine, pH6.0, 260 mM sucrose) |

TABLE 24-continued

Stability of ICOS.33 IgG1f S267E

| Property | Method | Results |
|---|---|---|
| Agitation Stability Study | 350 rpm at RT in buffer (20 mM histidine, pH6.0, 260 mM sucrose) +/− 0.05% PS80 for 7 days (50 and 10 mg/mL) | No aggregation issues observed |

Example 11

ICOS.33 IgG1f S267E Binding Affinity for Human FcγRs by Surface Plasmon Resonance The binding of human FcγRs to ICOS.33 IgG1f S267E was studied by surface plasmon resonance (SPR) and compared to control antibody anti-ICOS IgG1f. Antibodies were captured on a protein A sensor surface, and a titration series of FcγRs were injected as analytes.

For these studies, protein A was immobilized on flow cells 1-4 of the CM5 sensor chip using standard ethyl (dimethylaminopropyl) carbodiimide (EDC)/N-hydroxysuccinimide (NHS) chemistry, with ethanolamine blocking, in a running buffer of 10 mM HEPES pH 7.4, 150 mM NaCl, 3 mM EDTA, 0.05% surfactant p20, to a density of ~3000 RU. ICOS.33 IgG1f S267E (3 µg/mL) or hIgG1f control antibody (3 µg/mL) were captured on the protein A surface to a density of ~400-500 RU, and the binding of FcγR analytes was tested in running buffer consisting of 10 mM NaPO4, 130 mM NaCl, 0.05% p20, buffer (PBS-T) pH 7.1 at 25° C., using 120 second association time and 180 second dissociation time at a flow rate of 30 µL/min. To determine the kinetics and affinity of binding, an FcγR concentration series (3:1 dilution) from 1 µM down to 0.15 nM (CD64 proteins) or 10 µM down to 1.5 nM (all other FcγRs) was tested. The kinetic data were fit to either a 1:1 Langmuir model or to a steady-state model using Biacore T200 evaluation software.

Sensorgram data that demonstrated very rapid association and dissociation rates with steady-state binding were fit to a 1:1 steady state affinity model, while those that demonstrated slower kinetics were fit to a 1:1 Langmuir model. Data at single analyte concentrations (hCD64 at 0.11 µM and hCD32a-H131, hCD32a-R131, hCD32b, hCD16a-V158, hCD16a-F158, hCD16b-NA1, and hCD16b-NA21 at 1.1 µM) were compared for anti-ICOS control antibody and ICOS.33 IgG1f S267E, with ICOS.33 IgG1f S267E showing a higher binding response and slower dissociation rate for several of the FcγRs, with hCD32a-R131 and hCD32b having the most notable increases in binding and slower dissociation rates.

The best fit kinetic and affinity values are shown in Table 25. These data quantitatively demonstrated that the S267E mutation changes the binding affinity for several FcRs compared to hIgG1f control antibody. For example, binding to hCD32a-R131 improved from a $K_D$ of 1500 nM (hIgG1f control) to 34 nM (ICOS.33 IgG1f S267E), which was an improvement of more than 40-fold, and binding to hCD32b improved from a $K_D$ of greater than 5000 nM (hIgG1f control) to 170 nM (ICOS.33 IgG1f S267E), which was an improvement of at least 29-fold. Binding to cyno CD32a and CD32b was lower than that seen for human CD32a and CD32b.

TABLE 25

Kinetic and Affinity Data for the Binding of ICOS.33 IgG1f S267E to Human FcγRs

| Ligand | FcγRs | ka (1/Ms) | kd (1/s) | $K_D$ (nM) | Model |
|---|---|---|---|---|---|
| Anti-ICOS Control Antibody | hCD64 | $1.1 \times 10^6$ | $6.0 \times 10^{-3}$ | 0.1 | 1:1 Langmuir Fit |
| | hCD32a-H131 | | | 1100 | Steady State Affinity |
| | hCD32a-R131 | | | 1500 | Steady State Affinity |
| | hCD32b | | | >5000 | Steady State Affinity |
| | hCD16a-V158 | | | 560 | Steady State Affinity |
| | hCD16a-F158 | | | >5000 | Steady State Affinity |
| | hCD16B-NA1 | | | 3500 | Steady State Affinity |
| | hCD16B-NA2 | | | >5000 | Steady State Affinity |
| ICOS.33 IgG1fS267E | hCD64 | $1.6 \times 10^6$ | $5.1 \times 10^{-3}$ | 0.03 | 1:1 Langmuir Fit |
| | hCD32a-H131 | | | 840 | Steady State Affinity |
| | hCD32a-R131 | | | 34 | Steady State Affinity |
| | hCD32b | | | 170 | Steady State Affinity |
| | hCD16a-V158 | | | 1400 | Steady State Affinity |
| | hCD16a-F158 | | | >5000 | Steady State Affinity |
| | hCD16B-NA1 | | | 1400 | Steady State Affinity |
| | hCD16B-NA2 | | | >5000 | Steady State Affinity |
| | cyCD64 | | | .88 | 1:1 Langmuir Fit |
| | cyCD32a | | | 4000 | Steady State Affinity |
| | cyCD32b | | | 2300 | Steady State Affinity |
| | cyCD16 | | | 1700 | Steady State Affinity |

Example 12

Pharmacokinetics (PK) of ICOS.33 IgG1f S267E

The PK parameters obtained from a single-dose PK/PD and tolerability study with ICOS.33 IgG1f S267E are summarized in Table 26. The exposure was dose-proportional between 1 mg/kg and 10 mg/kg, with a half-life of 13-14 days. Anti-drug antibodies (ADA) were detected at seven days post dose in three out of four cynomolgus monkeys in the 1 mg/kg dose group and continued to increase up to 42 days post dose. The increase in the ADA signal corresponded with the rapid clearance of the antibody in these monkeys, and this portion of the data affected by ADA were not included in the PK data analysis.

TABLE 26

Pharmacokinetic Parameters of ICOS.33 IgG1f S267E after Intravenous (IV) Administration to Cynomolgus Monkeys

| Study | Monkey number | Dose (mg/kg) | Area Under the Curve (AUC)(0-INF) (µM × d) | T½ (half-life) (days) | Clearance (CLT) (mL/d/kg) | Volume at steady state (Vss) (mL/kg) |
|---|---|---|---|---|---|---|
| DT15107 | 4 (2 Female/ 2 Male) | 1 | 2.2 ± 0.4 | 13 ± 2.8 | 3.1 ± 0.46 | 57 ± 3.9 |
| | 4 (2 Female/ 2 Male) | 10 | 23 ± 3.8 | 14 ± 3.3 | 2.9 ± 0.48 | 66 ± 11 |

Pharmacokinetics of Mouse Surrogate Antibody in Mice

The pharmacokinetics of an anti-mouse ICOS surrogate mAb (ICOS.4, mouse IgG1 variant of the parental hamster antibody) following a single intravenous dose at 1 mg/kg and a single intraperitoneal administration (at 0.1 mg/kg, 1 mg/kg, and 10 mg/kg) were evaluated in non-tumor-bearing BALB/c mice, which is an albino, laboratory-bred strain of the house mouse. The antibody showed a greater-than-dose-proportional increase in exposure over a 1 mg/kg-10 mg/kg dose range, as shown in Table 27. The half-life ranged from 0.53 days at the lowest 1 mg/kg dose to 1.5 days at the highest 10 mg/g dose. The nonlinear PK in mice appeared to be due at least in part to target-mediated drug disposition.

TABLE 27

Pharmacokinetics Parameters of ICOS.4 mouse IgG1 after Intraperitoneal Administration to Mice

| Route of administration | Dose (mg/kg) | Cmax (nM) | AUC(0-INF) (µM × d) | T½ (d) | CLT (mL/d/kg) | Vss (mL/kg) |
|---|---|---|---|---|---|---|
| IV | 1 | | 0.15 | 0.65 | 43.2 | 101.4 |
| IP | 0.1 | 4.1 | 0.005 | 0.55 | | |
| IP | 1 | 51 | 0.187 | 0.53 | | |
| IP | 10 | 703 | 3.3 | 1.5 | | |

Example 13

Cross-Reactivity and Tissue Staining

Binding assays have demonstrated that ICOS.33 IgG1f S267E affinity (EC50) to activated CD4+ T cells was similar in mice, rats, cynomolgus monkeys, and humans.

In tissue cross-reactivity analysis, FITC-conjugated ICOS.33 IgG1f S267E was applied to frozen sections (acetone or acetone/formalin fixed) from 20 normal human tissues, one to four donors each. Specific staining was observed in subsets of lymphocytes in lymphoid (thymus, tonsil, and spleen) and lymphoid-rich tissues (stomach and small intestine), as well as scattered very rare mononuclear cells (MNCs) in several tissues (thyroid, skin, lung, uterus, and testis), which are largely associated with underlying inflammation. No positive labeling was seen in cerebrum, cerebellum, heart, liver, kidney, pancreas, peripheral nerve, colon, pituitary, and prostate. In lymphoid tissues, positive lymphocytes were primarily distributed in the medulla of the thymus, and the light zone of the germinal center and interfollicular region of the tonsil. These results are consistent with previous immunohistochemistry (IHC) with the parent antibody ICOS.4.

ICOS.33 IgG1f S267E-FITC staining was also evaluated by immunohistochemistry (IHC) in frozen sections from 10 normal cynomolgus monkey tissues, including cerebrum, heart, liver, lung, kidney, spleen, thymus, tonsil, skin, and testis. Overall, the staining patterns were similar to that in human tissues. Specific staining was observed in subsets of lymphocytes in lymphoid tissues (tonsil, spleen, and thymus). No unexpected staining was seen in the tissues examined.

Example 14

Cytokine Release, Complement Activation, and Tolerability

Cytokine release in human whole blood treated with ICOS. 33 IgG1f S267E This study was designed to assess cytokine responses in human peripheral blood cells after treatment with ICOS.33 IgG1f S267E on fresh whole blood samples.

Fresh normal sodium-heparinized whole blood (100 µL) was added to 96-well round bottom plates. 100 µL of ICOS.33 IgG1f S267E or ICOS.33 diluted in AIM V serum-free medium, isotype control anti-KLH-hIgG1-2F5 mAb, or TGN (5.11A1) anti-CD28 mAb were added to the wells to obtain a final antibody concentration of 10 µg/mL per well and a final volume of 200 µL per well. SEB (100 µL) diluted in AIM V medium was added to the wells for a final concentration of 100 ng/mL SEB to obtain a final volume of 200 µL per well. CD3-CD28 (100 µL) diluted in AIM V medium was added to the wells for a final concentration of 1 µg/mL CD3-CD28 and a final volume of 200 µL per well. LPS (100 µL) diluted in AIM V medium was added to the wells for a final concentration of 10 µg/mL LPS and a final volume of 200 µL per well. Plates were incubated in an incubator at 5% to 7% $CO_2$ atmosphere for 20 hours at 37° C. Plasma cell culture supernatants from each well were harvested after 20 hours and stored at −20° C. Samples were shipped to BMS Lawrenceville, N.J. (LVL) in a dry-ice container for assay performance.

To assess for cytokine secretion, 12 µL of premixed standards, controls, and samples were transferred to the assay plates. Magnetic beads (6 µL) were added to each 384-well plate, then sealed and incubated for two hours at room temperature on a plate shaker. After two hours of incubation, the magnetic beads were washed twice, and 6 µL of detection antibodies were added into each well. Plates were sealed again and incubated at room temperature on a plate shaker. Streptavidin-phycoerythrin (6 µL) was added to each well containing the detection antibodies, then incubated for 30 minutes at room temperature, and washed twice using a plate washer. Sheath fluid (80 µL) was added to each well, and beads were re-suspended for five minutes on a plate shaker. Plate samples were read by using the Bioplex 3D instrument array system. Raw data were measured as mean fluorescent intensity (MFI). Concentration (pg/mL) was calculated by Xponent software.

A panel of 75 cytokines was assessed in blood from eight human normal donors for cytokine release mediated by ICOS.33 IgG1f S267E. Addition of ICOS.33 IgG1f S267E to donor whole blood did not mediate cytokine secretion in comparison to the isotype control. These data showed that ICOS.33 IgG1f S267E treatment does not lead to cytokine release syndrome (CRS) in whole blood.

Intermittent-Dose Intravenous Toxicity Study in Monkeys

This study was conducted to determine the potential toxicity and the biological activity of ICOS.33 IgG1f S267E when given intravenously to monkeys either once weekly or once every three weeks for a one-month period to evaluate the reversibility of any observed changes, to determine systemic exposures to ICOS.33 IgG1f S267E, to assess immune responses, and to provide data to support the use of ICOS.33 IgG1f S267E in humans. ICOS.33 IgG1f S267E was administered intravenously as a slow bolus injection at doses of 0 (vehicle, once weekly on Days 1, 8, 15, 22, and 29), 1.5 mg/kg (once every 3 weeks on Days 1 and 22), 15 mg/kg (once weekly), or 75 mg/kg (once weekly) to groups of five female monkeys and five male monkeys. All doses were administered at 2 mL/kg in a vehicle/carrier consisting of 20 mM histidine, 260 mM sucrose, 50 µM diethylene triamine pentaacetic acid and 0.05% (w/v) polysorbate 80 (pH 6.0). As potential pharmacodynamics measures at least in part, all monkeys were immunized with keyhole limpet hemocyanin (KLH, immunogen to stimulate primary response), viral vectors Adenovirus-5 (Ad5)-Gag and Ad5-Nef (immunogen to stimulate antigen-specific CD8 T cell response), and tetanus toxoid (immunogen to stimulate secondary response) on Day 1. For example, immunizing with tetanus toxoid allows expansion of the number of T cells specific to tetanus toxoid, and allows PK/PD evaluation of an antigen-specific population.

Criteria for evaluation included survival, toxicokinetics, clinical observations (including feeding behavior), body weights, physical (including respiratory, cardiovascular, and neurologic) and ophthalmologic examinations, clinical pathology evaluations, immunogenicity assessment (of anti-ICOS.33 IgG1f S267E antibody; ADA), immunotoxicological and pharmacological assessments (including receptor occupancy and receptor expression on CD4 helper T cells, T-cell-dependent antibody response (TDAR) to KLH or tetanus toxoid, peripheral blood lymphocyte phenotyping, T-cell activation, antigen-specific T-cell phenotyping, and ex vivo recall response to KLH, Gag, or Nef peptides), organ weights, and gross and microscopic pathology analyses. Scheduled necropsies were conducted after 1 month (three/ group/sex) and following an 8-week recovery period (two/ group/sex).

After repeated dosing, mean ICOS.33 IgG1f S267E systemic exposures (AUC[0-T]) increased approximately dose proportionally from 15 mg/kg to 75 mg/kg (once weekly) with no substantial sex differences observed at all doses. After repeated dosing at 1.5 mg/kg (once every three weeks), mean ICOS.33 IgG1f S267E systemic exposures (AUC[0-504h]) were lower (0.4×) than those following dosing on Day 1, whereas AUC(0-168h) values after repeated dosing at 15 mg/kg and 75 mg/kg (QW) were slightly higher (2.1-fold to 2.6-fold) than those following dosing on Day 1 suggesting accumulation.

Treatment-emergent ADA responses were detected in 8 and 2 of 10 monkeys/group at 1.5 mg/kg (once every three weeks) and 15 mg/kg (once weekly), respectively, on or after Day 8. During the recovery phase, ADAs were only detected in monkeys at 1.5 mg/kg. After repeated dosing, serum ICOS.33 IgG1f S267E concentrations in monkeys with ADAs were generally immeasurable (i.e., <lower limit of quantification; LLOQ) or lower than those in monkeys with no ADAs at 1.5 mg/kg and 15 mg/kg, and the presence of ADAs contributed to lower mean AUC value at 1.5 mg/kg.

The toxicokinetic summary for ICOS.33 IgG1f S267E is presented in Table 28.

TABLE 28

Toxicokinetic Summary - Mean Sex-Combined Values

| | | ICOS.33 IgG1f S267E | | |
|---|---|---|---|---|
| Parameter | Period | 1.5 mg/kg (Q3W) | 15 mg/kg (QW) | 75 mg/kg (QW) |
| Cmax | Day 1 | 42.6 | 377 | 2,010 |
| (µg/mL) | Day 22 | 39.2/47.4$^a$ | 680/733$^a$ | 3,790 |
| AUC(0-168 h) | Day 1 | 3,520 | 34,200 | 176,000 |
| (µg · h/mL) | Day 22 | 2,860$^b$/4,610$^a$ | 71,800/84,600$^a$ | 452,000 |
| AUC(0-504 h) | Day 1 | 6,240$^c$ | NA | NA |
| (µg · h/mL) | Day 22 | 2,510$^d$/NA$^a$ | NA | NA |

$^a$Values were calculated with the inclusion/exclusion of the data from animals with detectable treatment-emergent ADAs on or/and after Day 8 (168 hours following the first dose).
$^b$Mean systemic exposure value was averaged from individual AUC(0-72 h) and AUC (0.168 h) values.
$^c$Mean systemic exposure value was averaged from individual AUC(0-168 h), and AUC(0.336 h), and AUC(0-504 h) values.
$^d$Mean systemic exposure value was averaged from individual AUC(0-72 h), AUC(0-168 h), AUC(0-336 h), and AUC(0-504 h) values.
NA = Not applicable ICOS.33 IgG1f S267E was well tolerated at all doses with no ICOS.33 IgG1f S267E-related clinical observations or effects on body weight, physical (including respiratory, cardiovascular, and neurologic) and ophthalmologic evaluations, hematology, coagulation, serum chemistry, urinalysis, organ weights, and gross or microscopic pathology. In addition, there were no ICOS.33 IgG1f S267E-related effects on TDAR to tetanus toxoid, absolute numbers of cytotoxic T cells, B cells, and NK cells, T cell subtypes (including naive CD4 T cells, effector memory CD4 T cells, CD25+ activated CD4 T cells, HLA-DR+ activated CD4 T cells, naive CD8 T cells, effector memory CD8 T cells, CD25+ activated CD8 T cells, and HLA-DR+ activated CD8 T cells), CD8+ T cell proliferation, and ex vivo recall responses at any dose tested.

Evidence of ICOS.33 IgG1f S267E-mediated effects was noted at all doses. ICOS receptor expression on CD4 helper T cells was close to 0% at four hours post dose on Day 1 at all doses, which suggested down regulation and/or internalization of the ICOS receptor, and generally stayed low through the dosing and recovery period at ≥15 mg/kg. Low ICOS receptor expression precluded meaningful assessment of ICOS receptor occupancy. At 1.5 mg/kg administered once every three weeks, ICOS receptor expression on CD4 helper T cells began to recover after Day 8, increased to 41% prior to dosing on Day 22, decreased to 4% following dosing on Day 22, and increased to 42% on Day 29. A full recovery of receptor expression was observed by Day 43 (91%). Receptor occupancy generally correlated with receptor expression (e.g., 71% and 85% RO on Days 22 [prior to dosing] and 29). In general, ICOS receptor expression levels were inversely correlated with serum ICOS.33 IgG1f S267E concentrations. This was consistent with the conclusion that the ICOS.33 IgG1f S267E antibody has caused loss of the receptor.

There was dose-independent suppression of keyhole limpet hemocyannin (KLH)-specific IgM (up to 52% on Day 8) and IgG responses (up to 78% on Day 29) relative to vehicle control. Suppression of T-cell-dependent antibody response to KLH by ICOS.33 IgG1f S267E may represent an alternative mode of action, and has been observed in a previous study in cynomolgus monkeys. Although not bound by any mechanism, suppression of TDAR by an agonist of the ICOS co-stimulatory pathway may relate to impaired agonism of T helper cells as a result of early and sustained downregulation of ICOS expression.

Other ICOS.33 IgG1f S267E-related effects at all or some of the dose levels during dosing and/or recovery period included decreases in mean absolute numbers of total T cells and CD4 helper T cells, percent CD4 T regulatory cells, percent central memory CD4+ T cells, percent central memory CD8+ T cells, percent Ki67+ CD4+ T cells, and percent Gag+ and Nef+ CD8 T cells.

In conclusion, ICOS.33 IgG1f S267E was clinically tolerated by monkeys for one month at intravenous doses ≤75 mg/kg administered once weekly. ICOS.33 IgG1f S267E-related effects were noted at all doses, as demonstrated by ICOS receptor expression and receptor occupancy changes, suppression of T-cell-dependent antibody response to KLH, decreased levels of certain T cell subsets, decreased CD4-T cell activation, and decreased percentages of antigen specific CD8 T cells. Many of these changes were still apparent by the end of the recovery period at ≥15 mg/kg QW consistent with continued ICOS.33 IgG1f S267E exposure throughout the recovery period and the subsequent sustained downregulation of ICOS receptor expression at these doses. The lower dose of 1.5 mg/kg administered once every three weeks resulted in lower serum ICOS.33 IgG1f S267E concentrations after the first dose and allowed receptor recovery on the cell surface before the second dose. There were no adverse ICOS.33 IgG1f S267E-related findings. Thus, the no-observed-adverse-effect level (NOAEL) was considered to be 75 mg/kg (mean AUC[0-168 h] of 452,000 μg·h/mL). In addition, for potential determination of the maximum recommended human starting dose, 75 mg/kg was also considered the highest non-severely toxic dose (HNSTD).

Single-Dose Intravenous Pharmacokinetics and Receptor Occupancy Study in Monkeys The pharmacokinetics of ICOS.33 IgG1f S267E was evaluated in protein naive monkeys. All monkeys were immunized intramuscularly with 2.5 mg of keyhole limpet hemocyanin (KLH). Following the immunization, monkeys were intravenously administered ICOS.33 IgG1f S267E in 20 mM histidine (pH 6.0), 250 mM sucrose buffer, 50 μM pentetic acid (DPTA) and 0.05% polysorbate 80 at doses of 0, 1 mg/kg, or 10 mg/kg (N=2/sex for vehicle and 1 mg/kg and 10 mg/kg groups) via femoral vein. Serial blood samples (about 0.5 mL) were collected at pre-dose and 6, 24, 72, 168, 240, 336, 408, 504, 672, 840, and 1008 hours post dose. Blood samples were allowed to coagulate and then centrifuged at 4° C. (1500-2000×g) to obtain serum. Serum samples were stored at −20° C. and delivered for analysis on dry ice. Samples not analyzed on the day of receipt were stored frozen in a freezer set to maintain a temperature of ≤70° C. until analyzed.

Cynomolgus monkey serum samples were analyzed using a qualified Gyros® immunoassay for the detection of ICOS.33 IgG1f S267E. Biotinylated human ICOS mG1 (Lot No 22Oct2015-Biotin) was used as a capture molecule for ICOS.33 IgG1f S267E. Samples, standards, and QCs were brought up to a final matrix concentration of 10% cynomolgus serum and loaded into Gyrolab. Wash 2 V2 Wizard method with Gyrolab Bioaffy 200 CD was used. After final wash steps the captured ICOS.33 IgG1f S267E was detected using an Alexa 647 labeled mouse anti-Hu IgG Fc-specific monoclonal antibody, clone 1007 (Lot No 15C3483473-1007A) as the detection molecule. The concentration of ICOS.33 IgG1f S267E in cynomolgus serum samples was calculated from fluorescence intensity as measured by Gyrolab using a 4-parameter logistic (4-PL) calibration curve generated from ICOS.33 IgG1f S267E calibrators.

The range of the ICOS.33 IgG1f S267E calibration curve was from 3 ng/mL to 30,000 ng/mL in cynomolgus monkey serum. The upper and lower limits of quantification were 30,000 ng/mL and 3 ng/mL, respectively (i.e., ULOQ 30000 ng/mL, LLOQ 3 ng/mL). Quality control samples were prepared at 20 ng/mL, 200 ng/mL, 2,000 ng/mL, and 20,000 ng/mL in cynomolgus monkey serum and analyzed on each CD to ensure acceptable assay performance. Calibrators, QCs, and samples were diluted 10-fold in PTB. Assay performance was within the acceptable range: % CV of the standards was below 25%, and QC recovery was within ±30% of the nominal values.

Monkey serum samples were analyzed by ABO/BAS, Lawrenceville, N.J., using a qualified electrochemiluminescence immunoassay on the Meso Scale Discovery (MSD) platform for the presence of anti-ICOS.33 IgG1f S267E ADA. ICOS.33 IgG1f S267E mouse anti-idiotypic antibody cell supernatant was used to prepare positive control (PC). Biotinylated ICOS.33 IgG1f S267E was used as a capture molecule and ICOS.33 IgG1f S267E labeled with Sulfo Tag was used as a detection reagent. The biotinylated ICOS.33 IgG1f S267E and Sulfo Tag-labeled ICOS.33 IgG1f S267E were diluted in PTB and combined to generate a master mix with final concentration of biotinylated ICOS.33 IgG1f S267E of 1,000 ng/mL and 1,000 ng/mL of Sulfo Tag-labeled ICOS.33 IgG1f S267E. Samples were diluted at 10% minimum required dilution (MRD) in the master mix and incubated at 22° C. for 2 hours. The master mix was then transferred into a streptavidin-coated MSD plate at 50 μL/well. After another hour of incubation at 22° C., the plate was washed and was added with the MSD read buffer. The plate was then read immediately on the MSD Sector Imager 6000. The presence of detectable anti-ICOS.33 IgG1f S267E antibodies in monkey serum samples was determined using the ratio of sample signal to negative sample signal.

Monkey serum samples were analyzed by BAR, Lawrenceville, N.J. Cynomolgus monkey serum samples were analyzed for "total" ICOS.33 IgG1f S267E using direct trypsin digestion reversed phased liquid chromatography tandem mass spectrometry (LC/MS/MS). Monkey serum samples were also analyzed for deamidated and unmodified ICOS.33 IgG1f S267E at position N329 using immunoaffinty enrichment target capture LC/MS/MS. Standard curves defining the range of the assay were prepared in commercially-obtained cyno serum and analyzed with the study samples as a complete analytical set. Concentrations for "total" ICOS.33 IgG1f S267E were reported in μg/ml via Excel spreadsheet for toxicokinetic and pharmacokinetic interpretation.

PK parameter values were calculated using noncompartmental analysis method (Phoenix WinNonlin 6.4, Certara, Princeton, N.J.). Exposure values below the lower limit of quantification (LLOQ: <10 ng/mL (0.07 nM) for ICOS.33 IgG1f S267E) were not used in the analysis. The area under the curve from time 0 to the last sampling time (AUC(0-T)) were calculated using a combination of linear and log trapezoidal summations.

The PK parameters of ICOS.33 IgG1f S267E following a single intravenous dose of 1 mg/kg and 10 mg/kg to cynomolgus monkeys are summarized in Table 29. After intravenous administration, the plasma concentrations of ICOS.33 IgG1f S267E exhibited a bi-exponential decline. Accelerated clearance was observed in three out of four monkeys in 1 mg/kg group after Day 7. As a result, only the concentration time data up to Day 14 were used for all animals in the 1 mg/kg dose group for analysis, and AUC (0-14d) was reported to eliminate influence of ADAs. Immunogenicity testing of the plasma samples suggested that five out of eight monkeys enrolled in the study developed ADAs, and that the monkeys with higher ADA levels showed faster clearance at the 1 mg/kg dose. AUC (0-42d) was reported for the 10 mg/kg group. ICOS.33 IgG1f S267E exhibited close to dose-proportional increase in Cmax and AUC(0-T) and AUC(0-INF). With the dose increment at the ratio of 1:10, the Cmax in male and female monkeys increased at the ratio of 1:8 and 1:8, respectively; and the AUC(0-T) increased at the ratio 1:16 and 1:11, respectively, and the AUC(0-INF) increased at the ratio 1:11 and 1:11, respectively.

The concentrations of intact ICOS.33 IgG1f S267E, and the deamidated product after a 10 mg/kg intravenous dose were quantified using LCMS/MS. The concentrations of the deamidated product ranged between 0.5% to 8% of total ICOS.33 IgG1f S267E at all measured time points. The AUC (0-42d) for the deamidated product was 2.9% of exposure of total ICOS.33 IgG1f S267E.

TABLE 29

Pharmacokinetic Summary

| | ICOS.33IgG1fS267E | | | | | |
|---|---|---|---|---|---|---|
| | 1 mg/kg$^{a,c}$ | | | 10 mg/kg$^{b,c}$ | | |
| Parameter | M | F | Mean | M | F | Mean |
| Cmax (µM) | 0.168 ± 0.006 | 0.161 ± 0.006 | 0.165 ± 0.006 | 1.4 ± 0.019 | 1.3 ± 0.046 | 1.38 ± 0.02 |
| Thalf (day) | 14 ± 3 | 11 ± 0.7 | 13 ± 2.7 | 14 ± 5.2 | 14 ± 2.3 | 14 ± 2.7 |
| AUC(0-T) (µM · day) | 1.28 ± 0.2 | 1.5 ± 0.7 | 1.2 ± 0.1 | 21 ± 0.5 | 16.9 ± 0.5 | 19 ± 0.5 |
| AUC(0-INF) (µM · day) | 2.3 ± 0.5$^d$ | 2 ± 0.09$^d$ | 2.17 ± 0.2$^d$ | 25.9 ± 2.5 | 20.4 ± 2.3 | 23 ± 3.8 |

$^a$AUC(0-T) truncated at 14 days in 1 mg/kg dose group
$^b$AUC(0-42 d) reported for animals in 10 mg/kg dose group
$^c$Number of monkeys = 2/sex
$^d$>20% of the AUC is extrapolated Although increased C1q binding was observed in vitro, the absence of overt clinical signs in the single-dose study in monkeys, and absence of hemodynamic effects in a cardiovascular instrumented monkey model showed low risk for complement activation. ICOS.33 IgG1f S267E was well tolerated when given intravenously as a single dose at 1 mg/kg or 10 mg/kg to cynomolgus monkeys with a dose proportional increase in exposure. No adverse clinical pathology findings were observed.

Example 15

Anti-ICOS Antibody Binding Competition

Epitope binning experiments were conducted to determine which anti-ICOS antibodies compete with which others for binding to huICOS. Epitope binning is a process that uses a competitive immunoassay to test antibodies in a pairwise combinatorial manner, and antibodies that compete for the same binding region, that is, the same or a closely related epitope of an antigen, are grouped together into bins. Pairwise competition between anti-huICOS antibodies was determined as follows. A reference antibody (i.e., ICOS.33, 20H4, 27B9, 23B6, 12D10, 23A10, 15B7, 12F3, 13B4, 17H9, 26E11, 23H5, 6D1, 12A9, 5C4, 10B10, 17C4, 1D7, 21E1, 9F11, 15H11, 25B10, 8A10, 4D11, 6D5, 7C6, 26E9, 3E8, 16H4, 25E4, or 2644) was bound to the surface of a sensor chip, a test antibody was pre-incubated with a huICOS polypeptide construct in a mixture, and the pre-incubated mixture was flowed over the sensor chip to determine the degree to which the test antibody interferes with binding of the huICOS polypeptide construct to the reference antibody on the chip surface. Competition experiments were performed using a BIACORE® Surface Plasmon Resonance (SPR) instrument. Specifically, a reference anti-huICOS antibody was immobilized onto Sensor Chip CM5 chip (Series S, GE Healthcare CAT #BR-1005-30) surfaces, flowcell2, flowcell3 & flowcell4 (5000 resonance units, RUs), and flowcell1 was used as a negative control. A test antibody (i.e., ICOS.33, 20H4, 27B9, 23B6, 12D10, 23A10, 15B7, 12F3, 13B4, 17H9, 26E11, 23H5, 6D1, 12A9, 5C4, 10B10, 17C4, 1D7, 21E1, 9F11, 15H11, 25B10, 8A10, 4D11, 6D5, 7C6, 26E9, 3E8, 16H4, 25E4, or 2644) was diluted to 120 µg/mL (2×) at starting concentration. A series of dilutions of the test antibody was made by diluting 1:3 concentration of antibody with buffer for seven different concentrations and a control sample (with 0 µg/ml) to obtain a titration curve. Each antibody concentration series was divided in half. In the first half of the concentration series, 40 nM (2×) human ICOS antigen (e.g. huICOS/Fc) was added to make the final concentration series (60 µg/ml-0.0 µg/ml) and 20 nM of final antigen concentration in each well. In the second half of the concentration series, in place of antigen, buffer was added to have the antibody diluted to the same concentration, and this half was treated as the blank. Complexes of the test anti-ICOS antibodies and huICOS/Fc were incubated for two hours. 40 µL complexes were injected on the reference antibody-coated surface at a 30 µL/min. A BIACORE® T200 SPR instrument was used and the running buffer in HBE-EP, GE Healthcare CAT #BR-1001-88, filtered, degassed, 0.01 M HEPES, pH 7.4, 0.15 NaCl, 3 mM EDTA, 0.005% Surfactant P20. The surface was regenerated with 25 mM NaOH (order code: BR-1003-58, GE Healthcare) at 100 µL/min for five seconds. The data were analyzed using Microsoft Excel where the concentration of test antibodies was plotted against the corresponding response unit to obtain titration curves.

The binding competition experiments determined that antibodies ICOS.33, 20H4, 27B9, 23B6, 12D10, 23A10, 15B7, 12F3, 13B4, 17H9, 26E11, 23H5, 6D1, 12A9, 5C4, 10B10, 17C4, 1D7, 21E1, 9F11, 15H11, 25B10, 8A10, 4D11, 6D5, 7C6 and 26E9 cross-compete with each other, and block ligand (B7-H2; ICOS-L) binding to huICOS. Antibodies 3E8, 16H4 and 25E4 cross-compete with each other but do not block ligand binding to huICOS. In contrast, while antibody 2644 was found to cross-compete with antibody 3E8, it was also able to block ligand binding to ICOS.

Example 16

Anti-ICOS Antibody Epitope Mapping

Anti LCOS Antibody Epitope Mapping by Yeast Display

The epitopes for anti-huICOS antibodies 3E8 and ICOS.4 were determined by displaying randomly mutagenized variants of the extracellular domain of human ICOS (residues 21-134 of NP_036224.1, provided as SEQ ID NO: 173) by yeast cells (Saccharomyces cerevisiae), and sorting the yeast cells based on their binding or not binding to particular antibodies. Selected yeast cells were amplified and subjected to additional rounds of selection based on their ability to bind to anti-ICOS antibodies tested. See, e.g., Chao et al. (2004) J. Mol. Biol. 342:539. Sequences for huICOS variants were determined for the resulting yeast and analyzed for the effects of each residue on antibody binding. The binding epitope for the antibodies of the present invention was determined as the loci within the huICOS sequence where single amino acid mutations disrupt binding to the anti-huICOS antibodies of the present invention.

Briefly, error-prone PCR was used to clone human ICOS-encoding DNA (encoding residues 21-134 of SEQ ID NO: 1) into constructs allowing expression of the huICOS variants as the amino-terminal portions of fusion proteins further comprising a c-myc tag sequence and yeast cell wall protein Aga1p. Such constructs, when expressed in yeast (Saccharomyces cerevisiae), display the variant huICOS polypeptides on the surface of yeast cells, anchored to the cell surface by the Aga1p polypeptide. The c-myc tag was used as a positive control to sort yeast cells displaying huICOS fusion proteins. These yeast cells were then further sorted for those that expressed properly folded huICOS-fusion proteins (as determined by binding of a control mouse anti-huICOS antibody detected by an allophycocyanin (APC)-labeled goat anti-mouse IgG secondary), but did not bind to the antibodies of the present invention (as determined by detection with a phycoerythrin (PE) labeled goat anti-human IgG as a secondary). These selected yeast cells were pooled, amplified, and used in a subsequent round of selection. The huICOS sequence was determined for constructs from yeast remaining after selection.

Yeast populations binding to ICOS.4 and 3E8 show distinct mutation patterns, indicating different epitopes were recognized by these two antibodies. Analogous experiments were performed with antibody 9D5, which blocks ICOS-ligand binding to ICOS and which competes with ICOS.4. For the 9D5 experiments, a molecular model of the three dimensional structure of ICOS based on the crystal structure of the CTLA-4/B7-2 complex (e.g. Stamper et al. (2001) Nature 410:608) was used to distinguish which amino acid residues are buried and which are surface-exposed to determine which of the selected mutations were most likely antibody-specific contact residues (i.e., epitope residues) as opposed to mere structurally disruptive mutations. The yeast display inferred epitopes for ICOS.4, 3E8 and 9D5 are provided in Table 30. Epitopes in Table 30 are presented as a list of residues in huICOS of SEQ ID NO: 1, which includes the 20 amino acid signal sequence. Accordingly, residue numbers for mature huICOS (i.e., ICOS protein without the signal sequence) would be the residues indicated in Table 30 reduced by 20 (e.g., V48 with the signal sequences or V28 without the signal sequence).

TABLE 30

Anti-ICOS mAb Epitopes

| Clone | ICOS Residues (SEQ ID NO: 1) |
|---|---|
| ICOS.4 | V48, Q50, G70, S71, G72, F114, D115, P116, P117, P118, L123 |
| 3E8 | D64, K78, S79, L80, K81, F82, S85 |
| 9D5 | P45, I47, P117, P118, K120 |

Analogous yeast display experiments were performed with ICOS-L (B7-H2) in place of anti-ICOS mAbs to determine which residues on ICOS are critical to the ICOS/ICOS-L interaction, i.e. the binding site for ICOS-L on ICOS. The ICOS-L binding site was determined to reside at residues Q50, K52, F114, P117, P118, and F119 of ICOS, as provided at SEQ ID NO: 1. Inspection of the epitopes for anti-ICOS mAbs in Table 30 suggests that ICOS.4 and 9D5 should block ICOS-L binding, whereas 3E8 may not, which is consistent with what was observed experimentally (as discussed in Example 15 above).

Anti LCOS Antibody Epitope Mapping by HDX-MS

Deuterium exchange experiments with antibodies ICOS.4 and 9D5 confirmed that the region from S112 and L123 is contacted when ICOS is bound to ICOS-L, which suggested a functional epitope region of residues 112-123 of ICOS (SEQ ID NO: 1), or SIFDPPPFKVTL (SEQ ID NO: 203). This region overlaps with the C-terminal portion of the epitope determined by yeast display, and represents the largest cluster of residues along the primary sequence.

The epitopes for anti-huICOS antibodies ICOS.4 and 9D5 were determined by hydrogen/deuterium exchange mass spectrometry (HDX-MS) see, e.g., Epitope Mapping Protocols in Methods in Molecular Biology, Vol. 66, G. E. Morris, Ed. (1996) as described herein. ICOS-Fc was mixed with mAbs at 1:1 ratio and HDX-MS was run for one minute, 10 minutes, 4 hours in duplicate.

Results show that ICOS.4 and 9D5 bind to the same discontinuous epitope, which is shown below (epitope is underlined) and in FIG. 1.

(SEQ ID NO: 1)

MKSGLWYFFLFCLRIKVLTGEINGSANYEMFIFHNGGVQILCKYPDIVQQFKMQLLKGGQ    60

ILCDLTKTKGSGNIVSIKSLKFCHSQLSNNSVSFFLYNLDHSHANYYFCNLSIFDPPPFK  120

VTLTGGYLHIYESQLCCQLKFWLPIGCAAFVVVCILGCILICWLTKKKYSSSVHDPNGEY  180

MFMRAVNTAKKSRLTDVTL                                            199

Example 17

Expression of ICOS on Peripheral Blood and Tumor-Infiltrating Lymphocytes from Lung, Kidney, and Colon Cancer Patients Understanding ICOS expression on tumor-infiltrating lymphocytes (TIL) in different tumor types and patient populations helped identify the relevant disease indication and patient population for effective ICOS.33 IgG1f S267E therapy, especially in combination with anti-PD-1 agents such as nivolumab. The frequency and magnitude of ICOS and PD-1 expression on peripheral blood cells and TIL (CD8+ and CD4+ T cells) were profiled in non-small cell lung, renal cell, and colorectal carcinoma (CRC) specimens. Fresh tumor tissues and matching peripheral blood samples were obtained from patients with lung cancer, kidney cancer, or CRC (ConversantBio, MT Group, Benaroya) and shipped overnight at 4° C. in hypothermosol FRS (Biolife Solutions) and ACD Solution A (BD Biosciences), respectively. All samples were processed and stained within 24 hours of surgery. Tumor tissues were weighed and dissociated using the Miltenyi dissociation kit (Miltenyi, Catalog 130-095-929), whereas peripheral blood cells were isolated after lysis of red blood cells (RBC) in RBC Lysis Buffer (BioLegend, Catalog 420301). Cell suspensions (from tumor tissues or peripheral blood) were washed two times in HBSS (no Ca, no Mg), stained with NIR Viability Dye (Molecular Probes by Life Technologies, Catalog L34976), blocked with human AB serum in Dulbecco's phosphate-buffered saline (dPBS), and added to wells containing cocktails of antibodies (Table 31) for incubation on ice in the dark for 45 minutes. The cells were then washed twice with dPBS/BSA/Na azide, fixed, and permeabilized using the FOXP3 buffer kit (BioLegend, Catalog 421403). Fluorescence minus one (FMO) controls were prepared for all antibodies and used to determine positive cell populations. Samples were acquired on the Fortessa flow cytometer (BD Biosciences) and data were analyzed using FlowJo Software (TreeStar).

As shown in Table 31, a panel was devised to examine expression of multiple markers, and ICOS expression on CD8+ and CD4+ T cells was analyzed.

TABLE 31

Antibodies Used For Immunofluorescence Staining For T Cell Subsets

| Marker | Clone | Fluorophore | Vendor | Catalog |
|---|---|---|---|---|
| CD3 | SK7 | BUV 395 | BD Biosciences | 564001 |
| CD4 | OKT4 | BV 785 | BioLegend | 317442 |
| FOXP3 | 206D | AF647 | BioLegend | 320114 |
| CD25 | 4E3 | PE-e610 | eBioscience | 61-0257-42 |
| CD152 | BN13 | BV 421 | BD Biosciences | 562743 |
| CD45 | HI30 | AF700 | BD Biosciences | 560566 |
| Viability | — | Near IR | ThermoFisher Scienitific | L10119 |
| 2B4 | C1.7 | AF488 | BioLegend | 329506 |
| CD8a | SK1 | BV605 | BD Biosciences | 564116 |
| ICOS | C398.4A | BV510 | BioLegend | 313525 |
| CD56 | NCAM16.2 | BV650 | BioLegend | 318343 |
| PD-1 | EH12.1 | PE | BioLegend | 560795 |

For Treg, Teff, B cell, and NK cell staining, fresh tumors from head and neck, lung, CRC, and endometrial cancers were placed in a 6-well plate rested on ice, immersed in 1-2 mL of dissociation media. The tumors were cut into small pieces, and the tumor solution was placed into the Dounce homogenizer for dissociation. Tumor solutions were filtered through a 70 μm filter with additional dissociation media and centrifuged. Resulting cells were re-suspended in staining buffer. Fresh omentum metastatic tumor tissue sample was dissociated using the Miltenyi dissociation kit (Miltenyi, Catalog 130-095-929). Frozen tumor samples were thawed and DNAase added dropwise (2 mL DNAase solution). Thaw medium (8 mL warmed in 37° C. bath) was added to the tumor and DNAase solution, and filtered through a 70 μm filter. Cells were centrifuged and re-suspended in staining buffer.

ICOS expression on TIL was assessed by FACS analysis. Tumor derived cell suspensions were blocked with staining buffer containing the Near-IR Dead Cell stain. Surface cell population markers were stained with antibodies (as shown in Table 32) to determine positive cell populations followed by intracellular staining of FOXP3 after fixation and permeabilization. Flow cytometric data was collected using a Fortessa X-20 flow cytometer. After gating on FSC-SSC-Live/Dead markers parameters to exclude debris and dead cells, the frequency of ICOS+ cells were determined for CD4+ Teff, Treg, CD8+ T cell, B cell, and NK cell subsets. Cd4+ Flow cytometric analysis was performed with FlowJo analysis software.

TABLE 32

Antibodies Used For Immunofluorescence Staining of B Cells, NK Cells, and T Cell Subsets

| Conjugate | Target | Company | Catalog | Clone |
|---|---|---|---|---|
| Alexa Fluor® 700 | CD8 | BioLegend | 301028 | RPA-T8 |
| BUV395 | CD8 | BD Biosciences | 563795 | RPA-T8 |
| BUV737 | CD14 | BD Biosciences | 564444 | M5E2 |
| BUV805 | CD4 | BD Biosciences | 564910 | SK3 |
| BV421 | ICOS | BioLegend | 313524 | C398.4A |
| BV510 | CD45 | BioLegend | 304036 | HI30 |
| BV510 | CD45RA | BioLegend | 304142 | HI100 |
| BV605 | CD11c | BioLegend | 301636 | 3.9 |
| BV650 | CD15 | BioLegend | 323034 | W6D3 |
| BV650 | CD45 | BD Biosciences | 563717 | HI30 |
| BV711 | PD1 | BD Biosciences | 564017 | EH12.1 |
| BV786 | CD3 | BD Biosciences | 563800 | SK7 |
| PE/Cy5 | CD19 | BioLegend | 302210 | HIB19 |
| PE/Cy7 | FOXP3 | eBioscience | 25-4777-42 | 236A/E7 |
| PE-eFluro® 610 | CD56 | eBioscience | 61-0567-42 | CMSSB |
| PerCP/Cy5.5 | HLADR | BD Bioscience | 560652 | G46-6 |

ICOS expression was evaluated using the anti-ICOS C398.4a clone in whole blood samples from 16 healthy donors and 14 lung cancer, 22 RCC, and 14 CRC patients. Compared to healthy donors, the frequencies of ICOS+ CD4+ T cells obtained from cancer patients were higher (Table 33, P<0.001 for all cancer patient groups compared to healthy donors, Mann-Whitney test). Frequencies of ICOS+ CD8+ T cells from RCC patients were significantly higher compared to healthy donors (Table 33, P<0.01, Mann-Whitney). In lung cancer and CRC patient blood samples, the percentages of ICOS+CD8+ T cells were also higher than in healthy donor samples without reaching statistical significance (Table 33).

Because higher frequencies were observed than reported in literature and because the C398.4a clone positively stained more T cells than the other commonly used clone ISA-3,6,7,8,9,10 the frequencies of cells that express high levels of ICOS (ICOShi) were also analyzed. Consistent with the literature, CD8+ T cells expressed minimal amounts of ICOShi, comparable to background (Table 33). In CD4+ T cells, however, the frequencies of ICOShi cells ranged on average from 3.0% in healthy donors to 4.9% in patients with RCC (Table 33, RCC vs. healthy: P<0.05, Mann-Whitney).

Next, ICOS expression was evaluated in TIL of 11 lung cancer, 21 RCC, and 8 CRC patients. Frequencies of ICOS+ CD4+ and ICOS+CD8+ TIL were similar across tumor types (Table 34). As in peripheral blood, high expression of ICOS by CD4+ and CD8+ TIL T cells was measured. On average, a greater percentage of CD4+ T cells expressed high levels of ICOS than CD8+ T cells (Table 34). Co-expression of ICOS and PD-1 in TIL was also measured. High levels of PD-1 (PD-1hi) were expressed by ICOShi CD4+ TIL with large interpatient variability (Table 34). Compared to ICOShi CD4+ TIL, a higher proportion of ICOShi CD8+ T cells co-expressed high levels of PD-1 (Table 34).

TABLE 33

Mean Frequencies ± SD of ICOS+ and ICOShi CD4+ and CD8+ T Cells in Peripheral Blood Samples From Healthy Donors and Patients with Cancer

|  | Healthy (N = 16) | NSCLC (N = 14) | RCC (N = 22) | CRC (N = 14) |
| --- | --- | --- | --- | --- |
| % ICOS+ CD4+ T cells | 21 ± 7 | 43 ± 15 | 39 ± 16 | 42 ± 19 |
| % ICOS+ CD8+ T cells | 14 ± 8 | 23 ± 14 | 25 ± 12 | 23 ± 14 |
| % ICOS$^{hi}$ CD4+ T cells | 3.0 ± 1.8 | 3.5 ± 1.8 | 4.9 ± 2.9 | 3.7 ± 2.4 |
| % ICOS$^{hi}$ CD8+ T cells | 0.9 ± 0.7 | 0.9 ± 0.8 | 1.3 ± 0.9 | 0.9 ± 0.7 |

Abbreviations:
ICOShi: Cells expressing high levels of ICOS;
N: Number of samples;
SD: Standard deviation;
NSCLC: Non-small cell lung cancer;
RCC: Renal cell carcinoma;
CRC: Colorectal carcinoma

TABLE 34

Mean Frequencies ± SD of ICOS+, ICOShi, and PD-1hi ICOShi CD4+ and CD8+ T Cells in TIL From Patients with Cancer

|  | NSCLC (N = 11) | RCC (N = 21) | CRC (N = 8) |
| --- | --- | --- | --- |
| % ICOS+ CD4+ T cells | 59 ± 21 | 53 ± 19 | 63 ± 14 |
| % ICOS+ CD8+ T cells | 35 ± 19 | 35 ± 20 | 27 ± 21 |
| % ICOS$^{hi}$ CD4+ T cells | 28 ± 15 | 19 ± 20 | 29 ± 12 |
| % ICOS$^{hi}$ CD4+ T cells | 8.3 ± 7.2 | 6.5 ± 8.5 | 4.8 ± 4.5 |
| % PD-1$^{hi}$ ICOS$^{hi}$ CD4+ T cells | 43 ± 18 | 48 ± 23 | 33 ± 17 |
| % PD-1$^{hi}$ ICOS$^{hi}$ CD8+ T cells | 63 ± 16 | 71 ± 29 | 62 ± 23 |

Abbreviations:
SD: Standard deviation;
ICOShi: Cells expressing high levels of ICOS;
PD-1: Cells expressing high levels of PD-1;
TIL; Tumor-infiltrating lymphocytes;
NSCLC: Non-small cell lung cancer;
RCC: Renal cell carcinoma;
CRC: Colorectal carcinoma;
N: Number of samples Human tumor samples from patients with two lung adenocarcinomas, one endometrial adenocarcinoma, one omentum metastasis of serous papillary carcinoma, one liver metastasis of colorectal adenocarcinoma, and one head and neck squamous cell carcinoma were dissociated and stained for flow cytometric analysis of ICOS expression on various lymphocyte populations. Of the five different lymphocyte populations depicted (CD4+ Teff, Tregs, CD8+ T cells, B cells, NK cells), CD4+ Teff and Tregs expressed the highest frequencies of ICOS. On cell populations that expressed ICOS (CD4 Teff, Tregs, CD8 T cells, and NK cells), Tregs expressed more ICOS on a per cell basis compared to other cell types.

In summary, ICOS was expressed at higher levels on CD4+ T cells than in CD8+ T cells on peripheral blood and TIL. ICOS expression was variable across patients and was similar for the three tumor types tested. On average, 33% to 48% of ICOShi CD4+ TIL and 62% to 71% of ICOShi CD8+ TIL co-expressed high levels of PD-1. In addition, Tregs expressed higher levels of ICOS than CD4+ Teffs, CD8+ T cells, NK cells, and B cells in the human tumor microenvironment.

Example 18

A Dose Escalation and Combination Cohort Study to Evaluate the Safety and Tolerability, Pharmacokinetics, and Efficacy of ICOS.33 IgG1f S267E Alone or in Combination with One or More Anti-PD-1 Antibody, One or More Anti-PD-L1 Antibody, and/or One or More Anti-CTLA-4 Antibody in Patients with Advanced Solid Tumors Phase 1/2, open-label, study of ICOS.33 IgG1f S267E administered as a monotherapy or in combination with an anti-PD-1 antibody, an anti-PD-L1 antibody, and/or an anti-CTLA-4 antibody (for example nivolumab and/or ipilimumab) is conducted in participants with advanced solid tumors. The study includes the following parts:

1) dose-escalation monotherapy (Preliminary Safety Cohorts and Part A);
2) dose-escalation combination therapy with either nivolumab (Part B) or ipilimumab (Part C); and
3) dose expansion phase with either nivolumab (Part D) or ipilimumab (Part E).

Objectives

The primary objective of this study is to characterize the safety and tolerability of ICOS.33 IgG1f S267E administered alone and in combination with nivolumab or ipilimumab in participants with advanced solid tumors.

Secondary objectives include exploring the preliminary efficacy of ICOS.33 IgG1f S267E administered alone and in combination with either nivolumab or ipilimumab in participants with advanced solid tumors; characterizing the PK of ICOS.33 IgG1f S267E when administered alone and in combination with nivolumab or ipilimumab in participants with advanced solid tumors; characterizing the immunogenicity of ICOS.33 IgG1f S267E when administered alone and in combination with nivolumab or ipilimumab in participants with advanced solid tumors; and monitoring target engagement of ICOS.33 IgG1f S267E administered alone and in combination with either nivolumab or ipilimumab in participants with advanced solid tumors.

In addition, exploratory objectives include examining the association between anti-tumor activity and specific biomarker measures in the tumor tissue and in peripheral blood prior to treatment and following administration of ICOS.33 IgG1f S267E alone and in combination with either nivolumab or ipilimumab; characterizing the relationship(s) between ICOS.33 IgG1f S267E PK alone and in combination with nivolumab PK or ipilimumab PK, and safety, efficacy, and/or clinical biomarkers; assessing the overall survival rate (OSR) in participants treated with ICOS.33 IgG1f S267E alone and in combination with either nivolumab or ipilimumab; characterizing the PK and immunogenicity of nivolumab and ipilimumab when administered in combination with ICOS.33 IgG1f S267E; characterizing the immunogenicity of nivolumab and ipilimumab when administered in combination with ICOS.33 IgG1f S267E; assessing the potential effect of ICOS.33 IgG1f S267E on QT interval corrected (QTc); and exploring associations between select peripheral blood biomarkers and incidence of adverse events (AEs) and serious adverse events (SAEs).

Overall Design

Figure 27:
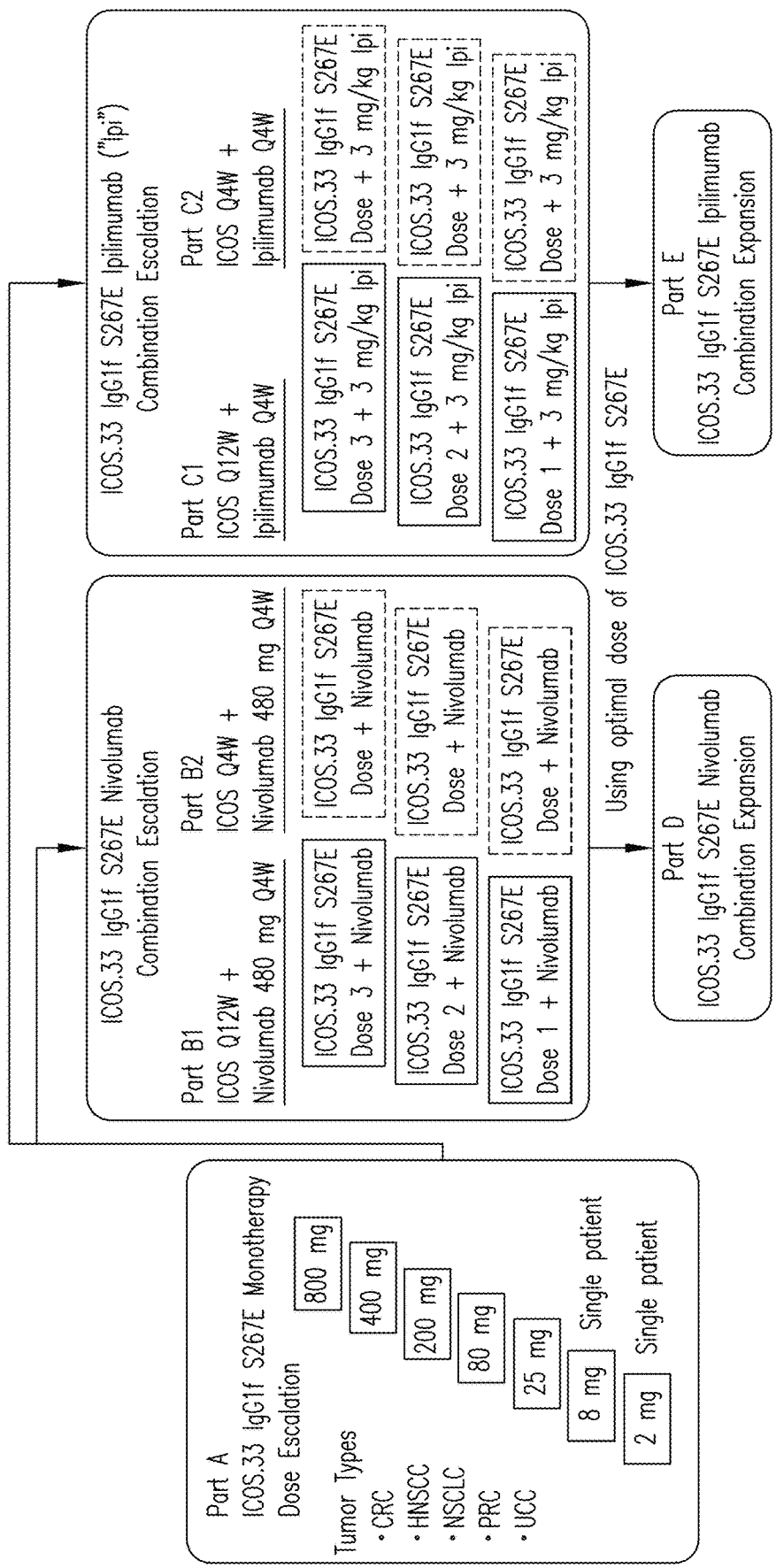
FIG. 27 is a schematic illustrating a dose escalation clinical trial study using anti-ICOS antibody in combination with anti-PD-1 antibody and/or anti-CTLA-4 antibody.

A schematic for the study design is shown in FIG. 27. Monotherapy consists of two different cohorts as follows:
Preliminary Safety Cohorts: ICOS.33 IgG1f S267E administered as monotherapy at 2 mg and 8 mg once every four weeks for 24 weeks.
Part A: ICOS.33 IgG1f S267E administered at 25 mg, 80 mg, 200 mg, 400 mg, and 800 mg once every four weeks for 24 weeks.

Parts B and C consist of different combination cohorts comprising:
B1: ICOS.33 IgG1f S267E administered once every 12 weeks+nivolumab 480 mg once every 4 weeks at a starting dose level of ICOS.33 IgG1f S267E recommended by the Bayesian Logistic Regression Model (BLRM)-Copula model and available PK/PD data from Part A.
B2: ICOS.33 IgG1f S267E once every 4 weeks+ nivolumab 480 mg once every 4 weeks at a dose level of ICOS.33 IgG1f S267E recommended by the Bayesian Logistic Regression Model (BLRM)-Copula model (BLRM-RD) and available PK/PD data from Part A.
C1: ICOS.33 IgG1f S267E once every 12 weeks+ipilimumab 3 mg/kg once every 4 weeks at a starting dose level of ICOS.33 IgG1f S267E recommended by the Bayesian Logistic Regression Model (BLRM)-Copula model and available PK/PD data from Part A.
C2: ICOS.33 IgG1f S267E once every 4 weeks+ipilimumab 3 mg/kg once every 4 weeks at a dose level of ICOS.33 IgG1f S267E recommended by the Bayesian Logistic Regression Model (BLRM)-Copula model and available PK/PD data from Part A.
Parts B1 and C1 are enrolled concurrently. Parts B2 and C2 are enrolled only if additional safety, PK, or PD data is required to optimize dose and/or schedule selection.

The doses of ICOS.33 IgG1f S267E for Parts B and C (combination with nivolumab or ipilimumab) are determined using all available safety (clinical and laboratory), PK, and target engagement/pharmacodynamic biomarker data, as well as modeling recommendation within Bayesian hierarchical modeling framework, i.e., the BLRM-Copula model, by incorporating single-agent toxicity profiles of both ICOS.33 IgG1f S267E (Preliminary Safety Cohorts and Part A) and nivolumab or ipilimumab and any available combination toxicity profiles from Parts B and C (for subsequent doses of ICOS.33 IgG1f S267E in Parts B and C), PK/PD modeling, and do not exceed the maximum administered dose (MAD) of ICOS.33 IgG1f S267E monotherapy in the Preliminary Safety Cohorts and Part A. A dose level of ICOS.33 IgG1f S267E recommended by the BLRM-Copula model, i.e., BLRM-RD, is defined as a generic concept such that a BLRM-RD for any cohort is always based on all available and most updated information.

At no point does the dose of ICOS.33 IgG1f S267E administered in combination with nivolumab or ipilimumab (Parts B and C) exceed the dose of ICOS.33 IgG1f S267E that is demonstrated to be safe in the monotherapy dose-escalation arm (Part A), nor at any point during combination therapy in Parts B and C does the ICOS.33 IgG1f S267E dose exceed the highest dose determined to be tolerated in the monotherapy dose-escalation arm (Part A). In addition, the starting dose level of ICOS.33 IgG1f S267E used in combination with nivolumab or ipilimumab (Parts B and C) is one dose level lower than a monotherapy (Part A) dose that has cleared the DLT period.

Parts B1 and C1 consist of a PK/pharmacodynamic substudy aimed to explore the kinetics of ICOS-receptor downregulation and re-expression (and/or change in selected target engagement/pharmacodynamic biomarkers) following administration of ICOS.33 IgG1f S267E in the presence of multiple doses of nivolumab once every 4 weeks (Part B1) or ipilimumab once every 4 weeks (Part C1).

Different doses of ICOS.33 IgG1f S267E are administered in Parts B1 and C1:
Doses that induce or are predicted to induce different levels of ICOS receptor downregulation, including at least one dose that induces near-complete receptor downregulation (and/or change in selected target engagement/pharmacodynamic biomarkers) for a duration of at least 4 weeks. These dose levels allow characterization of the ICOS receptor re-expression kinetics after near-complete downregulation for a period of time equal to, less than, and/or exceeding the dosing intervals used in Part A. By understanding ICOS receptor kinetics, it may help inform testing ICOS.33 IgG1f S267E dosing intervals in future study(ies).
BLRM-RD: Dose levels are determined based on all available safety (clinical and laboratory) and PK data, as well as changes in peripheral target engagement markers (e.g., ICOS downregulation on T cells and ICOS+B cells) from previous and completed portions of current cohorts, and/or the BLRM/BLRM-Copula model whenever applicable.

After 24 weeks of monotherapy treatment, or two years of combination therapy, the participant may be eligible for retreatment. For Part A, scans are collected centrally and may be reviewed by blinded independent central review (BICR) at a later date, or at any time during the study. For Parts B and C, scans are collected centrally to be reviewed in real time by BICR.

Physical examinations, vital sign measurements, 12-lead electrocardiogram (ECG), and clinical laboratory evaluations are performed at selected times throughout the dosing interval.

Participants are closely monitored for AEs throughout the study. Blood is collected at 30-, 60-, and 100-day follow-up visits after study treatment administration for PK analysis.

Participants complete up to four phases of the study: screening, treatment, safety follow-up, and response/survival follow-up, as described below. Total duration of participation in the study is approximately 2 years.

Tetanus Vaccine

All patients in Parts A, B, and C receive an approved tetanus vaccine. Administration of a potent recall antigen such as tetanus toxoid primes the immune system, induces an immune response, and promotes a more immunogenic state.

The ability of ICOS.33 IgG1f S267E to enhance a recall response will be determined by monitoring antibodies to tetanus and proliferative and cytokine responses by CD4+ T-cells after tetanus vaccination. Approximately 70% of the general population has protective antibodies to tetanus. However, cellular immune responses are usually detectable in the peripheral blood one month after tetanus vaccine. Tetanus has been used as a reporter antigen in cancer patients receiving immunotherapy with vaccines and can be easily monitored. Consequently, tetanus vaccination may provide potent recall response with ICOS.33 IgG1f S267E alone and in combination with nivolumab or ipilimumab.

Screening

The screening phase lasts for up to 28 days and take place prior to the first administration of study treatment. During the screening phase, the participant's initial eligibility is established, and written informed consent is obtained. Tumor biopsies are collected for all participants, centrally evaluated for ICOS expression by immunohistochemistry, and results are evaluated before administration of the first dose of study treatment. Participants are enrolled using the Interactive Response Technology (IRT).

Treatment Phase

The treatment phase in the Preliminary Safety Cohort and Part A consists of up to six four-week treatment cycles (1 cycle=28 days). In the Preliminary Safety Cohort and Part A, each treatment cycle consists of ICOS.33 IgG1f S267E monotherapy for a total of 24 weeks.

Dose levels for Parts B and C are determined based on all available safety (clinical and laboratory) and PK data, as well as changes in peripheral target engagement markers (e.g., ICOS downregulation on T cells and ICOS+B cells) from previous and completed portion of current cohorts, and are guided by the BLRM/BLRM-Copula model whenever applicable.

In Parts B1 and C1, four week cycles are used, such that ICOS.33 IgG1f S267E+nivolumab or ipilimumab are administered starting on Cycle 1 Day 1. Nivolumab and ipilimumab are administered on Day 1 of each cycle. ICOS.33 IgG1f S267E is administered once every 12 weeks, or on Day 1 of every third cycle (Cycle 1 Day1, Cycle 4, Day1, Cycle 7 Day1, etc.). Participants on Parts B1 and C1 continue treatment for up to a total of 2 years.

The treatment phase in Parts B2 and C2 consists of ICOS.33 IgG1f S267E+nivolumab or ipilimumab administered on Day 1 of each cycle for up to a total of 2 years, and are only enrolled if additional safety, PK, or PD data is required to optimize dose and/or schedule selection.

Following each treatment cycle, the decision to treat a participant with additional cycles of study treatment is based on tumor assessment evaluations performed every 12 weeks (once every 12 weeks±1 week) and completed before the first dose in the next cycle. Tumor progression or response endpoints are assessed using Response Evaluation Criteria In Solid Tumors (RECIST) v1.1 or Prostate Cancer Working Group 3 (PCGW3) Guidelines, for prostate only (Scher et al., 2016. Trial Design and Objectives for Castration-Resistant Prostate Cancer: Updated Recommendations From the Prostate Cancer Clinical Trials Working Group 3. *Clin Oncol*. 34(12):1402-1418).

Treatment beyond progression with additional cycles of study treatment is allowed for up to a maximum of 24 weeks for Part A and two years for Parts B, C, D, and E in select participants with initial RECIST v1.1 or PCGW3 (prostate only) defined PD after discussion and agreement between the Principal Investigator and the BMS Medical Monitor/Study Director that the benefit/risk assessment favors continued administration of the study treatment (e.g., participants are continuing to experience clinical benefit as assessed by the investigator, tolerating treatment, and meeting other specific criteria).

Participants with a response of unconfirmed progressive disease (PD), stable disease (SD), partial response (PR), or complete response (CR) at the end of a given cycle continue to the next treatment cycle. Participants are generally allowed to continue study treatment until the first occurrence of 1) completion of the maximum number of cycles, 2) confirmed PD, 3) clinical deterioration suggesting that no further benefit from treatment is likely, 4) intolerability to therapy, or 5) a participant meeting criteria for discontinuation of study treatment. Individual participants with confirmed CR are given the option to discontinue study treatment on a case-by-case basis after specific consultation and agreement between the investigator and BMS Medical Monitor/Study Director in settings where benefit/risk justify discontinuation of study treatment.

Safety Follow-Up

Upon completion of 24 weeks of study treatment for Part A (or up to a maximum of 48 weeks if applicable) or two years for Parts B, C, D, and E (or up to a maximum of four years, if applicable), the decision is made to discontinue the participant from study treatment (e.g., at end of treatment [EOT]) and all participants enter the safety follow-up period.

For participants who complete all scheduled cycles of therapy, the EOT visit is the same as the last scheduled and completed on-treatment visit and the start of the Week 1 safety follow-up visit. For participants who do not complete all scheduled cycles of study treatment, the EOT visit is the most recent on-treatment visit (with all available safety and response data) and is considered the start of the safety follow-up visit.

After the EOT visit, all participants are evaluated for any new AEs for at least 100 days after the last dose of study treatment. Follow-up visits to monitor for AEs occur at Days 30, 60, and 100 after the last dose or on the date of discontinuation (±7 days). All participants are required to complete the 3 clinical safety follow-up visits regardless of whether or not they start new anti-cancer treatment, except those participants who withdraw consent for study participation.

Survival Follow-Up

After completion of the safety follow-up visits, all participants treated with monotherapy and combination therapy enter the survival follow-up period. Participants are followed approximately every 3 months (12 weeks) until death, loss to follow-up, withdrawal of consent, or conclusion of the study, whichever comes first. The duration of this phase is up to two years from the first dose of study treatment, although a longer follow-up period is considered in selected cases if an efficacy signal is apparent.

Response Follow-Up

After completion of the Safety Follow-up period, participants with ongoing SD, PR, or CR at the EOT visit enter the Response Follow-up period. This period occurs simultaneously with the Survival Follow-up period for the mentioned participants. Participants continue to have radiologic and clinical tumor assessments approximately every 3 months (12 weeks) until death, loss to follow-up, withdrawal of consent, or conclusion of the study, whichever comes first. Radiological tumor assessments for participants who have ongoing clinical benefit continues to be collected after participants complete the survival phase of the study. Participants who have disease progression following initial course of study treatment are not evaluated for response beyond the EOT visit and are allowed to receive other tumor-directed therapy as required. If the participant discontinues treatment for any reason other than PD, radiological follow-up continues until the participant receives additional treatment.

Treatment with Additional Cycles Beyond 24 Weeks

All participants are treated for 24 weeks of monotherapy or combination therapy unless criteria for study treatment discontinuation are met earlier. All participants completing treatment with ongoing disease control (CR, PR, or SD) or unconfirmed PD are eligible for an additional 24 weeks of study treatment for Part A or for a total of two years for combination therapy on a case-by-case basis after careful evaluation and discussion with the BMS Medical Monitor/Study Director to determine whether the risk/benefit ratio supports administration of further study treatment. Upon completion of the additional study treatment period all participants enter the safety follow-up period.

Treatment Beyond Progression

Treatment beyond progression is allowed in select participants with initial RECIST v1.1 or PCGW3 (prostate only) defined PD after discussion and agreement with the BMS Medical Monitor/Study Director that the benefit/risk assessment favors continued administration of study treatment (e.g., participants are continuing to experience clinical benefit as assessed by the investigator, tolerating treatment, and meeting other criteria).

Participants are re-consented with an informed consent form (ICF) addendum to continue treatment beyond progression. Treatment beyond progression requires continued tumor assessments.

Retreatment During Response Follow-Up

Retreatment is allowed in this study with disease progression during the Response Follow-up period. Participants completing approximately 24 weeks of study treatment (or up to a maximum of 48 weeks if applicable) for Part A and approximately two years of study treatment (or up to a maximum of 4 years, if applicable) for Parts B, C, D, and E or less in case of discontinuation due to CR, who enter the Response Follow-up period with ongoing disease control (CR, PR, or SD) and without any significant toxicity are eligible for retreatment upon subsequent confirmed disease progression within 12 months of the last dose of study treatment on a case-by-case basis after careful evaluation and discussion with the BMS Medical Monitor/Study Director to determine whether the risk/benefit ratio supports administration of further study treatment and the participant continues to meet eligibility criteria for treatment with study treatment.

Participants meeting criteria for retreatment are treated with the originally assigned monotherapy or combination therapy regimen (e.g., the same dose and dose schedule administered during the first 24 weeks), unless that dose(s) and schedule are subsequently found to exceed the latest BLRM-RD, in which case the participant is treated with the BLRM-RD. Participants entering this phase follow the procedural schedule. Samples for PK and pharmacodynamics are collected less frequently (at predose of each treatment cycle). During retreatment, pharmacodynamic biomarker samples obtained from blood are collected.

Type of Participant and Target Disease Characteristics
  a) Participants must be at least 18 years old and have histological or cytological confirmation of metastatic and/or unresectable colorectal cancer (CRC), head and neck squamous cell carcinoma (HNSCC), non-small cell lung cancer (NSCLC), adenocarcinoma of the prostate (PRC), and urothelial carcinoma (UCC) with measureable disease per RECIST v1.1 or PCGW3 (prostate only) and have at least 1 lesion accessible for biopsy in addition to the target lesion.
  b) Presence of at least 1 lesion with measurable disease as defined by RECIST v1.1 or PCGW3 (prostate only) for solid tumors for response assessment. Participants with lesions in a previously irradiated field as the sole site of measurable disease are permitted to enroll provided the lesion(s) have demonstrated clear progression and can be measured.
  c) Participants must have received, and then progressed or been intolerant to, at least 1 standard treatment regimen in the advanced or metastatic setting, if such a therapy exists, and have been considered for all other potentially efficacious therapies prior to enrollment.
  d) Participants with prior exposure to therapy with any agent specifically targeting checkpoint pathway inhibition (such as anti-PD-1, anti-PD-L1, or anti-CTLA-4) are permitted after a washout period of any time greater than 4 weeks from the last treatment.

Tumor Types
a) colorectal cancer (CRC)
  i) Histologically confirmed CRC that is metastatic or recurrent with documented disease progression.
  ii) Document microsatellite instability, mismatch repair, KRAS, and BRAF status if known.
  iii) Prior therapy requirement: Participants must have received at least 1, but no more than 3, prior systemic therapies for metastatic and/or unresectable disease (or have progressed within 6 months of adjuvant therapy).
  iv) Participant must have incurable metastatic disease (i.e., patients with disease that is potentially curable by surgical resection are not eligible for treatment).
b) head and neck squamous cell carcinoma (HNSCC) (oral cavity, pharynx, larynx)
  i) Histologically confirmed incurable locally advanced, recurrent, or metastatic HNSCC (oral cavity, pharynx, larynx), Stage III or IV and not amenable to local therapy with curative intent (surgery or radiation therapy with or without chemotherapy).
  ii) Must have documented HPV status and subtype, particularly HPV16 and HPV18.
  iii) Participants must have received and then progressed or have been intolerant or refractory to at least 1 but no more than 2 prior systemic therapies (e.g., platinum-based chemotherapy) regimen for the treatment of metastatic or locally advanced un-resectable disease.
  iv) Prior curative radiation therapy must have been completed at least 4 weeks prior to study treatment administration. Prior focal palliative radiotherapy must have been completed at least 2 weeks before study treatment administration.
c) non-small cell lung cancer (NSCLC)
  i) Participants must have histologic or cytologic confirmation of NSCLC (per the seventh International Association for the Study of Lung Cancer [IASLC]) with squamous or nonsquamous histology that is advanced (metastatic and/or unresectable).
    (1). Participants must have had at least 1, but not more than 2, prior systemic therapies for NSCLC. Maintenance, adjuvant, or neoadjuvant (chemotherapy or chemoradiation) therapy do not count as an additional line of treatment.
    (2). Participants should have been offered a platinum-based chemotherapy for NSCLC. The platinum-based chemotherapy may have been in the adjuvant, neoadjuvant, or chemoradiation setting. Participants with recurrent/metastatic disease that has recurred within 6 months of completing such treatment are considered eligible for study treatment. Prior adjuvant or neoadjuvant chemotherapy is permitted as long as the last administration of the prior regimen occurred at least 4 weeks prior to enrollment.
    (3). Prior definitive chemoradiation for locally advanced disease is also permitted as long as the last administration of chemotherapy or radiotherapy (whichever was given last) occurred at least 4 weeks prior to enrollment.

(4). Participants with known EGFR mutations or ALK rearrangements must have received EGFR or ALK inhibitors, respectively. EGFR, ALK, KRAS, and ROS1 mutational status must be documented, if known.
d) adenocarcinoma of the prostate (PRC)
   i) Histologic or cytologic confirmation of adenocarcinoma of the prostate.
   ii) Participants have been treated by orchiectomy or are receiving a luteinizing hormone-releasing hormone analog, and have a testosterone level ≤50 ng/dL.
   iii) Metastatic disease by any 1 of the following modalities: computerized tomography (CT), magnetic resonance imaging (MRI), and bone scan.
e) urothelial carcinoma (UCC)
   i) Histological or cytological evidence of metastatic or surgically unresectable transitional cell carcinoma of the urothelium involving the bladder, urethra, ureter, or renal pelvis.

ICOS. 33 IgG1F S267E DOSE-LIMITING TOXICITIES (DLTs)

For the purpose of guiding dose escalation, DLTs are defined based on the incidence, intensity, and duration of AEs for which no clear alternative cause is identified. The DLT period is be 35 days (5 weeks).

In the Preliminary Safety Cohorts, participants who receive 1 dose of ICOS.33 IgG1f S267E and complete, or who discontinue due to a DLT in the 4-week DLT period, are considered as DLT-evaluable participants for ICOS.33 IgG1f S267E monotherapy.

In Part A, participants who receive 2 doses of ICOS.33 IgG1f S267E and complete, or who discontinue due to a DLT in the 5-week DLT period, are considered as DLT-evaluable participants for ICOS.33 IgG1f S267E monotherapy.

In Parts B, C, D and E, participants receiving either 1 dose of ICOS.33 IgG1f S267E or 2 doses of either nivolumab or ipilimumab, or participants who discontinue due to a DLT in the 5-week combination treatment DLT period, are considered as DLT-evaluable participants for combination treatment. Participants who withdraw from the study during the DLT evaluation period or receive less than 2 doses for reasons other than a DLT in the monotherapy (Part A) or 1 dose in combination therapy (Parts B, C, D, E), are not considered as DLT-evaluable participants and are not replaced with a new participant at the same dose level. Participants in Part A who are dose delayed during the DLT evaluation period for reasons other than a DLT are considered as DLT-evaluable participants if they receive at least 2 doses of therapy.

For the purpose of participant management, any AE that meets DLT criteria, regardless of the cycle in which it occurs, leads to discontinuation of study treatment. Participants who withdraw from the study during the 5-week DLT evaluation period for reasons other than a DLT may be replaced with a new participant at the same dose level. The incidence of DLT(s) during the 5-week DLT evaluation period is used in dose escalation decisions and to define the BLRM-RD. AEs occurring after the DLT period are considered for the purposes of defining the BLRM-RD upon agreement between the Sponsor, Medical Monitor/Study Director, and investigators.

Participants experiencing a DLT enter the safety follow-up period of the study. DLTs occurring after the 4-week DLT observation period for the Preliminary Safety Cohorts or 5-week DLT observation period for Parts A, B, and C are accounted for in determining the maximum administered dose (MAD) for the combination part.

This study will show that the anti-ICOS antibodies as administered are safe and effective in treating cancer.

Example 19

Combination Effects of Increasing Doses of Anti-ICOS Antibody on Tumor Growth

Figure 28:
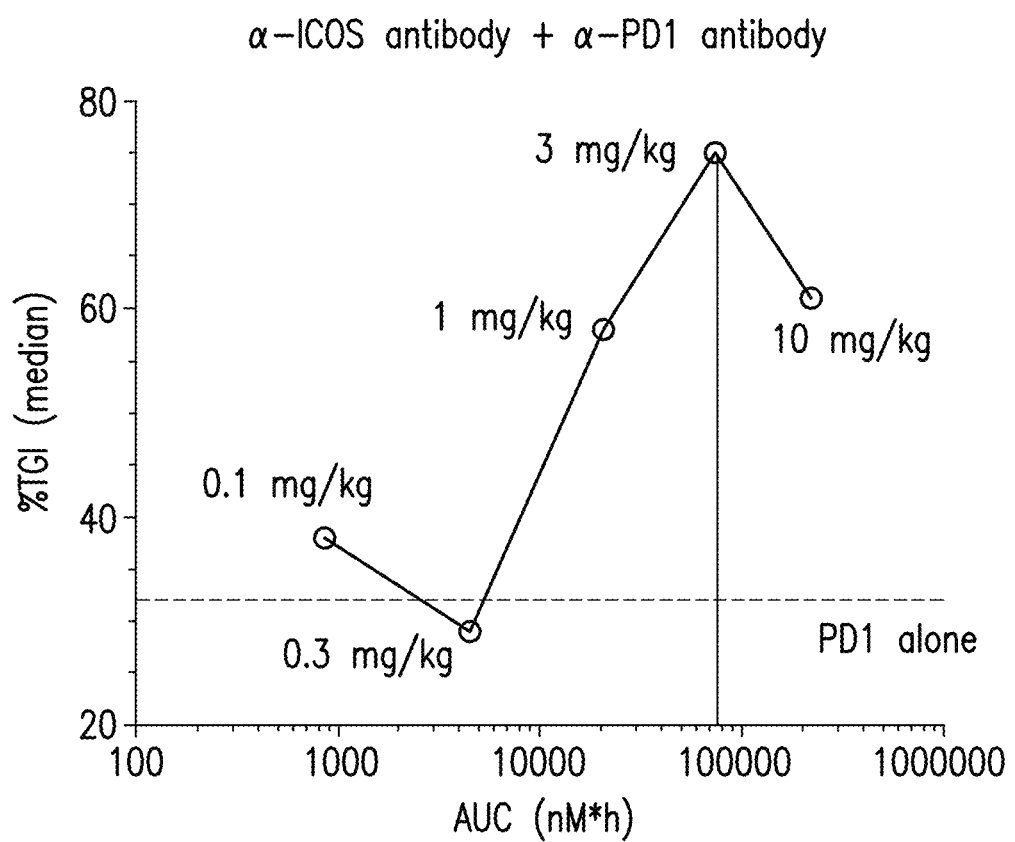
FIG. 28 is a graph showing the effects of increasing doses of anti-ICOS antibody, ICOS.33 IgG1f S267E, in combination with an anti-PD1 antibody and the effect on tumor growth inhibition in a mouse model.

The effect of increasing doses of agonistic anti-ICOS antibody, ICOS.33 IgG1f S267E, in combination with an anti-PD-1 antibody was assessed on tumor growth inhibition in a mouse model. As shown in FIG. 28, the combination exhibited reduced efficacy at higher doses, i.e., the "hook effect," wherein near-saturating or saturating concentrations of the antibody result in diminished efficacy compared to the efficacy of the antibody at lower concentrations, i.e., concentrations that do not result in saturation.

Briefly, mice (averaging about 20 mg in weight) with established CT26 tumors were treated by either anti-PD-1 monotherapy or in combination with ICOS.33 IgG1f S267E. Anti-ICOS dose escalation was started from 0.1 mg/kg with three-fold increase to 10 mg/kg (or a maximum dose of approximately 200 μg/mouse flat dose). Anti-PD-1 antibody was dosed at 10 mg/kg (or a maximum dose of approximately 200 μg/mouse flat dose). Anti-ICOS and anti-PD1 antibody were administered in the same schedule (i.e., every 4 days starting on day 7) following tumor implantation.

As shown in FIG. 28, maximal tumor growth inhibition (TGI) in anti-ICOS and anti-PD1 combination therapy was observed at a lower dose of the anti-ICOS antibody (3 mg/kg) than the maximal dose tested (10 mg/kg), demonstrating a decrease in TGI at doses greater than 3 mg/kg, i.e., maximal efficacy is achieved at sub-saturating doses.

TABLE 35

Summary of Sequence Listing

| SEQ ID NO | Sequence Name | Sequence | | | | |
|---|---|---|---|---|---|---|
| 1 | Human ICOS (NP_036224.1) | MKSGLWYFFL | FCLRIKVLTG | EINGSANYEM | FIFHNGGVQI | 40 |
| | | LCKYPDIVQQ | FKMQLLKGGQ | ILCDLTKTKG | SGNTVSIKSL | 80 |
| | | KFCHSQLSNN | SVSFFLYNLD | HSHANYYFCN | LSIFDPPPFK | 120 |
| | | VTLTGGYLHI | YESQLCCQLK | FWLPIGCAAF | VVVCILGCIL | 160 |
| | | ICWLTKKKYS | SSVHDPNGEY | MFMRAVNTAK | KSRLTDVTL | 199 |
| 2 | Human ICOS-L (NP_001269979.1) | MRLGSPGLLF | LLFSSLRADT | QEKEVRAMVG | SDVELSCACP | 40 |
| | | EGSRFDLNDV | YVYWQTSESK | TVVTYHIPQN | SSLENVDSRY | 80 |
| | | RNRALMSPAG | MLRGDFSLRL | FNVTPQDEQK | FHCLVLSQSL | 120 |
| | | GFQEVLSVEV | TLHVAANFSV | PVVSAPHSPS | QDELTFTCTS | 160 |

TABLE 35-continued

Summary of Sequence Listing

| SEQ ID NO | Sequence Name | Sequence | |
|---|---|---|---|
| | | INGYPRPNVY WINKTDNSLL DQALQNDTVF LNMRGLYDVV | 200 |
| | | SVLRIARTPS VNIGCCIENV LLQQNLTVGS QTGNDIGERD | 240 |
| | | KITENPVSTG EKNAATWSIL AVLCLLVVVA VAIGWVCRDR | 280 |
| | | CLQHSYAGAW AVSPETELTE SWNLLLLLS | 309 |
| 3 | Parental hamster antibody Heavy Chain | EVQLVESGGG LVKPAGSLTL SCVASGFTFS DYFMHWVRQA | 40 |
| | | PGKGLEWVAV IDTKSFNYAT YYSDLVKGRF TVSRDDSQGM | 80 |
| | | VYLQMNNLRK EDTATYYCTA TIAVPYYFDY WGQGTMVTVS | 120 |
| | | SATTTAPSVY PLAPACDSTT STTNTVTLGC LVKGYFPEPV | 160 |
| | | TVSWNSGALT SGVHTFPSVL HSGLYSLSSS VTVPSSTWPS | 200 |
| | | QTVTCNVAHP ASSTKVDKKI VPGDGSGCKP CTCPGPEVSS | 240 |
| | | VFIFPPKPKD VLTISLSPKV TCVVVDISQD DPEVQFSWFI | 280 |
| | | DGKEVHTAVT QPREEQFNST YRMVSVLPIL HQDWLNGKEF | 320 |
| | | KCKVNSPAFP VPIEKTISKR RGQLQVPQVY TMPPPKEQLT | 360 |
| | | QSQVSLTCMI KGFYPEDIDV AWQKNGQPEQ SFKNTPPVLD | 400 |
| | | TDETYFLYSK LDVKKDDWEK GDTFTCSVVH EALHNHHTEK | 440 |
| | | TLSQRPGK | 448 |
| 4 | Parental hamster antibody Light Chain | DIQMTQSPSS LPASLGDRVT INCQASQDIS NYLSWYQQKP | 40 |
| | | GKAPKLLIYY TNLLADGVPS RFSGSGSGRD YSFTISSLES | 80 |
| | | EDIGSYYCQQ YYNYRTFGPG TKLEIKRADA KPTVSIFPPS | 120 |
| | | SEQLGTGSAT LVCFVNNFYP KDINVKWKVD GSEKRDGVLQ | 160 |
| | | SVTDQDSKDS TYSLSSTLSL TKADYERHNL YTCEVTHKTS | 200 |
| | | TAAIVKTLNR NEC | 213 |
| 5 | ICOS.33 IgG1f S267E Heavy Chain Variable Domain | EVQLVESGGG LVKPGGSLRL SCAASGFTFS DYFMHWVRQA | 40 |
| | | PGKGLEWVGV IDTKSFNYAT YYSDLVKGRF TISRDDSKNT | 80 |
| | | LYLQMNSLKT EDTAVYYCTA TIAVPYYFDY WGQGTLVTVS | 120 |
| | | S | 121 |
| 6 | ICOS.33 IgG1f S267E Light Chain Variable Domain | DIQMTQSPSS LSASVGDRVT ITCQASQDIS NYLSWYQQKP | 40 |
| | | GKAPKLLIYY TNLLAEGVPS RFSGSGSGTD FTFTISSLQP | 80 |
| | | EDIATYYCQQ YYNYRTFGPG TKVDIK | 106 |
| 7 | ICOS.33 IgG1f S267E Heavy Chain | EVQLVESGGG LVKPGGSLRL SCAASGFTFS DYFMHWVRQA | 40 |
| | | PGKGLEWVGV IDTKSFNYAT YYSDLVKGRF TISRDDSKNT | 80 |
| | | LYLQMNSLKT EDTAVYYCTA TIAVPYYFDY WGQGTLVTVS | 120 |
| | | SASTKGPSVF PLAPSSKSTS GGTAALGCLV KDYFPEPVTV | 160 |
| | | SWNSGALTSG VHTFPAVLQS SGLYSLSSVV TVPSSSLGTQ | 200 |
| | | TYICNVNHKP SNTKVDKRVE PKSCDKTHTC PPCPAPELLG | 240 |
| | | GPSVFLFPPK PKDTLMISRT PEVTCVVVDV EHEDPEVKFN | 280 |
| | | WYVDGVEVHN AKTKPREEQY NSTYRVVSVL TVLHQDWLNG | 320 |
| | | KEYKCKVSNK ALPAPIEKTI SKAKGQPREP QVYTLPPSRE | 360 |
| | | EMTKNQVSLT CLVKGFYPSD IAVEWESNGQ PENNYKTTPP | 400 |
| | | VLDSDGSFFL YSKLTVDKSR WQQGNVFSCS VMHEALHNHY | 440 |
| | | TQKSLSLSPG | 450 |
| 8 | ICOS.33 IgG1f S267E Light Chain | DIQMTQSPSS LSASVGDRVT ITCQASQDIS NYLSWYQQKP | 40 |
| | | GKAPKLLIYY TNLLAEGVPS RFSGSGSGTD FTFTISSLQP | 80 |
| | | EDIATYYCQQ YYNYRTFGPG TKVDIKRTVA APSVFIFPPS | 120 |
| | | DEQLKSGTAS VVCLLNNFYP REAKVQWKVD NALQSGNSQE | 160 |
| | | SVTEQDSKDS TYSLSSTLTL SKADYEKHKV YACEVTHQGL | 200 |
| | | SSPVTKSFNR GEC | 213 |
| 9 | ICOS.33 IgG1f S267E CDRH1 | DYFMH | 5 |
| 10 | ICOS.33 IgG1f S267E CDRH2 | VIDTKSFNYA TYYSDLVKG | 19 |
| 11 | ICOS.33 IgG1f S267E CDRH3 | TIAVPYYFDY | 10 |
| 12 | ICOS.33 IgG1f S267E CDRL1 | QASQDISNYL S | 11 |
| 13 | Parental hamster antibody CDRL2 | YTNLLAD | 7 |
| 14 | ICOS.33 IgG1f S267E CDRL2 | YTNLLAE | 7 |

TABLE 35-continued

Summary of Sequence Listing

| SEQ ID NO | Sequence Name | Sequence | |
|---|---|---|---|
| 15 | ICOS.33 IgG1f S267E CDRL3 | QQYYNYRT | 8 |
| 16 | 17C4 Heavy Chain Variable Domain | MDILCSTLLL LTVPSWVLSQ VTLRESGPAL VKPTQTLTLT<br>CTFSGFSLST SGMCVSWIRQ PPGKALEWLA LIDWDDDKFY<br>STSLKTRLTI SKDTSKNQVV LTMTNMDPVD TATYYCARMS<br>TPTYYGLDVW GQGTTVTSS | 40<br>80<br>120<br>140 |
| 17 | 17C4 Light Chain Variable Domain | MRVLAQLLGL LLLCFPGARC DIQMTQSPSS LSASVGDRVT<br>ITCRASQGIS SWLAWYQQKP EKAPKSLIYA ASSLQSGVPS<br>RFSGSGSGTD FTLTISSLQP EDFATYYCQQ YNSYPLTFGG<br>GTKVEIK | 40<br>80<br>120<br>127 |
| 18 | 17C4 CDRH1 | TSGMCVS | 7 |
| 19 | 17C4 CDRH2 | LIDWDDDKFY STSLKT | 16 |
| 20 | 17C4 CDRH3 | MSTPTYYGLD V | 11 |
| 21 | 17C4 CDRL1 | RASQGISSWL A | 11 |
| 22 | 17C4 CDRL2 | AASSLQS | 7 |
| 23 | 17C4 CDRL3 | QQYNSYPLT | 9 |
| 24 | 9D5 Heavy Chain Variable Domain | MDTLCSTLLL LTIPSWVLSQ ITLKESGPTL VKPTQTLTLT<br>CTFSGFSLGT SGLGVGWIRQ PPGKALEWLA FIYWDDDKRY<br>SPSLKSRLTI TKDTSKNQVV LTMTNMDPVD TATYYCAHRR<br>GFFDYWGQGT LVTVSS | 40<br>80<br>120<br>136 |
| 25 | 9D5 Light Chain Variable Domain | MRVLAQLLGL LLLCFPGARC DIQMTQSPSS LSASVGDRVT<br>ITCRASQGIS SWLAWYQQKP EKAPKSLIYA ASSLQSGVPS<br>RFSGSGSGTD FTLTISSLQP EDFATYYCQQ YNSYPLTFGG<br>GTKVEIK | 40<br>80<br>120<br>127 |
| 26 | 9D5 CDRH1 | TSGLGVG | 7 |
| 27 | 9D5 CDRH2 | FIYWDDDKRY SPSLKS | 16 |
| 28 | 9D5 CDRH3 | RRGFFDY | 7 |
| 29 | 9D5 CDRL1 | RASQGISSWL A | 11 |
| 30 | 9D5 CDRL2 | AASSLQS | 7 |
| 31 | 9D5 CDRL3 | QQYNSYPLT | 9 |
| 32 | 3E8 Heavy Chain Variable Domain | MEFGLTWVFL VALLRGVQCQ VQLVESGGGV VQPGMSLRLS<br>CAASGFTFST YGMQWVRQAP GKGLEWVTVI WHDGSHKDYA<br>DSVKGRFTIS RDNSKNTMYL QMNSLRAEDT AVYYCARDRQ<br>TGEGYFDFWG QGTLVTVSS | 40<br>80<br>120<br>139 |
| 33 | 3E8 Light Chain Variable Domain | MRVLAQLLGL LLLCFPGARC DIQMTQSPSS LSASVGDRVT<br>ITCRASQGIS SWLAWYQQKP EKAPKSLIYA ASSLQSGVPS<br>RFSGSGSGTD FTLTISSLQP EDFATYYCQQ YNSYPYTFGQ<br>GTKLEIK | 40<br>80<br>120<br>127 |
| 34 | 3E8 CDRH1 | TYGMQ | 5 |
| 35 | 3E8 CDRH2 | VIWHDGSHKD YADSVKG | 17 |
| 36 | 3E8 CDRH3 | DRQTGEGYFD F | 11 |
| 37 | 3E8 CDRL1 | RASQGISSWL A | 11 |
| 38 | 3E8 CDRL2 | AASSLQS | 7 |
| 39 | 3E8 CDRL3 | QQYNSYPYT | 9 |
| 40 | 1D7 Heavy Chain Variable Domain | MDTLCSTLLL LTIPSWVLSQ ITLKESGPTL VKPTQTLTLT<br>CTFSGFSLGS NGLGVGWIRQ PPGKALEWLA LIYWDDDKRY<br>SPSLKSRLTI TKDSSKNQVV LTMTNMDPVD TATYYCAHRN<br>SGFDYWGQGI LVTVSS | 40<br>80<br>120<br>136 |

TABLE 35-continued

Summary of Sequence Listing

| SEQ ID NO | Sequence Name | Sequence | |
|---|---|---|---|
| 41 | 1D7 Light Chain-a Variable Domain | MRVLAQLLGL LLLCFPGARC DIQMTQSPSS LSASVGDRVT<br>ITCRASQGFS SWLAWYQQKP EKAPKSLIYA ASSLQSGVPS<br>RFSGSGSGTD FTLTISSLQP EDFATYYCQQ YNSYPYTFGQ<br>GTKLEIK | 40<br>80<br>120<br>127 |
| 42 | 1D7 CDRH1 | SNGLGVG | 7 |
| 43 | 1D7 CDRH2 | LIYWDDDKRY SPSLKS | 16 |
| 44 | 1D7 CDRH3 | RNSGFDY | 7 |
| 45 | 1D7 CDRL1-a | RASQGFSSWL A | 11 |
| 46 | 1D7 CDRL2-a | AASSLQS | 7 |
| 47 | 1D7 CDRL3-a | QQYNSYPYT | 9 |
| 48 | 1D7 Light Chain-b Variable Domain | MRVLAQLLGL LLLCFPGARC DIQMTQSPSS LSASVGDRVT<br>ITCRASQGIS SWLAWYQQKP EKAPKSLIYA ASSLQSGVPS<br>RFSGSGSGTD FTLTISSLQP EDFATYYCQQ YNSYPLTFGG<br>GTKVEIK | 40<br>80<br>120<br>127 |
| 49 | 1D7 CDRL1-b | RASQGISSWL A | 11 |
| 50 | 1D7 CDRL2-b | AASSLQS | 7 |
| 51 | 1D7 CDRL3-b | QQYNSYPLT | 9 |
| 52 | huIgG1f Heavy Chain Constant Domain | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKRVEP KSCDKTHTCP PCPAPELLGG<br>PSVFLFPPKP KDTLMISRTP EVTCVVVDVS HEDPEVKFNW<br>YVDGVEVHNA KTKPREEQYN STYRVVSVLT VLHQDWLNGK<br>EYKCKVSNKA LPAPIEKTIS KAKGQPREPQ VYTLPPSREE<br>MTKNQVSLTC LVKGFYPSDI AVEWESNGQP ENNYKTTPPV<br>LDSDGSFFLY SKLTVDKSRW QQGNVFSCSV MHEALHNHYT<br>QKSLSLSPG | 40<br>80<br>120<br>160<br>200<br>240<br>280<br>320<br>329 |
| 53 | huIgG1f S267E ("SE") Heavy Chain Constant Domain | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKRVEP KSCDKTHTCP PCPAPELLGG<br>PSVFLFPPKP KDTLMISRTP EVTCVVVDVE HEDPEVKFNW<br>YVDGVEVHNA KTKPREEQYN STYRVVSVLT VLHQDWLNGK<br>EYKCKVSNKA LPAPIEKTIS KAKGQPREPQ VYTLPPSREE<br>MTKNQVSLTC LVKGFYPSDI AVEWESNGQP ENNYKTTPPV<br>LDSDGSFFLY SKLTVDKSRW QQGNVFSCSV MHEALHNHYT<br>QKSLSLSPG | 40<br>80<br>120<br>160<br>200<br>240<br>280<br>320<br>329 |
| 54 | huIgG1f S267E/L328F ("SELF") Heavy Chain Constant Domain | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKRVEP KSCDKTHTCP PCPAPELLGG<br>PSVFLFPPKP KDTLMISRTP EVTCVVVDVE HEDPEVKFNW<br>YVDGVEVHNA KTKPREEQYN STYRVVSVLT VLHQDWLNGK<br>EYKCKVSNKA FPAPIEKTIS KAKGQPREPQ VYTLPPSREE<br>MTKNQVSLTC LVKGFYPSDI AVEWESNGQP ENNYKTTPPV<br>LDSDGSFFLY SKLTVDKSRW QQGNVFSCSV MHEALHNHYT<br>QKSLSLSPG | 40<br>80<br>120<br>160<br>200<br>240<br>280<br>320<br>329 |
| 55 | huIgG1f P238D Heavy Chain Constant Domain | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKRVEP KSCDKTHTCP PCPAPELLGG<br>DSVFLFPPKP KDTLMISRTP EVTCVVVDVS HEDPEVKFNW<br>YVDGVEVHNA KTKPREEQYN STYRVVSVLT VLHQDWLNGK<br>EYKCKVSNKA LPAPIEKTIS KAKGQPREPQ VYTLPPSREE<br>MTKNQVSLTC LVKGFYPSDI AVEWESNGQP ENNYKTTPPV<br>LDSDGSFFLY SKLTVDKSRW QQGNVFSCSV MHEALHNHYT<br>QKSLSLSPG | 40<br>80<br>120<br>160<br>200<br>240<br>280<br>320<br>329 |
| 56 | huIgG1f P238D/P271G ("V4") Heavy Chain Constant Domain | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKRVEP KSCDKTHTCP PCPAPELLGG<br>DSVFLFPPKP KDTLMISRTP EVTCVVVDVS HEDGEVKFNW<br>YVDGVEVHNA KTKPREEQYN STYRVVSVLT VLHQDWLNGK<br>EYKCKVSNKA LPAPIEKTIS KAKGQPREPQ VYTLPPSREE | 40<br>80<br>120<br>160<br>200<br>240 |

TABLE 35-continued

Summary of Sequence Listing

| SEQ ID NO | Sequence Name | Sequence | |
|---|---|---|---|
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |
| 57 | huIgG1f P238D/P271G ("V4") D270E Heavy Chain Constant Domain | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGG | 120 |
| | | DSVFLFPPKP KDTLMISRTP EVTCVVVDVS HEEGEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |
| 58 | huIgG1f E233D/P238D/ P271G/A330R ("V7") Heavy Chain Constant Domain | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPDLLGG | 120 |
| | | DSVFLFPPKP KDTLMISRTP EVTCVVVDVS HEDGEVKFNW | 160 |
| | | YVDGVEVHNA KTKPREEQYN STYRVVSVLT VLHQDWLNGK | 200 |
| | | EYKCKVSNKA LPRPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |
| 59 | huIgG1f G237D/P238D/ H268D//P271G ("V8") Heavy Chain Constant Domain | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGD | 120 |
| | | DSVFLFPPKP KDTLMISRTP EVTCVVVDVS DEDGEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |
| 60 | huIgG1f G237D/P238D/ P271G/A330R ("V9") Heavy Chain Constant Domain | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGD | 120 |
| | | DSVFLFPPKP KDTLMISRTP EVTCVVVDVS HEDGEVKFNW | 160 |
| | | YVDGVEVHNA KTKPREEQYN STYRVVSVLT VLHQDWLNGK | 200 |
| | | EYKCKVSNKA LPRPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |
| 61 | huIgG1f G237D/P238D/ P271G/A330R ("V9") D270E Heavy Chain Constant Domain | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGD | 120 |
| | | DSVFLFPPKP KDTLMISRTP EVTCVVVDVS HEEGEVKFNW | 160 |
| | | YVDGVEVHNA KTKPREEQYN STYRVVSVLT VLHQDWLNGK | 200 |
| | | EYKCKVSNKA LPRPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |
| 62 | huIgG1f G237D/P238D/ H268D/P271G/ A330R ("V11") Heavy Chain Constant Domain | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGD | 120 |
| | | DSVFLFPPKP KDTLMISRTP EVTCVVVDVS DEDGEVKFNW | 160 |
| | | YVDGVEVHNA KTKPREEQYN STYRVVSVLT VLHQDWLNGK | 200 |
| | | EYKCKVSNKA LPRPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |
| 63 | huIgG1f E233D/G237D/ P238D/H268D/ P271G/A330R ("V12") Heavy Chain Constant Domain | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPDLLGD | 120 |
| | | DSVFLFPPKP KDTLMISRTP EVTCVVVDVS DEDGEVKFNW | 160 |
| | | YVDGVEVHNA KTKPREEQYN STYRVVSVLT VLHQDWLNGK | 200 |
| | | EYKCKVSNKA LPRPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |

TABLE 35-continued

Summary of Sequence Listing

| SEQ ID NO | Sequence Name | Sequence | |
|---|---|---|---|
| 64 | huKappa Light Chain Constant Domain | RTVAAPSVFI FPPSDEQLKS GTASVVCLLN NFYPREAKVQ<br>WKVDNALQSG NSQESVTEQD SKDSTYSLSS TLTLSKADYE<br>KHKVYACEVT HQGLSSPVTK SFNRGEC | 40<br>80<br>107 |
| 65 | Signal Sequence | MRAWIFFLLC LAGRALA | 17 |
| 66 | IgG1 C-terminal CH1 (same for IgG3 (17-15-15-15), igG3 (17-15-15), IgG3 (17-15), IgG3 (15-15-15), IgG3 (15), and IgG4 | VDKRV | 5 |
| 67 | IgG1 upper hinge | EPKSCDKTHT | 10 |
| 68 | IgG1 middle hinge | CPPCP | 5 |
| 69 | IgG1 lower hinge (same for IgG3 (17-15-15-15), IgG3 (17-15-15), IgG3 (17-15), IgG3 (15-15-15), IgG3 (15), and IgG4) | APELLGG | 7 |
| 70 | IgG2 C-terminal CH1 | VDKTV | 5 |
| 71 | IgG2 middle hinge | CCVECPPCP | 9 |
| 72 | IgG2 lower hinge | APPVAG | 6 |
| 73 | IgG3 (17-15-15-15) upper hinge (same for IgG3 (17-15-15) and IgG3 (17-15)) | ELKTPLGDTT HT | 12 |
| 74 | IgG3 (17-15-15-15) middle hinge | CPRCPEPKSC DTPPPCPRCP EPKSCDTPPP CPRCPEPKSC<br>DTPPPCPRCP | 40<br>50 |
| 75 | IgG3 (17-15-15) middle hinge | CPRCPEPKSC DTPPPCPRCP EPKSCDTPPP CPRCP | 35 |
| 76 | IgG3 (17-15) middle hinge | CPRCPEPKSC DTPPPCPRCP | 20 |
| 77 | IgG3 (15-15-15) upper hinge (same for IgG3(15)) | EPKS | 4 |
| 78 | IgG3 (15-15-15) middle hinge | CDTPPPCPRC PEPKSCDTPP PCPRCPEPKS CDTPPPCPRC<br>P | 40<br>41 |
| 79 | IgG3 (15) middle hinge | CDTPPPCPRC P | 11 |
| 80 | IgG4 upper hinge | ESKYGPP | 7 |
| 81 | IgG4 middle hinge | CPSCP | 5 |
| 82 | IgG4 lower hinge | APEFLGG | 7 |

TABLE 35-continued

Summary of Sequence Listing

| SEQ ID NO | Sequence Name | Sequence | |
|---|---|---|---|
| 83 | Wildtype human IgG1 CH1 | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKV | 40<br>80<br>98 |
| 84 | Wildtype human IgG2 CH1 | ASTKGPSVFP LAPCSRSTSE STAALGCLVK DYFPEPVTVS<br>WNSGALTSGV HTFPAVLQSS GLYSLSSVVT VPSSNFGTQT<br>YTCNVDHKPS NTKVDKTV | 40<br>80<br>98 |
| 85 | Wildtype human IgG1 CH2 | PSVFLFPPKP KDTLMISRTP EVTCVVVDVS HEDPEVKFNW<br>YVDGVEVHNA KTKPREEQYN STYRVVSVLT VLHQDWLNGK<br>EYKCKVSNKA LPAPIEKTIS KAK | 40<br>80<br>103 |
| 86 | Human IgG1 CH2 with A330S/P331S | PSVFLFPPKP KDTLMISRTP EVTCVVVDVS HEDPEVKFNW<br>YVDGVEVHNA KTKPREEQYN STYRVVSVLT VLHQDWLNGK<br>EYKCKVSNKA LPSSIEKTIS KAK | 40<br>80<br>103 |
| 87 | Wildtype human IgG1 CH3 | GQPREPQVYT LPPSREEMTK NQVSLTCLVK GFYPSDIAVE<br>WESNGQPENN YKTTPPVLDS DGSFFLYSKL TVDKSRWQQG<br>NVFSCSVMHE ALHNHYTQKS LSLSPG | 40<br>80<br>106 |
| 88 | IgG1-IgG2-IgG1f | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVER KCCVECPPCP APELLGGPSV<br>FLFPPKPKDT LMISRTPEVT CVVVDVSHED PEVKFNWYVD<br>GVEVHNAKTK PREEQYNSTY RVVSVLTVLH QDWLNGKEYK<br>CKVSNKALPA PIEKTISKAK GQPREPQVYT LPPSREEMTK<br>NQVSLTCLVK GFYPSDIAVE WESNGQPENN YKTTPPVLDS<br>DGSFFLYSKL TVDKSRWQQG NVFSCSVMHE ALHNHYTQKS<br>LSLSPG | 40<br>80<br>120<br>160<br>200<br>240<br>280<br>320<br>326 |
| 89 | IgG1-IgG2CS-IgG1f | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVER KSCVECPPCP APPVAGPSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPAP IEKTISKAKG QPREPQVYTL PPSREEMTKN<br>QVSLTCLVKG FYPSDIAVEW ESNGQPENNY KTTPPVLDSD<br>GSFFLYSKLT VDKSRWQQGN VFSCSVMHEA LHNHYTQKSL<br>SLSPG | 40<br>80<br>120<br>160<br>200<br>240<br>280<br>320<br>325 |
| 90 | IgG1-IgG2-IgG1.1f | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVER KCCVECPPCP APPVAGPSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPSS IEKTISKAKG QPREPQVYTL PPSRREMTKN<br>QVSLTCLVKG FYPSDIAVEW ESNGQPENNY KTTPPVLDSD<br>GSFFLYSKLT VDKSRWQQGN VFSCSVMHEA LHNHYTQKSL<br>SLSPG | 40<br>80<br>120<br>160<br>200<br>240<br>280<br>320<br>325 |
| 91 | IgG1-IgG2CS-IgG1.1f | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVER KSCVECPPCP APPVAGPSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPSS IEKTISKAKG QPREPQVYTL PPSREEMTKN<br>QVSLTCLVKG FYPSDIAVEW ESNGQPENNY KTTPPVLDSD<br>GSFFLYSKLT VDKSRWQQGN VFSCSVMHEA LHNHYTQKSL<br>SLSPG | 40<br>80<br>120<br>160<br>200<br>240<br>280<br>320<br>325 |
| 92 | IgG1-IgG2-1gG1f2 | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVER KCCVECPPCP APPVAGPSVF<br>LFPPKPKDTL MISRTPEVTC VVVDVSHEDP EVKFNWYVDG<br>VEVHNAKTKP REEQYNSTYR VVSVLTVLHQ DWLNGKEYKC<br>KVSNKALPAP IEKTISKAKG QPREPQVYTL PPSREEMTKN<br>QVSLTCLVKG FYPSDIAVEW ESNGQPENNY KTTPPVLDSD<br>GSFFLYSKLT VDKSRWQQGN VFSCSVMHEA LHNHYTQKSL<br>SLSPG | 40<br>80<br>120<br>160<br>200<br>240<br>280<br>320<br>325 |
| 93 | IgG1-IgG2(C219S)-IgG1f2 | ASTKGPSVFP LAPSSKSTSG GTAALGCLVK DYFPEPVTVS<br>WNSGALTSGV HTFPAVLQSS GLYSLSSVVT VPSSSLGTQT<br>YICNVNHKPS NTKVDKKVER KSCVECPPCP APPVAGPSVF | 40<br>80<br>120 |

TABLE 35-continued

Summary of Sequence Listing

| SEQ ID NO | Sequence Name | Sequence | |
|---|---|---|---|
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPG | 325 |
| 94 | IgG2-IgG1F2 | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPG | 325 |
| 95 | IgG2(C219S)-IgG1f2 | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPG | 325 |
| 96 | WT human IgG2 hinge | ERKCCVECPP CPAPPVAG | 18 |
| 97 | Human IgG2 hinge with C219S | ERKSCVECPP CPAPPVAG | 18 |
| 98 | IgG2/IgG1 hinge | ERKCCVECPP CPAPELLGG | 19 |
| 99 | IgG2 (C219S)/IgG1 hinge | ERKSCVECPP CPAPELLGG | 19 |
| 100 | Wild type human IgG1 hinge | EPKSCDKTHT CPPCPAPELL GG | 22 |
| 101 | IgG1.1 Hinge (L234A/L235E/G237A) | EPKSCDKTHT CPPCPAPEAE GA | 22 |
| 102 | Wildtype human IgG2 CH2 | PSVFLFPPKP KDTLMISRTP EVTCVVVDVS HEDPEVQFNW | 40 |
| | | YVDGVEVHNA KTKPREEQFN STFRVVSVLT VVHQDWLNGK | 80 |
| | | EYKCKVSNKG LPAPIEKTIS KTK | 103 |
| 103 | Wildtype human IgG2 CH3 | GQPREPQVYT LPPSREEMTK NQVSLTCLVK GFYPSDIAVE | 40 |
| | | WESNGQPENN YKTTPPMLDS DGSFFLYSKL TVDKSRWQQG | 80 |
| | | NVFSCSVMHE ALHNHYTQKS LSLSPGK | 107 |
| 104 | IgG1f with C-terminal K | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 105 | IgG2.3 | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |

TABLE 35-continued

Summary of Sequence Listing

| SEQ ID NO | Sequence Name | Sequence | |
|---|---|---|---|
| | | SLSPGK | 326 |
| 106 | IgG2.3G1-AY | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APELLGGPSV | 120 |
| | | FLFPPKPKDT LMISRTPEVT CVVVDVSHED PEVKFNWYVD | 160 |
| | | GVEVHNAKTK PREEQYNSTY RVVSVLTVLH QDWLNGKEYK | 200 |
| | | CKVSNKALPA PIEKTISKAK GQPREPQVYT LPPSREEMTK | 240 |
| | | NQVSLTCLVK GFYPSDIAVE WESNGQPENN YKTTPPVLDS | 280 |
| | | DGSFFLYSKL TVDKSRWQQG NVFSCSVMHE ALHNHYTQKS | 320 |
| | | LSLSPGK | 327 |
| 107 | IgG2.3G1-KH | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPGK | 326 |
| 108 | IgG2.5 | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCCVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 109 | IgG1.1f | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPEAEGA | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPSSIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 110 | IgG2.3G1.1f-KH | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPSS IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPGK | 326 |
| 111 | IgG1-deltaTHT | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKCPPCP APELLGGPSV | 120 |
| | | FLFPPKPKDT LMISRTPEVT CVVVDVSHED PEVKFNWYVD | 160 |
| | | GVEVHNAKTK PREEQYNSTY RVVSVLTVLH QDWLNGKEYK | 200 |
| | | CKVSNKALPA PIEKTISKAK GQPREPQVYT LPPSREEMTK | 240 |
| | | NQVSLTCLVK GFYPSDIAVE WESNGQPENN YKTTPPVLDS | 280 |
| | | DGSFFLYSKL TVDKSRWQQG NVFSCSVMHE ALHNHYTQKS | 320 |
| | | LSLSPGK | 327 |
| 112 | IgG2.3-plusTHT | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVETHTCP PCPAPPVAGP | 120 |
| | | SVFLFPPKPK DTLMISRTPE VTCVVVDVSH EDPEVQFNWY | 160 |
| | | VDGVEVHNAK TKPREEQFNS TFRVVSVLTV VHQDWLNGKE | 200 |
| | | YKCKVSNKGL PAPIEKTISK TKGQPREPQV YTLPPSREEM | 240 |
| | | TKNQVSLTCL VKGFYPSDIA VEWESNGQPE NNYKTTPPML | 280 |
| | | DSDGSFFLYS KLTVDKSRWQ QGNVFSCSVM HEALHNHYTQ | 320 |
| | | KSLSLSPGK | 329 |
| 113 | IgG2.3-plusGGG | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |

TABLE 35-continued

Summary of Sequence Listing

| SEQ ID NO | Sequence Name | Sequence | |
|---|---|---|---|
| | | YTCNVDHKPS NTKVDKTVER KSCVEGGGCP PCPAPPVAGP | 120 |
| | | SVFLFPPKPK DTLMISRTPE VTCVVVDVSH EDPEVQFNWY | 160 |
| | | VDGVEVHNAK TKPREEQFNS TFRVVSVLTV VHQDWLNGKE | 200 |
| | | YKCKVSNKGL PAPIEKTISK TKGQPREPQV YTLPPSREEM | 240 |
| | | TKNQVSLTCL VKGFYPSDIA VEWESNGQPE NNYKTTPPML | 280 |
| | | DSDGSFFLYS KLTVDKSRWQ QGNVFSCSVM HEALHNHYTQ | 320 |
| | | KSLSLSPGK | 329 |
| 114 | IgG2.5G1.1f-KH | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPSS IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPGK | 326 |
| 115 | IgG2.5G1-AY | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCCVECPPCP APELLGGPSV | 120 |
| | | FLFPPKPKDT LMISRTPEVT CVVVDVSHED PEVKFNWYVD | 160 |
| | | GVEVHNAKTK PREEQYNSTY RVVSVLTVLH QDWLNGKEYK | 200 |
| | | CKVSNKALPA PIEKTISKAK GQPREPQVYT LPPSREEMTK | 240 |
| | | NQVSLTCLVK GFYPSDIAVE WESNGQPENN YKTTPPVLDS | 280 |
| | | DGSFFLYSKL TVDKSRWQQG NVFSCSVMHE ALHNHYTQKS | 320 |
| | | LSLSPGK | 327 |
| 116 | IgG2.5G1-KH | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPGK | 326 |
| 117 | IgG2.5-plusTHT | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCCVETHTCP PCPAPPVAGP | 120 |
| | | SVFLFPPKPK DTLMISRTPE VTCVVVDVSH EDPEVQFNWY | 160 |
| | | VDGVEVHNAK TKPREEQFNS TFRVVSVLTV VHQDWLNGKE | 200 |
| | | YKCKVSNKGL PAPIEKTISK TKGQPREPQV YTLPPSREEM | 240 |
| | | TKNQVSLTCL VKGFYPSDIA VEWESNGQPE NNYKTTPPML | 280 |
| | | DSDGSFFLYS KLTVDKSRWQ QGNVFSCSVM HEALHNHYTQ | 320 |
| | | KSLSLSPGK | 329 |
| 118 | IgG1-G2.3G1-AY | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVER KSCVECPPCP APELLGGPSV | 120 |
| | | FLFPPKPKDT LMISRTPEVT CVVVDVSHED PEVKFNWYVD | 160 |
| | | GVEVHNAKTK PREEQYNSTY RVVSVLTVLH QDWLNGKEYK | 200 |
| | | CKVSNKALPA PIEKTISKAK GQPREPQVYT LPPSREEMTK | 240 |
| | | NQVSLTCLVK GFYPSDIAVE WESNGQPENN YKTTPPVLDS | 280 |
| | | DGSFFLYSKL TVDKSRWQQG NVFSCSVMHE ALHNHYTQKS | 320 |
| | | LSLSPGK | 327 |
| 119 | IgG1-G2.3G1-KH | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVER KSCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPGK | 326 |
| 120 | G2-G1-G1-G1 | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |

TABLE 35-continued

Summary of Sequence Listing

| SEQ ID NO | Sequence Name | Sequence | |
|---|---|---|---|
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 121 | G2.5-G1-G1-G1 | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 122 | G1-G2.3-G2-G2 | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 123 | G1-KRGEGSSNLF | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YICNVNHKPS NTKVDKRVEP KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 124 | G1-KRGEGS | ASTKGPSVFP LAPSSRSTSE STAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 125 | G1-SNLF | ASTKGPSVFP LAPSSKSTSG GTAALGCLVK DYFPEPVTVS | 40 |
| | | WNSGALTSGV HTFPAVLQSS GLYSLSSVVT VPSSNFGTQT | 80 |
| | | YICNVNHKPS NTKVDKRVEP KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 126 | IgG1-ITNDRTPR | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YTCNVDHKPS NTKVDKTVER KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 127 | G1-SNLFPR | ASTKGPSVFP LAPSSKSTSG GTAALGCLVK DYFPEPVTVS | 40 |
| | | WNSGALTSGV HTFPAVLQSS GLYSLSSVVT VPSSNFGTQT | 80 |
| | | YICNVNHKPS NTKVDKRVER KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |

TABLE 35-continued

Summary of Sequence Listing

| SEQ ID NO | Sequence Name | Sequence | |
|---|---|---|---|
| 128 | G2-RKEGSGNSFL | ASTKGPSVFP LAPCSKSTSG GTAALGCLVK DYFPEPVTVS | 40 |
| | | WNSGALTSGV HTFPAVLQSS GLYSLSSVVT VPSSSLGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 129 | G2-RKEGSG | ASTKGPSVFP LAPCSKSTSG GTAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 130 | G2-NSFL | ASTKGPSVFP LAPCSRSTSE STAALGCLVK DYFPEPVTVS | 40 |
| | | WNSGALTSGV HTFPAVLQSS GLYSLSSVVT VPSSSLGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 131 | IgG2-TIDNTRRP | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YICNVNHKPS NTKVDKRVEP KSCVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 132 | G2-NSFLRP | ASTKGPSVFP LAPCSRSTSE STAALGCLVK DYFPEPVTVS | 40 |
| | | WNSGALTSGV HTFPAVLQSS GLYSLSSVVT VPSSSLGTQT | 80 |
| | | YTCNVDHKPS NTKVDKTVEP KSCVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 133 | G1-G1-G2-G1-AY | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGG | 120 |
| | | PSVFLFPPKP KDTLMISRTP EVTCVVVDVS HEDPEVQFNW | 160 |
| | | YVDGVEVHNA KTKPREEQFN STFRVVSVLT VVHQDWLNGK | 200 |
| | | EYKCKVSNKG LPAPIEKTIS KTKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 134 | G1-G1-G2-G1-KH | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPPVAGP | 120 |
| | | SVFLFPPKPK DTLMISRTPE VTCVVVDVSH EDPEVQFNWY | 160 |
| | | VDGVEVHNAK TKPREEQFNS TFRVVSVLTV VHQDWLNGKE | 200 |
| | | YKCKVSNKGL PAPIEKTISK TKGQPREPQV YTLPPSREEM | 240 |
| | | TKNQVSLTCL VKGFYPSDIA VEWESNGQPE NNYKTTPPVL | 280 |
| | | DSDGSFFLYS KLTVDKSRWQ QGNVFSCSVM HEALHNHYTQ | 320 |
| | | KSLSLSPGK | 329 |
| 135 | G2-G2.3-G1-G2-KH | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVKFNWYVDG | 160 |

TABLE 35-continued

Summary of Sequence Listing

| SEQ ID NO | Sequence Name | Sequence | |
|---|---|---|---|
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 136 | G2.5-G2.3-G1-G2-KH | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 137 | G2-G2.3-G1-G2-AY | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APELLGGPSV | 120 |
| | | FLFPPKPKDT LMISRTPEVT CVVVDVSHED PEVKFNWYVD | 160 |
| | | GVEVHNAKTK PREEQYNSTY RVVSVLTVLH QDWLNGKEYK | 200 |
| | | CKVSNKALPA PIEKTISKAK GQPREPQVYT LPPSREEMTK | 240 |
| | | NQVSLTCLVK GFYPSDIAVE WESNGQPENN YKTTPPMLDS | 280 |
| | | DGSFFLYSKL TVDKSRWQQG NVFSCSVMHE ALHNHYTQKS | 320 |
| | | LSLSPG | 326 |
| 138 | G2.5-G2.3-G1-G2-AY | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APELLGGPSV | 120 |
| | | FLFPPKPKDT LMISRTPEVT CVVVDVSHED PEVKFNWYVD | 160 |
| | | GVEVHNAKTK PREEQYNSTY RVVSVLTVLH QDWLNGKEYK | 200 |
| | | CKVSNKALPA PIEKTISKAK GQPREPQVYT LPPSREEMTK | 240 |
| | | NQVSLTCLVK GFYPSDIAVE WESNGQPENN YKTTPPMLDS | 280 |
| | | DGSFFLYSKL TVDKSRWQQG NVFSCSVMHE ALHNHYTQKS | 320 |
| | | LSLSPGK | 327 |
| 139 | G1-G2.3-G1-G1-KH | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCVECPPCP APPVAGPSVF | 120 |
| | | LFPPKPKDTL MISRTPEVTC VVVDVSHEDP EVKFNWYVDG | 160 |
| | | VEVHNAKTKP REEQYNSTYR VVSVLTVLHQ DWLNGKEYKC | 200 |
| | | KVSNKALPAP IEKTISKAKG QPREPQVYTL PPSREEMTKN | 240 |
| | | QVSLTCLVKG FYPSDIAVEW ESNGQPENNY KTTPPVLDSD | 280 |
| | | GSFFLYSKLT VDKSRWQQGN VFSCSVMHEA LHNHYTQKSL | 320 |
| | | SLSPGK | 326 |
| 140 | G2-G1-G2-G2-AY | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCDKTHTCP PCPAPELLGG | 120 |
| | | PSVFLFPPKP KDTLMISRTP EVTCVVVDVS HEDPEVQFNW | 160 |
| | | YVDGVEVHNA KTKPREEQFN STFRVVSVLT VVHQDWLNGK | 200 |
| | | EYKCKVSNKG LPAPIEKTIS KTKGQPREPQ VYTLPPSREE | 240 |
| | | MTKNQVSLTC LVKGFYPSDI AVEWESNGQP ENNYKTTPPM | 280 |
| | | LDSDGSFFLY SKLTVDKSRW QQGNVFSCSV MHEALHNHYT | 320 |
| | | QKSLSLSPGK | 330 |
| 141 | G2.5-G1-G2-G2-AY | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCDKTHTCP PCPAPELLGG | 120 |
| | | PSVFLFPPKP KDTLMISRTP EVTCVVVDVS HEDPEVQFNW | 160 |
| | | YVDGVEVHNA KTKPREEQFN STFRVVSVLT VVHQDWLNGK | 200 |
| | | EYKCKVSNKG LPAPIEKTIS KTKGQPREPQ VYTLPPSREE | 240 |
| | | MTKNQVSLTC LVKGFYPSDI AVEWESNGQP ENNYKTTPPM | 280 |
| | | LDSDGSFFLY SKLTVDKSRW QQGNVFSCSV MHEALHNHYT | 320 |
| | | QKSLSLSPGK | 330 |
| 142 | G1-G2-G1-G1-AY | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCVECPPCP APELLGGPSV | 120 |
| | | FLFPPKPKDT LMISRTPEVT CVVVDVSHED PEVKFNWYVD | 160 |
| | | GVEVHNAKTK PREEQYNSTY RVVSVLTVLH QDWLNGKEYK | 200 |
| | | CKVSNKALPA PIEKTISKAK GQPREPQVYT LPPSREEMTK | 240 |

TABLE 35-continued

Summary of Sequence Listing

| SEQ ID NO | Sequence Name | Sequence | |
|---|---|---|---|
| | | NQVSLTCLVK GFYPSDIAVE WESNGQPENN YKTTPPVLDS | 280 |
| | | DGSFFLYSKL TVDKSRWQQG NVFSCSVMHE ALHNHYTQKS | 320 |
| | | LSLSPGK | 327 |
| 143 | G2-G1-G2-G2-KH | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCDKTHTCP PCPAPPVAGP | 120 |
| | | SVFLFPPKPK DTLMISRTPE VTCVVVDVSH EDPEVQFNWY | 160 |
| | | VDGVEVHNAK TKPREEQFNS TFRVVSVLTV VHQDWLNGKE | 200 |
| | | YKCKVSNKGL PAPIEKTISK TKGQPREPQV YTLPPSREEM | 240 |
| | | TKNQVSLTCL VKGFYPSDIA VEWESNGQPE NNYKTTPPML | 280 |
| | | DSDGSFFLYS KLTVDKSRWQ QGNVFSCSVM HEALHNHYTQ | 320 |
| | | KSLSLSPG | 328 |
| 144 | G2.5-G1-G2-G2-KH | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCDKTHTCP PCPAPPVAGP | 120 |
| | | SVFLFPPKPK DTLMISRTPE VTCVVVDVSH EDPEVQFNWY | 160 |
| | | VDGVEVHNAK TKPREEQFNS TFRVVSVLTV VHQDWLNGKE | 200 |
| | | YKCKVSNKGL PAPIEKTISK TKGQPREPQV YTLPPSREEM | 240 |
| | | TKNQVSLTCL VKGFYPSDIA VEWESNGQPE NNYKTTPPML | 280 |
| | | DSDGSFFLYS KLTVDKSRWQ QGNVFSCSVM HEALHNHYTQ | 320 |
| | | KSLSLSPGK | 329 |
| 145 | IgG1-deltaHinge | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KCPPCPAPEL LGGPSVFLFP | 120 |
| | | PKPKDTLMIS RTPEVTCVVV DVSHEDPEVK FNWYVDGVEV | 160 |
| | | HNAKTKPREE QYNSTYRVVS VLTVLHQDWL NGKEYKCKVS | 200 |
| | | NKALPAPIEK TISKAKGQPR EPQVYTLPPS REEMTKNQVS | 240 |
| | | LTCLVKGFYP SDIAVEWESN GQPENNYKTT PPVLDSDGSF | 280 |
| | | FLYSKLTVDK SRWQQGNVFS CSVMHEALHN HYTQKSLSLS | 320 |
| | | PGK | 323 |
| 146 | IgG2-deltaHinge | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCPPCPAPPV AGPSVFLFPP | 120 |
| | | KPKDTLMISR TPEVTCVVVD VSHEDPEVQF NWYVDGVEVH | 160 |
| | | NAKTKPREEQ FNSTFRVVSV LTVVHQDWLN GKEYKCKVSN | 200 |
| | | KGLPAPIEKT ISKTKGQPRE PQVYTLPPSR EEMTKNQVSL | 240 |
| | | TCLVKGFYPS DIAVEWESNG QPENNYKTTP PMLDSDGSFF | 280 |
| | | LYSKLTVDKS RWQQGNVFSC SVMHEALHNH YTQKSLSLSP | 320 |
| | | GK | 322 |
| 147 | IgG2.5-deltaHinge | ASTKGPSVFP LAPSSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCPPCPAPPV AGPSVFLFPP | 120 |
| | | KPKDTLMISR TPEVTCVVVD VSHEDPEVQF NWYVDGVEVH | 160 |
| | | NAKTKPREEQ FNSTFRVVSV LTVVHQDWLN GKEYKCKVSN | 200 |
| | | KGLPAPIEKT ISKTKGQPRE PQVYTLPPSR EEMTKNQVSL | 240 |
| | | TCLVKGFYPS DIAVEWESNG QPENNYKTTP PMLDSDGSFF | 280 |
| | | LYSKLTVDKS RWQQGNVFSC SVMHEALHNH YTQKSLSLSP | 320 |
| | | GK | 322 |
| 148 | IgG1-deltaG237 | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGP | 120 |
| | | SVFLFPPKPK DTLMISRTPE VTCVVVDVSH EDPEVKFNWY | 160 |
| | | VDGVEVHNAK TKPREEQYNS TYRVVSVLTV LHQDWLNGKE | 200 |
| | | YKCKVSNKAL PAPIEKTISK AKGQPREPQV YTLPPSREEM | 240 |
| | | TKNQVSLTCL VKGFYPSDIA VEWESNGQPE NNYKTTPPVL | 280 |
| | | DSDGSFFLYS KLTVDKSRWQ QGNVFSCSVM HEALHNHYTQ | 320 |
| | | KSLSLSPG | 328 |
| 149 | IgG2-plusG237 | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSCVECPPCP APPVAGGPSV | 120 |
| | | FLFPPKPKDT LMISRTPEVT CVVVDVSHED PEVQFNWYVD | 160 |
| | | GVEVHNAKTK PREEQFNSTF RVVSVLTVVH QDWLNGKEYK | 200 |
| | | CKVSNKGLPA PIEKTISKTK GQPREPQVYT LPPSREEMTK | 240 |
| | | NQVSLTCLVK GFYPSDIAVE WESNGQPENN YKTTPPMLDS | 280 |
| | | DGSFFLYSKL TVDKSRWQQG NVFSCSVMHE ALHNHYTQKS | 320 |
| | | LSLSPGK | 327 |

TABLE 35-continued

Summary of Sequence Listing

| SEQ ID NO | Sequence Name | Sequence | |
|---|---|---|---|
| 150 | IgG2.4 | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCSVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 151 | IgG2.3/4 | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KSSVECPPCP APPVAGPSVF | 120 |
| | | LFPPKPKDTL MISRTPEVTC VVVDVSHEDP EVQFNWYVDG | 160 |
| | | VEVHNAKTKP REEQFNSTFR VVSVLTVVHQ DWLNGKEYKC | 200 |
| | | KVSNKGLPAP IEKTISKTKG QPREPQVYTL PPSREEMTKN | 240 |
| | | QVSLTCLVKG FYPSDIAVEW ESNGQPENNY KTTPPMLDSD | 280 |
| | | GSFFLYSKLT VDKSRWQQGN VFSCSVMHEA LHNHYTQKSL | 320 |
| | | SLSPGK | 326 |
| 152 | Hinge IgG2 C220S | ERKCSVECPP CPAPPVAG | 18 |
| 153 | IgG2/IgG1 hybrid hinge C220S | ERKCSVECPP CPAPELLGG | 19 |
| 154 | Wildtype IgG2 hinge portion | ERKCCVECPP CPAP | 14 |
| 155 | IgG2 hinge portion C219S | ERKSCVECPP CPAP | 14 |
| 156 | IgG2 hinge portion C220S | ERKCSVECPP CPAP | 14 |
| 157 | IgG2 hinge portion C219X | ERKXCVECPP CPAP | 14 |
| 158 | IgG2 hinge portion C220X | ERKCXVECPP CPAP | 14 |
| 159 | IgG2 CH1 + IgG2 hinge (wildtype) | ASTKGPSVFP LAPCSRSTSE STAALGCLVK DYFPEPVTVS | 40 |
| | | WNSGALTSGV HTFPAVLQSS GLYSLSSVVT VPSSNFGTQT | 80 |
| | | YTCNVDHKPS NTKVDKTVER KCCVECPPCP APPVAG | 116 |
| 160 | IgG2 with C219X | ERKXCVECPP CPAPPVAG | 18 |
| 161 | IgG2 with C220X | ERKCXVECPP CPAPPVAG | 18 |
| 162 | IgG2/IgG1 hybrid with C219X | ERKXCVECPP CPAPELLGG | 19 |
| 163 | IgG2/IgG1 hybrid with C220X | ERKCXVECPP CPAPELLGG | 19 |
| 164 | IgG2/IgG1 hybrid deltaG | ERKCCVECPP CPAPELLG | 18 |
| 165 | IgG2/IgG1 hybrid with C219S deltaG | ERKSCVECPP CPAPELLG | 18 |
| 166 | IgG2/IgG1 hybrid with C220S deltaG | ERKCSVECPP CPAPELLG | 18 |
| 167 | IgG2/IgG1 hybrid with C219X deltaG | ERKXCVECPP CPAPELLG | 18 |

TABLE 35-continued

Summary of Sequence Listing

| SEQ ID NO | Sequence Name | Sequence | |
|---|---|---|---|
| 168 | IgG2/IgG1 hybrid with C220X deltaG | ERKCXVECPP CPAPELLG | 18 |
| 169 | IgG2 hinge portion | PVAG | 4 |
| 170 | IgG1 hinge portion | SCDKTHT | 7 |
| 171 | IgG1 hinge portion 1 | ELLG | 4 |
| 172 | IgG1 hinge portion 2 | ELLGG | 5 |
| 173 | Mature huICOS Extracellular Domain (21-134 of NP_036224.1) | EINGSANYEM FIFHNGGVQI LCKYPDIVQQ FKMQLLKGGQ<br>ILCDLTKTKG SGNTVSIKSL KFCHSQLSNN SVSFFLYNLD<br>HSHANYYFCN LSIFDPPPFK VTLTGGYLHI YESQ | 40<br>80<br>114 |
| 174 | 3E8 Heavy Chain Variable Domain Nucleotide Sequence | ATG GAG TTT GGG CTG ACC TGG GTT TTC CTC GTT GCT<br>CTT TTA AGA GGT GTC CAG TGT CAG GTG CAG CTG GTG<br>GAG TCT GGG GGA GGC GTG GTC CAG CCT GGG ATG TCC<br>CTG AGA CTC TCC TGT GCA GCG TCT GGA TTC ACC TTC<br>AGT ACC TAT GGC ATG CAG TGG GTC CGC CAG GCT CCA<br>GGC AAG GGG CTG GAG TGG GTG ACA GTT ATA TGG CAT<br>GAT GGA AGT CAT AAA GAC TAT GCA GAC TCC GTG AAG<br>GGC CGA TTC ACC ATC TCC AGA GAC AAT TCC AAG AAC<br>ACG ATG TAT CTG CAA ATG AAC AGC CTG AGA GCC GAG<br>GAC ACG GCT GTG TAT TAC TGT GCG AGA GAT CGG CAA<br>ACT GGG GAG GGC TAC TTT GAC TTC TGG GGC CAG GGA<br>ACC CTG GTC ACC GTC TCC TCA | 36<br>72<br>108<br>144<br>180<br>216<br>252<br>288<br>324<br>360<br>396<br>417 |
| 175 | 3E8 Light Chain Variable Domain Nucleotide Sequence | ATG AGG GTC CTC GCT CAG CTC CTG GGG CTC CTG CTG<br>CTC TGT TTC CCA GGT GCC AGA TGT GAC ATC CAG ATG<br>ACC CAG TCT CCA TCC TCA CTG TCT GCA TCT GTA GGA<br>GAC AGA GTC ACC ATC ACT TGT CGG GCG AGT CAG GGT<br>ATT AGC AGC TGG TTA GCC TGG TAT CAG CAG AAA CCA<br>GAG AAA GCC CCT AAG TCC CTG ATC TAT GCT GCA TCC<br>AGT TTG CAA AGT GGG GTC CCA TCA AGG TTC AGC GGC<br>AGT GGA TCT GGG ACA GAT TTC ACT CTC ACC ATC AGC<br>AGC CTG CAG CCT GAA GAT TTT GCA ACT TAT TAC TGC<br>CAA CAG TAT AAT AGT TAC CCG TAC ACT TTT GGC CAG<br>GGG ACC AAG CTG GAG ATC AAA | 36<br>72<br>108<br>144<br>180<br>216<br>252<br>288<br>324<br>360<br>381 |
| 176 | 17C4 Heavy Chain Variable Domain Nucleotide Sequence | ATG GAC ATA CTT TGT TCC ACG CTC CTG CTA CTG ACT<br>GTC CCG TCC TGG GTC TTA TCC CAG GTC ACC TTG AGG<br>GAG TCT GGT CCT GCG CTG GTG AAA CCC ACA CAG ACC<br>CTC ACA CTG ACC TGC ACC TTC TCT GGG TTC TCA CTC<br>AGC ACT AGT GGA ATG TGT GTG AGC TGG ATC CGT CAG<br>CCC CCA GGG AAG GCC CTG GAG TGG CTT GCA CTC ATT<br>GAT TGG GAT GAT GAT AAA TTC TAC AGC ACA TCT CTG<br>AAG ACC AGG CTC ACC ATC TCC AAG GAC ACC TCC AAA<br>AAC CAG GTG GTC CTT ACA ATG ACC AAC ATG GAC CCT<br>GTG GAC ACA GCC ACG TAT TAC TGT GCA CGG ATG TCA<br>ACA CCT ACC TAC TAC GGT TTG GAC GTC TGG GGC CAA<br>GGG ACC ACG GTC ACC GTC TCC TCA | 36<br>72<br>108<br>144<br>180<br>216<br>252<br>288<br>324<br>360<br>396<br>420 |
| 177 | 17C4 Light Chain Variable Domain Nucleotide Sequence | ATG AGG GTC CTC GCT CAG CTC CTG GGG CTC CTG CTG<br>CTC TGT TTC CCA GGT GCC AGA TGT GAC ATC CAG ATG<br>ACC CAG TCT CCA TCC TCA CTG TCT GCA TCT GTA GGA<br>GAC AGA GTC ACC ATC ACT TGT CGG GCG AGT CAG GGT<br>ATT AGC AGC TGG TTA GCC TGG TAT CAG CAG AAA CCA<br>GAG AAA GCC CCT AAG TCC CTG ATC TAT GCT GCA TCC<br>AGT TTG CAA AGT GGG GTC CCA TCA AGG TTC AGC GGC<br>AGT GGA TCT GGG ACA GAT TTC ACT CTC ACC ATC AGC<br>AGC CTG CAG CCT GAA GAT TTT GCA ACT TAT TAC TGC<br>CAA CAG TAT AAT AGT TAC CCT CTC ACT TTC GGC GGA<br>GGG ACC AAG GTG GAG ATC AAA | 36<br>72<br>108<br>144<br>180<br>216<br>252<br>288<br>324<br>360<br>381 |

TABLE 35-continued

Summary of Sequence Listing

| SEQ ID NO | Sequence Name | Sequence | |
|---|---|---|---|
| 178 | 1D7 Heavy Chain Variable Domain Nucleotide Sequence | ATG GAC ACA CTT TGC TCC ACG CTC CTG CTG CTG ACC<br>ATC CCT TCA TGG GTC TTG TCC CAG ATC ACC TTG AAG<br>GAG TCT GGT CCT ACG CTG GTG AAA CCC ACA CAG ACC<br>GAC AGA GTC ACC ATC ACT TGT CGG GCG AGT CAG GGT<br>TTT AGC AGC TGG TTA GCC TGG TAT CAG CAG AAA CCA<br>GAG AAA GCC CCT AAG TCC CTG ATC TAT GCT GCA TCC<br>AGT TTG CAA AGT GGG GTC CCA TCA AGG TTC AGC GGC<br>AGT GGA TCT GGG ACA GAT TTC ACT CTC ACC ATC AGC<br>AGC CTG CAG CCT GAA GAT TTT GCA ACT TAT TAC TGC<br>CAA CAG TAT AAT AGT TAC CCT TAC ACT TTT GGC CAG<br>GGG ACC AAG CTG GAG ATC AAA | 36<br>72<br>108<br>144<br>180<br>216<br>252<br>288<br>324<br>360<br>381 |
| 180 | 1D7 Light Chain-b Variable Domain Nucleotide Sequence | ATG AGG GTC CTC GCT CAG CTC CTG GGG CTC CTG CTG<br>CTC TGT TTC CCA GGT GCC AGA TGT GAC ATC CAG ATG<br>ACC CAG TCT CCA TCC TCA CTG TCT GCA TCT GTA GGA<br>GAC AGA GTC ACC ATC ACT TGT CGG GCG AGT CAG GGT<br>ATT AGC AGC TGG TTA GCC TGG TAT CAG CAG AAA CCA<br>GAG AAA GCC CCT AAG TCC CTG ATC TAT GCT GCA TCC<br>AGT TTG CAA AGT GGG GTC CCA TCA AGG TTC AGC GGC<br>AGT GGA TCT GGG ACA GAT TTC ACT CTC ACC ATC AGC<br>AGC CTG CAG CCT GAA GAT TTT GCA ACT TAT TAC TGC<br>CAA CAG TAT AAT AGT TAC CCT CTC ACT TTC GGC GGA<br>GGG ACC AAG GTG GAG ATC AAA | 36<br>72<br>108<br>144<br>180<br>216<br>252<br>288<br>324<br>360<br>381 |
| 181 | 9D5 Heavy Chain Variable Domain Nucleotide Sequence | ATG GAC ACA CTT TGC TCC ACG CTC CTG CTG CTG ACC<br>ATC CCT TCA TGG GTC TTG TCC CAG ATC ACC TTG AAG<br>GAG TCT GGT CCT ACG CTG GTG AAA CCC ACA CAG ACC<br>CTC ACG CTG ACC TGC ACC TTC TCT GGG TTC TCA CTC<br>GGC ACT AGT GGA CTG GGT GTG GGC TGG ATC CGT CAG<br>CCC CCA GGA AAG GCC CTG GAG TGG CTT GCA TTC ATT<br>TAT TGG GAT GAT GAT AAG CGC TAC AGC CCA TCT CTG<br>AAG AGC AGG CTC ACC ATC ACC AAG GAC ACC TCC AAA<br>AAC CAG GTG GTC CTT ACA ATG ACC AAC ATG GAC CCT<br>GTG GAC ACA GCC ACA TAT TAC TGT GCA CAC AGA CGG<br>GGC TTT TTT GAC TAC TGG GGC CAG GGA ACC CTG GTC<br>ACC GTC TCC TCA | 36<br>72<br>108<br>144<br>180<br>216<br>252<br>288<br>324<br>360<br>396<br>408 |
| 182 | 9D5 Light Chain Variable Domain Nucleotide Sequence | ATG AGG GTC CTC GCT CAG CTC CTG GGG CTC CTG CTG<br>CTC TGT TTC CCA GGT GCC AGA TGT GAC ATC CAG ATG<br>ACC CAG TCT CCA TCC TCA CTG TCT GCA TCT GTA GGA<br>GAC AGA GTC ACC ATC ACT TGT CGG GCG AGT CAG GGT<br>ATT AGC AGC TGG TTA GCC TGG TAT CAG CAG AAA CCA<br>GAG AAA GCC CCT AAG TCC CTG ATC TAT GCT GCA TCC<br>AGT TTG CAA AGT GGG GTC CCA TCA AGG TTC AGC GGC<br>AGT GGA TCT GGG ACA GAT TTC ACT CTC ACC ATC AGC<br>TTC GGC CCT GGG ACC AAA GTG GAT ATC AAA CGT ACG<br>GTG GCT GCA CCA TCT GTC TTC ATC TTC CCG CCA TCT<br>GAT GAG CAG TTG AAA TCT GGA ACT GCC TCT GTT GTG<br>TGC CTG CTG AAT AAC TTC TAT CCC AGA GAG GCC AAA<br>GTA CAG TGG AAG GTG GAT AAC GCC CTC CAA TCG GGT<br>AAC TCC CAG GAG AGT GTC ACA GAG CAG GAC AGC AAG<br>GAC AGC ACC TAC AGC CTC AGC AGC ACC CTG ACG CTG<br>AGC AAA GCA GAC TAC GAG AAA CAC AAA GTC TAC GCC<br>TGC GAA GTC ACC CAT CAG GGC CTG AGC TCG CCC GTC<br>ACA AAG AGC TTC AAC AGG GGA GAG TGT TAG | 36<br>72<br>108<br>144<br>180<br>216<br>252<br>288<br>324<br>360<br>396<br>432<br>468<br>504<br>540<br>576<br>612<br>642 |
| 184 | ICOS.33-g1f-S267E Nucleotide Sequence | GAG GTG CAG CTG GTG GAG TCT GGG GGA GGC TTG GTA<br>AAG CCT GGG GGG TCC CTT AGA CTC TCC TGT GCA GCC<br>TCT GGA TTC ACT TTC AGT GAC TAT TTC ATG CAC TGG<br>GTC CGC CAG GCT CCA GGG AAG GGG CTG GAG TGG GTT<br>GGC GTC ATA GAC ACT AAA AGT TTT AAT TAT GCA ACC<br>TAT TAC TCT GAT TTG GTG AAA GGC AGA TTC ACC ATC<br>TCA AGA GAT GAT TCA AAA AAC ACG CTG TAT CTG CAA<br>ATG AAC AGC CTG AAA ACC GAG GAC ACA GCC GTG TAT<br>TAC TGT ACC GCA ACC ATC GCT GTC CCA TAT TAC TTC<br>GAT TAC TGG GGC CAG GGA ACC CTG GTC ACC GTC TCC<br>TCA GCT AGC ACC AAG GGC CCA TCG GTC TTC CCC CTG<br>GCA CCC TCC TCC AAG AGC ACC TCT GGG GGC ACA GCG<br>GCC CTG GGC TGC CTG GTC AAG GAC TAC TTC CCC GAA<br>CCG GTG ACG GTG TCG TGG AAC TCA GGC GCC CTG ACC<br>AGC GGC GTG CAC ACC TTC CCG GCT GTC CTA CAG TCC<br>TCA GGA CTC TAC TCC CTC AGC AGC GTG GTG ACC GTG<br>CCC TCC AGC AGC TTG GGC ACC CAG ACC TAC ATC TGC | 36<br>72<br>108<br>144<br>180<br>216<br>252<br>288<br>324<br>360<br>396<br>432<br>468<br>504<br>540<br>576<br>612 |

TABLE 35-continued

Summary of Sequence Listing

| SEQ ID NO | Sequence Name | Sequence | |
|---|---|---|---|
| | | AAC GTG AAT CAC AAG CCC AGC AAC ACC AAG GTG GAC | 648 |
| | | AAG AGA GTT GAG CCC AAA TCT TGT GAC AAA ACT CAC | 684 |
| | | ACA TGC CCA CCG TGC CCA GCA CCT GAA CTC CTG GGG | 720 |
| | | GGA CCG TCA GTC TTC CTC TTC CCC CCA AAA CCC AAG | 756 |
| | | GAC ACC CTC ATG ATC TCC CGG ACC CCT GAG GTC ACA | 792 |
| | | TGC GTG GTG GTG GAC GTG AGC CAC GAA GAC CCT GAG | 828 |
| | | GTC AAG TTC AAC TGG TAC GTG GAC GGC GTG GAG GTG | 864 |
| | | CAT AAT GCC AAG ACA AAG CCG CGG GAG GAG CAG TAC | 900 |
| | | AAC AGC ACG TAC CGT GTG GTC AGC GTC CTC ACC GTC | 936 |
| | | CTG CAC CAG GAC TGG CTG AAT GGC AAG GAG TAC AAG | 972 |
| | | TGC AAG GTC TCC AAC AAA GCC CTC CCA GCC CCC ATC | 1008 |
| | | GAG AAA ACC ATC TCC AAA GCC AAA GGG CAG CCC CGA | 1044 |
| | | GAA CCA CAG GTG TAC ACC CTG CCC CCA TCC CGG GAG | 1080 |
| | | GAG ATG ACC AAG AAC CAG GTC AGC CTG ACC TGC CTG | 1116 |
| | | GTC AAA GGC TTC TAT CCC AGC GAC ATC GCC GTG GAG | 1152 |
| | | TGG GAG AGC AAT GGG CAG CCG GAG AAC AAC TAC AAG | 1188 |
| | | ACC ACG CCT CCC GTG CTG GAC TCC GAC GGC TCC TTC | 1224 |
| | | TTC CTC TAT AGC AAG CTC ACC GTG GAC AAG AGC AGG | 1260 |
| | | TGG CAG CAG GGG AAC GTC TTC TCA TGC TCC GTG ATG | 1296 |
| | | CAT GAG GCT CTG CAC AAC CAC TAC ACG CAG AAG AGC | 1332 |
| | | CTC TCC CTG TCC CCG GGT TGA | 1353 |
| 185 | IgG-2644 Heavy Chain Amino Add Sequence | EVQLLESGGG LVQPGGSLRL SCEASGFIFK YYAMSWVRQA | 40 |
| | | PGKGLEWVSG ISGSGGSTYY ADSVKGRFTI SRDNSKHTLY | 80 |
| | | LQMNSLRAED TAVYYCAKDG DFDWIHYYYG MDVWGQGTTV | 120 |
| | | TVSSASTKGP SVFPLAPSSK STSGGTAALG CLVKDYFPEP | 160 |
| | | VTVSWNSGAL TSGVHTFPAV LQSSGLYSLS SVVTVPSSSL | 200 |
| | | GTQTYICNVN HKPSNTKVDK RVEPKSCDKT HTCPPCPAPE | 240 |
| | | LLGGPSVFLF PPKPKDTLMI SRTPEVTCVV VDVSHEDPEV | 280 |
| | | KFNWYVDGVE VHNAKTKPRE EQYNSTYRVV SVLTVLHQDW | 320 |
| | | LNGKEYKCKV SNKALPAPIE KTISKAKGQP REPQVYTLPP | 360 |
| | | SREEMTKNQV SLTCLVKGFY PSDIAVEWES NGQPENNYKT | 400 |
| | | TPPVLDSDGS FFLYSKLTVD KSRWQQGNVF SCSVMHEALH | 440 |
| | | NHYTQKSLSL SPG | 453 |
| 186 | IgG-2644 Heavy Chain Variable Domain Amino Acid Sequence | EVQLLESGGG LVQPGGSLRL SCEASGFIFK YYAMSWVRQA | 40 |
| | | PGKGLEWVSG ISGSGGSTYY ADSVKGRFTI SRDNSKHTLY | 80 |
| | | LQMNSLRAED TAVYYCAKDG DFDWIHYYYG MDVWGQGTTV | 120 |
| | | TVSS | 124 |
| 187 | IgG-2644 Heavy Chain Constant Domain Amino Acid Sequence | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKRVEP KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPG | 329 |
| 188 | IgG-2644 Light Chain Amino Acid Sequence | AIQLTQSPSS LSASVGDRVT ITCRASQGIS SALAWYQQKP | 40 |
| | | GKAPKLLIYD ASSLESGVPS RFSGSGSGTD FTLTISSLQP | 80 |
| | | EDFATYYCQQ FNSYPHTFGG GTKVEIKRTV AAPSVFIFPP | 120 |
| | | SDEQLKSGTA SVVCLLNNFY PREAKVQWKV DNALQSGNSQ | 160 |
| | | ESVTEQDSKD STYSLSSTLT LSKADYEKHK VYACEVTHQG | 200 |
| | | LSSPVTKSFN RGEC | 214 |
| 189 | IgG-2644 Light Chain Variable Domain Amino Acid Sequence | AIQLTQSPSS LSASVGDRVT ITCRASQGIS SALAWYQQKP | 40 |
| | | GKAPKLLIYD ASSLESGVPS RFSGSGSGTD FTLTISSLQP | 80 |
| | | EDFATYYCQQ FNSYPHTFGG GTKVEIK | 107 |
| 190 | IgG-2644 Light Chain Constant Domain Amino Acid Sequence | RTVAAPSVFI FPPSDEQLKS GTASVVCLLN NFYPREAKVQ | 40 |
| | | WKVDNALQSG NSQESVTEQD SKDSTYSLSS TLTLSKADYE | 80 |
| | | KHKVYACEVT HQGLSSPVTK SFNRGEC | 107 |
| 191 | IgG-2644 CDRH1 Amino Acid Sequence | YYAMS | 5 |
| 192 | IgG-2644 CDRH2 Amino Acid Sequence | GISGSGGSTY YADSVKG | 17 |

TABLE 35-continued

Summary of Sequence Listing

| SEQ ID NO | Sequence Name | Sequence | |
|---|---|---|---|
| 193 | IgG-2644 CDRH3 Amino Acid Sequence | DGDFDWIHYY YGMDV | 15 |
| 194 | IgG-2644 CDRL1 Amino Acid Sequence | RASQGISSAL A | 11 |
| 195 | IgG-2644 CDRL2 Amino Acid Sequence | DASSLES | 7 |
| 196 | IgG-2644 CDRL3 Amino Acid Sequence | QQFNSYPHT | 9 |
| 197 | IgG-2644 Heavy Chain Nucleotide Sequence | GAG GTG CAG CTG TTG GAG TCT GGG GGA GGC TTG GTA<br>CAG CCT GGG GGG TCC CTG AGA CTC TCC TGT GAA GCC<br>TCT GGA TTC ATC TTT AAA TAC TAT GCC ATG AGC TGG<br>GTC CGC CAG GCT CCA GGG AAG GGG CTG GAG TGG GTC<br>TCA GGT ATT AGT GGT AGT GGT GGT AGC ACA TAC TAC<br>GCA GAC TCC GTG AAG GGC CGG TTC ACC ATC TCC AGA<br>GAC AAT TCC AAG CAC ACG CTG TAT CTG CAA ATG AAC<br>AGC CTG AGA GCC GAG GAC ACG GCC GTT TAT TAC TGT<br>GCG AAA GAT GGG GAT TTT GAC TGG ATC CAC TAT TAC<br>TAT GGT ATG GAC GTC TGG GGC CAA GGG ACC ACG GTC<br>ACC GTC TCC TCA GCG TCG ACC AAG GGC CCA TCC GTC<br>TTC CCC CTG GCA CCC TCC TCC AAG AGC ACC TCT GGG<br>GGC ACA GCG GCC CTG GGC TGC CTG GTC AAG GAC TAC<br>TTC CCC GAA CCG GTG ACG GTG TCG TGG AAC TCA GGC<br>GCC CTG ACC AGC GGC GTG CAC ACC TTC CCG GCT GTC<br>CTA CAG TCC TCA GGA CTC TAC TCC CTC AGC AGC GTG<br>GTG ACC GTG CCC TCC AGC AGC TTG GGC ACC CAG ACC<br>TAC ATC TGC AAC GTG AAT CAC AAG CCC AGC AAC ACC<br>AAG GTG GAC AAG AGA GTT GAG CCC AAA TCT TGT GAC<br>AAA ACT CAC ACA TGC CCA CCG TGC CCA GCA CCT GAA<br>CTC CTG GGG GGA CCG TCA GTC TTC CTC TTC CCC CCA<br>AAA CCC AAG GAC ACC CTC ATG ATC TCC CGG ACC CCT<br>GAG GTC ACA TGC GTG GTG GTG GAC GTG AGC CAC GAA<br>GAC CCT GAG GTC AAG TTC AAC TGG TAC GTG GAC GGC<br>GTG GAG GTG CAT AAT GCC AAG ACA AAG CCG CGG GAG<br>GAG CAG TAC AAC AGC ACG TAC CGT GTG GTC AGC GTC<br>CTC ACC GTC CTG CAC CAG GAC TGG CTG AAT GGC AAG<br>GAG TAC AAG TGC AAG GTC TCC AAC AAA GCC CTC CCA<br>GCC CCC ATC GAG AAA ACC ATC TCC AAA GCC AAA GGG<br>CAG CCC CGA GAA CCA CAG GTG TAC ACC CTG CCC CCA<br>TCC CGG GAG GAG ATG ACC AAG AAC CAG GTC AGC CTG<br>ACC TGC CTG GTC AAA GGC TTC TAT CCC AGC GAC ATC<br>GCC GTG GAG TGG GAG AGC AAT GGG CAG CCG GAG AAC<br>AAC TAC AAG ACC ACG CCT CCC GTG CTG GAC TCC GAC<br>GGC TCC TTC TTC CTC TAT AGC AAG CTC ACC GTG GAC<br>AAG AGC AGG TGG CAG CAG GGG AAC GTC TTC TCA TGC<br>TCC GTG ATG CAT GAG GCT CTG CAC AAC CAC TAC ACG<br>CAG AAG AGC CTC TCC CTG TCC CCG GGT | 36<br>72<br>108<br>144<br>180<br>216<br>252<br>288<br>324<br>360<br>396<br>432<br>468<br>504<br>540<br>576<br>612<br>648<br>684<br>720<br>756<br>792<br>828<br>864<br>900<br>936<br>972<br>1008<br>1044<br>1080<br>1116<br>1152<br>1188<br>1224<br>1260<br>1296<br>1332<br>1359 |
| 198 | IgG-2644 Heavy Chain Variable Domain Nucleotide Sequence | GAG GTG CAG CTG TTG GAG TCT GGG GGA GGC TTG GTA<br>CAG CCT GGG GGG TCC CTG AGA CTC TCC TGT GAA GCC<br>TCT GGA TTC ATC TTT AAA TAC TAT GCC ATG AGC TGG<br>GTC CGC CAG GCT CCA GGG AAG GGG CTG GAG TGG GTC<br>TCA GGT ATT AGT GGT AGT GGT GGT AGC ACA TAC TAC<br>GCA GAC TCC GTG AAG GGC CGG TTC ACC ATC TCC AGA<br>GAC AAT TCC AAG CAC ACG CTG TAT CTG CAA ATG AAC<br>AGC CTG AGA GCC GAG GAC ACG GCC GTT TAT TAC TGT<br>GCG AAA GAT GGG GAT TTT GAC TGG ATC CAC TAT TAC<br>TAT GGT ATG GAC GTC TGG GGC CAA GGG ACC ACG GTC<br>ACC GTC TCC TCA | 36<br>72<br>108<br>144<br>180<br>216<br>252<br>288<br>324<br>360<br>372 |
| 199 | IgG-2644 Heavy Chain Constant Domain Nucleotide Sequence | CCC TCC TCC AAG AGC ACC TCT GGG GGC ACA GCG GCC<br>CTG GGC TGC CTG GTC AAG GAC TAC TTC CCC GAA CCG<br>GTG ACG GTG TCG TGG AAC TCA GGC GCC CTG ACC AGC<br>GGC GTG CAC ACC TTC CCG GCT GTC CTA CAG TCC TCA<br>GGA CTC TAC TCC CTC AGC AGC GTG GTG ACC GTG CCC<br>TCC AGC AGC TTG GGC ACC CAG ACC TAC ATC TGC AAC | 72<br>108<br>144<br>180<br>216<br>252 |

TABLE 35-continued

Summary of Sequence Listing

| SEQ ID NO | Sequence Name | Sequence | |
|---|---|---|---|
| | | GTG AAT CAC AAG CCC AGC AAC ACC AAG GTG GAC AAG | 288 |
| | | AGA GTT GAG CCC AAA TCT TGT GAC AAA ACT CAC ACA | 324 |
| | | TGC CCA CCG TGC CCA GCA CCT GAA CTC CTG GGG GGA | 360 |
| | | CCG TCA GTC TTC CTC TTC CCC CCA AAA CCC AAG GAC | 396 |
| | | ACC CTC ATG ATC TCC CGG ACC CCT GAG GTC ACA TGC | 432 |
| | | GTG GTG GTG GAC GTG AGC CAC GAA GAC CCT GAG GTC | 468 |
| | | AAG TTC AAC TGG TAC GTG GAC GGC GTG GAG GTG CAT | 504 |
| | | AAT GCC AAG ACA AAG CCG CGG GAG GAG CAG TAC AAC | 540 |
| | | AGC ACG TAC CGT GTG GTC AGC GTC CTC ACC GTC CTG | 576 |
| | | CAC CAG GAC TGG CTG AAT GGC AAG GAG TAC AAG TGC | 612 |
| | | AAG GTC TCC AAC AAA GCC CTC CCA GCC CCC ATC GAG | 648 |
| | | AAA ACC ATC TCC AAA GCC AAA GGG CAG CCC CGA GAA | 684 |
| | | CCA CAG GTG TAC ACC CTG CCC CCA TCC CGG GAG GAG | 720 |
| | | ATG ACC AAG AAC CAG GTC AGC CTG ACC TGC CTG GTC | 756 |
| | | AAA GGC TTC TAT CCC AGC GAC ATC GCC GTG GAG TGG | 792 |
| | | GAG AGC AAT GGG CAG CCG GAG AAC AAC TAC AAG ACC | 828 |
| | | ACG CCT CCC GTG CTG GAC TCC GAC GGC TCC TTC TTC | 864 |
| | | CTC TAT AGC AAG CTC ACC GTG GAC AAG AGC AGG TGG | 900 |
| | | CAG CAG GGG AAC GTC TTC TCA TGC TCC GTG ATG CAT | 936 |
| | | GAG GCT CTG CAC AAC CAC TAC ACG CAG AAG AGC CTC | 972 |
| | | TCC CTG TCC CCG GGT | 987 |
| 200 | IgG-2644 Light Chain Nucleotide Sequence | GCC ATC CAG TTG ACC CAG TCT CCA TCC TCC CTG TCT | 36 |
| | | GCA TCT GTA GGA GAC AGA GTC ACC ATC ACT TGC CGG | 72 |
| | | GCA AGT CAG GGC ATT AGC AGT GCT TTA GCC TGG TAT | 108 |
| | | CAG CAG AAA CCA GGG AAA GCT CCT AAG CTC CTG ATC | 144 |
| | | TAT GAT GCC TCC AGT TTG GAA AGT GGG GTC CCA TCA | 180 |
| | | AGG TTC AGC GGC AGT GGA TCT GGG ACA GAT TTC ACT | 216 |
| | | CTC ACC ATC AGC AGC CTG CAG CCT GAA GAT TTT GCA | 252 |
| | | ACT TAT TAC TGT CAA CAG TTT AAT AGT TAC CCT CAC | 288 |
| | | ACT TTC GGC GGA GGG ACC AAG GTG GAG ATC AAA CGT | 324 |
| | | ACG GTG GCT GCA CCA TCT GTC TTC ATC TTC CCG CCA | 360 |
| | | TCT GAT GAG CAG TTG AAA TCT GGA ACT GCC TCT GTT | 396 |
| | | GTG TGC CTG CTG AAT AAC TTC TAT CCC AGA GAG GCC | 432 |
| | | AAA GTA CAG TGG AAG GTG GAT AAC GCC CTC CAA TCG | 468 |
| | | GGT AAC TCC CAG GAG AGT GTC ACA GAG CAG GAC AGC | 504 |
| | | AAG GAC AGC ACC TAC AGC CTC AGC AGC ACC CTG ACG | 540 |
| | | CTG AGC AAA GCA GAC TAC GAG AAA CAC AAA GTC TAC | 576 |
| | | GCC TGC GAA GTC ACC CAT CAG GGC CTG AGC TCG CCC | 612 |
| | | GTC ACA AAG AGC TTC AAC AGG GGA GAG TGT | 642 |
| 201 | IgG-2644 Light Chain Variable Domain Nucleotide Sequence | GCC ATC CAG TTG ACC CAG TCT CCA TCC TCC CTG TCT | 36 |
| | | GCA TCT GTA GGA GAC AGA GTC ACC ATC ACT TGC CGG | 72 |
| | | GCA AGT CAG GGC ATT AGC AGT GCT TTA GCC TGG TAT | 108 |
| | | CAG CAG AAA CCA GGG AAA GCT CCT AAG CTC CTG ATC | 144 |
| | | TAT GAT GCC TCC AGT TTG GAA AGT GGG GTC CCA TCA | 180 |
| | | AGG TTC AGC GGC AGT GGA TCT GGG ACA GAT TTC ACT | 216 |
| | | CTC ACC ATC AGC AGC CTG CAG CCT GAA GAT TTT GCA | 252 |
| | | ACT TAT TAC TGT CAA CAG TTT AAT AGT TAC CCT CAC | 288 |
| | | ACT TTC GGC GGA GGG ACC AAG GTG GAG ATC AAA | 321 |
| 202 | IgG-2644 Light Chain Constant Domain Nucleotide Sequence | CGT ACG GTG GCT GCA CCA TCT GTC TTC ATC TTC CCG | 36 |
| | | CCA TCT GAT GAG CAG TTG AAA TCT GGA ACT GCC TCT | 72 |
| | | GTT GTG TGC CTG CTG AAT AAC TTC TAT CCC AGA GAG | 108 |
| | | GCC AAA GTA CAG TGG AAG GTG GAT AAC GCC CTC CAA | 144 |
| | | TCG GGT AAC TCC CAG GAG AGT GTC ACA GAG CAG GAC | 180 |
| | | AGC AAG GAC AGC ACC TAC AGC CTC AGC AGC ACC CTG | 216 |
| | | ACG CTG AGC AAA GCA GAC TAC GAG AAA CAC AAA GTC | 252 |
| | | TAC GCC TGC GAA GTC ACC CAT CAG GGC CTG AGC TCG | 288 |
| | | CCC GTC ACA AAG AGC TTC AAC AGG GGA GAG TGT | 321 |
| 203 | ICOS.4 Epitope Amino Acid Sequence | SIFDPPPFKV TL | 12 |
| 204 | hulgG1f Heavy Chain Constant Domain with C-terminal lysine | ASTKGPSVFP LAPSSKSTSG GTAALGCLVK DYFPEPVTVS | 40 |
| | | WNSGALTSGV HTPAVLQSS GLYSLSSVVT VPSSSLGTQT | 80 |
| | | YICNVNHKPS NTKVDKRVEP KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSREE | 240 |
| | | MTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |

TABLE 35-continued

Summary of Sequence Listing

| SEQ ID NO | Sequence Name | Sequence | |
|---|---|---|---|
| 205 | Isoform 2 (Q9Y6W8-2) | MKSGLWYFFL FCLRIKVLTG EINGSANYEM FIFHNGGVQI | 40 |
| | | LCKYPDIVQQ FKMQLLKGGQ ILCDLTKTKG SGNTVSIKSL | 80 |
| | | KFCHSQLSNN SVSFFLYNLD HSHANYYFCN LSIFDPPPFK | 120 |
| | | VTLTGGYLHI YESQLCCQLK FWLPIGCAAF VVVCILGCIL | 160 |
| | | ICWLTKKM | 168 |
| 206 | Human IgG1 (P01857-1) | ASTKGPSVFP LAPSSKSTSG GTAALGCLVK DYFPEPVTVS | 40 |
| | | WNSGALTSGV HTFPAVLQSS GLYSLSSVVT VPSSSLGTQT | 80 |
| | | YICNVNHKPS NTKVDKKVEP KSCDKTHTCP PCPAPELLGG | 120 |
| | | PSVFLFPPKP KDTLMISRTP EVTCVVVDVS HEDPEVKFNW | 160 |
| | | YVDGVEVHNA KTKPREEQYN STYRVVSVLT VLHQDWLNGK | 200 |
| | | EYKCKVSNKA LPAPIEKTIS KAKGQPREPQ VYTLPPSRDE | 240 |
| | | LTKNQVSLTC LVKGFYPSDI AVEWESNGQP ENNYKTTPPV | 280 |
| | | LDSDGSFFLY SKLTVDKSRW QQGNVFSCSV MHEALHNHYT | 320 |
| | | QKSLSLSPGK | 330 |
| 207 | VKI O18 | DIQMTQSPSS LSASVGDRVT ITCQASQDIS NYLNWYQQKP | 40 |
| | | GKAPKLLIYD ASNLETGVPS RFSGSGSGTD FTFTISSLQP | 80 |
| | | EDIATYYCQQ YDNLP | 95 |
| 208 | JK3 | FTFGPGTKVD IK | 12 |
| 209 | VH3-15 | EVQLVESGGG LVKPGGSLRL SCAASGFTFS NAWMSWVRQA | 40 |
| | | PGKGLEWVGR IKSKTDGGTT DYAAPVKGRF TISRDDSKNT | 80 |
| | | LYLQMNSLKT EDTAVYYCTT | 100 |
| 210 | JH4 | YFDYWGQGTL VTVSS | 15 |
| 211 | mICOS.1-mG1 Heavy Chain | EVDLVETGGG LVQPGGSLKL SCVASGFTFS RYWMFWIRQA | 40 |
| | | PGKGLEWVSS VSTDGRSTYY PDSVQGRFTI SRNDAENTVY | 80 |
| | | LQMNSLRSED TATYYCAKEG YYDGSYYAYY FDYWGQGVTV | 120 |
| | | TVSSAKTTPP SVYPLAPGSA AQTNSMVTLG CLVKGYFPEP | 160 |
| | | VTVTWNSGSL SSGVHTFPAV LQSDLYTLSS SVTVPSSTWP | 200 |
| | | SETVTCNVAH PASSTKVDKK IVPRDCGCKP CICTVPEVSS | 240 |
| | | VFIFPPKPKD VLTITLTPKV TCVVVDISKD DPEVQFSWFV | 280 |
| | | DDVEVHTAQT QPREEQFNST FRSVSELPIM HQDWLNGKEF | 320 |
| | | KCRVNSAAFP APIEKTISKT KGRPKAPQVY TIPPPKEQMA | 360 |
| | | KDKVSLTCMI TDFFPEDITV EWQWNGQPAE NYKNTQPIMD | 400 |
| | | TDGSYFVYSK LNVQKSNWEA GNTFTCSVLH EGLHNHHTEK | 440 |
| | | SLSHSPGK | 448 |
| 212 | mICOS.1-mG1 Light Chain | DVQMAQSPSS LAASPGESVS INCKASKSIS KYLAWYQQKP | 40 |
| | | GKANKLLIYS GSTLQSGTPS RFSGSGSGTD FTLTIRNLEP | 80 |
| | | EDFGLYYCQQ HNAYPPTFGT GTKLELKRAD AAPTVSIFPP | 120 |
| | | SSEQLTSGGA SVVCFLNNFY PKDINVKWKI DGSERQNGVL | 160 |
| | | NSWTDQDSKD STYSMSSTLT LTKDEYERHN SYTCEATHKT | 200 |
| | | STSPIVKSFN RNEC | 214 |
| 213 | ICOS.4-mG1 Heavy Chain | EVQLVESGGG LVKPAGSLTL SCVASGFTFS DYFMHWVRQA | 40 |
| | | PGKGLEWVAV IDTKSFNYAT YYSDLVKGRF TVSRDDSQGM | 80 |
| | | VYLQMNNLRK EDTATYYCTA TIAVPYYFDY WGQGTMVTVS | 120 |
| | | SAKTTPPSVY PLAPGSAAQT NSMVTLGCLV KGYFPEPVTV | 160 |
| | | TWNSGSLSSG VHTFPAVLQS DLYTLSSSVT VPSSTWPSET | 200 |
| | | VTCNVAHPAS STKVDKKIVP RDCGCKPCIC TVPEVSSVFI | 240 |
| | | FPPKPKDVLT ITLTPKVTCV VVDISKDDPE VQFSWFVDDV | 280 |
| | | EVHTAQTQPR EEQFNSTFRS VSELPIMHQD WLNGKEFKCR | 320 |
| | | VNSAAFPAPI EKTISKTKGR PKAPQVYTIP PPKEQMAKDK | 360 |
| | | VSLTCMITDF FPEDITVEWQ WNGQPAENYK NTQPIMDTDG | 400 |
| | | SYFVYSKLNV QKSNWEAGNT FTCSVLHEGL HNHHTEKSLS | 440 |
| | | HSPGK | 445 |
| 214 | ICOS.4-mG1 Light Chain | DIQMTQSPSS LPASLGDRVT INCQASQDIS NYLSWYQQKP | 40 |
| | | GKAPKLLIYY TNLLADGVPS RFSGSGSGRD YSFTISSLES | 80 |
| | | EDIGSYYCQQ YYNYRTFGPG TKLEIKRADA APTVSIFPPS | 120 |
| | | SEQLTSGGAS VVCFLNNFYP KDINVKWKID GSERQNGVLN | 160 |
| | | SWTDQDSKDS TYSMSSTLTL TKDEYERHNS YTCEATHKTS | 200 |
| | | TSPIVKSFNR NEC | 213 |
| 215 | ICOS.34-G1f Heavy Chain | EVQLVESGGG LVKPGGSLRL SCAASGFTFS DYFMHWVRQA | 40 |
| | | PGKGLEWVGV IDTKSFNYAT YYSDLVKGRF TISRDDSKNT | 80 |
| | | LYLQMNSLKT EDTAVYYCTT TIAVPYYFDY WGQGTLVTVS | 120 |
| | | SASTKGPSVF PLAPSSKSTS GGTAALGCLV KDYFPEPVTV | 160 |
| | | SWNSGALTSG VHTFPAVLQS SGLYSLSSVV TVPSSSLGTQ | 200 |

TABLE 35-continued

Summary of Sequence Listing

| SEQ ID NO | Sequence Name | Sequence | |
|---|---|---|---|
| | | TYICNVNHKP SNTKVDKRVE PKSCDKTHTC PPCPAPELLG | 240 |
| | | GPSVFLFPPK PKDTLMISRT PEVTCVVVDV SHEDPEVKFN | 280 |
| | | WYVDGVEVHN AKTKPREEQY NSTYRVVSVL TVLHQDWLNG | 320 |
| | | KEYKCKVSNK ALPAPIEKTI SKAKGQPREP QVYTLPPSRE | 360 |
| | | EMTKNQVSLT CLVKGFYPSD IAVEWESNGQ PENNYKTTPP | 400 |
| | | VLDSDGSFFL YSKLTVDKSR WQQGNVFSCS VMHEALHNHY | 440 |
| | | TQKSLSLSPG | 450 |
| 216 | ICOS.34-G1f Light Chain | DIQMTQSPSS LSASVGDRVT ITCQASQDIS NYLSWYQQKP | 40 |
| | | GKAPKLLIYY TNLLADGVPS RFSGSGSGTD FTFTISSLQP | 80 |
| | | EDIATYYCQQ YYNYRTFGPG TKVDIKRTVA APSVFIFPPS | 120 |
| | | DEQLKSGTAS VVCLLNNFYP REAKVQWKVD NALQSGNSQE | 160 |
| | | SVTEQDSKDS TYSLSSTLTL SKADYEKHKV YACEVTHQGL | 200 |
| | | SSPVTKSFNR GEC | 213 |
| 217 | ICOS.35-G1f Heavy Chain | EVQLVESGGG LVKPGGSLRL SCAASGFTFS DYFMHWVRQA | 40 |
| | | PGKGLEWVGV IDTKSFNYAT YYSDLVKGRF TISRDDSKNT | 80 |
| | | LYLQMNSLKT EDTAVYYCTA TIAVPYYFDY WGQGTLVTVS | 120 |
| | | SASTKGPSVF PLAPSSKSTS GGTAALGCLV KDYFPEPVTV | 160 |
| | | SWNSGALTSG VHTFPAVLQS SGLYSLSSVV TVPSSSLGTQ | 200 |
| | | TYICNVNHKP SNTKVDKRVE PKSCDKTHTC PPCPAPELLG | 240 |
| | | GPSVFLFPPK PKDTLMISRT PEVTCVVVDV SHEDPEVKFN | 280 |
| | | WYVDGVEVHN AKTKPREEQY NSTYRVVSVL TVLHQDWLNG | 320 |
| | | KEYKCKVSNK ALPAPIEKTI SKAKGQPREP QVYTLPPSRE | 360 |
| | | EMTKNQVSLT CLVKGFYPSD IAVEWESNGQ PENNYKTTPP | 400 |
| | | VLDSDGSFFL YSKLTVDKSR WQQGNVFSCS VMHEALHNHY | 440 |
| | | TQKSLSLSPG | 450 |
| 218 | ICOS.35-G1f Light Chain | DIQMTQSPSS LSASVGDRVT ITCQASQDIS NYLSWYQQKP | 40 |
| | | GKAPKLLIYY TNLLADGVPS RFSGSGSGTD FTFTISSLQP | 80 |
| | | EDIATYYCQQ YYNYRTFGPG TKVDIKRTVA APSVFIFPPS | 120 |
| | | DEQLKSGTAS VVCLLNNFYP REAKVQWKVD NALQSGNSQE | 160 |
| | | SVTEQDSKDS TYSLSSTLTL SKADYEKHKV YACEVTHQGL | 200 |
| | | SSPVTKSFNR GEC | 213 |
| 219 | NKTR-214 IL-2 pathway agonist | FTSSSTKKTQ LQLEHLLLDL QMILNGINNY KNPKLTRMLT | 40 |
| | | FKFYMPKKAT ELKHLQCLEE ELKPLEEVLN LAQSKNFHLR | 80 |
| | | PRDLISNINV IVLELKGSET TFMCEYADET ATIVEFLNRW | 120 |
| | | ITFSQSIIST LT | 132 |

We claim:

1. An isolated monoclonal antibody that binds to human Inducible COStimulator molecule (ICOS), wherein the antibody comprises a heavy chain variable domain comprising the amino acid sequences of SEQ ID NOs: 9, 10, 11, and a light chain variable domain comprising the amino acid sequences of SEQ ID NOs: 12, 14, 15, wherein the antibody binds to human CD32b with a dissociation constant ($K_D$) of 170 nM or less as measured by surface plasmon resonance.

2. An isolated monoclonal antibody that binds to human ICOS, wherein the antibody comprises heavy and light chain variable domains comprising the amino acid sequences of SEQ ID NOs: 5 and 6, respectively, wherein the antibody binds to human CD32b with a $K_D$ of 170 nM or less as measured by surface plasmon resonance.

3. The antibody of claim 2, wherein the antibody comprises heavy and light chains comprising the amino acid sequences of SEQ ID NOs: 7 and 8, respectively.

4. The antibody of claim 1, wherein the antibody is a humanized antibody.

5. The antibody of claim 2, wherein the antibody is a humanized antibody.

6. The antibody of claim 1, wherein the antibody further comprises a heavy chain constant region comprising the amino acid sequence of SEQ ID NO: 53.

7. The antibody of claim 2, wherein the antibody further comprises a heavy chain constant region comprising the amino acid sequence of SEQ ID NO: 53.

8. The antibody of claim 1, wherein the antibody blocks the binding and/or the interaction of an ICOS ligand to human ICOS.

9. The antibody of claim 2, wherein the antibody blocks the binding and/or the interaction of an ICOS ligand to human ICOS.

10. An isolated, humanized monoclonal antibody that binds to human ICOS, wherein the antibody comprises a heavy chain variable domain comprising the amino acid sequences of SEQ ID NOs: 9, 10 and 11, and a light chain variable domain comprising the amino acid sequences of SEQ ID NOs: 12, 14 and 15, wherein the antibody binds to human CD32b with a $K_D$ of 170 nM or less as measured by surface plasmon resonance.

11. The antibody of claim 10, wherein the antibody further comprises a heavy chain constant region comprising the amino acid sequence of SEQ ID NO: 53.

12. The antibody of claim 10, wherein the antibody comprises a heavy chain variable domain comprising the amino acid sequence of SEQ ID NO: 5, and a light chain variable domain comprising the amino acid sequence of SEQ ID NO. 6.

13. The antibody of claim 12, wherein the heavy chain variable domain consists essentially of the amino acid sequence of SEQ ID NO: 5, and the light chain variable domain consists essentially of the amino acid sequence of SEQ ID NO: 6.

14. An isolated, humanized monoclonal antibody that binds to human ICOS, wherein the antibody comprises:
a heavy chain variable domain comprising the amino acid sequence of SEQ ID NO: 5,
a light chain variable domain comprising the amino acid sequence of SEQ ID NO: 6, and
a heavy chain constant region comprising the amino acid sequence of SEQ ID NO: 53,
wherein the antibody exhibits a greater than 29-fold increase in binding affinity to human CD32b as measured by surface plasmon resonance compared to an antibody comprising a heavy chain variable domain comprising the amino acid sequence of SEQ ID NO: 5, a light chain variable domain comprising the amino acid sequence of SEQ ID NO. 6, and a wild-type human IgG1 constant region.

15. The antibody of claim 14, wherein the heavy chain consists essentially of the amino acid sequence of SEQ ID NO: 7, and the light chain consists essentially of the amino acid sequence of SEQ ID NO. 8.

16. The antibody of claim 14, wherein the antibody blocks the binding and/or the interaction of ICOS ligand to human ICOS.

17. The antibody of claim 15, wherein the antibody blocks the binding and/or the interaction of ICOS ligand to human ICOS.

18. A composition comprising the antibody of claim 1 and a pharmaceutically acceptable carrier.

19. A composition comprising the antibody of claim 2 and a pharmaceutically acceptable carrier.

20. A composition comprising the antibody of claim 3 and a pharmaceutically acceptable carrier.

21. A composition comprising the antibody of claim 10 and a pharmaceutically acceptable carrier.

22. A composition comprising the antibody of claim 14 and a pharmaceutically acceptable carrier.

23. The composition of claim 18, further comprising an additional therapeutic agent, wherein the additional therapeutic agent is an anti-cancer therapeutic agent, an immunostimulatory therapeutic agent, a chemotherapeutic agent, a radiotherapeutic agent, an immunotherapeutic agent, and/or an immunogenic therapeutic agent.

24. The composition of claim 19, further comprising an additional therapeutic agent, wherein the additional therapeutic agent is an anti-cancer therapeutic agent, an immunostimulatory therapeutic agent, a chemotherapeutic agent, a radiotherapeutic agent, an immunotherapeutic agent, and/or an immunogenic therapeutic agent.

25. The composition of claim 20, further comprising an additional therapeutic agent, wherein the additional therapeutic agent is an anti-cancer therapeutic agent, an immunostimulatory therapeutic agent, a chemotherapeutic agent, a radiotherapeutic agent, an immunotherapeutic agent, and/or an immunogenic therapeutic agent.

26. The composition of claim 21, further comprising an additional therapeutic agent, wherein the additional therapeutic agent is an anti-cancer therapeutic agent, an immunostimulatory therapeutic agent, a chemotherapeutic agent, a radiotherapeutic agent, an immunotherapeutic agent, and/or an immunogenic therapeutic agent.

27. The composition of claim 22, further comprising an additional therapeutic agent, wherein the additional therapeutic agent is an anti-cancer therapeutic agent, an immunostimulatory therapeutic agent, a chemotherapeutic agent, a radiotherapeutic agent, an immunotherapeutic agent, and/or an immunogenic therapeutic agent.

28. The composition of claim 23, wherein the additional therapeutic agent is an anti-programmed death protein 1 (PD-1) antibody, anti-programmed death ligand 1 (PD-L1) antibody, and/or an anti-cytotoxic T-lymphocyte-associated protein 4 (CTLA-4) antibody.

29. The composition of claim 24, wherein the additional therapeutic agent is an anti-PD-1 antibody, anti-PD-L1 antibody, and/or an anti-CTLA-4 antibody.

30. The composition of claim 25, wherein the additional therapeutic agent is an anti-PD-1 antibody, anti-PD-L1 antibody, and/or an anti-CTLA-4 antibody.

31. The composition of claim 26, wherein the additional therapeutic agent is an anti-PD-1 antibody, anti-PD-L1 antibody, and/or an anti-CTLA-4 antibody.

32. The composition of claim 27, wherein the additional therapeutic agent is an anti-PD-1 antibody, anti-PD-L1 antibody, and/or an anti-CTLA-4 antibody.

* * * * *

SEQUENCE LISTING

<160> NUMBER OF SEQ ID NOS: 219

<210> SEQ ID NO 1
<211> LENGTH: 199
<212> TYPE: PRT
<213> ORGANISM: Homo sapiens

<400> SEQUENCE: 1

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

```
Tyr Asn Leu Asp His Ser His Ala Asn Tyr Tyr Phe Cys Asn Leu Ser
            100                 105                 110

Ile Phe Asp Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
        130                 135                 140

Ile Gly Cys Ala Ala Phe Val Val Cys Ile Leu Gly Cys Ile Leu
145                 150                 155                 160

Ile Cys Trp Leu Thr Lys Lys Lys Tyr Ser Ser Val His Asp Pro
                165                 170                 175

Asn Gly Glu Tyr Met Phe Met Arg Ala Val Asn Thr Ala Lys Lys Ser
            180                 185                 190

Arg Leu Thr Asp Val Thr Leu
            195

<210> SEQ ID NO 2
<211> LENGTH: 309
<212> TYPE: PRT
<213> ORGANISM: Homo sapiens

<400> SEQUENCE: 2

Met Arg Leu Gly Ser Pro Gly Leu Leu Phe Leu Leu Phe Ser Ser Leu
1               5                   10                  15

Arg Ala Asp Thr Gln Glu Lys Glu Val Arg Ala Met Val Gly Ser Asp
            20                  25                  30

Val Glu Leu Ser Cys Ala Cys Pro Glu Gly Ser Arg Phe Asp Leu Asn
        35                  40                  45

Asp Val Tyr Val Tyr Trp Gln Thr Ser Glu Ser Lys Thr Val Val Thr
50                  55                  60

Tyr His Ile Pro Gln Asn Ser Ser Leu Glu Asn Val Asp Ser Arg Tyr
65                  70                  75                  80

Arg Asn Arg Ala Leu Met Ser Pro Ala Gly Met Leu Arg Gly Asp Phe
                85                  90                  95

Ser Leu Arg Leu Phe Asn Val Thr Pro Gln Asp Glu Gln Lys Phe His
            100                 105                 110

Cys Leu Val Leu Ser Gln Ser Leu Gly Phe Gln Glu Val Leu Ser Val
        115                 120                 125

Glu Val Thr Leu His Val Ala Ala Asn Phe Ser Val Pro Val Val Ser
130                 135                 140

Ala Pro His Ser Pro Ser Gln Asp Glu Leu Thr Phe Thr Cys Thr Ser
145                 150                 155                 160

Ile Asn Gly Tyr Pro Arg Pro Asn Val Tyr Trp Ile Asn Lys Thr Asp
                165                 170                 175

Asn Ser Leu Leu Asp Gln Ala Leu Gln Asn Asp Thr Val Phe Leu Asn
            180                 185                 190

Met Arg Gly Leu Tyr Asp Val Val Ser Val Leu Arg Ile Ala Arg Thr
            195                 200                 205

Pro Ser Val Asn Ile Gly Cys Cys Ile Glu Asn Val Leu Leu Gln Gln
210                 215                 220

Asn Leu Thr Val Gly Ser Gln Thr Gly Asn Asp Ile Gly Glu Arg Asp
225                 230                 235                 240

Lys Ile Thr Glu Asn Pro Val Ser Thr Gly Glu Lys Asn Ala Ala Thr
                245                 250                 255

Trp Ser Ile Leu Ala Val Leu Cys Leu Leu Val Val Val Ala Val Ala
            260                 265                 270
```

```
Ile Gly Trp Val Cys Arg Asp Arg Cys Leu Gln His Ser Tyr Ala Gly
        275                 280                 285

Ala Trp Ala Val Ser Pro Glu Thr Glu Leu Thr Glu Ser Trp Asn Leu
290                 295                 300

Leu Leu Leu Leu Ser
305

<210> SEQ ID NO 3
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Glu Val Gln Leu Val Glu Ser Gly Gly Gly Leu Val Lys Pro Ala Gly
1               5                   10                  15

Ser Leu Thr Leu Ser Cys Val Ala Ser Gly Phe Thr Phe Ser Asp Tyr
            20                  25                  30

Phe Met His Trp Val Arg Gln Ala Pro Gly Lys Gly Leu Glu Trp Val
        35                  40                  45

Ala Val Ile Asp Thr Lys Ser Phe Asn Tyr Ala Thr Tyr Tyr Ser Asp
    50                  55                  60

Leu Val Lys Gly Arg Phe Thr Val Ser Arg Asp Asp Ser Gln Gly Met
65                  70                  75                  80

Val Tyr Leu Gln Met Asn Asn Leu Arg Lys Glu Asp Thr Ala Thr Tyr
                85                  90                  95

Tyr Cys Thr Ala Thr Ile Ala Val Pro Tyr Tyr Phe Asp Tyr Trp Gly
            100                 105                 110

Gln Gly Thr Met Val Thr Val Ser Ser Ala Thr Thr Ala Pro Ser
        115                 120                 125

Val Tyr Pro Leu Ala Pro Ala Cys Asp Ser Thr Thr Ser Thr Thr Asn
    130                 135                 140

Thr Val Thr Leu Gly Cys Leu Val Lys Gly Tyr Phe Pro Glu Pro Val
145                 150                 155                 160

Thr Val Ser Trp Asn Ser Gly Ala Leu Thr Ser Gly Val His Thr Phe
                165                 170                 175

Pro Ser Val Leu His Ser Gly Leu Tyr Ser Leu Ser Ser Val Thr
            180                 185                 190

Val Pro Ser Ser Thr Trp Pro Ser Gln Thr Val Thr Cys Asn Val Ala
    195                 200                 205

His Pro Ala Ser Ser Thr Lys Val Asp Lys Lys Ile Val Pro Gly Asp
    210                 215                 220

Gly Ser Gly Cys Lys Pro Cys Thr Cys Pro Gly Pro Glu Val Ser Ser
225                 230                 235                 240

Val Phe Ile Phe Pro Pro Lys Pro Lys Asp Val Leu Thr Ile Ser Leu
                245                 250                 255

Ser Pro Lys Val Thr Cys Val Val Asp Ile Ser Gln Asp Asp Pro
            260                 265                 270

Glu Val Gln Phe Ser Trp Phe Ile Asp Gly Lys Glu Val His Thr Ala
        275                 280                 285

Val Thr Gln Pro Arg Glu Glu Gln Phe Asn Ser Thr Tyr Arg Met Val
    290                 295                 300
```

Ser Val Leu Pro Ile Leu His Gln Asp Trp Leu Asn Gly Lys Glu Phe
305                 310                 315                 320

Lys Cys Lys Val Asn Ser Pro Ala Phe Pro Val Pro Ile Glu Lys Thr
            325                 330                 335

Ile Ser Lys Arg Arg Gly Gln Leu Gln Val Pro Gln Val Tyr Thr Met
            340                 345                 350

Pro Pro Pro Lys Glu Gln Leu Thr Gln Ser Gln Val Ser Leu Thr Cys
            355                 360                 365

Met Ile Lys Gly Phe Tyr Pro Glu Asp Ile Asp Val Ala Trp Gln Lys
        370                 375                 380

Asn Gly Gln Pro Glu Gln Ser Phe Lys Asn Thr Pro Pro Val Leu Asp
385                 390                 395                 400

Thr Asp Glu Thr Tyr Phe Leu Tyr Ser Lys Leu Asp Val Lys Lys Asp
                405                 410                 415

Asp Trp Glu Lys Gly Asp Thr Phe Thr Cys Ser Val Val His Glu Ala
            420                 425                 430

Leu His Asn His His Thr Glu Lys Thr Leu Ser Gln Arg Pro Gly Lys
        435                 440                 445

<210> SEQ ID NO 4
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Gln Met Thr Gln Ser Pro Ser Ser Leu Pro Ala Ser Leu Gly
1               5                   10                  15

Asp Arg Val Thr Ile Asn Cys Gln Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Asn Leu Leu Ala Asp Gly Val Pro Ser Arg Phe Ser Gly
    50                  55                  60

Ser Gly Ser Gly Arg Asp Tyr Ser Phe Thr Ile Ser Ser Leu Glu Ser
65                  70                  75                  80

Glu Asp Ile Gly Ser Tyr Tyr Cys Gln Gln Tyr Tyr Asn Tyr Arg Thr
                85                  90                  95

Phe Gly Pro Gly Thr Lys Leu Glu Ile Lys Arg Ala Asp Ala Lys Pro
            100                 105                 110

Thr Val Ser Ile Phe Pro Pro Ser Glu Gln Leu Gly Thr Gly Ser
        115                 120                 125

Ala Thr Leu Val Cys Phe Val Asn Asn Phe Tyr Pro Lys Asp Ile Asn
    130                 135                 140

Val Lys Trp Lys Val Asp Gly Ser Glu Lys Arg Asp Gly Val Leu Gln
145                 150                 155                 160

Ser Val Thr Asp Gln Asp Ser Lys Asp Ser Thr Tyr Ser Leu Ser Ser
                165                 170                 175

Thr Leu Ser Leu Thr Lys Ala Asp Tyr Glu Arg His Asn Leu Tyr Thr
            180                 185                 190

Cys Glu Val Thr His Lys Thr Ser Thr Ala Ala Ile Val Lys Thr Leu
            195                 200                 205

Asn Arg Asn Glu Cys
    210

<210> SEQ ID NO 5
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met His Trp Val Arg Gln Ala Pro Gly Lys Gly Leu Glu Trp Val
        35                  40                  45

Gly Val Ile Asp Thr Lys Ser Phe Asn Tyr Ala Thr Tyr Tyr Ser Asp
    50                  55                  60

Leu Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ala Thr Ile Ala Val Pro Tyr Tyr Phe Asp Tyr Trp Gly
            100                 105                 110

Gln Gly Thr Leu Val Thr Val Ser Ser
        115                 120

<210> SEQ ID NO 6
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Asn Leu Leu Ala Glu Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Asn Tyr Arg Thr
                85                  90                  95

Phe Gly Pro Gly Thr Lys Val Asp Ile Lys
            100                 105

<210> SEQ ID NO 7
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met His Trp Val Arg Gln Ala Pro Gly Lys Gly Leu Glu Trp Val
        35                  40                  45

Gly Val Ile Asp Thr Lys Ser Phe Asn Tyr Ala Thr Tyr Tyr Ser Asp
    50                  55                  60

Leu Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ala Thr Ile Ala Val Pro Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Glu His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380
```

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 8
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Asn Leu Leu Ala Glu Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Tyr Asn Tyr Arg Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 9
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 9

Asp Tyr Phe Met His
1               5

<210> SEQ ID NO 10
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Val Ile Asp Thr Lys Ser Phe Asn Tyr Ala Thr Tyr Tyr Ser Asp Leu
1               5                   10                  15

Val Lys Gly

<210> SEQ ID NO 11
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Thr Ile Ala Val Pro Tyr Tyr Phe Asp Tyr
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Ala Ser Gln Asp Ile Ser Asn Tyr Leu Ser
1               5                   10

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Thr Asn Leu Leu Ala Asp
1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Tyr Thr Asn Leu Leu Ala Glu
1               5
```

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 15

Gln Gln Tyr Tyr Asn Tyr Arg Thr
1               5

<210> SEQ ID NO 16
<211> LENGTH: 140
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Met Asp Ile Leu Cys Ser Thr Leu Leu Leu Thr Val Pro Ser Trp
1               5                   10                  15

Val Leu Ser Gln Val Thr Leu Arg Glu Ser Gly Pro Ala Leu Val Lys
            20                  25                  30

Pro Thr Gln Thr Leu Thr Leu Thr Cys Thr Phe Ser Gly Phe Ser Leu
        35                  40                  45

Ser Thr Ser Gly Met Cys Val Ser Trp Ile Arg Gln Pro Pro Gly Lys
    50                  55                  60

Ala Leu Glu Trp Leu Ala Leu Ile Asp Trp Asp Asp Lys Phe Tyr
65                  70                  75                  80

Ser Thr Ser Leu Lys Thr Arg Leu Thr Ile Ser Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala Arg Met Ser Thr Pro Thr Tyr Tyr Gly Leu Asp
        115                 120                 125

Val Trp Gly Gln Gly Thr Thr Val Thr Val Ser Ser
    130                 135                 140

<210> SEQ ID NO 17
<211> LENGTH: 127
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Ser Trp Leu Ala Trp Tyr Gln Gln Lys Pro Glu Lys Ala Pro
    50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

```
Ser Leu Gln Pro Glu Asp Phe Ala Thr Tyr Tyr Cys Gln Gln Tyr Asn
        100                 105                 110

Ser Tyr Pro Leu Thr Phe Gly Gly Gly Thr Lys Val Glu Ile Lys
        115                 120                 125

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Ser Gly Met Cys Val Ser
1               5

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Ile Asp Trp Asp Asp Asp Lys Phe Tyr Ser Thr Ser Leu Lys Thr
1               5                   10                  15

<210> SEQ ID NO 20
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Ser Thr Pro Thr Tyr Tyr Gly Leu Asp Val
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Ala Ser Gln Gly Ile Ser Ser Trp Leu Ala
1               5                   10

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ala Ala Ser Ser Leu Gln Ser
1               5

<210> SEQ ID NO 23
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Gln Tyr Asn Ser Tyr Pro Leu Thr
1               5

<210> SEQ ID NO 24
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Thr Leu Cys Ser Thr Leu Leu Leu Thr Ile Pro Ser Trp
1               5                   10                  15

Val Leu Ser Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Gly Thr Ser Gly Leu Gly Val Gly Trp Ile Arg Gln Pro Pro Gly Lys
    50                  55                  60

Ala Leu Glu Trp Leu Ala Phe Ile Tyr Trp Asp Asp Lys Arg Tyr
65                  70                  75                  80

Ser Pro Ser Leu Lys Ser Arg Leu Thr Ile Thr Lys Asp Thr Ser Lys
                85                  90                  95

Asn Gln Val Val Leu Thr Met Thr Asn Met Asp Pro Val Asp Thr Ala
            100                 105                 110

Thr Tyr Tyr Cys Ala His Arg Arg Gly Phe Phe Asp Tyr Trp Gly Gln
        115                 120                 125

Gly Thr Leu Val Thr Val Ser Ser
    130                 135

<210> SEQ ID NO 25
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Ser Trp Leu Ala Trp Tyr Gln Gln Lys Pro Glu Lys Ala Pro
    50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95
```

Ser Leu Gln Pro Glu Asp Phe Ala Thr Tyr Tyr Cys Gln Gln Tyr Asn
            100                 105                 110

Ser Tyr Pro Leu Thr Phe Gly Gly Gly Thr Lys Val Glu Ile Lys
        115                 120                 125

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Thr Ser Gly Leu Gly Val Gly
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Phe Ile Tyr Trp Asp Asp Asp Lys Arg Tyr Ser Pro Ser Leu Lys Ser
1               5                   10                  15

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Arg Arg Gly Phe Phe Asp Tyr
1               5

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Ala Ser Gln Gly Ile Ser Ser Trp Leu Ala
1               5                   10

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Ala Ser Ser Leu Gln Ser
1               5

<210> SEQ ID NO 31
<211> LENGTH: 9

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gln Gln Tyr Asn Ser Tyr Pro Leu Thr
1               5

<210> SEQ ID NO 32
<211> LENGTH: 139
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Met Glu Phe Gly Leu Thr Trp Val Phe Leu Val Ala Leu Leu Arg Gly
1               5                   10                  15

Val Gln Cys Gln Val Gln Leu Val Glu Ser Gly Gly Val Val Gln
            20                  25                  30

Pro Gly Met Ser Leu Arg Leu Ser Cys Ala Ala Ser Gly Phe Thr Phe
            35                  40                  45

Ser Thr Tyr Gly Met Gln Trp Val Arg Gln Ala Pro Gly Lys Gly Leu
        50                  55                  60

Glu Trp Val Thr Val Ile Trp His Asp Gly Ser His Lys Asp Tyr Ala
65                  70                  75                  80

Asp Ser Val Lys Gly Arg Phe Thr Ile Ser Arg Asp Asn Ser Lys Asn
                85                  90                  95

Thr Met Tyr Leu Gln Met Asn Ser Leu Arg Ala Glu Asp Thr Ala Val
            100                 105                 110

Tyr Tyr Cys Ala Arg Asp Arg Gln Thr Gly Glu Gly Tyr Phe Asp Phe
        115                 120                 125

Trp Gly Gln Gly Thr Leu Val Thr Val Ser Ser
    130                 135

<210> SEQ ID NO 33
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Ser Trp Leu Ala Trp Tyr Gln Gln Lys Pro Glu Lys Ala Pro
    50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95
```

```
Ser Leu Gln Pro Glu Asp Phe Ala Thr Tyr Tyr Cys Gln Gln Tyr Asn
            100                 105                 110

Ser Tyr Pro Tyr Thr Phe Gly Gln Gly Thr Lys Leu Glu Ile Lys
        115                 120                 125

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Thr Tyr Gly Met Gln
1               5

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Val Ile Trp His Asp Gly Ser His Lys Asp Tyr Ala Asp Ser Val Lys
1               5                   10                  15

Gly

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Asp Arg Gln Thr Gly Glu Gly Tyr Phe Asp Phe
1               5                   10

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Arg Ala Ser Gln Gly Ile Ser Ser Trp Leu Ala
1               5                   10

<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ala Ala Ser Ser Leu Gln Ser
1               5
```

-continued

```
<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Gln Tyr Asn Ser Tyr Pro Tyr Thr
1               5

<210> SEQ ID NO 40
<211> LENGTH: 136
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Met Asp Thr Leu Cys Ser Thr Leu Leu Leu Thr Ile Pro Ser Trp
1               5                   10                  15

Val Leu Ser Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Gly Ser Asn Gly Leu Gly Val Gly Trp Ile Arg Gln Pro Pro Gly Lys
    50                  55                  60

Ala Leu Glu Trp Leu Ala Leu Ile Tyr Trp Asp Asp Asp Lys Arg Tyr
65                  70                  75                  80

Ser Pro Ser Leu Lys Ser Arg Leu Thr Ile Thr Lys Asp Ser Ser Lys
                85                  90                  95

Asn Gln Val Val Leu Thr Met Thr Asn Met Asp Pro Val Asp Thr Ala
            100                 105                 110

Thr Tyr Tyr Cys Ala His Arg Asn Ser Gly Phe Asp Tyr Trp Gly Gln
        115                 120                 125

Gly Ile Leu Val Thr Val Ser Ser
    130                 135

<210> SEQ ID NO 41
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Phe Ser Ser Trp Leu Ala Trp Tyr Gln Gln Lys Pro Glu Lys Ala Pro
    50                  55                  60

Lys Ser Leu Ile Tyr Ala Ala Ser Ser Leu Gln Ser Gly Val Pro Ser
65                  70                  75                  80
```

```
Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Tyr Thr Phe Gly Gln Gly Thr Lys Leu Glu Ile Lys
        115                 120                 125
```

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Ser Asn Gly Leu Gly Val Gly
1               5
```

<210> SEQ ID NO 43
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

```
Leu Ile Tyr Trp Asp Asp Asp Lys Arg Tyr Ser Pro Ser Leu Lys Ser
1               5                   10                  15
```

<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

```
Arg Asn Ser Gly Phe Asp Tyr
1               5
```

<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

```
Arg Ala Ser Gln Gly Phe Ser Ser Trp Leu Ala
1               5                   10
```

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

```
Ala Ala Ser Ser Leu Gln Ser
1               5
```

```
<210> SEQ ID NO 47
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gln Gln Tyr Asn Ser Tyr Pro Tyr Thr
1               5

<210> SEQ ID NO 48
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Met Arg Val Leu Ala Gln Leu Leu Gly Leu Leu Leu Leu Cys Phe Pro
1               5                   10                  15

Gly Ala Arg Cys Asp Ile Gln Met Thr Gln Ser Pro Ser Ser Leu Ser
            20                  25                  30

Ala Ser Val Gly Asp Arg Val Thr Ile Thr Cys Arg Ala Ser Gln Gly
        35                  40                  45

Ile Ser Ser Trp Leu Ala Trp Tyr Gln Gln Lys Pro Glu Lys Ala Pro
    50                  55                  60

Lys Ser Leu Ile Tyr Ala Ala Ser Ser Leu Gln Ser Gly Val Pro Ser
65                  70                  75                  80

Arg Phe Ser Gly Ser Gly Ser Gly Thr Asp Phe Thr Leu Thr Ile Ser
                85                  90                  95

Ser Leu Gln Pro Glu Asp Phe Ala Thr Tyr Tyr Cys Gln Gln Tyr Asn
            100                 105                 110

Ser Tyr Pro Leu Thr Phe Gly Gly Gly Thr Lys Val Glu Ile Lys
        115                 120                 125

<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Arg Ala Ser Gln Gly Ile Ser Ser Trp Leu Ala
1               5                   10

<210> SEQ ID NO 50
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Ala Ser Ser Leu Gln Ser
1               5
```

```
<210> SEQ ID NO 51
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Gln Tyr Asn Ser Tyr Pro Leu Thr
1               5

<210> SEQ ID NO 52
<211> LENGTH: 329
<212> TYPE: PRT
<213> ORGANISM: Homo sapiens

<400> SEQUENCE: 52

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 53
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320
```

```
Gln Lys Ser Leu Ser Leu Ser Pro Gly
                325

<210> SEQ ID NO 54
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Glu His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Phe Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

```
<210> SEQ ID NO 55
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 56
<211> LENGTH: 329
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 56

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 57
<211> LENGTH: 329
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 57

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Asp Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Glu Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 58
<211> LENGTH: 329
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Asp Leu Leu Gly Gly Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 59
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Asp Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser Asp Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 60
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
                100                 105                 110

Pro Ala Pro Glu Leu Leu Gly Asp Asp Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
                195                 200                 205

Lys Ala Leu Pro Arg Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
                275                 280                 285

Leu Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 61
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Glu Gly Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 62
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Asp Asp Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser Asp Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Arg Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 63
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Arg Val Glu Pro Lys Ser Cys Asp Lys Thr His Thr Cys Pro Pro Cys
            100                 105                 110

Pro Ala Pro Asp Leu Leu Gly Asp Asp Ser Val Phe Leu Phe Pro Pro
            115                 120                 125

Lys Pro Lys Asp Thr Leu Met Ile Ser Arg Thr Pro Glu Val Thr Cys
            130                 135                 140

Val Val Val Asp Val Ser Asp Glu Asp Gly Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Arg Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 64
<211> LENGTH: 107
<212> TYPE: PRT
<213> ORGANISM: Homo sapiens

<400> SEQUENCE: 64

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 65
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 65

Met Arg Ala Trp Ile Phe Phe Leu Leu Cys Leu Ala Gly Arg Ala Leu
1               5                   10                  15

Ala

<210> SEQ ID NO 66
<211> LENGTH: 5
<212> TYPE: PRT
<213> ORGANISM: Homo sapiens

<400> SEQUENCE: 66

Val Asp Lys Arg Val
1               5

<210> SEQ ID NO 67
<211> LENGTH: 10
<212> TYPE: PRT
<213> ORGANISM: Homo sapiens

<400> SEQUENCE: 67

Glu Pro Lys Ser Cys Asp Lys Thr His Thr
1               5                   10

<210> SEQ ID NO 68
<211> LENGTH: 5
<212> TYPE: PRT
<213> ORGANISM: Homo sapiens

<400> SEQUENCE: 68

Cys Pro Pro Cys Pro
1               5

<210> SEQ ID NO 69
<211> LENGTH: 7
<212> TYPE: PRT
<213> ORGANISM: Homo sapiens

<400> SEQUENCE: 69

Ala Pro Glu Leu Leu Gly Gly
1               5

<210> SEQ ID NO 70
<211> LENGTH: 5
<212> TYPE: PRT
<213> ORGANISM: Homo sapiens

<400> SEQUENCE: 70

Val Asp Lys Thr Val
1               5

<210> SEQ ID NO 71
<211> LENGTH: 9
<212> TYPE: PRT
<213> ORGANISM: Homo sapiens

<400> SEQUENCE: 71

Cys Cys Val Glu Cys Pro Pro Cys Pro
1               5
```

<210> SEQ ID NO 72
<211> LENGTH: 6
<212> TYPE: PRT
<213> ORGANISM: Homo sapiens

<400> SEQUENCE: 72

Ala Pro Pro Val Ala Gly
1               5

<210> SEQ ID NO 73
<211> LENGTH: 12
<212> TYPE: PRT
<213> ORGANISM: Homo sapiens

<400> SEQUENCE: 73

Glu Leu Lys Thr Pro Leu Gly Asp Thr Thr His Thr
1               5                   10

<210> SEQ ID NO 74
<211> LENGTH: 50
<212> TYPE: PRT
<213> ORGANISM: Homo sapiens

<400> SEQUENCE: 74

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro Glu Pro Lys Ser Cys Asp Thr Pro Pro Pro Cys Pro Arg
        35                  40                  45

Cys Pro
    50

<210> SEQ ID NO 75
<211> LENGTH: 35
<212> TYPE: PRT
<213> ORGANISM: Homo sapiens

<400> SEQUENCE: 75

Cys Pro Arg Cys Pro Glu Pro Lys Ser Cys Asp Thr Pro Pro Pro Cys
1               5                   10                  15

Pro Arg Cys Pro Glu Pro Lys Ser Cys Asp Thr Pro Pro Pro Cys Pro
            20                  25                  30

Arg Cys Pro
        35

<210> SEQ ID NO 76
<211> LENGTH: 20
<212> TYPE: PRT
<213> ORGANISM: Homo sapiens

<400> SEQUENCE: 76

Cys Pro Arg Cys Pro Glu Pro Lys Ser Cys Asp Thr Pro Pro Pro Cys
1               5                   10                  15

Pro Arg Cys Pro
            20

<210> SEQ ID NO 77
<211> LENGTH: 4
<212> TYPE: PRT
<213> ORGANISM: Homo sapiens

```
<400> SEQUENCE: 77

Glu Pro Lys Ser
1

<210> SEQ ID NO 78
<211> LENGTH: 41
<212> TYPE: PRT
<213> ORGANISM: Homo sapiens

<400> SEQUENCE: 78

Cys Asp Thr Pro Pro Pro Cys Pro Arg Cys Pro Glu Pro Lys Ser Cys
1               5                   10                  15

Asp Thr Pro Pro Pro Cys Pro Arg Cys Pro Glu Pro Lys Ser Cys Asp
            20                  25                  30

Thr Pro Pro Pro Cys Pro Arg Cys Pro
        35                  40

<210> SEQ ID NO 79
<211> LENGTH: 11
<212> TYPE: PRT
<213> ORGANISM: Homo sapiens

<400> SEQUENCE: 79

Cys Asp Thr Pro Pro Pro Cys Pro Arg Cys Pro
1               5                   10

<210> SEQ ID NO 80
<211> LENGTH: 7
<212> TYPE: PRT
<213> ORGANISM: Homo sapiens

<400> SEQUENCE: 80

Glu Ser Lys Tyr Gly Pro Pro
1               5

<210> SEQ ID NO 81
<211> LENGTH: 5
<212> TYPE: PRT
<213> ORGANISM: Homo sapiens

<400> SEQUENCE: 81

Cys Pro Ser Cys Pro
1               5

<210> SEQ ID NO 82
<211> LENGTH: 7
<212> TYPE: PRT
<213> ORGANISM: Homo sapiens

<400> SEQUENCE: 82

Ala Pro Glu Phe Leu Gly Gly
1               5

<210> SEQ ID NO 83
<211> LENGTH: 98
<212> TYPE: PRT
<213> ORGANISM: Homo sapiens

<400> SEQUENCE: 83

Ala Ser Thr Lys Gly Pro Ser Val Phe Pro Leu Ala Pro Ser Ser Lys
1               5                   10                  15
```

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 84
<211> LENGTH: 98
<212> TYPE: PRT
<213> ORGANISM: Homo sapiens

<400> SEQUENCE: 84

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 85
<211> LENGTH: 103
<212> TYPE: PRT
<213> ORGANISM: Homo sapiens

<400> SEQUENCE: 85

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
            35                  40                  45

Asn Ala Lys Thr Lys Pro Arg Glu Glu Gln Tyr Asn Ser Thr Tyr Arg
        50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys
            100

<210> SEQ ID NO 86
<211> LENGTH: 103
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 86

```
Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ser Ser Ile Glu
                85                  90                  95

Lys Thr Ile Ser Lys Ala Lys
            100
```

<210> SEQ ID NO 87
<211> LENGTH: 106
<212> TYPE: PRT
<213> ORGANISM: Homo sapiens

<400> SEQUENCE: 87

```
Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105
```

<210> SEQ ID NO 88
<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60
```

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Cys Cys Val Glu Cys Pro Pro Cys Pro Ala Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 89
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 90
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95
```

```
Lys Val Glu Arg Lys Cys Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Arg Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 91
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Ser Cys Val Glu Cys Pro Pro Cys Pro Ala Pro
                100                 105                 110
```

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ser Ser Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 92
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

```
Thr Leu Met Ile Ser Arg Thr Pro Glu Val Thr Cys Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 93
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
            165                 170                 175

Ser Thr Tyr Arg Val Val Ser Val Leu Thr Val Leu His Gln Asp Trp
        180                 185                 190

Leu Asn Gly Lys Glu Tyr Lys Cys Lys Val Ser Asn Lys Ala Leu Pro
    195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 94
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160
```

Val Glu Val His Asn Ala Lys Thr Lys Pro Arg Glu Glu Gln Tyr Asn
            165                 170                 175

Ser Thr Tyr Arg Val Val Ser Val Leu Thr Val Leu His Gln Asp Trp
        180                 185                 190

Leu Asn Gly Lys Glu Tyr Lys Cys Lys Val Ser Asn Lys Ala Leu Pro
    195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 95
<211> LENGTH: 325
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly
                325

<210> SEQ ID NO 96
<211> LENGTH: 18
<212> TYPE: PRT
<213> ORGANISM: Homo sapiens

<400> SEQUENCE: 96

Glu Arg Lys Cys Cys Val Glu Cys Pro Pro Cys Pro Ala Pro Pro Val
1               5                   10                  15

Ala Gly

<210> SEQ ID NO 97
<211> LENGTH: 18
<212> TYPE: PRT
<213> ORGANISM: Homo sapiens

<400> SEQUENCE: 97

Glu Arg Lys Ser Cys Val Glu Cys Pro Pro Cys Pro Ala Pro Pro Val
1               5                   10                  15

Ala Gly

<210> SEQ ID NO 98
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Glu Arg Lys Cys Cys Val Glu Cys Pro Pro Cys Pro Ala Pro Glu Leu
1               5                   10                  15

Leu Gly Gly

<210> SEQ ID NO 99
<211> LENGTH: 19
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 99

Glu Arg Lys Ser Cys Val Glu Cys Pro Pro Cys Pro Ala Pro Glu Leu
1               5                   10                  15

Leu Gly Gly

<210> SEQ ID NO 100
<211> LENGTH: 22
<212> TYPE: PRT
<213> ORGANISM: Homo sapiens

<400> SEQUENCE: 100

Glu Pro Lys Ser Cys Asp Lys Thr His Thr Cys Pro Pro Cys Pro Ala
1               5                   10                  15

Pro Glu Leu Leu Gly Gly
            20

<210> SEQ ID NO 101
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Glu Pro Lys Ser Cys Asp Lys Thr His Thr Cys Pro Pro Cys Pro Ala
1               5                   10                  15

Pro Glu Ala Glu Gly Ala
            20

<210> SEQ ID NO 102
<211> LENGTH: 103
<212> TYPE: PRT
<213> ORGANISM: Homo sapiens

<400> SEQUENCE: 102

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Gln Phe Asn Trp Tyr Val Asp Gly Val Glu Val His
        35                  40                  45

Asn Ala Lys Thr Lys Pro Arg Glu Glu Gln Phe Asn Ser Thr Phe Arg
    50                  55                  60

Val Val Ser Val Leu Thr Val Val His Gln Asp Trp Leu Asn Gly Lys
65                  70                  75                  80

Glu Tyr Lys Cys Lys Val Ser Asn Lys Gly Leu Pro Ala Pro Ile Glu
                85                  90                  95

Lys Thr Ile Ser Lys Thr Lys
            100

<210> SEQ ID NO 103
<211> LENGTH: 107
<212> TYPE: PRT
<213> ORGANISM: Homo sapiens

<400> SEQUENCE: 103

Gly Gln Pro Arg Glu Pro Gln Val Tyr Thr Leu Pro Pro Ser Arg Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Met Leu Asp Ser Asp Gly Ser Phe
50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly Lys
            100                 105

<210> SEQ ID NO 104
<211> LENGTH: 330
<212> TYPE: PRT
<213> ORGANISM: Homo sapiens

<400> SEQUENCE: 104

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 105
<211> LENGTH: 326
<212> TYPE: PRT
<213> ORGANISM: Homo sapiens

<400> SEQUENCE: 105

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285
```

```
Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 106
<211> LENGTH: 327
<212> TYPE: PRT
<213> ORGANISM: Homo sapiens

<400> SEQUENCE: 106

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300
```

```
Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 107
<211> LENGTH: 326
<212> TYPE: PRT
<213> ORGANISM: Homo sapiens

<400> SEQUENCE: 107

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 108
<211> LENGTH: 326
<212> TYPE: PRT
<213> ORGANISM: Homo sapiens

<400> SEQUENCE: 108

```
Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 109
<211> LENGTH: 330
<212> TYPE: PRT
<213> ORGANISM: Homo sapiens

<400> SEQUENCE: 109

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Glu Gly Ala Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ser Ser Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 110
<211> LENGTH: 326
<212> TYPE: PRT
<213> ORGANISM: Homo sapiens

<400> SEQUENCE: 110

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Pro Val Ala Gly Pro Ser Val Phe Leu Phe Pro Pro Lys Pro Lys Asp
                115                 120                 125

Thr Leu Met Ile Ser Arg Thr Pro Glu Val Thr Cys Val Val Val Asp
            130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ser Ser Ile Glu Lys Thr Ile Ser Lys Ala Lys Gly Gln Pro Arg Glu
            210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
                260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 111
<211> LENGTH: 327
<212> TYPE: PRT
<213> ORGANISM: Homo sapiens

<400> SEQUENCE: 111

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Cys Pro Pro Cys Pro Ala Pro
            100                 105                 110

Glu Leu Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 112
<211> LENGTH: 329
<212> TYPE: PRT
<213> ORGANISM: Homo sapiens

<400> SEQUENCE: 112

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Thr His Thr Cys Pro Pro Cys
100                 105                 110

Pro Ala Pro Pro Val Ala Gly Pro Ser Val Phe Leu Phe Pro Pro Lys
            115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
            165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
            195                 200                 205

Gly Leu Pro Ala Pro Ile Glu Lys Thr Ile Ser Lys Thr Lys Gly Gln
210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
            245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 113
<211> LENGTH: 329
<212> TYPE: PRT
<213> ORGANISM: Homo sapiens

<400> SEQUENCE: 113

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Ser Cys Val Glu Gly Gly Gly Cys Pro Pro Cys
            100                 105                 110

Pro Ala Pro Pro Val Ala Gly Pro Ser Val Phe Leu Phe Pro Pro Lys
            115                 120                 125

```
Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 114
<211> LENGTH: 326
<212> TYPE: PRT
<213> ORGANISM: Homo sapiens

<400> SEQUENCE: 114

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160
```

Val Glu Val His Asn Ala Lys Thr Lys Pro Arg Glu Gln Tyr Asn
            165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
            195                 200                 205

Ser Ser Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
            245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
            325

<210> SEQ ID NO 115
<211> LENGTH: 327
<212> TYPE: PRT
<213> ORGANISM: Homo sapiens

<400> SEQUENCE: 115

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

```
Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 116
<211> LENGTH: 326
<212> TYPE: PRT
<213> ORGANISM: Homo sapiens

<400> SEQUENCE: 116

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 117
<211> LENGTH: 329
<212> TYPE: PRT
<213> ORGANISM: Homo sapiens

<400> SEQUENCE: 117

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255
```

Ser Asp Ile Ala Val Glu Trp Glu Ser Asn Gly Gln Pro Glu Asn Asn
        260                 265                 270

Tyr Lys Thr Thr Pro Pro Met Leu Asp Ser Asp Gly Ser Phe Phe Leu
            275                 280                 285

Tyr Ser Lys Leu Thr Val Asp Lys Ser Arg Trp Gln Gln Gly Asn Val
        290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 118
<211> LENGTH: 327
<212> TYPE: PRT
<213> ORGANISM: Homo sapiens

<400> SEQUENCE: 118

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

```
Lys Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 119
<211> LENGTH: 326
<212> TYPE: PRT
<213> ORGANISM: Homo sapiens

<400> SEQUENCE: 119

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Gly Lys
                325

<210> SEQ ID NO 120
<211> LENGTH: 330
<212> TYPE: PRT
<213> ORGANISM: Homo sapiens

<400> SEQUENCE: 120

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 121
<211> LENGTH: 330
<212> TYPE: PRT
<213> ORGANISM: Homo sapiens

<400> SEQUENCE: 121

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 122
<211> LENGTH: 326
<212> TYPE: PRT
<213> ORGANISM: Homo sapiens
```

<400> SEQUENCE: 122

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65              70                  75                  80

Tyr Ile Cys Asn Val Asn His Lys Pro Ser Asn Thr Lys Val Asp Lys
                85                  90                  95

Arg Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 123
<211> LENGTH: 330
<212> TYPE: PRT
<213> ORGANISM: Homo sapiens

<400> SEQUENCE: 123

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
65                   70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 124
<211> LENGTH: 330
<212> TYPE: PRT
<213> ORGANISM: Homo sapiens

<400> SEQUENCE: 124

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 125
<211> LENGTH: 330
<212> TYPE: PRT
<213> ORGANISM: Homo sapiens

<400> SEQUENCE: 125

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Ile Cys Asn Val Asn His Lys Pro Ser Asn Thr Lys Val Asp Lys
                85                  90                  95

```
Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 126
<211> LENGTH: 330
<212> TYPE: PRT
<213> ORGANISM: Homo sapiens

<400> SEQUENCE: 126

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125
```

```
Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 127
<211> LENGTH: 329
<212> TYPE: PRT
<213> ORGANISM: Homo sapiens

<400> SEQUENCE: 127

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Ile Cys Asn Val Asn His Lys Pro Ser Asn Thr Lys Val Asp Lys
                85                  90                  95

Arg Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160
```

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly
            325

<210> SEQ ID NO 128
<211> LENGTH: 326
<212> TYPE: PRT
<213> ORGANISM: Homo sapiens

<400> SEQUENCE: 128

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
            130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
            180                 185                 190
```

```
Leu Asn Gly Lys Glu Tyr Lys Cys Lys Val Ser Asn Lys Gly Leu Pro
            195                 200                 205

Ala Pro Ile Glu Lys Thr Ile Ser Lys Thr Lys Gly Gln Pro Arg Glu
        210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 129
<211> LENGTH: 326
<212> TYPE: PRT
<213> ORGANISM: Homo sapiens

<400> SEQUENCE: 129

Ala Ser Thr Lys Gly Pro Ser Val Phe Pro Leu Ala Pro Cys Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
        210                 215                 220
```

```
Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 130
<211> LENGTH: 326
<212> TYPE: PRT
<213> ORGANISM: Homo sapiens

<400> SEQUENCE: 130

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
                100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255
```

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
            290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 131
<211> LENGTH: 326
<212> TYPE: PRT
<213> ORGANISM: Homo sapiens

<400> SEQUENCE: 131

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

```
Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 132
<211> LENGTH: 326
<212> TYPE: PRT
<213> ORGANISM: Homo sapiens

<400> SEQUENCE: 132

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Thr Cys Asn Val Asp His Lys Pro Ser Asn Thr Lys Val Asp Lys
                85                  90                  95

Thr Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300
```

```
Ser Val Met His Glu Ala Leu His Asn His Tyr Thr Gln Lys Ser Leu
305                 310                 315                 320

Ser Leu Ser Pro Gly Lys
                325

<210> SEQ ID NO 133
<211> LENGTH: 330
<212> TYPE: PRT
<213> ORGANISM: Homo sapiens

<400> SEQUENCE: 133

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
                165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
        195                 200                 205

Lys Gly Leu Pro Ala Pro Ile Glu Lys Thr Ile Ser Lys Thr Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 134
<211> LENGTH: 329
<212> TYPE: PRT
<213> ORGANISM: Homo sapiens

<400> SEQUENCE: 134

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 135
<211> LENGTH: 326
<212> TYPE: PRT
<213> ORGANISM: Homo sapiens
```

<400> SEQUENCE: 135

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 136
<211> LENGTH: 326
<212> TYPE: PRT
<213> ORGANISM: Homo sapiens

<400> SEQUENCE: 136

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
                20                  25                  30

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

Tyr Thr Cys Asn Val Asp His Lys Pro Ser Asn Thr Lys Val Asp Lys
                 85                  90                  95

Thr Val Glu Arg Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 137
<211> LENGTH: 326
<212> TYPE: PRT
<213> ORGANISM: Homo sapiens

<400> SEQUENCE: 137

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
 50                  55                  60
```

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
    210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Pro Gly
                325

<210> SEQ ID NO 138
<211> LENGTH: 327
<212> TYPE: PRT
<213> ORGANISM: Homo sapiens

<400> SEQUENCE: 138

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Val Glu Cys Pro Pro Cys Pro Ala Pro
            100                 105                 110

Glu Leu Leu Gly Gly Pro Ser Val Phe Leu Phe Pro Lys Pro Lys
            115                 120                 125

Asp Thr Leu Met Ile Ser Arg Thr Pro Glu Val Thr Cys Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
            195                 200                 205

Pro Ala Pro Ile Glu Lys Thr Ile Ser Lys Ala Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
            275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 139
<211> LENGTH: 326
<212> TYPE: PRT
<213> ORGANISM: Homo sapiens

<400> SEQUENCE: 139

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

```
Thr Leu Met Ile Ser Arg Thr Pro Glu Val Thr Cys Val Val Asp
    130                 135                 140

Val Ser His Glu Asp Pro Glu Val Lys Phe Asn Trp Tyr Val Asp Gly
145                 150                 155                 160

Val Glu Val His Asn Ala Lys Thr Lys Pro Arg Glu Glu Gln Tyr Asn
                165                 170                 175

Ser Thr Tyr Arg Val Val Ser Val Leu Thr Val Leu His Gln Asp Trp
            180                 185                 190

Leu Asn Gly Lys Glu Tyr Lys Cys Lys Val Ser Asn Lys Ala Leu Pro
        195                 200                 205

Ala Pro Ile Glu Lys Thr Ile Ser Lys Ala Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Val Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 140
<211> LENGTH: 330
<212> TYPE: PRT
<213> ORGANISM: Homo sapiens

<400> SEQUENCE: 140

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Gln Phe Asn Trp
145                 150                 155                 160
```

Tyr Val Asp Gly Val Glu Val His Asn Ala Lys Thr Lys Pro Arg Glu
            165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
            195                 200                 205

Lys Gly Leu Pro Ala Pro Ile Glu Lys Thr Ile Ser Lys Thr Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 141
<211> LENGTH: 330
<212> TYPE: PRT
<213> ORGANISM: Homo sapiens

<400> SEQUENCE: 141

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
            85                  90                  95

Thr Val Glu Arg Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Gln Phe Asn Trp
145                 150                 155                 160

Tyr Val Asp Gly Val Glu Val His Asn Ala Lys Thr Lys Pro Arg Glu
            165                 170                 175

Glu Gln Phe Asn Ser Thr Phe Arg Val Val Ser Val Leu Thr Val Val
            180                 185                 190

His Gln Asp Trp Leu Asn Gly Lys Glu Tyr Lys Cys Lys Val Ser Asn
            195                 200                 205

Lys Gly Leu Pro Ala Pro Ile Glu Lys Thr Ile Ser Lys Thr Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Met Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 142
<211> LENGTH: 327
<212> TYPE: PRT
<213> ORGANISM: Homo sapiens

<400> SEQUENCE: 142

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Val Glu Cys Pro Pro Cys Pro Ala Pro
            100                 105                 110

Glu Leu Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser His Glu Asp Pro Glu Val Lys Phe Asn Trp Tyr Val Asp
145                 150                 155                 160

Gly Val Glu Val His Asn Ala Lys Thr Lys Pro Arg Glu Glu Gln Tyr
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Ala Leu
        195                 200                 205

Pro Ala Pro Ile Glu Lys Thr Ile Ser Lys Ala Lys Gly Gln Pro Arg
210                 215                 220

-continued

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
            325

<210> SEQ ID NO 143
<211> LENGTH: 328
<212> TYPE: PRT
<213> ORGANISM: Homo sapiens

<400> SEQUENCE: 143

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

```
Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
            275                 280                 285

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly
                325

<210> SEQ ID NO 144
<211> LENGTH: 329
<212> TYPE: PRT
<213> ORGANISM: Homo sapiens

<400> SEQUENCE: 144

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
            275                 280                 285
```

Tyr Ser Lys Leu Thr Val Asp Lys Ser Arg Trp Gln Gln Gly Asn Val
            290                 295                 300

Phe Ser Cys Ser Val Met His Glu Ala Leu His Asn His Tyr Thr Gln
305                 310                 315                 320

Lys Ser Leu Ser Leu Ser Pro Gly Lys
            325

<210> SEQ ID NO 145
<211> LENGTH: 323
<212> TYPE: PRT
<213> ORGANISM: Homo sapiens

<400> SEQUENCE: 145

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Cys Pro Pro Cys Pro Ala Pro Glu Leu Leu Gly
            100                 105                 110

Gly Pro Ser Val Phe Leu Phe Pro Pro Lys Pro Lys Asp Thr Leu Met
        115                 120                 125

Ile Ser Arg Thr Pro Glu Val Thr Cys Val Val Val Asp Val Ser His
130                 135                 140

Glu Asp Pro Glu Val Lys Phe Asn Trp Tyr Val Asp Gly Val Glu Val
145                 150                 155                 160

His Asn Ala Lys Thr Lys Pro Arg Glu Glu Gln Tyr Asn Ser Thr Tyr
                165                 170                 175

Arg Val Val Ser Val Leu Thr Val Leu His Gln Asp Trp Leu Asn Gly
            180                 185                 190

Lys Glu Tyr Lys Cys Lys Val Ser Asn Lys Ala Leu Pro Ala Pro Ile
        195                 200                 205

Glu Lys Thr Ile Ser Lys Ala Lys Gly Gln Pro Arg Glu Pro Gln Val
210                 215                 220

Tyr Thr Leu Pro Pro Ser Arg Glu Glu Met Thr Lys Asn Gln Val Ser
225                 230                 235                 240

Leu Thr Cys Leu Val Lys Gly Phe Tyr Pro Ser Asp Ile Ala Val Glu
                245                 250                 255

Trp Glu Ser Asn Gly Gln Pro Glu Asn Asn Tyr Lys Thr Thr Pro Pro
            260                 265                 270

Val Leu Asp Ser Asp Gly Ser Phe Phe Leu Tyr Ser Lys Leu Thr Val
        275                 280                 285

Asp Lys Ser Arg Trp Gln Gln Gly Asn Val Phe Ser Cys Ser Val Met
290                 295                 300

His Glu Ala Leu His Asn His Tyr Thr Gln Lys Ser Leu Ser Leu Ser
305                 310                 315                 320

Pro Gly Lys

<210> SEQ ID NO 146
<211> LENGTH: 322
<212> TYPE: PRT
<213> ORGANISM: Homo sapiens

<400> SEQUENCE: 146

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Pro Cys Pro Ala Pro Pro Val Ala Gly
            100                 105                 110

Pro Ser Val Phe Leu Phe Pro Pro Lys Pro Lys Asp Thr Leu Met Ile
        115                 120                 125

Ser Arg Thr Pro Glu Val Thr Cys Val Val Val Asp Val Ser His Glu
    130                 135                 140

Asp Pro Glu Val Gln Phe Asn Trp Tyr Val Asp Gly Val Glu Val His
145                 150                 155                 160

Asn Ala Lys Thr Lys Pro Arg Glu Glu Gln Phe Asn Ser Thr Phe Arg
                165                 170                 175

Val Val Ser Val Leu Thr Val Val His Gln Asp Trp Leu Asn Gly Lys
            180                 185                 190

Glu Tyr Lys Cys Lys Val Ser Asn Lys Gly Leu Pro Ala Pro Ile Glu
        195                 200                 205

Lys Thr Ile Ser Lys Thr Lys Gly Gln Pro Arg Glu Pro Gln Val Tyr
    210                 215                 220

Thr Leu Pro Pro Ser Arg Glu Glu Met Thr Lys Asn Gln Val Ser Leu
225                 230                 235                 240

Thr Cys Leu Val Lys Gly Phe Tyr Pro Ser Asp Ile Ala Val Glu Trp
                245                 250                 255

Glu Ser Asn Gly Gln Pro Glu Asn Asn Tyr Lys Thr Thr Pro Pro Met
            260                 265                 270

Leu Asp Ser Asp Gly Ser Phe Phe Leu Tyr Ser Lys Leu Thr Val Asp
        275                 280                 285

Lys Ser Arg Trp Gln Gln Gly Asn Val Phe Ser Cys Ser Val Met His
    290                 295                 300

Glu Ala Leu His Asn His Tyr Thr Gln Lys Ser Leu Ser Leu Ser Pro
305                 310                 315                 320

Gly Lys
```

<210> SEQ ID NO 147
<211> LENGTH: 322
<212> TYPE: PRT
<213> ORGANISM: Homo sapiens

<400> SEQUENCE: 147

Ala Ser Thr Lys Gly Pro Ser Val Phe Pro Leu Ala Pro Ser Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Pro Pro Cys Pro Ala Pro Val Ala Gly
            100                 105                 110

Pro Ser Val Phe Leu Phe Pro Pro Lys Pro Lys Asp Thr Leu Met Ile
            115                 120                 125

Ser Arg Thr Pro Glu Val Thr Cys Val Val Asp Val Ser His Glu
    130                 135                 140

Asp Pro Glu Val Gln Phe Asn Trp Tyr Val Asp Gly Val Glu Val His
145                 150                 155                 160

Asn Ala Lys Thr Lys Pro Arg Glu Glu Gln Phe Asn Ser Thr Phe Arg
                165                 170                 175

Val Val Ser Val Leu Thr Val Val His Gln Asp Trp Leu Asn Gly Lys
            180                 185                 190

Glu Tyr Lys Cys Lys Val Ser Asn Lys Gly Leu Pro Ala Pro Ile Glu
        195                 200                 205

Lys Thr Ile Ser Lys Thr Lys Gly Gln Pro Arg Glu Pro Gln Val Tyr
    210                 215                 220

Thr Leu Pro Pro Ser Arg Glu Glu Met Thr Lys Asn Gln Val Ser Leu
225                 230                 235                 240

Thr Cys Leu Val Lys Gly Phe Tyr Pro Ser Asp Ile Ala Val Glu Trp
                245                 250                 255

Glu Ser Asn Gly Gln Pro Glu Asn Asn Tyr Lys Thr Thr Pro Pro Met
            260                 265                 270

Leu Asp Ser Asp Gly Ser Phe Phe Leu Tyr Ser Lys Leu Thr Val Asp
        275                 280                 285

Lys Ser Arg Trp Gln Gln Gly Asn Val Phe Ser Cys Ser Val Met His
    290                 295                 300

Glu Ala Leu His Asn His Tyr Thr Gln Lys Ser Leu Ser Leu Ser Pro
305                 310                 315                 320

Gly Lys

<210> SEQ ID NO 148
<211> LENGTH: 328
<212> TYPE: PRT
<213> ORGANISM: Homo sapiens

<400> SEQUENCE: 148

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Pro Ser Val Phe Leu Phe Pro Pro Lys
            115                 120                 125

Pro Lys Asp Thr Leu Met Ile Ser Arg Thr Pro Glu Val Thr Cys Val
            130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
            195                 200                 205

Ala Leu Pro Ala Pro Ile Glu Lys Thr Ile Ser Lys Ala Lys Gly Gln
            210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
            275                 280                 285

Tyr Ser Lys Leu Thr Val Asp Lys Ser Arg Trp Gln Gln Gly Asn Val
290                 295                 300

Phe Ser Cys Ser Val Met His Glu Ala Leu His Asn His Tyr Thr Gln
305                 310                 315                 320

Lys Ser Leu Ser Leu Ser Pro Gly
            325

<210> SEQ ID NO 149
<211> LENGTH: 327
<212> TYPE: PRT
<213> ORGANISM: Homo sapiens

<400> SEQUENCE: 149

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Asn Phe Gly Thr Gln Thr
 65                  70                  75                  80

```
Tyr Thr Cys Asn Val Asp His Lys Pro Ser Asn Thr Lys Val Asp Lys
                85                  90                  95

Thr Val Glu Arg Lys Ser Cys Val Glu Cys Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser His Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Phe Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ala Pro Ile Glu Lys Thr Ile Ser Lys Thr Lys Gly Gln Pro Arg
210                 215                 220

Glu Pro Gln Val Tyr Thr Leu Pro Pro Ser Arg Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Met Leu Asp Ser Asp Gly Ser Phe Phe Leu Tyr Ser
        275                 280                 285

Lys Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Pro Gly Lys
                325

<210> SEQ ID NO 150
<211> LENGTH: 326
<212> TYPE: PRT
<213> ORGANISM: Homo sapiens

<400> SEQUENCE: 150

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Ser Val Glu Cys Pro Pro Cys Pro Ala Pro
            100                 105                 110
```

```
Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 151
<211> LENGTH: 326
<212> TYPE: PRT
<213> ORGANISM: Homo sapiens

<400> SEQUENCE: 151

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Ser Ser Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140
```

```
Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
            165                 170                 175

Ser Thr Phe Arg Val Val Ser Val Leu Thr Val Val His Gln Asp Trp
        180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 152
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Glu Arg Lys Cys Ser Val Glu Cys Pro Pro Cys Pro Ala Pro Pro Val
1               5                   10                  15

Ala Gly

<210> SEQ ID NO 153
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

Glu Arg Lys Cys Ser Val Glu Cys Pro Pro Cys Pro Ala Pro Glu Leu
1               5                   10                  15

Leu Gly Gly

<210> SEQ ID NO 154
<211> LENGTH: 14
<212> TYPE: PRT
<213> ORGANISM: Homo sapiens

<400> SEQUENCE: 154

Glu Arg Lys Cys Cys Val Glu Cys Pro Pro Cys Pro Ala Pro
1               5                   10
```

```
<210> SEQ ID NO 155
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Glu Arg Lys Ser Cys Val Glu Cys Pro Pro Cys Pro Ala Pro
1               5                   10

<210> SEQ ID NO 156
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Glu Arg Lys Cys Ser Val Glu Cys Pro Pro Cys Pro Ala Pro
1               5                   10

<210> SEQ ID NO 157
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 157

Glu Arg Lys Xaa Cys Val Glu Cys Pro Pro Cys Pro Ala Pro
1               5                   10

<210> SEQ ID NO 158
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 158

Glu Arg Lys Cys Xaa Val Glu Cys Pro Pro Cys Pro Ala Pro
1               5                   10

<210> SEQ ID NO 159
<211> LENGTH: 116
<212> TYPE: PRT
<213> ORGANISM: Homo sapiens

<400> SEQUENCE: 159

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
 50                  55                  60
Leu Ser Ser Val Val Thr Val Pro Ser Ser Asn Phe Gly Thr Gln Thr
 65                  70                  75                  80
Tyr Thr Cys Asn Val Asp His Lys Pro Ser Asn Thr Lys Val Asp Lys
                 85                  90                  95
Thr Val Glu Arg Lys Cys Cys Val Glu Cys Pro Pro Cys Pro Ala Pro
            100                 105                 110
Pro Val Ala Gly
        115

<210> SEQ ID NO 160
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 160

Glu Arg Lys Xaa Cys Val Glu Cys Pro Pro Cys Pro Ala Pro Val
1               5                   10                  15
Ala Gly

<210> SEQ ID NO 161
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 161

Glu Arg Lys Cys Xaa Val Glu Cys Pro Pro Cys Pro Ala Pro Val
1               5                   10                  15
Ala Gly

<210> SEQ ID NO 162
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid

<400> SEQUENCE: 162

Glu Arg Lys Xaa Cys Val Glu Cys Pro Pro Cys Pro Ala Pro Glu Leu
1               5                   10                  15
Leu Gly Gly
```

```
<210> SEQ ID NO 163
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 163

Glu Arg Lys Cys Xaa Val Glu Cys Pro Pro Cys Pro Ala Pro Glu Leu
1               5                   10                  15

Leu Gly Gly

<210> SEQ ID NO 164
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Glu Arg Lys Cys Cys Val Glu Cys Pro Pro Cys Pro Ala Pro Glu Leu
1               5                   10                  15

Leu Gly

<210> SEQ ID NO 165
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165

Glu Arg Lys Ser Cys Val Glu Cys Pro Pro Cys Pro Ala Pro Glu Leu
1               5                   10                  15

Leu Gly

<210> SEQ ID NO 166
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Glu Arg Lys Cys Ser Val Glu Cys Pro Pro Cys Pro Ala Pro Glu Leu
1               5                   10                  15

Leu Gly

<210> SEQ ID NO 167
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any amino acid
```

```
<400> SEQUENCE: 167

Glu Arg Lys Xaa Cys Val Glu Cys Pro Pro Cys Pro Ala Pro Glu Leu
1               5                   10                  15

Leu Gly

<210> SEQ ID NO 168
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Any amino acid

<400> SEQUENCE: 168

Glu Arg Lys Cys Xaa Val Glu Cys Pro Pro Cys Pro Ala Pro Glu Leu
1               5                   10                  15

Leu Gly

<210> SEQ ID NO 169
<211> LENGTH: 4
<212> TYPE: PRT
<213> ORGANISM: Homo sapiens

<400> SEQUENCE: 169

Pro Val Ala Gly
1

<210> SEQ ID NO 170
<211> LENGTH: 7
<212> TYPE: PRT
<213> ORGANISM: Homo sapiens

<400> SEQUENCE: 170

Ser Cys Asp Lys Thr His Thr
1               5

<210> SEQ ID NO 171
<211> LENGTH: 4
<212> TYPE: PRT
<213> ORGANISM: Homo sapiens

<400> SEQUENCE: 171

Glu Leu Leu Gly
1

<210> SEQ ID NO 172
<211> LENGTH: 5
<212> TYPE: PRT
<213> ORGANISM: Homo sapiens

<400> SEQUENCE: 172

Glu Leu Leu Gly Gly
1               5

<210> SEQ ID NO 173
<211> LENGTH: 114
<212> TYPE: PRT
<213> ORGANISM: Homo sapiens
```

<400> SEQUENCE: 173

Glu Ile Asn Gly Ser Ala Asn Tyr Glu Met Phe Ile Phe His Asn Gly
1               5                   10                  15

Gly Val Gln Ile Leu Cys Lys Tyr Pro Asp Ile Val Gln Gln Phe Lys
            20                  25                  30

Met Gln Leu Leu Lys Gly Gly Gln Ile Leu Cys Asp Leu Thr Lys Thr
        35                  40                  45

Lys Gly Ser Gly Asn Thr Val Ser Ile Lys Ser Leu Lys Phe Cys His
50                  55                  60

Ser Gln Leu Ser Asn Asn Ser Val Ser Phe Phe Leu Tyr Asn Leu Asp
65                  70                  75                  80

His Ser His Ala Asn Tyr Tyr Phe Cys Asn Leu Ser Ile Phe Asp Pro
                85                  90                  95

Pro Pro Phe Lys Val Thr Leu Thr Gly Gly Tyr Leu His Ile Tyr Glu
            100                 105                 110

Ser Gln

<210> SEQ ID NO 174
<211> LENGTH: 417
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 174
atggagtttg ggctgacctg ggttttcctc gttgctcttt taagaggtgt ccagtgtcag      60
gtgcagctgg tggagtctgg gggaggcgtg gtccagcctg gcatgtccct gagactctcc     120
tgtgcagcgt ctggattcac cttcagtacc tatggcatgc agtgggtccg ccaggctcca     180
ggcaaggggc tggagtgggt gacagttata tggcatgatg aagtcataaa agactatgca     240
gactccgtga agggccgatt caccatctcc agagacaatt ccaagaacac gatgtatctg     300
caaatgaaca gcctgagagc cgaggacacg gctgtgtatt actgtgcgag agatcggcaa     360
actggggagg gctactttga cttctggggc caggaacccc tggtcaccgt ctcctca       417

<210> SEQ ID NO 175
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 175
atgagggtcc tcgctcagct cctggggctc ctgctgctct gtttcccagg tgccagatgt      60
gacatccaga tgacccagtc tccatcctca ctgtctgcat ctgtaggaga cagagtcacc     120
atcacttgtc gggcgagtca gggtattagc agctggttag cctggtatca gcagaaacca     180
gagaaagccc ctaagtccct gatctatgct gcatccagtt tgcaaagtgg ggtcccatca     240
aggttcagcg gcagtggatc tgggacagat ttcactctca ccatcagcag cctgcagcct     300
gaagattttg caacttatta ctgccaacag tataatagtt acccgtacac ttttggccag     360
gggaccaagc tggagatcaa a                                                381

<210> SEQ ID NO 176
<211> LENGTH: 420

```
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 176
atggacatac tttgttccac gctcctgcta ctgactgtcc cgtcctgggt cttatcccag    60
gtcaccttga gggagtctgg tcctgcgctg gtgaaaccca cacagaccct cacactgacc   120
tgcaccttct ctgggttctc actcagcact agtggaatgt gtgtgagctg gatccgtcag   180
ccccagggaa ggccctgga gtggcttgca ctcattgatt gggatgatga taaattctac    240
agcacatctc tgaagaccag gctcaccatc tccaaggaca cctccaaaaa ccaggtggtc   300
cttacaatga ccaacatgga ccctgtggac acagccacgt attactgtgc acggatgtca   360
acacctacct actacggttt ggacgtctgg ggccaaggga ccacggtcac cgtctcctca   420

<210> SEQ ID NO 177
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 177
atgagggtcc tcgctcagct cctggggctc ctgctgctct gtttccagg tgccagatgt     60 gacatccaga tgacccagtc tccatcctca ctgtctgcat ctgtaggaga cagagtcacc   120
atcacttgtc gggcgagtca gggtattagc agctggttag cctggtatca gcagaaacca   180
gagaaagccc ctaagtccct gatctatgct gcatccagtt tgcaaagtgg ggtcccatca   240
aggttcagcg gcagtggatc tgggacagat ttcactctca ccatcagcag cctgcagcct   300
gaagattttg caacttatta ctgccaacag tataatagtt accctctcac tttcggcgga   360
gggaccaagg tggagatcaa a                                              381

<210> SEQ ID NO 178
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
atggacacac tttgctccac gctcctgctg ctgaccatcc cttcatgggt cttgtcccag    60
atcaccttga aggagtctgg tcctacgctg gtgaaaccca cacagaccct cacgctgacc   120
tgcaccttct ctgggttctc actcggctct aatggactgg gtgtgggctg gatccgtcag   180 ccccaggaa aggccctgga gtggcttgca ctcatttatt gggatgatga taagcgctac    240
agtccatctc tgaagagcag gctcaccatc accaaggact cctccaaaaa ccaggtggtc   300
cttacaatga ccaacatgga ccctgtggac acagccacgt attactgtgc acacaggaac   360
agtggctttg actactgggg ccagggaatc ctggtcaccg tctcctca                408

<210> SEQ ID NO 179
<211> LENGTH: 381
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 179

```
atgagggtcc tcgctcagct cctggggctc ctgctgctct gtttcccagg tgccagatgt    60
gacatccaga tgacccagtc tccatcctca ctgtctgcat ctgtaggaga cagagtcacc   120
atcacttgtc gggcgagtca gggttttagc agctggttag cctggtatca gcagaaacca   180
gagaaagccc ctaagtccct gatctatgct gcatccagtt tgcaaagtgg ggtcccatca   240
aggttcagcg gcagtggatc tgggacagat ttcactctca ccatcagcag cctgcagcct   300
gaagattttg caacttatta ctgccaacag tataatagtt accccttacac ttttggccag   360
gggaccaagc tggagatcaa a                                              381
```

<210> SEQ ID NO 180
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 180

```
atgagggtcc tcgctcagct cctggggctc ctgctgctct gtttcccagg tgccagatgt    60
gacatccaga tgacccagtc tccatcctca ctgtctgcat ctgtaggaga cagagtcacc   120
atcacttgtc gggcgagtca gggtattagc agctggttag cctggtatca gcagaaacca   180
gagaaagccc ctaagtccct gatctatgct gcatccagtt tgcaaagtgg ggtcccatca   240
aggttcagcg gcagtggatc tgggacagat ttcactctca ccatcagcag cctgcagcct   300
gaagattttg caacttatta ctgccaacag tataatagtt accctctcac tttcggcgga   360
gggaccaagg tggagatcaa a                                              381
```

<210> SEQ ID NO 181
<211> LENGTH: 408
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181

```
atggacacac tttgctccac gctcctgctg ctgaccatcc cttcatgggt cttgtcccag    60
atcaccttga aggagtctgg tcctacgctg gtgaaaccca cacagaccct cacgctgacc   120
tgcaccttct ctgggttctc actcggcact agtggactgg gtgtgggctg gatccgtcag   180
cccccaggaa aggccctgga gtggcttgca ttcatttatt gggatgatga taagcgctac   240
agcccatctc tgaagagcag gctcaccatc accaaggaca cctccaaaaa ccaggtggtc   300
cttacaatga ccaacatgga ccctgtggac acagccacat attactgtgc acacagacgg   360
ggcttttttg actactgggg ccagggaacc ctggtcaccg tctcctca                408
```

<210> SEQ ID NO 182
<211> LENGTH: 381
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 182

| atgagggtcc tcgctcagct cctggggctc ctgctgctct gtttcccagg tgccagatgt | 60 |
| --- | --- |
| gacatccaga tgacccagtc tccatcctca ctgtctgcat ctgtaggaga cagagtcacc | 120 |
| atcacttgtc gggcgagtca gggtattagc agctggttag cctggtatca gcagaaacca | 180 |
| gagaaagccc ctaagtccct gatctatgct gcatccagtt tgcaaagtgg ggtcccatca | 240 |
| aggttcagcg gcagtggatc tgggacagat ttcactctca ccatcagcag cctgcagcct | 300 |
| gaagattttg caacttatta ctgccaacag tataatagtt acccgctcac tttcggcgga | 360 |
| gggaccaagg tggagatcaa a | 381 |

<210> SEQ ID NO 183
<211> LENGTH: 642
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 183

| gacatccaga tgacccagtc tccatcctcc ctgtctgcat ctgtaggaga cagagtcacc | 60 |
| --- | --- |
| atcacttgcc aggccagtca ggacattagc aattatttaa gctggtatca gcagaaacca | 120 |
| gggaaagccc ctaagctcct gatctactat acaaatctat ggcagaagg ggtcccatca | 180 |
| aggttcagtg gaagtggatc tgggacagat tttactttca ccatcagcag cctgcagcct | 240 |
| gaagatattg caacatatta ctgtcaacag tattataact atcggacgtt cggccctggg | 300 |
| accaaagtgg atatcaaacg tacggtggct gcaccatctg tcttcatctt cccgccatct | 360 |
| gatgagcagt tgaaatctgg aactgcctct gttgtgtgcc tgctgaataa cttctatccc | 420 |
| agagaggcca agtacagtg gaaggtggat aacgccctcc aatcgggtaa ctcccaggag | 480 |
| agtgtcacag agcaggacag caaggacagc acctacagcc tcagcagcac cctgacgctg | 540 |
| agcaaagcag actacgagaa acacaaagtc tacgcctgcg aagtcaccca tcagggcctg | 600 |
| agctcgcccg tcacaaagag cttcaacagg ggagagtgtt ag | 642 |

<210> SEQ ID NO 184
<211> LENGTH: 1353
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 184

| gaggtgcagc tggtggagtc tgggggaggc ttggtaaagc ctgggggtc ccttagactc | 60 |
| --- | --- |
| tcctgtgcag cctctggatt cactttcagt gactatttca tgcactgggt ccgccaggct | 120 |
| ccagggaagg gctgagtg ggttggcgtc atagacacta aaagttttaa ttatgcaacc | 180 |
| tattactctg atttggtgaa aggcagattc accatctcaa gagatgattc aaaaaacacg | 240 |
| ctgtatctgc aaatgaacag cctgaaaacc gaggacacag ccgtgtatta ctgtaccgca | 300 |
| accatcgctg tccatatta cttcgattac tggggccagg gaaccctggt caccgtctcc | 360 |
| tcagctagca ccaagggccc atcggtcttc cccctggcac cctcctccaa gagcacctct | 420 |
| gggggcacag cggccctggg ctgcctggtc aaggactact ccccgaacc ggtgacggtg | 480 |
| tcgtggaact caggcgccct gaccagcggc gtgcacacct tcccggctgt cctacagtcc | 540 |

```
tcaggactct actccctcag cagcgtggtg accgtgccct ccagcagctt gggcacccag    600
acctacatct gcaacgtgaa tcacaagccc agcaacacca aggtggacaa gagagttgag    660
cccaaatctt gtgacaaaac tcacacatgc ccaccgtgcc cagcacctga actcctgggg    720
ggaccgtcag tcttcctctt ccccccaaaa cccaaggaca ccctcatgat ctcccggacc    780
cctgaggtca catgcgtggt ggtggacgtg agccacgaag accctgaggt caagttcaac    840
tggtacgtgg acggcgtgga ggtgcataat gccaagacaa agccgcggga ggagcagtac    900
aacagcacgt accgtgtggt cagcgtcctc accgtcctgc accaggactg gctgaatggc    960
aaggagtaca agtgcaaggt ctccaacaaa gccctcccag cccccatcga gaaaaccatc   1020
tccaaagcca agggcagcc cgagaaccca ggtgtaca ccctgccccc atcccgggag     1080
gagatgacca gaaccaggt cagcctgacc tgcctggtca aaggcttcta tcccagcgac    1140
atcgccgtgg agtgggagag caatgggcag ccggagaaca actacaagac cacgcctccc    1200
gtgctggact ccgacggctc cttcttcctc tatagcaagc tcaccgtgga caagagcagg    1260
tggcagcagg ggaacgtctt ctcatgctcc gtgatgcatg aggctctgca caaccactac    1320
acgcagaaga gcctctccct gtccccgggt tga                                 1353
```

<210> SEQ ID NO 185
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 185

```
Glu Val Gln Leu Leu Glu Ser Gly Gly Gly Leu Val Gln Pro Gly Gly
1               5                   10                  15

Ser Leu Arg Leu Ser Cys Glu Ala Ser Gly Phe Ile Phe Lys Tyr Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys His Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Gly Asp Phe Asp Trp Ile His Tyr Tyr Gly Met Asp
            100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205
```

Val Asn His Lys Pro Ser Asn Thr Lys Val Asp Lys Arg Val Glu Pro
             210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
             245                 250                 255

Thr Leu Met Ile Ser Arg Thr Pro Glu Val Thr Cys Val Val Val Asp
             260                 265                 270

Val Ser His Glu Asp Pro Glu Val Lys Phe Asn Trp Tyr Val Asp Gly
         275                 280                 285

Val Glu Val His Asn Ala Lys Thr Lys Pro Arg Glu Glu Gln Tyr Asn
     290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
             325                 330                 335

Ala Pro Ile Glu Lys Thr Ile Ser Lys Ala Lys Gly Gln Pro Arg Glu
             340                 345                 350

Pro Gln Val Tyr Thr Leu Pro Pro Ser Arg Glu Glu Met Thr Lys Asn
         355                 360                 365

Gln Val Ser Leu Thr Cys Leu Val Lys Gly Phe Tyr Pro Ser Asp Ile
370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
             405                 410                 415

Leu Thr Val Asp Lys Ser Arg Trp Gln Gln Gly Asn Val Phe Ser Cys
             420                 425                 430

Ser Val Met His Glu Ala Leu His Asn His Tyr Thr Gln Lys Ser Leu
         435                 440                 445

Ser Leu Ser Pro Gly
    450

<210> SEQ ID NO 186
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Val Gln Leu Leu Glu Ser Gly Gly Gly Leu Val Gln Pro Gly Gly
1               5                   10                  15

Ser Leu Arg Leu Ser Cys Glu Ala Ser Gly Phe Ile Phe Lys Tyr Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Ser Thr Tyr Tyr Ala Asp Ser Val
    50                  55                  60

Lys Gly Arg Phe Thr Ile Ser Arg Asp Asn Ser Lys His Thr Leu Tyr
65                  70                  75                  80

Leu Gln Met Asn Ser Leu Arg Ala Glu Asp Thr Ala Val Tyr Tyr Cys
                85                  90                  95

```
Ala Lys Asp Gly Asp Phe Asp Trp Ile His Tyr Tyr Gly Met Asp
                100                 105                 110

Val Trp Gly Gln Gly Thr Thr Val Thr Val Ser Ser
            115                 120

<210> SEQ ID NO 187
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 187

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300
```

```
Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 188
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 189
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45
```

Tyr Asp Ala Ser Ser Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro His
                85                  90                  95

Thr Phe Gly Gly Gly Thr Lys Val Glu Ile Lys
            100                 105

<210> SEQ ID NO 190
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 191
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Tyr Tyr Ala Met Ser
1               5

<210> SEQ ID NO 192
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Ile Ser Gly Ser Gly Gly Ser Thr Tyr Tyr Ala Asp Ser Val Lys
1               5                   10                  15

Gly

<210> SEQ ID NO 193
<211> LENGTH: 15
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 193

Asp Gly Asp Phe Asp Trp Ile His Tyr Tyr Tyr Gly Met Asp Val
1               5                   10                  15

<210> SEQ ID NO 194
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Ala Ser Gln Gly Ile Ser Ser Ala Leu Ala
1               5                   10

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Asp Ala Ser Ser Leu Glu Ser
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Gln Gln Phe Asn Ser Tyr Pro His Thr
1               5

<210> SEQ ID NO 197
<211> LENGTH: 1359
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 197
gaggtgcagc tgttggagtc tgggggaggc ttggtacagc ctgggggtc cctgagactc      60 tcctgtgaag cctctggatt catctttaaa tactatgcca tgagctgggt ccgccaggct    120
ccagggaagg ggctggagtg ggtctcaggt attagtggta gtggtggtag cacatactac    180
gcagactccg tgaagggccg gttcaccatc tccagagaca attccaagca cacgctgtat    240
ctgcaaatga acagcctgag agccgaggac acggccgttt attactgtgc gaaagatggg    300
gattttgact ggatccacta ttactatggt atggacgtct ggggccaagg gaccacggtc    360
accgtctcct cagcgtcgac caagggccca tccgtcttcc ccctggcacc ctcctccaag    420
agcacctctg ggggcacagc ggccctgggc tgcctggtca aggactactt ccccgaaccg    480

```
gtgacggtgt cgtggaactc aggcgccctg accagcggcg tgcacacctt cccggctgtc      540
ctacagtcct caggactcta ctccctcagc agcgtggtga ccgtgccctc agcagcttg       600 ggcacccaga cctacatctg caacgtgaat cacaagccca gcaacaccaa ggtggacaag      660
agagttgagc ccaaatcttg tgacaaaact cacacatgcc caccgtgccc agcacctgaa     720
ctcctggggg gaccgtcagt cttcctcttc cccccaaaac ccaaggacac cctcatgatc      780
tcccggaccc ctgaggtcac atgcgtggtg gtggacgtga gccacgaaga ccctgaggtc      840
aagttcaact ggtacgtgga cggcgtggag gtgcataatg ccaagacaaa gccgcgggag      900
gagcagtaca acagcacgta ccgtgtggtc agcgtcctca ccgtcctgca ccaggactgg      960
ctgaatggca aggagtacaa gtgcaaggtc tccaacaaag ccctcccagc ccccatcgag     1020
aaaaccatct ccaaagccaa agggcagccc cgagaaccac aggtgtacac cctgccccca     1080
tcccgggagg agatgaccaa gaaccaggtc agcctgacct gcctggtcaa aggcttctat     1140
cccagcgaca tcgccgtgga gtgggagagc aatgggcagc cggagaacaa ctacaagacc     1200
acgcctcccg tgctggactc cgacggctcc ttcttcctct atagcaagct caccgtggac     1260
aagagcaggt ggcagcaggg gaacgtcttc tcatgctccg tgatgcatga ggctctgcac     1320
aaccactaca cgcagaagag cctctccctg tccccgggt                            1359

<210> SEQ ID NO 198
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 198
gaggtgcagc tgttggagtc tgggggaggc ttggtacagc ctgggggtc cctgagactc       60 tcctgtgaag cctctggatt catctttaaa tactatgcca tgagctgggt ccgccaggct     120
ccagggaagg ggctggagtg ggtctcaggt attagtggta gtggtggtag cacatactac      180
gcagactccg tgaagggccg gttcaccatc tccagagaca attccaagca cacgctgtat      240
ctgcaaatga acagcctgag agccgaggac acggccgttt attactgtgc gaaagatggg     300
gattttgact ggatccacta ttactatggt atggacgtct ggggccaagg gaccacggtc      360
accgtctcct ca                                                          372

<210> SEQ ID NO 199
<211> LENGTH: 987
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 199
gcgtcgacca agggcccatc cgtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca      180
ggactctact ccctcagcag cgtggtgacc gtgccctcca gcagcttggg cacccagacc      240
tacatctgca acgtgaatca caagcccagc aacaccaagg tggacaagag agttgagccc      300
aaatcttgtg acaaaactca cacatgccca ccgtgcccag cacctgaact cctgggggga      360
ccgtcagtct tcctcttccc cccaaaaccc aaggacaccc tcatgatctc ccggacccct      420
```

```
gaggtcacat gcgtggtggt ggacgtgagc cacgaagacc ctgaggtcaa gttcaactgg    480
tacgtggacg gcgtggaggt gcataatgcc aagacaaagc cgcgggagga gcagtacaac    540
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgcccccatc ccgggaggag    720
atgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctat agcaagctca ccgtggacaa gagcaggtgg    900
cagcagggga acgtcttctc atgctccgtg atgcatgagg ctctgcacaa ccactacacg    960
cagaagagcc tctccctgtc cccgggt                                        987

<210> SEQ ID NO 200
<211> LENGTH: 642
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 200
gccatccagt tgacccagtc tccatcctcc ctgtctgcat ctgtaggaga cagagtcacc     60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctcacac tttcggcgga    300
gggaccaagg tggagatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacccctgacg    540 ctgagcaaag cagactacga gaaacacaaa gtctacgcct gcgaagtcac ccatcagggc    600
ctgagctcgc ccgtcacaaa gagcttcaac aggggagagt gt                       642

<210> SEQ ID NO 201
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 201
gccatccagt tgacccagtc tccatcctcc ctgtctgcat ctgtaggaga cagagtcacc     60
atcacttgcc gggcaagtca gggcattagc agtgctttag cctggtatca gcagaaacca    120
gggaaagctc ctaagctcct gatctatgat gcctccagtt tggaaagtgg ggtcccatca    180
aggttcagcg gcagtggatc tgggacagat ttcactctca ccatcagcag cctgcagcct    240
gaagattttg caacttatta ctgtcaacag tttaatagtt accctcacac tttcggcgga    300
gggaccaagg tggagatcaa a                                              321

<210> SEQ ID NO 202
```

<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 202

```
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321
```

<210> SEQ ID NO 203
<211> LENGTH: 12
<212> TYPE: PRT
<213> ORGANISM: Homo sapiens

<400> SEQUENCE: 203

```
Ser Ile Phe Asp Pro Pro Pro Phe Lys Val Thr Leu
1               5                   10
```

<210> SEQ ID NO 204
<211> LENGTH: 330
<212> TYPE: PRT
<213> ORGANISM: Homo sapiens

<400> SEQUENCE: 204

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205
```

```
Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 205
<211> LENGTH: 168
<212> TYPE: PRT
<213> ORGANISM: Homo sapiens

<400> SEQUENCE: 205

Met Lys Ser Gly Leu Trp Tyr Phe Phe Leu Phe Cys Leu Arg Ile Lys
1               5                   10                  15

Val Leu Thr Gly Glu Ile Asn Gly Ser Ala Asn Tyr Glu Met Phe Ile
            20                  25                  30

Phe His Asn Gly Gly Val Gln Ile Leu Cys Lys Tyr Pro Asp Ile Val
        35                  40                  45

Gln Gln Phe Lys Met Gln Leu Leu Lys Gly Gly Gln Ile Leu Cys Asp
    50                  55                  60

Leu Thr Lys Thr Lys Gly Ser Gly Asn Thr Val Ser Ile Lys Ser Leu
65                  70                  75                  80

Lys Phe Cys His Ser Gln Leu Ser Asn Asn Ser Val Ser Phe Phe Leu
                85                  90                  95

Tyr Asn Leu Asp His Ser His Ala Asn Tyr Tyr Phe Cys Asn Leu Ser
            100                 105                 110

Ile Phe Asp Pro Pro Pro Phe Lys Val Thr Leu Thr Gly Gly Tyr Leu
        115                 120                 125

His Ile Tyr Glu Ser Gln Leu Cys Cys Gln Leu Lys Phe Trp Leu Pro
    130                 135                 140

Ile Gly Cys Ala Ala Phe Val Val Val Cys Ile Leu Gly Cys Ile Leu
145                 150                 155                 160

Ile Cys Trp Leu Thr Lys Lys Met
                165

<210> SEQ ID NO 206
<211> LENGTH: 330
<212> TYPE: PRT
<213> ORGANISM: Homo sapiens

<400> SEQUENCE: 206

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 207
<211> LENGTH: 95
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 207

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asp Asn Leu Pro
                85                  90                  95

<210> SEQ ID NO 208
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 208

Phe Thr Phe Gly Pro Gly Thr Lys Val Asp Ile Lys
1               5                   10

<210> SEQ ID NO 209
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 210
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Tyr Phe Asp Tyr Trp Gly Gln Gly Thr Leu Val Thr Val Ser Ser
1               5                   10                  15

<210> SEQ ID NO 211
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

```
Glu Val Asp Leu Val Glu Thr Gly Gly Gly Leu Val Gln Pro Gly Gly
1               5                   10                  15

Ser Leu Lys Leu Ser Cys Val Ala Ser Gly Phe Thr Phe Ser Arg Tyr
            20                  25                  30

Trp Met Phe Trp Ile Arg Gln Ala Pro Gly Lys Gly Leu Glu Trp Val
        35                  40                  45

Ser Ser Val Ser Thr Asp Gly Arg Ser Thr Tyr Tyr Pro Asp Ser Val
50                  55                  60

Gln Gly Arg Phe Thr Ile Ser Arg Asn Asp Ala Glu Asn Thr Val Tyr
65                  70                  75                  80

Leu Gln Met Asn Ser Leu Arg Ser Glu Asp Thr Ala Thr Tyr Tyr Cys
                85                  90                  95

Ala Lys Glu Gly Tyr Tyr Asp Gly Ser Tyr Tyr Ala Tyr Tyr Phe Asp
            100                 105                 110

Tyr Trp Gly Gln Gly Val Thr Val Thr Val Ser Ser Ala Lys Thr Thr
        115                 120                 125

Pro Pro Ser Val Tyr Pro Leu Ala Pro Gly Ser Ala Ala Gln Thr Asn
130                 135                 140

Ser Met Val Thr Leu Gly Cys Leu Val Lys Gly Tyr Phe Pro Glu Pro
145                 150                 155                 160

Val Thr Val Thr Trp Asn Ser Gly Ser Leu Ser Ser Gly Val His Thr
                165                 170                 175

Phe Pro Ala Val Leu Gln Ser Asp Leu Tyr Thr Leu Ser Ser Ser Val
            180                 185                 190

Thr Val Pro Ser Ser Thr Trp Pro Ser Glu Thr Val Thr Cys Asn Val
        195                 200                 205

Ala His Pro Ala Ser Ser Thr Lys Val Asp Lys Lys Ile Val Pro Arg
210                 215                 220

Asp Cys Gly Cys Lys Pro Cys Ile Cys Thr Val Pro Glu Val Ser Ser
225                 230                 235                 240

Val Phe Ile Phe Pro Pro Lys Pro Lys Asp Val Leu Thr Ile Thr Leu
                245                 250                 255

Thr Pro Lys Val Thr Cys Val Val Asp Ile Ser Lys Asp Asp Pro
            260                 265                 270

Glu Val Gln Phe Ser Trp Phe Val Asp Asp Val Glu Val His Thr Ala
        275                 280                 285

Gln Thr Gln Pro Arg Glu Glu Gln Phe Asn Ser Thr Phe Arg Ser Val
290                 295                 300

Ser Glu Leu Pro Ile Met His Gln Asp Trp Leu Asn Gly Lys Glu Phe
305                 310                 315                 320

Lys Cys Arg Val Asn Ser Ala Ala Phe Pro Ala Pro Ile Glu Lys Thr
                325                 330                 335

Ile Ser Lys Thr Lys Gly Arg Pro Lys Ala Pro Gln Val Tyr Thr Ile
            340                 345                 350

Pro Pro Pro Lys Glu Gln Met Ala Lys Asp Lys Val Ser Leu Thr Cys
        355                 360                 365

Met Ile Thr Asp Phe Phe Pro Glu Asp Ile Thr Val Glu Trp Gln Trp
370                 375                 380

Asn Gly Gln Pro Ala Glu Asn Tyr Lys Asn Thr Gln Pro Ile Met Asp
385                 390                 395                 400
```

Thr Asp Gly Ser Tyr Phe Val Tyr Ser Lys Leu Asn Val Gln Lys Ser
            405                 410                 415

Asn Trp Glu Ala Gly Asn Thr Phe Thr Cys Ser Val Leu His Glu Gly
            420                 425                 430

Leu His Asn His His Thr Glu Lys Ser Leu Ser His Ser Pro Gly Lys
            435                 440                 445

<210> SEQ ID NO 212
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Asp Val Gln Met Ala Gln Ser Pro Ser Ser Leu Ala Ala Ser Pro Gly
1               5                   10                  15

Glu Ser Val Ser Ile Asn Cys Lys Ala Ser Lys Ser Ile Ser Lys Tyr
            20                  25                  30

Leu Ala Trp Tyr Gln Gln Lys Pro Gly Lys Ala Asn Lys Leu Leu Ile
        35                  40                  45

Tyr Ser Gly Ser Thr Leu Gln Ser Gly Thr Pro Ser Arg Phe Ser Gly
    50                  55                  60

Ser Gly Ser Gly Thr Asp Phe Thr Leu Thr Ile Arg Asn Leu Glu Pro
65                  70                  75                  80

Glu Asp Phe Gly Leu Tyr Tyr Cys Gln Gln His Asn Ala Tyr Pro Pro
                85                  90                  95

Thr Phe Gly Thr Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 213
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Glu Val Gln Leu Val Glu Ser Gly Gly Gly Leu Val Lys Pro Ala Gly
1               5                   10                  15

Ser Leu Thr Leu Ser Cys Val Ala Ser Gly Phe Thr Phe Ser Asp Tyr
            20                  25                  30

Phe Met His Trp Val Arg Gln Ala Pro Gly Lys Gly Leu Glu Trp Val
          35                  40                  45

Ala Val Ile Asp Thr Lys Ser Phe Asn Tyr Ala Thr Tyr Tyr Ser Asp
 50                  55                  60

Leu Val Lys Gly Arg Phe Thr Val Ser Arg Asp Asp Ser Gln Gly Met
 65                  70                  75                  80

Val Tyr Leu Gln Met Asn Asn Leu Arg Lys Glu Asp Thr Ala Thr Tyr
                  85                  90                  95

Tyr Cys Thr Ala Thr Ile Ala Val Pro Tyr Tyr Phe Asp Tyr Trp Gly
                 100                 105                 110

Gln Gly Thr Met Val Thr Val Ser Ser Ala Lys Thr Thr Pro Pro Ser
                 115                 120                 125

Val Tyr Pro Leu Ala Pro Gly Ser Ala Ala Gln Thr Asn Ser Met Val
         130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                 165                 170                 175

Val Leu Gln Ser Asp Leu Tyr Thr Leu Ser Ser Ser Val Thr Val Pro
                 180                 185                 190

Ser Ser Thr Trp Pro Ser Glu Thr Val Thr Cys Asn Val Ala His Pro
                 195                 200                 205

Ala Ser Ser Thr Lys Val Asp Lys Lys Ile Val Pro Arg Asp Cys Gly
         210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                 245                 250                 255

Val Thr Cys Val Val Val Asp Ile Ser Lys Asp Asp Pro Glu Val Gln
                 260                 265                 270

Phe Ser Trp Phe Val Asp Asp Val Glu Val His Thr Ala Gln Thr Gln
         275                 280                 285

Pro Arg Glu Glu Gln Phe Asn Ser Thr Phe Arg Ser Val Ser Glu Leu
         290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                 325                 330                 335

Thr Lys Gly Arg Pro Lys Ala Pro Gln Val Tyr Thr Ile Pro Pro Pro
                 340                 345                 350

Lys Glu Gln Met Ala Lys Asp Lys Val Ser Leu Thr Cys Met Ile Thr
                 355                 360                 365

Asp Phe Phe Pro Glu Asp Ile Thr Val Glu Trp Gln Trp Asn Gly Gln
         370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
                 405                 410                 415

Ala Gly Asn Thr Phe Thr Cys Ser Val Leu His Glu Gly Leu His Asn
                 420                 425                 430

His His Thr Glu Lys Ser Leu Ser His Ser Pro Gly Lys
                 435                 440                 445

<210> SEQ ID NO 214
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 214

Asp Ile Gln Met Thr Gln Ser Pro Ser Ser Leu Pro Ala Ser Leu Gly
1               5                   10                  15

Asp Arg Val Thr Ile Asn Cys Gln Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Asn Leu Leu Ala Asp Gly Val Pro Ser Arg Phe Ser Gly
50                  55                  60

Ser Gly Ser Gly Arg Asp Tyr Ser Phe Thr Ile Ser Ser Leu Glu Ser
65                  70                  75                  80

Glu Asp Ile Gly Ser Tyr Tyr Cys Gln Gln Tyr Tyr Asn Tyr Arg Thr
                85                  90                  95

Phe Gly Pro Gly Thr Lys Leu Glu Ile Lys Arg Ala Asp Ala Ala Pro
            100                 105                 110

Thr Val Ser Ile Phe Pro Pro Ser Ser Glu Gln Leu Thr Ser Gly Gly
        115                 120                 125

Ala Ser Val Val Cys Phe Leu Asn Asn Phe Tyr Pro Lys Asp Ile Asn
130                 135                 140

Val Lys Trp Lys Ile Asp Gly Ser Glu Arg Gln Asn Gly Val Leu Asn
145                 150                 155                 160

Ser Trp Thr Asp Gln Asp Ser Lys Asp Ser Thr Tyr Ser Met Ser Ser
                165                 170                 175

Thr Leu Thr Leu Thr Lys Asp Glu Tyr Glu Arg His Asn Ser Tyr Thr
            180                 185                 190

Cys Glu Ala Thr His Lys Thr Ser Thr Ser Pro Ile Val Lys Ser Phe
        195                 200                 205

Asn Arg Asn Glu Cys
    210

<210> SEQ ID NO 215
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met His Trp Val Arg Gln Ala Pro Gly Lys Gly Leu Glu Trp Val
        35                  40                  45

Gly Val Ile Asp Thr Lys Ser Phe Asn Tyr Ala Thr Tyr Tyr Ser Asp
    50                  55                  60

Leu Val Lys Gly Arg Phe Thr Ile Ser Arg Asp Asp Ser Lys Asn Thr
65                  70                  75                  80

```
Leu Tyr Leu Gln Met Asn Ser Leu Lys Thr Glu Asp Thr Ala Val Tyr
                85                  90                  95

Tyr Cys Thr Thr Thr Ile Ala Val Pro Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 216
<211> LENGTH: 213
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 216

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Asn Leu Leu Ala Asp Gly Val Pro Ser Arg Phe Ser Gly
50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Tyr Arg Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 217
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Phe Met His Trp Val Arg Gln Ala Pro Gly Lys Gly Leu Glu Trp Val
        35                  40                  45

Gly Val Ile Asp Thr Lys Ser Phe Asn Tyr Ala Thr Tyr Tyr Ser Asp
50                  55                  60

Leu Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Ala Thr Ile Ala Val Pro Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 218
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

Asp Ile Gln Met Thr Gln Ser Pro Ser Ser Leu Ser Ala Ser Val Gly
1               5                   10                  15

```
Asp Arg Val Thr Ile Thr Cys Gln Ala Ser Gln Asp Ile Ser Asn Tyr
            20                  25                  30

Leu Ser Trp Tyr Gln Gln Lys Pro Gly Lys Ala Pro Lys Leu Leu Ile
        35                  40                  45

Tyr Tyr Thr Asn Leu Leu Ala Asp Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Tyr Asn Tyr Arg Thr
                85                  90                  95

Phe Gly Pro Gly Thr Lys Val Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
            165                 170                 175

Thr Leu Thr Leu Ser Lys Ala Asp Tyr Glu Lys His Lys Val Tyr Ala
        180                 185                 190

Cys Glu Val Thr His Gln Gly Leu Ser Ser Pro Val Thr Lys Ser Phe
            195                 200                 205

Asn Arg Gly Glu Cys
            210

<210> SEQ ID NO 219
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Pro Thr Ser Ser Ser Thr Lys Lys Thr Gln Leu Gln Leu Glu His Leu
1               5                   10                  15

Leu Leu Asp Leu Gln Met Ile Leu Asn Gly Ile Asn Asn Tyr Lys Asn
            20                  25                  30

Pro Lys Leu Thr Arg Met Leu Thr Phe Lys Phe Tyr Met Pro Lys Lys
        35                  40                  45

Ala Thr Glu Leu Lys His Leu Gln Cys Leu Glu Glu Glu Leu Lys Pro
    50                  55                  60

Leu Glu Glu Val Leu Asn Leu Ala Gln Ser Lys Asn Phe His Leu Arg
65                  70                  75                  80

Pro Arg Asp Leu Ile Ser Asn Ile Asn Val Ile Val Leu Glu Leu Lys
                85                  90                  95

Gly Ser Glu Thr Thr Phe Met Cys Glu Tyr Ala Asp Glu Thr Ala Thr
            100                 105                 110

Ile Val Glu Phe Leu Asn Arg Trp Ile Thr Phe Ser Gln Ser Ile Ile
        115                 120                 125

Ser Thr Leu Thr
130
```